United States Patent [19]
Pamukcu et al.

[11] Patent Number: 6,133,271
[45] Date of Patent: *Oct. 17, 2000

[54] METHOD FOR INHIBITING NEOPLASTIC CELLS AND RELATED CONDITIONS BY EXPOSURE THIENOPYRIMIDINE DERIVATIVES

[75] Inventors: Rifat Pamukcu, Spring House; Gary A. Piazza, Doylestown, both of Pa.

[73] Assignee: Cell Pathways, Inc., Horsham, Pa.

[ * ] Notice: This patent is subject to a terminal disclaimer.

[21] Appl. No.: 09/197,216

[22] Filed: Nov. 19, 1998

[51] Int. Cl.$^7$ .................................................. A61K 31/519

[52] U.S. Cl. .................. 514/258; 514/234.2; 514/252.02

[58] Field of Search ................................ 514/258, 234.2, 514/254, 252.02

[56] References Cited

U.S. PATENT DOCUMENTS

| | | | |
|---|---|---|---|
| 3,031,450 | 4/1962 | Fischer et al. | 260/247 S |
| 3,161,654 | 12/1964 | Shen | 260/119 |
| 3,322,755 | 5/1967 | Roch et al. | 260/246 |

(List continued on next page.)

FOREIGN PATENT DOCUMENTS

| | | |
|---|---|---|
| 0 330 004 A1 | 6/1989 | European Pat. Off. . |
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 722937 A1 | 7/1996 | European Pat. Off. . |
| 0 743304 A1 | 10/1996 | European Pat. Off. . |
| 3038166 | 5/1981 | Germany . |
| 274218 | 12/1989 | Germany . |
| 56-53659 | 5/1981 | Japan . |
| 57-167974 | 10/1982 | Japan . |
| 8-311035 | 11/1996 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 94/19351 | 9/1994 | WIPO . |
| WO 94/29277 | 12/1994 | WIPO . |
| WO 95 18969 | 7/1995 | WIPO . |
| WO 95/26743 | 10/1995 | WIPO . |
| WO 97/03070 | 1/1997 | WIPO . |
| WO 97/03985 | 2/1997 | WIPO . |
| WO 97/24334 | 7/1997 | WIPO . |
| WO 98/14448 | 4/1998 | WIPO . |
| WO 98/15530 | 4/1998 | WIPO . |
| WO 98/16224 | 4/1998 | WIPO . |
| WO 98/16521 | 4/1998 | WIPO . |
| WO 98/17668 | 4/1998 | WIPO . |
| WO 98/08848 | 5/1998 | WIPO . |
| WO 98/23597 | 6/1998 | WIPO . |
| WO 98/38168 | 9/1998 | WIPO . |
| WO 96/32379 | 10/1998 | WIPO . |
| WO 00/15222 | 3/2000 | WIPO . |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

(List continued on next page.)

*Primary Examiner*—Richard L. Raymond
*Attorney, Agent, or Firm*—Robert W. Stevenson

[57] ABSTRACT

Benzothienopyrimidine derivatives for inducing or promoting apoptosis and for arresting uncontrolled neoplastic cell proliferation, and specifically for arresting and treating neoplasia, including precancerous and cancerous lesions of formula I:

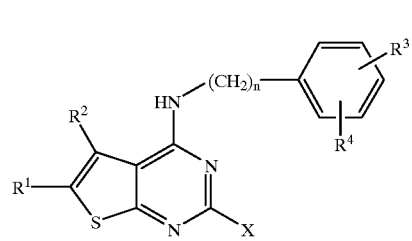

(I)

wherein $R_1$ and $R_2$ are independently selected from the group consisting of hydrogen, A, OA, alkenyl, alkynyl, —$NO_2$, —$CF_3$ or halogen, with the proviso that one of $R_1$ or $R_2$ is not hydrogen; $R_3$ and $R_4$ are independently selected from the group consisting of hydrogen, A, —OA, halogen, —$NO_2$, —$NH_2$, —NHA or —NAA', or $R_3$ and $R_4$ are together form a moiety selected from the group consisting of —O—$CH_2$—$CH_2$—, —O—$CH_2$—O— or —O—$CH_2$—$CH_2$—O; X is selected from the group consisting of an unsubstituted or a substituted 5–7 membered saturated or unsaturated ring, wherein the ring is selected from the group consisting of phenyl, cyclopentyl, cyclohexyl, cycloheptyl, furyl, dioxolanyl, thienyl, pyrrolyl, pyrrolidinyl, imidazolyl, pyrazolyl, pyridyl, piperidinyl, morpholinyl, pyranyl, dioxanyl, pyridazinyl, pyrimidinyl, piperazinyl, quinolyl, and isoquinolyl and wherein the substitutents on the "X" ring are one or two selected from the group consisting of lower alkyl, COOH, —COOA, —$CONH_2$, —CONAA', —CONHA, —CN, —$CH_2$COOH or —$CH_2CH_2$COOH; A and A' are independently selected from the group consisting of hydrogen or $C_{1-6}$ alkyl; and n is 0, 1, 2 or 3; and physiologically acceptable salts thereof.

12 Claims, No Drawings

U.S. PATENT DOCUMENTS

| | | | |
|---|---|---|---|
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/478 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,865,840 | 2/1975 | Carson | 260/326.46 |
| 3,920,636 | 11/1975 | Takahasi et al. | 260/240 J |
| 4,001,237 | 1/1977 | Partyka et al. | 260/256.4 B |
| 4,001,238 | 1/1977 | Partyka et al. | 260/256.4 B |
| 4,039,544 | 8/1977 | Broughton et al. | 260/256.4 F |
| 4,060,615 | 11/1977 | Matier et al. | 424/251 |
| 4,076,711 | 2/1978 | Ganguly et al. | 260/256.4 F |
| 4,079,057 | 3/1978 | Juby et al. | 260/256.4 F |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/283 |
| 4,138,561 | 2/1979 | Crenshaw et al. | 544/284 |
| 4,146,716 | 3/1979 | Cox et al. | 544/728 |
| 4,161,595 | 7/1979 | Kaplan et al. | 544/284 |
| 4,171,363 | 10/1979 | Crenshaw et al. | 424/251 |
| 4,196,207 | 4/1980 | Webber et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,457,927 | 7/1984 | Biere et al. | 424/245 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 4,971,972 | 11/1990 | Doll et al. | 514/265 |
| 5,073,559 | 12/1991 | Coates | 514/262 |
| 5,091,431 | 2/1992 | Tulshian et al. | 514/262 |
| 5,147,875 | 9/1992 | Coates et al. | 514/259 |
| 5,175,151 | 12/1992 | Afonso et al. | 514/63 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/344 |
| 5,280,026 | 1/1994 | Brown et al. | 514/258 |
| 5,358,952 | 10/1994 | Moschel et al. | 514/262 |
| 5,376,683 | 12/1994 | Klar et al. | 514/530 |
| 5,393,755 | 2/1995 | Neustadt et al. | 514/233.2 |
| 5,401,774 | 3/1995 | Pamukcu et al. | 514/569 |
| 5,439,895 | 8/1995 | Lee et al. | 514/63 |
| 5,488,055 | 1/1996 | Kumar et al. | 514/293 |
| 5,614,530 | 3/1997 | Kumar et al. | 514/293 |
| 5,614,627 | 3/1997 | Takase et al. | 544/293 |
| 5,696,159 | 12/1997 | Gross et al. | 514/468 |
| 5,728,563 | 3/1998 | Toshio et al. | 560/121 |
| 5,756,818 | 5/1998 | Buchmann et al. | 514/269 |
| 5,852,035 | 12/1998 | Pamukcu et al. | 514/293 |
| 5,858,694 | 1/1999 | Piazza et al. | 435/19 |
| 5,869,486 | 2/1999 | Lee et al. | 514/248 |
| 5,874,440 | 2/1999 | Pamukcu et al. | 514/293 |
| 5,984,911 | 9/1999 | Pamukcu et al. | 544/278 |

OTHER PUBLICATIONS

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$Colon Carcinoma, Science, vol. 175, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Rochus et al. CA Abstract Accession No. 1998:268506, 1998.

Rochus et al CA Abstract Accession No. 1998:126255, 1998.

Boehm et al. CA Abstract Accession No. 1987:156389, 1986.

Boehm et al. CA Abstract Accession No. 1986:186437, 1986.

Waddell, w.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–1999 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucldeotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, p. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, A Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R.B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89. (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Ho–Sam Ahn et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp 11693–11697.

J.D. Gaffen et al.: Increased killing of malignant cells by giving indomethacin with methotrexate, p. 30; column 1; XP002084860Chemical Abstract, vol. 106, No. 11, Mar. 16, 1987, abstract No. 78377, J.D.

Tsou, K–C. et al. 5'Nucleotide Phosphodiesterase Isozyme–V as a Marker for Liver Metastases in Breast Cancer Patients, Cancer 54:1788–1793, 1984.

Epstein P M et al.; Dep. Pharmacol., Univ. Tex. Med. Sch., M.D. Anderson Hosp., Houston, Tex. 88030, USA BIOSIS 78:140912, Increased Cyclic Nucleotide Phospho Di Esterase Activity Associated With Proliferation and Cancer in Human and Murine Lymphoid Cells, 1978.

Christian Schudt et al., "Phosphodiesterase Inhibitors" The Handbook of Immunopharmacology, Academic Press, 1996, pp. 65–134.

METHOD FOR INHIBITING NEOPLASTIC CELLS AND RELATED CONDITIONS BY EXPOSURE THIENOPYRIMIDINE DERIVATIVES

TECHNICAL FIELD

This invention relates to a method for the inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps that can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds of that are useful in the methods of this invention include those of Formula I:

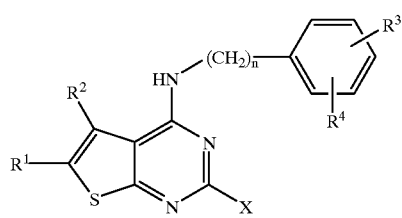

wherein $R_1$ and $R_2$ are independently selected from the group consisting of hydrogen, A, OA, alkenyl, alkynyl, $-NO_2$, $-CF_3$ or halogen, with the proviso that one of $R_1$ or $R_2$ is not hydrogen; or $R_1$ and $R_2$ together form a $C_{3-5}$ alkylene group;

$R_3$ and $R_4$ are independently selected from the group consisting of hydrogen, A, $-OA$, halogen, $-NO_2$, $-NH_2$, $-NHA$ or $-NAA'$, or $R_3$ and $R_4$ are together form a moiety selected from the group consisting of $-O-CH_2-CH_2-$, $-O-CH_2-O-$ or $-O-CH_2-CH_2-O$, X is selected from the group consisting of an unsubstituted or a substituted 5–7 membered saturated or unsaturated heterocyclic ring, wherein the ring is selected from the group consisting of phenyl, cyclopentyl, cyclohexyl, cycloheptyl, furyl, dioxolanyl, thienyl, pyrrolyl, pyrrolidinyl, imidazolyl, pyrazolyl, pyridyl, piperidinyl, morpholinyl, pyranyl, dioxanyl, pyridazinyl, pyrimidinyl, piperazinyl, quinolyl, and isoquinolyl and wherein the substitutents on the "X" ring are one or two selected from the group consisting of -lower alkyl, COOH, $-COOA$, $-CONH_2$, $-CONAA'$, $-CONHA$, $-CN$, $-CH_2COOH$ or $-CH_2CH_2COOH$;

A and A' are independently selected from the group consisting of hydrogen or $C_{1-6}$ alkyl; and n is 0, 1, 2 or 3n and physiologically acceptable salts thereof.

DETAILED DESCRIPTION OF THE INVENTION

The present invention also is a method of treating a patient with such lesions by administering to a patient a pharmacologically effective amount of a pharmaceutical composition that includes a compound of Formula I, wherein $R_1$ etc. are as defined above. Preferably, this composition is administered without therapeutic amounts of an NSAID.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein RI through $R_7$ and Y are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

As used herein, the term "halogen" means fluorine, chlorine, bromine, or iodine.

Compounds useful in the practice of this invention may be formulated into pharmaceutical compositions together with pharmaceutically acceptable carriers for oral administration in solid or liquid form, or for rectal or topical administration, although carriers for oral and parenteral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

When the present invention is used as a medicine for such diseases, it is administered by oral administration or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth.

In general the compounds useful in the practice of this invention are administered preferably in dosages between 1 and 500 mg, in particular between 5 and 100 mg per dosage unit. The daily dosage is preferably between approximately 0.02 and 10 mg/kg body weight. The specific dosage for each patient depends on various factors, e.g., on the efficacy of the used specific compound, on the age, the body weight, general health, gender, nutrition, the application time and method, elimination velocity, the pharmaceutical combination and the gravity of the respective disease for which the treatment is meant. Oral administration is preferred.

A and A' are independently preferably alkyl with 1–6 carbon atoms. In the preceding formulae "alkyl" can be linear, branched or cyclic, but preferably linear with 1–6 carbons and more preferably 1–5 carbons, most preferably methyl, ethyl or propyl. However, isopropyl, butyl, isobutyl, butyl or tert.-butyl, n-pentyl, neopentyl or isopentyl can be employed.

"Alkylene" is preferably linear and is most preferred propylene, butylene or pentylene.

Of the substituents $R_1$ and $R_2$, one is preferably hydrogen, while the other is preferably propyl or butyl, most preferred is ethyl or methyl. However, $R_1$ and $R_2$ can also together be propylene, butylene or pentylene.

"Halo" or "halogen" preferably refer to F, Cl or Br. However iodine can also be employed.

"Alkenyl" is preferably vinyl, 1- or 2-propenyl, 1-butenyl, isobutenyl, sec.-butenyl. However, 1-pentenyl, iso-pentenyl or 1-hexenyl can be employed.

"Alkinyl" is preferably ethyinyl, or propyn-1-yl. However, butyn-1-,butyn-2-yl, penyn-1-,pentyn-2- or pentyn-3-yl can be employed.

The substitutents $R_3$ and $R_4$ can be the same or different and are preferably, in position 3 or 4 of the phenyl ring. They are for example independently hydrogen, alkyl, alkoxy, nitro, amino, alkylamino (e.g., methylamino), dialkylamino (e.g., dimethylamino), or halo. Alternatively, $R_3$ and $R_4$ together are ethylenoxy, methylenedioxy or ethylendioxy. $R_3$ and $R_4$ also can be alkoxy (e.g., methoxy, ethoxy or propoxy).

X is preferably single or double substituted phenyl, cyclopentyl, cyclohexyl, cycloheptyl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or-5-pyrrolyl, 2,5-dihydro-1-, -2-, -3-, -4- or-5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3-, or 4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1,-2-,-3-,-4-,-5-,-6-,-7- or -8-isoquinolyl.

The substituent(s) on the "X" ring preferably are selected from the group consisting of lower alkyl, —COOH, —COOCH$_3$, —COOC$_2$H$_5$, —CONH$_2$, —CON(CH$_3$)$_2$, —CONHCH$_3$, —CN, —CH$_2$COOH or —CH$_2$CH$_2$COOH.

More preferred compounds useful in the practice of this invention are those in groups 1–5 below In group 1, X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH;

In Group 2, $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; X is as defined in Group 1; and n is 1.

In group 3, $R_1$ and $R_2$ are as defined in group 2; $R_3$ and $R_4$ are independently selected from the group consisting of hydrogen, A, OA, halogen, —NO$_2$, —NH$_2$, —NHA or —NAA'; X is as defined in group 1; and n is 1;

In group 4, $R_1$ and $R_2$ together form a $C_{3-5}$ alkylene, $R_3$ and $R_4$ together form a moiety selected from the group consisting of —O—CH$_2$—CH$_2$—, —O—CH$_2$—O— or —O—CH$_2$—CH$_2$—O, X is as defined in group 1; and n is 1;

Finally, in group 5, $R_1$, $R_2$ together form a $C_{3-5}$ alkylene; $R_3$ and $R_4$ are independently selected from the group consisting of hydrogen, A, OA, halogen, $NO_2$, $NH_2$, NHA or NAA'; X is as defined in group 1; and n is 1.

Processes for preparing compounds useful in this invention are described in PCT Patent Application No. 97/05530 (which is incorporated herein by reference). Those processes are set forth below. However, those processes, as well as processes for making the starting materials are reportedly known methods described in the literature (e.g., Houben-Weyl, Methods of Organic Chemistry, Georg Thieme, Stuttgart). The same reaction conditions as those known for the respective reactions can be employed.

Specifically, compounds useful in practicing this invention can be synthesized in several general ways, depending on the types of substitutions. For example, compounds of Formula I (as well as their salts) where X is a single or double substituted saturated 5–7 membered nitrogen-containing heterocycle which is connected via the nitrogen is made using a compound of Formula II

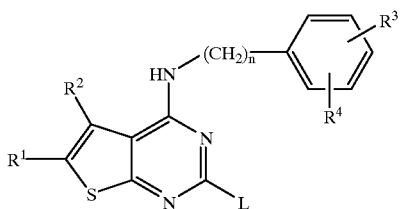

II wherein $R_1$, $R_2$, $R_3$, $R_4$ and n have the meanings above, but L is Cl, Br, OH, SCH$_3$ or a reactive esterfied OH-group. The compound of Formula II is allowed to react with a "$R_5$ substituted" saturated 5–7 membered nitrogen-containing heterocycle (where $R_5$ has the given designation).

Alternatively, the synthesis of compounds of Formula I (as well as their salts) where X is a substituted, unsaturated or saturated 5–7 membered isocycle which is connected a carbon atom on its ring to the theinopyrimidine ring is as follows. A compound of Formula III

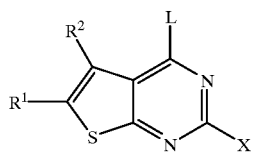

III wherein $R_1$, $R_2$ and X have the meanings described above and L is Cl, Br, OH, SCH$_3$ or a reactive esterified OH-group is allowed to react with a compound of Formula IV

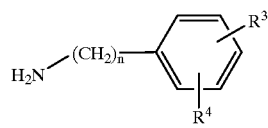

IV wherein $R_3$, $R_4$ and n have the given designations to obtain the desired compound.

In still another method to synthesize a compound of Formula I, one compound of Formula I can be converted to another. For example, a substituent $R_3$, $R_4$ and/or X can be transformed to another substituent $R_3$, $R_4$, and/or X, e.g., by the saponification of an ester, or by reduction of a nitro group. Also an acid compound of Formula I can be converted to one of its salts by treatment with a base.

If L is a reactive esterified OH-group, it is preferably alkylsulfonyloxy with $C_{1-6}$ (preferably methylsulfonyloxy) or arylsulfonyloxy with $C_{6-10}$ (preferably phenyl- or p-tolylsulfonyloxy, also 2-naphthalenesulfonyloxy).

The starting materials can also, if necessary, be made in situ, so that they are not isolated from the reaction mixture but are immediately allowed to react to compounds of Formula I. On the other hand, the reaction can also be done stepwise.

The compounds of Formula I, wherein X is connected via N to the thienopyrimidine ringsystem can preferably be obtained by the reaction of compounds of formula II with unsubstituted or single or double substituted (i.e., substituted with COOH, COOA, CONH$_2$, CONAA'. CONHA or CN) saturated 5–7 membered heterocyles.

The compounds of Formula II are generally known. To the extent they are not specifically known or described previously, they can be synthesized by known methods. Precursors to the compounds of Formula II can e.g., be synthesized by cyclisation or halogenation according to Med. Chem. 24, 374 (1981). Subsequent reaction with arylalkylamines yield compounds of Formula II.

In particular, the reaction of compounds of Formula II with the NH-containing heterocycle takes place in the presence or in the absence of an inert solvent at temperatures between approximately −20° C. and approximately 150° C., preferably between 20° C. and 100° C.

The addition of an acid binding agent, e.g., an alkali or alkaline earth metal hydroxide, carbonate or bicarbonate or of another salt of a weak acid of the alkali or alkaline earth metals, preferably of potassium, sodium or calcium, or the addition of an organic base like triethylamine, dimethylamine, pyridine or quinoline or an excess of the amine component can be enhancing.

As inert solvents the following can be used: hydrocarbons (e.g., hexane, petrolether, benzene, toluene, xylene), chlorinated hydrocarbons (e.g., trichloroethylene, 1,2-dichlorethane, carbontetrachloride, chloroform or dichloromethane), alcohols (e.g., methanol, ethanol, isopropanol, n-propano, n-butanol, tert. Butanol), ethers (e.g., diethylether, disopropylether, tetrahydrofurane (THF) or dioxane), glycolethers (e.g., ethyleneglycolmono methyl or monoethylether (methylglycol or ethylglycol), ethyleneglycoldimethylether (diglyme)), ketones (e.g., acetone or butanone), amides (e.g., acetamide, dimethylacetamide or dimethyl formamide (DMF)), nitriles (e.g., acetonitrile; sulfoxides like dimethysulfoxide (DMSO)), nitro compounds (e.g., nitromethane or nitrobenzene), esters (e.g., ethylacetate), or mixtures of these solvents.

Compounds of Formula III can be obtained from compounds derived from thiophenderivatives and CN-substituted heterocycles by reaction with POCl$_3$ (Eur. J. Med. Chem. 23, (1988).

The reactions of compounds of Formula III and compounds of Formula IV take place under similar conditions regarding reaction time temperature and solvent, as are described for the reactions of compounds of Formula II with NH-containing heterocycles.

To convert a substituent $R_3$ and/or $R_4$ of a compound of Formula I, to another substituent $R_3$ and/or $R_4$ e.g., by reduction of a nitrogroup (e.g., by hydration on Raney-nickel or Pd-charcoal in an inert solvent like methanol or ethanol) to an amino group or by hydrolysis of a cyano group to a carboxylic group.

An acid of formula I with a base can be converted to the corresponding addition salt e.g., by the reaction of equivalent amounts of acid and base in an inert solvent like ethanol and subsequent evaporation. For this reaction bases that yield physiologically non-toxic salts are to be used.

In this way, the acid of Formula I can be transformed with a base (e.g., sodium or potassium hydroxide or carbonate) to the corresponding metal, in particular alkali- or alkaline earth metal or the corresponding ammonium salt.

On the other hand, base of Formula I can be transformed with an acid to the corresponding acid addition salt, e.g., by reaction of equivalent amounts of base and acid in an inert solvent like ethanol and subsequent evaporation. For this reaction acids which give physiologically non-toxic salts can particularly be used, inorganic acids e.g., sulfuric acid, nitric acid, halogenhalides like hydrochloric acid or hydrobromic acid, phosphoric acids like orthophosphoric acid, sulfaminic acid; furthermore organic acids can be used, in particular aliphatic, alicyclic, araliphatic, aromatic or heterocyclic one or multiple base carbonic, sulfonic or sulfuric acids, e.g., formic acid, acetic acid, propionic acid, pivalinic acid, diethylacetic acid, malonic acid, succinic acid, pimelinic acid, fumatic acid, maleinic acid, lactic acid, tartaric acid, 2-hydroxysuccinic acid, citric acid, glucomic acid, ascorbic acid, nicotinic acid, isonicotinic acid, methan- or ethansulfonic acid, ethandisulfonic acid, 2-hydroxyethansulfonic acid, benzenesulfonic acid, p-toluene-sulfonic acid, naphthaline-mono- and disulfonic acids, laurylsulfuric acids. Salts with physiologically not acceptable acids, e.g., picrates, can be used for the isolation and/or purification of compounds of Formula I.

In the preceding and the following all temperatures are in ° C. In the following examples the "usual workup" means: if necessary, water is added, the pH is, if necessary, adjusted to values between 2 and 10, depending on the constituency of the product, extraction is done with ethylacetate or CH$_2$Cl$_2$, the phases are separated, the organic phase is dried over Na$_2$SO$_4$, evaporated and purified by chromatography on silicagel and/or crystallisation.

The foregoing may be better understood from the following examples from the aforesaid PCT patent application (which is incorporated herein by reference) that are presented for purposes illustrating compounds useful in practicing this invention and are not intended to limit the scope of the invention.

EXAMPLE 1

2-Chloro-6-Methyl-4-(3,4-Methylenedioxybenzylamino)-Thieno-[2,3-d]-Pyrimidine

A solution of 2,4-dichloro-6-methyl-thieno-[2,3-d]-pyrimidine (3.29 g) in dichloromethane (30 ml) is charged with 3,4-methylenedioxybenzylamine ("A") (3.02 g). Triethylamine (1.52 g) is added, and the mixture is stirred at room temperature. The solvent is removed, and the usual workup yields 2-chloro-6-methyl-4-(3,4-methylenedioxybenzylamino)-thieno-[2,3-d]-pyrimidine (3.38 g) Mp. 162° C.

EXAMPLE 2

2-Chloro-5-Methyl-4-(3,4-Methylenedioxybenzylamino)-Thieno-[2,3-d]-Pyrimidine

Following the procedure of Example 1, the reaction of 3,4-methylenedioxybenzylamine with 2,4-dichloro-5-methyl-thieno-[2,3-d]-pyrimidine gives 2-chloro-5-methyl-4-(3,4-methylenedioxybenzylamino)-thieno-[2,3-d]-pyrimidine

EXAMPLE 3

Following the procedure of Example 1, the reaction of 3,4-methylenedioxybenzylamine with 2,4-dichloro-5,6,7,8-tetrahydro-[1]-benzothieno-[2,3-d]-pyrimidine gives 2-chloro-5,6,7,8-tetrahydro-4-(3,4-methylenedioxybenzylamino)-[1]-benzothieno-[2,3-d]-pyrimidine Mp. 222° C.

EXAMPLE 4

Following the procedure of Example 1, the reaction of 3,4-methylenedioxybenzylamine with 2,4-dichloro-5,6-cyclopenteno-[1]-benzothieno-[2,3-d]-pyrimidine gives 2-chloro-5,6-cyclopenteno-4-(3,4-methylenedioxybenzylamino)-[1]-benzothieno-[2,3-d]-pyrimidine.

EXAMPLE 5

Following the procedure of Example 1, the reaction of 3,4-methylenedioxybenzylamine with 2,4-dichloro-5,6-cyclohepteno-[1]-benzothieno-[2,3-d]-pyrimidine gives 2-chloro-5,6-cyclohepteno-4-3,4-methylenedioxybenzylamino)-[1]-benzothieno-[2,3-d]-pyrimidine.

EXAMPLE 6

Following the procedure of Example 1, the reaction of 3,4-methylenedioxybenzylamine with 2,4-dichloro-6-ethyl-thieno-[2,3-d]-pyrimidine gives 2-chloro-6-ethyl-4-(3,4-methylenedioxybenzylamino)-thieno-[2,3-d]-pyrimidine Mp. 148° C.

EXAMPLE 7

Following the procedure of Example 1, the reaction of 3,4-methylenedioxybenzylamine with 2,4,6-trichloro-thieno-[2,3-d]-pyrimidine gives 2,6-dichloro-4-(3,4-methylenedioxybenzylamino)-thieno-[2,3-d]-pyrimidine

EXAMPLE 8

Following the procedure of Example 1, the reaction of 3,4-methylenedioxybenzylamine with 2,4,5-trichloro-6-methyl-thieno-[2,3-d]-pyrimidine gives 2,5-dichloro-6-methyl-4-93,4-methylenedioxybenzylamino)-thieno-[2,3-d]-pyrimidine

EXAMPLE 9

Following the procedure of Example 1, the reaction of 3,4-methylenedioxybenzylamine with 2,4-dichloro-6-nitrothieno-[2,3-d]-pyrimidine gives 2-chloro-6-nitro-4-(3,4-methylenedioxybenzylamino)-thieno-[2,3-d]-pyrimidine

EXAMPLE 10

Following the procedure of Example 1, the reaction of 3,4-methylenedioxybenzylamine with 2,4-dichloro-5,6-dimethyl-thieno-[2,3-d]-pyrimidine gives 2-chloro-5,6-dimethyl-4-(3,4-methylenedioxybenzylamino)-thieno-[2,3-d]-pyrimidine

EXAMPLE 11

Following the procedure of Example 1, the reaction of 3,4-methylenedioxybenzylamine with 2,4-dichloro-6-trifluoromethyl-thieno-[2,3-d]-pyrimidine gives 2-chloro-6-trifluoromethyl-4-(3,4-methylenedioxybenzylamino)-thieno-[2,3-d]-pyrimidine

EXAMPLE 12

Following the procedure of Example 1, the reaction of 3-chloro-4-methoxybenzylamine with 2,4-dichloro-6-methyl-thieno-[2,3-d]-pyrimidine yields 2-chloro-6-methyl-4-(3-chloro-4-methoxybenzylamino)-thieno-[2,3-d]-pyrimidine

EXAMPLE 13

Following the procedure of Example 1, the reaction of 3-chloro-4-methoxybenzylamine with 2,4-dichloro-5-methyl-thieno-[2,3-d]-pyrimidine yields 2-chloro-5-methyl-4-(3-chloro-4-methoxybenzylamino)-thieno-[2,3-d]-pyrimidine

EXAMPLE 14

Following the procedure of Example 1, the reaction of 3-chloro-4-methoxybenzylamine with 2,4-dichloro-5,6,7,8-tetrahydro-[1]-benzothieno-[2,3-d]-pyrimidine yields 2-chloro-5,6,7,8-tetrahydro-4-(3-chloro-4-methoxybenzylamino)-[1]-[1]-benzothieno-[2,3-d]-pyrimidine.

EXAMPLE 15

Following the procedure of Example 1, the reaction of 3-chloro-4-methoxybenzylamine with 2,4-dichloro-5,6-cyclopenteno-[1]-benzothieno-[2,3-d]-pyrimidine yields 2-chloro-5,6-cyclopenteno-4-(3-chloro-4-methoybenzylamino)-[1]-benzothieno-[2,3-d]-pyrimidine.

EXAMPLE 16

Following the procedure of Example 1, the reaction of 3-chloro-4-methoxybenzylamine with 2,4-dichloro-5,6-cyclohepteno-[1]-benzothieno-[2,3-d]-pyrimidine yields 2-chloro-5,6-cyclohepteno-4-(3-chloro-4-methoxybenzylamino)-[1]-benzothieno-[2,3-d]-pyrimidine.

EXAMPLE 17

Following the procedure of Example 1, the reaction of 3-chloro-4-methoxybenzylamine with 2,4-dichloro-6-ethyl-thieno-[2,3-d]-pyrimidine yields 2-chloro-6-ethyl-4-(3-chloro-4-methoxybenzylamino)-thieno-[2,3-d]-pyrimidine.

EXAMPLE 18

Following the procedure of Example 1, the reaction of 3-chloro-4-methoxybenzylamine with 2,4,6-trichloro-thieno-[2,3-d]-pyrimidine yields 2,6-dichloro-4-93-chloro-4-methoxybenzylamino0-thieno-[2,3-d]-pyrimidine.

EXAMPLE 19

Following the procedure of Example 1, the reaction of 3-chloro-4-methoxybenzylamine with 2,4,5-trichloro-6-methyl-thieno-[2,3-d]-pyrimidine yields 2,5-dichloro-6-methyl-4-93-chloro-4-methoxybenzylamino0-thieno-[2,3-d]-pyrimidine.

EXAMPLE 20

Following the procedure of Example 1, the reaction of 3-chloro-4-methoxybenzylamine with 2,4-dichloro-6-nitro-thieno-[2,3-d]-pyrimidine yields 2-chloro-6-nitro-4-93-chloro-4-methoxybenzylamino)-thieno-[2,3-d]-pyrimidine

EXAMPLE 21

Following the procedure of Example 1, the reaction of 3-chloro-4-methoxybenzylamine with 2,4-dichloro-5,6-dimethyl-thieno-[2,3-d]-pyrimidine yields 2-chloro-5,6-dimethyl-4-(3-chloro-4-methoxybenzylamino)-thieno-[2,3-d]-pyrimidine.

EXAMPLE 22

Following the procedure of Example 1, the reaction of 3-chloro-4-methoxybenzylamine with 2,4-dichloro-6-trifluoromethyl-thieno-[2,3-d]-pyrimidine yields 2-chloro-6-trifluoromethyl-4-(3-chloro-4-methoxybenzylamino0-thieno-[2,3-d]-pyrimidine.

EXAMPLE 23

Following the procedure of Example 1, the reaction of 3,4-dimethoxybenzylamine with 2,4-dichloro-6-methyl-thieno-[2,3-d]-pyrimidine yields 2-chloro-6-methyl-4-(3,4-dimethoxybenzylamino)-thieno-[2,3-d]-pyrimidine.

EXAMPLE 24

Following the procedure of Example 1, the reaction of 3,4-dimethoxybenzylamine with 2,4-dichloro-5-methyl-thieno-[2,3-d]-pyrimidine yields 2-chloro-5-methyl-4-(3,4-dimethoxybenzylamino0-thieno-[2,3-d]-pyrimidine.

EXAMPLE 25

Following the procedure of Example 1, the reaction of 3,4-dimethoxybenzylamine with 2,4-dichloro-5,6,7,8-tetrahydro-[1]-[1]-benzothieno-[2,3-d]-pyrimidine yields 2-chloro-5,6,7,8-tetrahydro-4-(3,4-dimethoxybenzylamino)-[1]-[1]-benzothieno-[2,3-d]-pyrimidine.

EXAMPLE 26

Following the procedure of Example 1, the reaction of 3,4-dimethoxybenzylamine with 2,4-dichloro-5,6-cyclopenteno-[1]-[1]-benzothieno-[2,3 -d]-pyrimidine yields 2-chloro-5,6-cyclopenteno-4-(3,4-dimethoxybenzylamino)-[1]-benzothieno-[2,3-d]-pyrimidine.

EXAMPLE 27

Following the procedure of Example 1, the reaction of 3,4-dimethoxybenzylamine with 2,4-dichloro-5,6-cyclopenteno-[1]-benzothieno-[2,3-d]-pyrimidine yields 2-chloro-5,6-cyclopenteno-4-(3,4-dimethoxybenzylamino)-[1]-benzothieno-[2,3-d]-pyrimidine.

EXAMPLE 28

Following the procedure of Example 1, the reaction of 3,4-dimethoxybenzylamine with 2,4-dichloro-6-ethylthieno-[2,3-d]-pyrimidine yields 2-chloro-6-ethyl-4-(3,4-dimethoxybenzylamino)-thieno-[2,3-d]-pyrimidine.

EXAMPLE 29

Following the procedure of Example 1, the reaction of 3,4-dimethoxybenzylamine with 2,4,6-trichloro-thieno-[2,3-d]-pyrimidine yields 2,6-dichloro-4-(3,4-dimethoxybenzylamino)-thieno-[2,3-d]-pyrimidine.

EXAMPLE 30

Following the procedure of Example 1, the reaction of 3,4-dimethoxybenzylamine with 2,4,5-trichloro-6-methyl-thieno-[2,3-d]-pyrimidine yields 2,5-dichloro-6-methyl-4-(3,4-dimethoxybenzylamino)-thieno-[2,3-d]-pyrimidine.

EXAMPLE 31

Following the procedure of Example 1, the reaction of 3,4-dimethoxybenzylamine with 2,4dichloro-6-nitro-thieno-[2,3-d]-pyrimidine yields 2-chloro-6-nitro-4-(3,4-dimethoxybenzylamino)-thieno-[2,3-d]-pyrimidine.

EXAMPLE 32

Following the procedure of Example 1, the reaction of 3,4-dimethoxybenzylamine with 2,4dichloro-5,6-dimethyl-thieno-[2,3-d]-pyrimidine yields 2-chloro-5,6-dimethyl-4-(3,4-dimethoxybenzylamino)-thieno-[2,3-d]-pyrimidine.

EXAMPLE 33

Following the procedure of Example 1, the reaction of 3,4-dimethoxybenzylamine with 2,4dichloro-6-trifluoromethyl-thieno-[2,3-d]-pyrimidine yields 2-chloro-6-trifluoromethyl-4-(3,4-dimethoxybenzylamino)-thieno-[2,3-d]-pyrimidine.

EXAMPLE 34

Following the procedure of Example 1, the reaction of benzylamine with 2,4-dichloro-6-methyl-thieno-[2,3-d]-pyrimidine yields 2-chloro-6-methyl-4-benzylamino-thieno-[2,3-d]-pyrimidine.

EXAMPLE 35

Following the procedure of Example 1, the reaction of benzylamine with 2,4-dichloro-5-methyl-thieno-[2,3-d]-pyrimidine yields 2-chloro-5-methyl-4-benzylamino-thieno-[2,3-d]-pyrimidine.

EXAMPLE 36

Following the procedure of Example 1, the reaction of benzylamine with 2,4-dichloro-5,6,7,8-tetrahydro-[1]-[1]-benzothieno-[2,3-d]-pyrimidine yields 2-chloro-5,6,7,8-tetrahydro-4-benzylamino-thieno-[1]-[1]-benzothieno-[2,3-d]-pyrimidine.

EXAMPLE 37

Following the procedure of Example 1, the reaction of benzylamine with 2,4-dichloro-5,6-cyclopenteno-[1]-benzothieno-[2,3-d]-pyrimidine yields 2-chloro-5,6-cyclopenteno-4-benzylamino-[2,3-d]-pyrimidine.

EXAMPLE 38

Following the procedure of Example 1, the reaction of benzylamine with 2,4-dichloro-5,6-cyclopenteno-[1]-benzothieno-[2,3-d]-pyrimidine yields 2-chloro-5,6-cyclopenteno-4-benzylamino-[1]-benzothieno-[2,3-d]-pyrimidine.

EXAMPLE 39

Following the procedure of Example 1, the reaction of benzylamine with 2,4-dichloro-6-ethyl-thieno-[2,3-d]-pyrimidine yields 2-chloro-6-ethyl-4-benzylamino-thieno-[2,3-d]-pyrimidine.

EXAMPLE 40

Following the procedure of Example 1, the reaction of benzylamine with 2,4,6-trichloro-thieno-[2,3-d]-pyrimidine yields 2,6-dichloro-6-4-benzylamino-thieno-[2,3-d]-pyrimidine.

EXAMPLE 41

Following the procedure of Example 1, the reaction of benzylamine with 2,4,5-trichloro-6-methyl-thieno-[2,3-d]-pyrimidine yields 2,5-dichloro-6-methyl-4-benzylamino-thieno-[2,3-d]-pyrimidine.

EXAMPLE 42

Following the procedure of Example 1, the reaction of benzylamine with 2,4-dichloro-6-nitro-thieno-[2,3-d]-pyrimidine yields 2-chloro-6-nitro-4-benzylamino-thieno-[2,3-d]-pyrimidine.

EXAMPLE 43

Following the procedure of Example 1, the reaction of benzylamine with 2,4-dichloro-5,6-dimethyl-thieno-[2,3-d]-pyrimidine yields 2-chloro-5,6-dimethyl-4-benzylamino-thieno-[2,3-d]-pyrimidine.

EXAMPLE 44

Following the procedure of Example 1, the reaction of benzylamine with 2,4-dichloro-6-trifluoromethyl-thieno-[2,3-d]-pyrimidine yields 2-chloro-6-trifluoromethyl-4-benzylamino-thieno-[2,3-d]-pyrimidine.

EXAMPLE 45

Following the procedure of Example 1, the reaction of 4-fluorobenzylamine with 2,4-dichloro-6-methyl-thieno-[2,3-d]-pyrimidine yields 2-chloro-6-methyl-4-(4-fluorobenzylamino)-thieno-[2,3-d]-pyrimidine with 2,4-dichloro-5-methyl-thieno-[2,3-d]-pyrimidine yields 2-chloro-5-methyl-4-(4-fluorobenzylamino)-thieno-[2,3-d]-pyrimidine.

EXAMPLE 46

Following the procedure of Example 1, the reaction of 4-fluorobenzylamine with 2,4-dichloro-5,6,7,8-tetrahydro-[1]-benzothieno-[2,3-d]-pyrimidine yields 2-chloro-5,6-7,8-tetrahydro-4-(4-fluorobenzylamino)-[1]-benzothieno-[2,3-d]-pyrimidine.

EXAMPLE 47

Following the procedure of Example 1, the reaction of 4-fluorobenzylamine with 2,4-dichloro-5,6-cyclopenteno-[1]-benzothieno-[2,3-d]-pyrimidine yields 2-chloro-5,6-cyclopenteno-4-(4-fluorobenzylamino)-[1]-benzothieno-[2,3-d]-pyrimidine.

EXAMPLE 48

Following the procedure of Example 1, the reaction of 4-fluorobenzylamine with 2,4-dichloro-5,6-cyclohepteno-

[1]-benzothieno-[2,3-d]-pyrimidine yields 2-chloro-5,6-cyclohepteno-4-(4-fluorobenzylamino)-[1]-benzothieno-[2,3-d]-pyrimidine.

EXAMPLE 49

Following the procedure of Example 1, the reaction of 4-fluorobenzylamine with 2,4-dichloro-6-ethyl-thieno-[2,3-d]-pyrimidine yields 2-chloro-6-ethyl-4-(4-fluorobenzylamino)-thieno-[2,3-d]-pyrimidine.

EXAMPLE 50

Following the procedure of Example 1, the reaction of 4-fluorobenzylamine with 2,4,6-trichloro-thieno-[2,3-d]-pyrimidine yields 2,6-dichloro-4-(4-fluorobenzylamino)-thieno-[2,3-d]-pyrimidine.

EXAMPLE 51

Following the procedure of Example 1, the reaction of 4-fluorobenzylamine with 2,4,5-trichloro-6-methyl-thieno-[2,3-d]-pyrimidine yields 2,5-dichloro-6-methyl-4-(4-fluorobenzylamino)-thieno-[2,3-d]-pyrimidine.

EXAMPLE 52

Following the procedure of Example 1, the reaction of 4-fluorobenzylamine with 2,4-dichloro-6-nitro-thieno-[2,3-d]-pyrimidine yields 2-chloro-6-nitro-4-(4-fluorobenzylamino)-thieno-[2,3-d]-pyrimidine.

EXAMPLE 53

Following the procedure of Example 1, the reaction of 4-fluorobenzylamine with 2,4-dichloro-5,6-dimethyl-thieno-[2,3-d]-pyrimidine yields 2-chloro-5,6-dimethyl-4-(4-fluorobenzylamino)-thieno-[2,3-d]-pyrimidine.

EXAMPLE 54

Following the procedure of Example 1, the reaction of 4-fluorobenzylamine with 2,4-dichloro-6-trifluoromethyl-thieno-[2,3-d]-pyrimidine yields 2-chloro-6-trifluoromethyl-4-(4-fluorobenzylamino)-thieno-[2,3-d]-pyrimidine.

EXAMPLE 55

Following the procedure of Example 1, the reaction of 3,4-dichlorobenzylamine with 2,4-dichloro-6-methyl-thieno-[2,3-d]-pyrimidine yields 2-chloro-6-methyl-4-(3,4-dichlorobenzylamino)-thieno-[2,3-d]-pyrimidine.

EXAMPLE 56

Following the procedure of Example 1, the reaction of 3,4-dichlorobenzylamine with 2,4-dichloro-5-methyl-thieno-[2,3-d]-pyrimidine yields 2-chloro-5-methyl-4-(3,4-dichlorobenzylamino)-thieno-[2,3-d]-pyrimidine.

EXAMPLE 57

Following the procedure of Example 1, the reaction of 3,4-dichlorobenzylamine with 2,4-dichloro-5,6,7,8-tetrahydro-[1]-benzothieno-[2,3-d]-pyrimidine yields 2-chloro-5,6,7,8-tetrahydro-4-(3,4-dichlorobenzylamino)-[1]-benzothieno-[2,3-d]-pyrimidine.

EXAMPLE 58

Following the procedure of Example 1, the reaction of 3,4-dichlorobenzylamine with 2,4-dichloro-5,6-cyclopenteno-[1]-benzothieno-[2,3-d]-pyrimidine yields 2-chloro-5,6-cyclopenteno-4-(3,4-dichlorobenzylamino)-[1]-benzothieno-[2,3-d]-pyrimidine.

EXAMPLE 59

Following the procedure of Example 1, the reaction of 3,4-dichlorobenzylamine with 2,4-dichloro-5,6-cyclopenteno-[1]-benzothieno-[2,3-d]-pyrimidine yields 2-chloro-5,6-cyclopenteno-4-(3,4-dichlorobenzylamino)-[1]-benzothieno-[2,3-d]-pyrimidine.

EXAMPLE 60

Following the procedure of Example 1, the reaction of 3,4-dichlorobenzylamine with 2,4-dichloro-6-ethyl-thieno-[2,3-d]-pyrimidine yields 2-chloro-6-ethyl-4-(3,4-dichlorobenzylamino)-thieno-[2,3-d]-pyrimidine.

EXAMPLE 61

Following the procedure of Example 1, the reaction of 3,4-dichlorobenzylamine with 2,4,6-trichloro-thieno-[2,3-d]-pyrimidine yields 2-6-dichloro-4-(3,4-dichlorobenzylamino)-thieno-[2,3-d]-pyrimidine.

EXAMPLE 62

Following the procedure of Example 1, the reaction of 3,4-dichlorobenzylamine with 2,4,5-trichloro-6-methyl-thieno-[2,3-d]-pyrimidine yields 2,5-dichloro-6-methyl-4-(3,4-dichlorobenzylamino)-thieno-[2,3-d]-pyrimidine.

EXAMPLE 63

Following the procedure of Example 1, the reaction of 3,4-dichlorobenzylamine with 2,4-dichloro-6-nitro-thieno-[2,3-d]-pyrimidine yields 2-chloro-6-nitro-4-(3,4-dichlorobenzylamino)-thieno-[2,3-d]-pyrimidine

EXAMPLE 64

Following the procedure of Example 1, the reaction of 3,4-dichlorobenzylamine with 2,4-dichloro-5,6-dimethyl-thieno-[2,3-d]-pyrimidine yields 2-chloro-5,6-dimethyl-4-(3,4-dichlorobenzylamino)-thieno-[2,3-d]-pyrimidine

EXAMPLE 65

Following the procedure of Example 1, the reaction of 3,4-dichlorobenzylamine with 2,4-dichloro-6-trifluoromethyl-thieno-[2,3-d]-pyrimidine yields 2-chloro-6-trifluoromethyl-4-(3,4-dichlorobenzylamino)-thieno-[2,3-d]-pyrimidine.

EXAMPLE 66

Following the procedure of Example 1, the reaction of 3-nitrobenzylamine with 2,4-dichloro-6-methyl-thieno-[2,3-d]-pyrimidine yields 2-chloro-6-methyl-4-(3-nitrobenzylamino)-thieno-[2,3-d]-pyrimidine

EXAMPLE 67

Following the procedure of Example 1, the reaction of 3-nitrobenzylamine with 2,4-dichloro-5-methyl-thieno-[2,3-d]-pyrimidine yields 2-chloro-5-methyl-4-(3-nitrobenzylamino)-thieno-[2,3-d]-pyrimidine.

EXAMPLE 68

Following the procedure of Example 1, the reaction of 3-nitrobenzylamine with 2,4-dichloro-5,6,7,8-tetrahydro-

[1]-benzothieno-[2,3-d]-pyrimidine yields 2-chloro-5,6,7,8-tetrahydro-4-(3-nitrobenzylamino)-[1]-benzothieno-[2,3-d]-pyrimidine.

EXAMPLE 69

Following the procedure of Example 1, the reaction of 3-nitrobenzylamine with 2,4-dichloro-5,6-cyclopenteno-[1]-benzothieno-[2,3-d]-pyrimidine yields 2-chloro-5,6-cyclopenteno-4-(3-nitrobenzylamino)-[1]-benzothieno-[2,3-d]-pyrimidine

EXAMPLE 70

Following the procedure of Example 1, the reaction of 3-nitrobenzylamine with 2,4-dichloro-5,6-cyclopenteno-[1]-benzothieno-[2,3-d]-pyrimidine yields 2-chloro-5,6-cyclopenteno-4-(3-nitrobenzylamino)-[1]-benzothieno-[2,3-d]-pyrimidine.

EXAMPLE 71

Following the procedure of Example 1, the reaction of 3-nitrobenzylamine with 2,4-dichloro-6-ethyl-thieno-[2,3-d]-pyrimidine yields 2-chloro-6-ethyl-4-(3-nitrobenzylamino)-thieno-[2,3-d]-pyrimidine

EXAMPLE 72

Following the procedure of Example 1, the reaction of 3-nitrobenzylamine with 2,4,6-trichloro-thieno-[2,3-d]-pyrimidine yields 2,6-dichloro-4-(3-nitrobenzylamino)-thieno-[2,3-d]-pyrimidine.

EXAMPLE 73

Following the procedure of Example 1, the reaction of 3-nitrobenzylamine with 2,4,5-trichloro-6-methyl-thieno-[2,3-d]-pyrimidine yields 2,5-dichloro-6-methyl-4-(3-nitrobenzylamino)-thieno-[2,3-d]-pyrimidine

EXAMPLE 74

Following the procedure of Example 1, the reaction of 3-nitrobenzylamine with 2,4-dichloro-6-nitro-thieno-[2,3-d]-pyrimidine yields 2-chloro-6-nitro-4-(3-nitrobenzylamino)-thieno-[2,3-d]-pyrimidine.

EXAMPLE 75

Following the procedure of Example 1, the reaction of 3-nitrobenzylamine with 2,4-dichloro-5,6-dimethyl-thieno-[2,3-d]-pyrimidine yields 2-chloro-5,6-dimethyl-4-(3-nitrobenzylamino)-thieno-[2,3-d]-pyrimidine

EXAMPLE 76

Following the procedure of Example 1, the reaction of 3-nitrobenzylamine with 2,4-dichloro-6-trifluoromethyl-thieno-[2,3-d]-pyrimidine yields 2-chloro-6-trifluoromethyl-4-(3-nitrobenzylamino)-thieno-[2,3-d]-pyrimidine.

EXAMPLE 77

Following the procedure of Example 1, the reaction of 3,4-methylenedioxyphenethylamine with 2,4-dichloro-6-methyl-thieno-[2,3-d]-pyrimidine yields 2-chloro-6-methyl-4-(3-nitrobenzylamino)-thieno-[2,3-d]-pyrimidine

EXAMPLE 78

Following the procedure of Example 1, the reaction of 3,4-methylenedioxyphenethylamine with 2,4-dichloro-5-methyl-thieno-[2,3-d]-pyrimidine yields 2-chloro-5-methyl-4-(3,4-methylenedioxyphenethylamino)-thieno-[2,3-d]-pyrimidine

EXAMPLE 79

Following the procedure of Example 1, the reaction of 3,4-methylenedioxyphenethylamine with 2,4-dichloro-5,6,7,8-tetrahydro-[1]-benzothieno-[2,3-d]-pyrimidine yields 2-chloro-5,6,7,8-tetrahydro-4-(3,4-methylenedioxyphenethylamino)-[1]-benzothieno-[2,3-d]-pyrimidine

EXAMPLE 80

Following the procedure of Example 1, the reaction of 3,4-methylenedioxyphenethylamine with 2,4-dichloro-5,6-cyclopenteno-[1]-benzothieno-[2,3-d]-pyrimidine yields 2-chloro-5,6-cyclopenteno-4-(3,4-methylenedioxyphenethylamino)-[1]-benzothieno-[2,3-d]-pyrimidine.

EXAMPLE 81

Following the procedure of Example 1, the reaction of 3,4-methylenedioxyphenethylamine with 2,4-dichloro-6-ethyl-thieno-[2,3-d]-pyrimidine yields 2-chloro-6-ethyl-4-(3,4-methylenedioxyphenethylamino)-thieno-[2,3-d]-pyrimidine.

EXAMPLE 82

Following the procedure of Example 1, the reaction of 3,4-methylenedioxyphenethylamine with 2,4,6-trichloro-thieno-[2,3-d]-pyrimidine yields 2,6-dichloro-4-(3,4-methylenedioxyphenethylamino)-thieno-[2,3-d]-pyrimidine.

EXAMPLE 83

Following the procedure of Example 1, the reaction of 3,4-methylenedioxyphenethylamine with 2,4,5-trichloro-6-methyl-thieno-[2,3-d]-pyrimidine yields 2,5-dichloro-6-methyl-4-(3,4-methylenedioxyphenethylamino)-thieno-[2,3-d]-pyrimidine.

EXAMPLE 84

Following the procedure of Example 1, the reaction of 3,4-methylenedioxyphenethylamine with 2,4-dichloro-6-nitro-thieno-[2,3-d]-pyrimidine yields 2-chloro-6-nitro-4-(3,4-methylenedioxyphenethylamino)-thieno-[2,3-d]-pyrimidine.

EXAMPLE 85

Following the procedure of Example 1, the reaction of 3,4-methylenedioxyphenethylamine with 2,4-dichloro-5,6-dimethyl-thieno-[2,3-d]-pyrimidine yields 2-chloro-5,6-dimethyl-4-(3,4-methylenedioxyphenethylamino)-thieno-[2,3-d]-pyrimidine.

EXAMPLE 86

Following the procedure of Example 1, the reaction of 3,4-methylenedioxyphenethylamine with 2,4-dichloro-6-trifluoromethyl-thieno-[2,3-d]-pyrimidine yields 2-chloro-6-trifluoromethyl-4-(3,4-methylenedioxyphenethylamino)-thieno-[2,3-d]-pyrimidine.

EXAMPLE 87

Following the procedure of Example 1, the reaction of 3,4-ethylendioxyphenethylamine with 2,4-dichloro-6- methyl-thieno-[2,3-d]-pyrimidine yields 2-chloro-6-methyl-4-(3,4-ethylendioxybenzylamino)-thieno-[2,3-d]-pyrimidine.

EXAMPLE 88

Following the procedure of Example 1, the reaction of 3,4-ethylendioxyphenethylamine with 2,4-dichloro-5-methyl-thieno-[2,3-d]-pyrimidine yields 2-chloro-5-methyl-4-(3,4-ethylendioxybenzylamino)-thieno-[2,3-d]-pyrimidine.

EXAMPLE 89

Following the procedure of Example 1, the reaction of 3,4-ethylendioxyphenethylamine with 2,4-dichloro-5,6,7,8-tetrahydro-[1]-benzothieno-[2,3-d]-pyrimidine yields 2-chloro-5,6,7,8-tetrahydro-4-(3,4-ethylendioxybenzylamino)-[1]-benzothieno-[2,3-d]-pyrimidine.

EXAMPLE 90

Following the procedure of Example 1, the reaction of 3,4-ethylendioxyphenethylamine with 2,4-dichloro-6-ethyl-thieno-[2,3-d]-pyrimidine yields 2-chloro-6-ethyl-4-(3,4-ethylendioxybenzylamino)-thieno-[2,3-d]-pyrimidine.

EXAMPLE 91

Following the procedure of Example 1, the reaction of 3,4-ethylendioxyphenethylamine with 2,4,6-trichloro-thieno-[2,3-d]-pyrimidine yields 2,6-dichloro-4-(3,4-ethylendioxybenzylamino)-thieno-[2,3-d]-pyrimidine.

EXAMPLE 92

Following the procedure of Example 1, the reaction of 3,4-ethylendioxyphenethylamine with 2,4,5-trichloro-6-methyl-thieno-[2,3-d]-pyrimidine yields 2,5-dichloro-6-methyl-4-(3,4-ethylendioxybenzylamino)-thieno-[2,3-d]-pyrimidine.

EXAMPLE 93

Following the procedure of Example 1, the reaction of 3,4-ethylendioxyphenethylamine with 2,4-dichloro-6-nitro-thieno-[2,3-d]-pyrimidine yields 2-chloro-6-nitro-4-(3,4-ethylendioxybenzylamino)-thieno-[2,3-d]-pyrimidine.

EXAMPLE 94

Following the procedure of Example 1, the reaction of 3,4-ethylendioxyphenethylamine with 2,4-dichloro-5,6-dimethyl-thieno-[2,3-d]-pyrimidine yields 2-chloro-5,6-dimethyl-4-(3,4-ethylendioxybenzylamino)-thieno-[2,3-d]-pyrimidine.

EXAMPLE 95

Following the procedure of Example 1, the reaction of 3,4-ethylendioxyphenethylamine with 2,4-dichloro-6-trimethyl-thieno-[2,3-d]-pyrimidine yields 2-chloro-6-trifluoromethyl-4-(3,4-ethylendioxybenzylamino)-thieno-[2,3-d]-pyrimidine.

EXAMPLE 96

2-Chloro-6-methyl-4-(3,4-methylenedioxybenzylamino)-thieno-[2,3-d]-pyrimidine (1.67 g) and piperidine-4-carboxylic acid ethylester (3 g) are heated to 130° C. After cooling, the residue is dissolved in dichloromethane. The usual workup yields 1-[6-methyl-4-(3,4-methyleneedioxybenzylamino)-thieno-[2,3-d]-2-yl-piperidine-4-carboxylic acid ethylester (0.5 g).

EXAMPLE 97

A solution of 2-chloro-6-methyl-4-(3,4-methylene dioxybenzylamino)-thieno-[2,3-d]-pyrimidine (1.67 g), imidazole (1.02 g) and phenol (2 g) are heated 5 hours at 150° C. After cooling, the residue is dissolved in $CH_2Cl_2$. The solvent is removed, and the usual workup yields 2-(imidazol-1-yl)-6-methyl-4-(3,4-methylenedioxybenzylamino)-thieno-[2,3-d]-pyrimidine (3.38 g) Mp. 162° C.

EXAMPLE 98

Following the procedure of Example 97, the reaction of imidazole with 2-chloro-5-methyl-4-(3,4-methylenedioxybenzylamino)-thieno-[2,3-d]-pyrimidine gives 2-(imidazol-1-yl)-5-methyl-4-(3,4-methylenedioxybenzylamino)-thieno-[2,3-d]-pyrimidine.

EXAMPLE 99

Following the procedure of Example 97, the reaction of imidazole with 2-chloro-5,6,7,8-tetrahydro-4-(3,4-methylenedioxybenzylamino)-[1]-benzothieno-[2,3-d]-pyrimidine gives 2-(imidazol-1-yl)-5,6,7,8-tetrahydro-4-(3,4-methylenedioxybenzylamino)-[1]-benzothieno-[2,3-d]-pyrimidine.

EXAMPLE 100

Following the procedure of Example 97, the reaction of imidazole with 2-chloro-5,6-cyclopenteno-4-(3,4-methylenedioxybenzylamino)-[1]-benzothieno-[2,3 -d]-pyrimidine gives 2-(imidazol-1-yl)-5,6-cyclopenteno-4-(3,4-methylenedioxybenzylamino)-[1]-benzothieno-[2,3-d]-pyrimidine.

EXAMPLE 101

Following the procedure of Example 97, the reaction of imidazole with 2-chloro-5,6-cyclohepteno-4-93,4-methylenedioxybenzylamino)-[1]-benzothieno-[2,3-d]-pyrimidine gives 2-(imidazol-1-yl)-5,6-cyclohepteno-4-93,4-methylenedioxybenzylamino)-[1]-benzothieno-[2,3-d]-pyrimidine.

EXAMPLE 102

Following the procedure of Example 97, the reaction of imidazole with 2-chloro-6-ethyl-4-(3,4-methylenedioxybenzylamino)-thieno-[2,3-d]-pyrimidine gives 2-(imidazol-1-yl)-6-ethyl-4-(3,4-methylenedioxybenzylamino)-thieno-[2,3-d]-pyrimidine.

EXAMPLE 103

Following the procedure of Example 97, the reaction of imidazole with 2,6-dichloro-4-(3,4-methylenedioxybenzylamino)-thieno-[2,3-d]-pyrimidine gives 2-(imidazol-1-yl)-6-chloro-4-(3,4-methylenedioxybenzylamino)-thieno-[2,3-d]-pyrimidine.

EXAMPLE 104

Following the procedure of Example 97, the reaction imidazole with 2,5-dichloro-6-methyl-4-93,4-methylenedioxybenzylamino)-thieno-[2,3-d]-pyrimidine gives 2-(imidazol-1-yl)-5-chloro-6-methyl-4-93,4-methylenedioxybenzylamino)-thieno-[2,3-d]-pyrimidine.

EXAMPLE 105

Following the procedure of Example 97, the reaction of imidazole with 2-chloro-6-nitro-4-(3,4-methylenedioxybenzylamino)-thieno-[2,3-d]-pyrimidine gives 2-(imidazol-1-yl)-6-nitro-4-(3,4-methylenedioxybenzylamino)-thieno-[2,3-d]-pyrimidine.

EXAMPLE 106

Following the procedure of Example 97, the reaction of imidazole with 2-chloro-5,6-dimethyl-4-(3,4-methylenedioxybenzylamino)-thieno-[2,3-d]-pyrimidine gives 2-(imidazol-1-yl)-5,6-dimethyl-4-(3,4-methylenedioxybenzylamino)-thieno-[2,3-d]-pyrimidine.

EXAMPLE 107

Following the procedure of Example 97, the reaction of imidazole with 2-chloro-6-trifluoromethyl-4-(3,4-methylenedioxybenzylamino)-thieno-[2,3-d]-pyrimidine gives 2-(imidazol-1-yl)-6-trifluoromethyl-4-(3,4-methylenedioxybenzylamino)-thieno-[2,3-d]-pyrimidine.

EXAMPLE 108

Following the procedure of Example 97, the reaction of imidazole with 2-chloro-6-methyl-4-(3-chloro-4-methoxybenzylamino)-thieno-[2,3-d]-pyrimidine gives 2-(imidazol-1-yl)-6-methyl-4-(3-chloro-4-methoxybenzylamino)-thieno-[2,3-d]-pyrimidine.

EXAMPLE 109

Following the procedure of Example 97, the reaction of imidazole with 2-chloro-5-methyl-4-(3-chloro-4-methoxybenzylamino)-thieno-[2,3-d]-pyrimidine gives 2-(imidazol-1-yl)-5-methyl-4-(3-chloro-4-methoxybenzylamino)-thieno-[2,3-d]-pyrimidine.

EXAMPLE 110

Following the procedure of Example 97, the reaction of imidazole with 2-chloro-5,6,7,8-tetrahydro-4-(3-chloro-4-methoxybenzylamino)-[1]-[1]-benzothieno-[2,3-d]-pyrimidine gives 2-(imidazol-1-yl)-5,6,7,8-tetrahydro-4-(3-chloro-4-methoxybenzylamino)-[1]-[1]-benzothieno-[2,3-d]-pyrimidine.

EXAMPLE 111

Following the procedure of Example 97, the reaction of imidazole with 2-chloro-5,6-cyclopenteno-4-(3-chloro-4-methoybenzylamino)-[1]-benzothieno-[2,3-d]-pyrimidine gives 2-(imidazol-1-yl)-5,6-cyclopenteno-4-(3-chloro-4-methoybenzylamino)-[1]-benzothieno-[2,3-d]-pyrimidine.

EXAMPLE 112

Following the procedure of Example 97, the reaction of imidazole with 2-chloro-5,6-cyclohepteno-4-(3-chloro-4-methoxybenzylamino)-[1]-benzothieno-[2,3-d]-pyrimidine gives 2-(imidazol-1-yl)-5,6-cyclohepteno-4-(3-chloro-4-methoxybenzylamino)-[1]-benzothieno-[2,3-d]-pyrimidine.

EXAMPLE 113

Following the procedure of Example 97, the reaction of imidazole with 2-chloro-6-ethyl-4-(3-chloro-4-methoxybenzylamino)-thieno-[2,3-d]-pyrimidine gives 2-(imidazol-1-yl)-6-ethyl-4-(3-chloro-4-methoxybenzylamino)-thieno-[2,3-d]-pyrimidine.

EXAMPLE 114

Following the procedure of Example 97, the reaction of imidazole with 2,6-dichloro-4-(3-chloro-4-methoxybenzylamino)-thieno-[2,3-d]-pyrimidine gives 2-(imidazol-1-yl)-6-chloro-4-(3-chloro-4-methoxybenzylamino)-thieno-[2,3-d]-pyrimidine.

EXAMPLE 115

Following the procedure of Example 97, the reaction of imidazole with 2,5-dichloro-6-methyl-4-(3-chloro-4-methoxybenzylamino)-thieno-[2,3-d]-pyrimidine gives 2-(imidazol-1-yl)-5-chloro-6-methyl-4-(3-chloro-4-methoxybenzylamino)-thieno-[2,3-d]-pyrimidine.

EXAMPLE 116

Following the procedure of Example 97, the reaction of imidazole with 2-chloro-6-nitro-4-(3-chloro-4-methoxybenzylamino)-thieno-[2,3-d]-pyrimidine gives 2-(imidazol-1-yl)-6-nitro-4-(3-chloro-4-methoxybenzylamino)-thieno-[2,3-d]-pyrimidine.

EXAMPLE 117

Following the procedure of Example 97, the reaction of imidazole with 2-chloro-5,6-dimethyl-4-(3-chloro-4-methoxybenzylamino)-thieno-[2,3-d]-pyrimidine gives 2-(imidazol-1-yl)-5,6-dimethyl-4-(3-chloro-4-methoxybenzylamino)-thieno-[2,3-d]-pyrimidine.

EXAMPLE 118

Following the procedure of Example 97, the reaction of imidazole with 2-<chloro-6-trifluoromethyl-4-(3-chloro-4-methoxybenzylamino0-thieno-[2,3-d]-pyrimidine gives 2-(imidazol-1-yl)-6-trifluoromethyl-4-(3-chloro-4-methoxybenzylamino0-thieno-[2,3-d]-pyrimidine.

EXAMPLE 119

Following the procedure of Example 97, the reaction of imidazole with 2-chloro-6-methyl-4-(3,4-dimenthoxybenzylamino)-thieno-[2,3-d]-pyrimidine gives 2-(imidazol-1-yl)-6-methyl-4-(3,4-dimethoxybenzylamino)-thieno-[2,3-d]-pyrimidine.

EXAMPLE 120

Following the procedure of Example 97, the reaction of imidazole with 2-chloro-5-methyl-4-(3,4-dimethoxybenzylamino)-thieno-[2,3-d]-pyrimidine gives 2-(imidazol-1-yl)-5-methyl-4-(3,4-dimethoxybenzylamino)-thieno-[2,3-d]-pyrimidine.

EXAMPLE 121

Following the procedure of Example 97, the reaction of imidazole with 2-chloro-5,6,7,8-tetrahydro-4-(3,4-dimethoxybenzylamino)-[1]-[1]-benzothieno-[2,3-d]-pyrimidine gives 2-(imidazol-1-yl)-5,6,7,8-tetrahydro-4-(3,4-dimethoxybenzylamino)-[1]-[1]-benzothieno-[2,3-d]-pyrimidine.

EXAMPLE 122

Following the procedure of Example 97, the reaction of imidazole with 2-chloro-5,6-cyclopenteno-4-(3,4- dimethoxybenzylamino)-[1]-benzothieno-[2,3-d]-pyrimidine gives 2-(imidazol-1-yl)-5,6-cyclopenteno-4-(3,4-dimethoxybenzylamino)-[1]-benzothieno-[2,3-d]-pyrimidine.

EXAMPLE 123

Following the procedure of Example 97, the reaction of imidazole with 2-chloro-5,6-cyclopenteno-4-(3,4-dimethoxybenzylamino)-[1]-benzothieno-[2,3-d]-pyrimidine gives 2-(imidazol-1-yl)-5,6-cyclopenteno-4-(3,4-dimethoxybenzylamino)-[1]-benzothieno-[2,3-d]-pyrimidine.

EXAMPLE 124

Following the procedure of Example 97, the reaction of imidazole with 2-chloro-6-ethyl-4-(3,4-dimethoxybenzylamino)-thieno-[2,3-d]-pyrimidine gives 2-(imidazol-1-yl)-6-ethyl-4-(3,4-dimethoxybenzylamino)-thieno-[2,3-d]-pyrimidine.

EXAMPLE 125

Following the procedure of Example 97, the reaction of imidazole with 2,6-dichloro-4-(3,4-dimethoxybenzylamino)-thieno-[2,3-d]-pyrimidine gives 2-(imidazol-1-yl)-6-chloro-4-(3,4-dimethoxybenzylamino)-thieno-[2,3-d]-pyrimidine.

EXAMPLE 126

Following the procedure of Example 97, the reaction of imidazole with 2,5-dichloro-6-methyl-4-(3,4-dimethoxybenzylamino)-thieno-[2,3-d]-pyrimidine gives 2-(imidazol-1-yl)-5-chloro-6-methyl-4-(3,4-dimethoxybenzylamino)-thieno-[2,3-d]-pyrimidine.

EXAMPLE 127

Following the procedure of Example 97, the reaction of imidazole with 2-chloro-6-nitro-4-(3,4-dimethoxybenzylamino)-thieno-[2,3-d]-pyrimidine gives 2-(imidazol-1-yl)-6-nitro-4-(3,4-dimethoxybenzylamino)-thieno-[2,3-d]-pyrimidine.

EXAMPLE 128

Following the procedure of Example 97, the reaction of imidazole with 2-chloro-5,6-dimethyl-4-(3,4-dimethoxybenzylamino)-thieno-[2,3-d]-pyrimidine gives 2-(imidazol-1-yl)-5,6-dimethyl-4-(3,4-dimethoxybenzylamino)-thieno-[2,3-d]-pyrimidine.

EXAMPLE 129

Following the procedure of Example 97, the reaction of imidazole with yields 2-chloro-6-trifluoromethyl-4-(3,4-dimethoxybenzylamino)-thieno-[2,3-d]-pyrimidine gives 2-(imidazol-1-yl)-6-trifluoromethyl-4-(3,4-dimethoxybenzylamino)-thieno-[2,3-d]-pyrimidine.

EXAMPLE 130

Following the procedure of Example 97, the reaction of imidazole with 2-chloro-6-methyl-4-benzylamino-thieno-[2,3-d]-pyrimidine gives 2-(imidazol-1-yl)-6-methyl-4-benzylamino-thieno-[2,3-d]-pyrimidine.

EXAMPLE 131

Following the procedure of Example 97, the reaction of imidazole with 2-chloro-5-methyl-4-benzylamino-thieno-[2,3-d]-pyrimidine gives 2-(imidazol-1-yl)-5-methyl-4-benzylamino-thieno-[2,3-d]-pyrimidine.

EXAMPLE 132

Following the procedure of Example 97, the reaction of imidazole with 2-chloro-5,6,7,8-tetrahydro-4-benzylamino-thieno-[1]-[1]-benzothieno-[2,3-d]-pyrimidine gives 2-(imidazol-1-yl)-5,6,7,8-tetrahydro-4-benzylamino-thieno-[1]-[1]-benzothieno-[2,3-d]-pyrimidine.

EXAMPLE 133

Following the procedure of Example 97, the reaction of imidazole with 2-chloro-5,6-cyclopenteno-4-benzylamino-[2,3-d]-pyrimidine gives 2-(imidazol-1-yl)-5,6-cyclopenteno-4-benzylamino-[2,3-d]-pyrimidine.

EXAMPLE 134

Following the procedure of Example 97, the reaction of imidazole with 2-chloro-5,6-cyclopenteno-4-benzylamino-[1]-benzothieno-[2,3-d]-pyrimidine gives 2-(imidazol-1-yl)-5,6-cyclopenteno-4-benzylamino-[1]-benzothieno-[2,3-d]-pyrimidine.

EXAMPLE 135

Following the procedure of Example 97, the reaction of imidazole with 2-chloro-6-ethyl-4-benzylamino-thieno-[2,3-d]-pyrimidine gives 2-(imidazol-1-yl)-6-ethyl-4-benzylamino-thieno-[2,3-d]-pyrimidine.

EXAMPLE 136

Following the procedure of Example 97, the reaction of imidazole with 2,6-dichloro-6-4-benzylamino-thieno-[2,3-d]-pyrimidine gives 2-(imidazol-1-yl)-6-chloro-6-4-benzylamino-thieno-[2,3-d]-pyrimidine.

EXAMPLE 137

Following the procedure of Example 97, the reaction of imidazole with 2,5-dichloro-6-methyl-4-benzylamino-thieno-[2,3-d]-pyrimidine gives 2-(imidazol-1-yl)-5-chloro-6-methyl-4-benzylamino-thieno-[2,3-d]-pyrimidine.

EXAMPLE 138

Following the procedure of Example 97, the reaction of imidazole with 2-chloro-6-nitro-4-benzylamino-thieno-[2,3-d]-pyrimidine gives 2-(imidazol-1-yl)-6-nitro-4-benzylamino-thieno-[2,3-d]-pyrimidine.

EXAMPLE 139

Following the procedure of Example 97, the reaction of imidazole with 2-chloro-5,6-dimethyl-4-benzylamino-thieno-[2,3-d]-pyrimidine gives 2-(imidazol-1-yl)-5,6-dimethyl-4-benzylamino-thieno-[2,3-d]-pyrimidine.

EXAMPLE 140

Following the procedure of Example 97, the reaction of imidazole with 2-chloro-6-trifluoromethyl-4-benzylamino-thieno-[2,3-d]-pyrimidine gives 2-(imidazol-1-yl)-6-trifluoromethyl-4-benzylamino-thieno-[2,3-d]-pyrimidine.

EXAMPLE 141

Following the procedure of Example 97, the reaction of imidazole with 2-chloro-6-methyl-4-(4- fluorobenzylamino)-thieno-[2,3-d]-pyrimidine gives 2-(imidazol-1-yl)-6-methyl-4-(4-fluorobenzylamino)-thieno-[2,3-d]-pyrimidine.

EXAMPLE 142

Following the procedure of Example 97, the reaction of imidazole with 2-chloro-5,6,7,8-tetrahydro-4-(4-fluorobenzylamino)-[1]-benzothieno-[2,3-d]-pyrimidine gives 2-(imidazol-1-yl)-5,6,7,8-tetrahydro-4-(4-fluorobenzylamino)-[1]-benzothieno-[2,3-d]-pyrimidine.

EXAMPLE 143

Following the procedure of Example 97, the reaction of imidazole with 2-chloro-5,6-cyclopenteno-4-(4-fluorobenzylamino)-[1]-benzothieno-[2,3-d]-pyrimidine gives 2-(imidazol-1-yl)-5,6-cyclopenteno-4-(4-fluorobenzylamino)-[1]-benzothieno-[2,3-d]-pyrimidine.

EXAMPLE 144

Following the procedure of Example 97, the reaction of imidazole with 2-chloro-5,6-cyclohepteno-4-(4-fluorobenzylamino)-[1]-benzothieno-[2,3-d]-pyrimidine gives 2-(imidazol-1-yl)-5,6-cyclohepteno-4-(4-fluorobenzylamino)-[1]-benzothieno-[2,3-d]-pyrimidine.

EXAMPLE 145

Following the procedure of Example 97, the reaction of imidazole with 2-chloro-6-ethyl-4-(4-fluorobenzylamino)-thieno-[2,3-d]-pyrimidine gives 2-(imidazol-1-yl)-6-ethyl-4-(4-fluorobenzylamino)-thieno-[2,3-d]-pyrimidine.

EXAMPLE 146

Following the procedure of Example 97, the reaction of imidazole with 2,6-dichloro-4-(4-fluorobenzylamino)-thieno-[2,3-d]-pyrimidine gives 2-(imidazol-1-yl)-6-dichloro-4-(4-fluorobenzylamino)-thieno-[2,3-d]-pyrimidine.

EXAMPLE 147

Following the procedure of Example 97, the reaction of imidazole with 2,5-dichloro-6-methyl-4-(4-fluorobenzylamino)-thieno-[2,3-d]-pyrimidine gives 2-(imidazol-1-yl)-5-chloro-6-methyl-4-(4-fluorobenzylamino)-thieno-[2,3-d]-pyrimidine.

EXAMPLE 148

Following the procedure of Example 97, the reaction of imidazole with 2-chloro-6-nitro-4-(4-fluorobenzylamino)-thieno-[2,3-d]-pyrimidine gives 2-(imidazol-1-yl)-6-nitro-4-(4-fluorobenzylamino)-thieno-[2,3-d]-pyrimidine.

EXAMPLE 149

Following the procedure of Example 97, the reaction of imidazole with 2-chloro-5,6-dimethyl-4-(4-fluorobenzylamino)-thieno-[2,3-d]-pyrimidine gives 2-(imidazol-1-yl)-5,6-dimethyl-4-(4-fluorobenzylamino)-thieno-[2,3-d]-pyrimidine.

EXAMPLE 150

Following the procedure of Example 97, the reaction of imidazole with 2-chloro-6-trifluoromethyl-4-(4-fluorobenzylamino)-thieno-[2,3-d]-pyrimidine gives 2-(imidazol-1-yl)-6-trifluoromethyl-4-(4-fluorobenzylamino)-thieno-[2,3-d]-pyrimidine.

EXAMPLE 151

Following the procedure of Example 97, the reaction of imidazole with 2-chloro-6-methyl-4-(3,4-dichlorobenzylamino)-thieno-[2,3-d]-pyrimidine gives 2-(imidazol-1-yl)-6-methyl-4-(3,4-dichlorobenzylamino)-thieno-[2,3-d]-pyrimidine.

EXAMPLE 152

Following the procedure of Example 97, the reaction of imidazole with 2-chloro-5-methyl-4-(3,4-dichlorobenzylamino)-thieno-[2,3-d]-pyrimidine gives 2-(imidazol-1-yl)-5-methyl-4-(3,4-dichlorobenzylamino)-thieno-[2,3-d]-pyrimidine.

EXAMPLE 153

Following the procedure of Example 97, the reaction of imidazole with 2-chloro-5,6,7,8-tetrahydro-4-(3,4-dichlorobenzylamino)-[1]-benzothieno-[2,3-d]-pyrimidine gives 2-(imidazol-1-yl)-5,6,7,8-tetrahydro-4-(3,4-dichlorobenzylamino)-[1]-benzothieno-[2,3-d]-pyrimidine.

EXAMPLE 154

Following the procedure of Example 97, the reaction of imidazole with 2-chloro-5,6-cyclopenteno-4-(3,4-dichlorobenzylamino)-[1]-benzothieno-[2,3-d]-pyrimidine gives 2-(imidazol-1-yl)-5,6-cyclopenteno-4-(3,4-dichlorobenzylamino)-[1]-benzothieno-[2,3-d]-pyrimidine.

EXAMPLE 155

Following the procedure of Example 97, the reaction of imidazole with 2-chloro-5,6-cyclopenteno-4-(3,4-dichlorobenzylamino)-[1]-benzothieno-[2,3-d]-pyrimidine gives 2-(imidazol-1-yl)-5,6-cyclopenteno-4-(3,4-dichlorobenzylamino)-[1]-benzothieno-[2,3-d]-pyrimidine.

EXAMPLE 156

Following the procedure of Example 97, the reaction of imidazole with 2-chloro-6-ethyl-4-(3,4-dichlorobenzylamino)-thieno-[2,3-d]-pyrimidine gives 2-(imidazol-1-yl)-6-ethyl-4-(3,4-dichlorobenzylamino)-thieno-[2,3-d]-pyrimidine.

EXAMPLE 157

Following the procedure of Example 97, the reaction of imidazole with 2–6-dichloro-4-(3,4-dichlorobenzylamino)-thieno-[2,3-d]-pyrimidine gives 2-(imidazol-1-yl)-6-chloro-4-(3,4-dichlorobenzylamino)-thieno-[2,3-d]-pyrimidine.

EXAMPLE 158

Following the procedure of Example 97, the reaction of imidazole with 2,5-dichloro-6-methyl-4-(3,4-dichlorobenzylamino)-thieno-[2,3-d]-pyrimidine gives 2-(imidazol-1-yl)-5-chloro-6-methyl-4-(3,4-dichlorobenzylamino)-thieno-[2,3-d]-pyrimidine.

EXAMPLE 159

Following the procedure of Example 97, the reaction of imidazole with 2-chloro-6-nitro-4-(3,4-dichlorobenzylamino)-thieno-[2,3-d]-pyrimidine gives 2-(imidazol-1-yl)-6-nitro-4-(3,4-dichlorobenzylamino)-thieno-[2,3-d]-pyrimidine.

EXAMPLE 160

Following the procedure of Example 97, the reaction of imidazole with 2-chloro-5,6-dimethyl-4-(3,4-

27 dichlorobenzylamino)-thieno-[2,3-d]-pyrimidine gives 2-(imidazol-1-yl)-5,6-dimethyl-4-(3,4-dichlorobenzylamino)-thieno-[2,3-d]-pyrimidine.

EXAMPLE 161

Following the procedure of Example 97, the reaction of imidazole with 2-chloro-6-trifluoromethyl-4-(3,4-dichlorobenzylamino)-thieno-[2,3-d]-pyrimidine gives 2-(imidazol-1-yl)-6-trifluoromethyl-4-(3,4-dichlorobenzylamino)-thieno-[2,3-d]-pyrimidine.

EXAMPLE 162

Following the procedure of Example 97, the reaction of imidazole with 2-chloro-6-methyl-4-(3-nitrobenzylamino)-thieno-[2,3-d]-pyrimidine gives 2-(imidazol-1-yl)-6-methyl-4-(3-nitrobenzylamino)-thieno-[2,3-d]-pyrimidine.

EXAMPLE 163

Following the procedure of Example 97, the reaction of imidazole with 2-chloro-5-methyl-4-(3-nitrobenzylamino)-thieno-[2,3-d]-pyrimidine gives 2-(imidazol-1-yl)-5-methyl-4-(3-nitrobenzylamino)-thieno-[2,3-d]-pyrimidine.

EXAMPLE 164

Following the procedure of Example 97, the reaction of imidazole with 2-chloro-5,6,7,8-tetrahydro-4-(3-nitrobenzylamino)-[1]-benzothieno-[2,3-d]-pyrimidine gives 2-(imidazol-1-yl)-5,6,7,8-tetrahydro-4-(3-nitrobenzylamino)-[1]-benzothieno-[2,3-d]-pyrimidine.

EXAMPLE 165

Following the procedure of Example 97, the reaction of imidazole with 2-chloro-5,6-cyclopenteno-4-(3-nitrobenzylamino)-[1]-benzothieno-[2,3-d]-pyrimidine gives 2-(imidazol-1-yl)-5,6-cyclopenteno-4-(3-nitrobenzylamino)-[1]-benzothieno-[2,3-d]-pyrimidine.

EXAMPLE 166

Following the procedure of Example 97, the reaction of imidazole with 2-chloro-5,6-cyclopenteno-4-(3-nitrobenzylamino)-[1]-benzothieno-[2,3-d]-pyrimidine gives 2-(imidazol-1-yl)-5,6-cyclopenteno-4-(3-nitrobenzylamino)-[1]-benzothieno-[2,3-d]-pyrimidine.

EXAMPLE 167

Following the procedure of Example 97, the reaction of imidazole with 2-chloro-6-ethyl-4-(3-nitrobenzylamino)-thieno-[2,3-d]-pyrimidine gives 2-(imidazol-1-yl)-6-ethyl-4-(3-nitrobenzylamino)-thieno-[2,3-d]-pyrimidine.

EXAMPLE 168

Following the procedure of Example 97, the reaction of imidazole with 6-chloro-4-(3-nitrobenzylamino)-thieno-[2,3-d]-pyrimidine gives 2-(imidazol-1-yl)-4-(3-nitrobenzylamino)-thieno-[2,3-d]-pyrimidine.

EXAMPLE 169

Following the procedure of Example 97, the reaction of imidazole with 5-chloro-6-methyl-4-(3-nitrobenzylamino)-thieno-[2,3-d]-pyrimidine gives 2-(imidazol-1-yl)-6-methyl-4-(3-nitrobenzylamino)-thieno-[2,3-d]-pyrimidine.

EXAMPLE 170

Following the procedure of Example 97, the reaction of imidazole with 2-chloro-6-nitro-4-(3-nitrobenzylamino)-thieno-[2,3-d]-pyrimidine gives 2-(imidazol-1-yl)-6-nitro-4-(3-nitrobenzylamino)-thieno-[2,3-d]-pyrimidine.

EXAMPLE 171

Following the procedure of Example 97, the reaction of imidazole with 2-chloro-5,6-dimethyl-4-(3-nitrobenzylamino)-thieno-[2,3-d]-pyrimidine gives 2-(imidazol-1-yl)-5,6-dimethyl-4-(3-nitrobenzylamino)-thieno-[2,3-d]-pyrimidine.

EXAMPLE 172

Following the procedure of Example 97, the reaction of imidazole with 2-chloro-6-trifluoromethyl-4-(3-nitrobenzylamino)-thieno-[2,3-d]-pyrimidine gives 2-(imidazol-1-yl)-6-trifluoromethyl-4-(3-nitrobenzylamino)-thieno-[2,3-d]-pyrimidine.

EXAMPLE 173

Following the procedure of Example 97, the reaction of imidazole with 2-chloro-6-methyl-4-(3-nitrobenzylamino)-thieno-[2,3-d]-pyrimidine gives 2-(imidazol-1-yl)-6-methyl-4-(3-nitrobenzylamino)-thieno-[2,3-d]-pyrimidine.

EXAMPLE 174

Following the procedure of Example 97, the reaction of imidazole with 2-chloro-5-methyl-4-(3,4-methylenedioxyphenethylamino)-thieno-[2,3-d]-pyrimidine gives 2-(imidazol-1-yl)-5-methyl-4-(3,4-methylenedioxyphenethylamino)-thieno-[2,3-d]-pyrimidine.

EXAMPLE 175

Following the procedure of Example 97, the reaction of imidazole with 2-chloro-5,6,7,8-tetrahydro-4-(3,4-methylenedioxyphenethylamino)-[1]-benzothieno-[2,3-d]-pyrimidine gives 2-(imidazol-1-yl)-5,6,7,8-tetrahydro-4-(3,4-methylenedioxyphenethylamino)-[1]-benzothieno-[2,3-d]-pyrimidine.

EXAMPLE 176

Following the procedure of Example 97, the reaction of imidazole with 2-chloro-5,6-cyclopenteno-4-(3,4-methylenedioxyphenethylamino)-[1]-benzothieno-[2,3-d]-pyrimidine gives 2-(imidazol-1-yl)-5,6-cyclopenteno-4-(3,4-methylenedioxyphenethylamino)-[1]-benzothieno-[2,3-d]-pyrimidine.

EXAMPLE 177

Following the procedure of Example 97, the reaction of imidazole with 2-chloro-6-ethyl-4-(3,4-methylenedioxyphenethylamino)-thieno-[2,3-d]-pyrimidine gives 2-(imidazol-1-yl)-6-ethyl-4-(3,4-methylenedioxyphenethylamino)-thieno-[2,3-d]-pyrimidine.

EXAMPLE 178

Following the procedure of Example 97, the reaction of imidazole with 6-chloro-4-(3,4-methylenedioxyphenethylamino)-thieno-[2,3-d]-pyrimidine gives 2-(imidazol-1-yl)-4-(3,4-methylenedioxyphenethylamino)-thieno-[2,3-d]-pyrimidine.

EXAMPLE 179

Following the procedure of Example 97, the reaction of imidazole with 5-chloro-6-methyl-4-(3,4- methylenedioxyphenethylamino)-thieno-[2,3-d]-pyrimidine gives 2-(imidazol-1-yl)-6-methyl-4-(3,4-methylenedioxyphenethylamino)-thieno-[2,3-d]-pyrimidine.

EXAMPLE 180

Following the procedure of Example 97, the reaction of imidazole with 2-chloro-6-nitro-4-(3,4-methylenedioxyphenethylamino)-thieno-[2,3-d]-pyrimidine gives 2-(imidazol-1-yl)-6-nitro-4-(3,4-methylenedioxyphenethylamino)-thieno-[2,3-d]-pyrimidine.

EXAMPLE 181

Following the procedure of Example 97, the reaction of imidazole with 2-chloro-5,6-dimethyl-4-(3,4-methylenedioxyphenethylamino)-thieno-[2,3-d]-pyrimidine gives 2-(imidazol-1-yl)-5,6-dimethyl-4-(3,4-methylenedioxyphenethylamino)-thieno-[2,3-d]-pyrimidine.

EXAMPLE 182

Following the procedure of Example 97, the reaction of imidazole with 2-chloro-6-trifluoromethyl-4-(3,4-methylenedioxyphenethylamino)-thieno-[2,3-d]-pyrimidine gives 2-(imidazol-1-yl)-6-trifluoromethyl-4-(3,4-methylenedioxyphenethylamino)-thieno-[2,3-d]-pyrimidine.

EXAMPLE 183

Following the procedure of Example 97, the reaction of imidazole with 2-chloro-6-methyl-4-(3,4-ethylendioxybenzylamino)-thieno-[2,3-d]-pyrimidine gives 2-(imidazol-1-yl)-6-methyl-4-(3,4-ethylendioxybenzylamino)-thieno-[2,3-d]-pyrimidine.

EXAMPLE 184

Following the procedure of Example 97, the reaction of imidazole with 2-chloro-5-methyl-4-(3,4-ethylendioxybenzylamino)-thieno-[2,3-d]-pyrimidine gives 2-(imidazol-1-yl)-5-methyl-4-(3,4-ethylendioxybenzylamino)-thieno-[2,3-d]-pyrimidine.

EXAMPLE 185

Following the procedure of Example 97, the reaction of imidazole with 2-chloro-5,6,7,8-tetrahydro-4-(3,4-ethylendioxybenzylamino)-[1]-benzothieno-[2,3-d]-pyrimidine gives 2-(imidazol-1-yl)-5,6,7,8-tetrahydro-4-(3,4-ethylendioxybenzylamino)-[1]-benzothieno-[2,3-d]-pyrimidine.

EXAMPLE 186

Following the procedure of Example 97, the reaction of imidazole with 2-chloro-6-ethyl-4-(3,4-ethylendioxybenzylamino)-thieno-[2,3-d]-pyrimidine gives 2-(imidazol-1-yl)-6-ethyl-4-(3,4-ethylendioxybenzylamino)-thieno-[2,3-d]-pyrimidine.

EXAMPLE 187

Following the procedure of Example 97, the reaction of imidazole with 2,6-dichloro-4-(3,4-ethylendioxybenzylamino)-thieno-[2,3-d]-pyrimidine gives 2-(imidazol-1-yl)-6-chloro-4-(3,4-ethylendioxybenzylamino)-thieno-[2,3-d]-pyrimidine.

EXAMPLE 188

Following the procedure of Example 97, the reaction of 2,5-dichloro-6-methyl-4-(3,4-ethylendioxybenzylamino)-thieno-[2,3-d]-pyrimidine gives 2-(imidazol-1-yl)-5-chloro-6-methyl-4-(3,4-ethylendioxybenzylamino)-thieno-[2,3-d]-pyrimidine.

EXAMPLE 189

Following the procedure of Example 97, the reaction of imidazole with 2-chloro-6-nitro-4-(3,4-ethylendioxybenzylamino)-thieno-[2,3-d]-pyrimidine gives 2-(imidazol-1-yl)-6-nitro-4-(3,4-ethylendioxybenzylamino)-thieno-[2,3-d]-pyrimidine.

EXAMPLE 190

Following the procedure of Example 97, the reaction of imidazole with 2-chloro-5,6-dimethyl-4-(3,4-ethylendioxybenzylamino)-thieno-[2,3-d]-pyrimidine gives 2-(imidazol-1-yl)-5,6-dimethyl-4-(3,4-ethylendioxybenzylamino)-thieno-[2,3-d]-pyrimidine.

EXAMPLE 191

Following the procedure of Example 97, the reaction of imidazole with 2-chloro-6-trifluoromethyl-4-(3,4-ethylendioxybenzylamino)-thieno-[2,3-d]-pyrimidine gives 2-(imidazol-1-yl)-6-trifluoromethyl-4-(3,4-ethylendioxybenzylamino)-thieno-[2,3-d]-pyrimidine.

EXAMPLE 192

Following the procedure of Example 97, the reaction of pyrazole with 2-chloro-6-methyl-4-(3,4-methylene dioxybenzylamino)-thieno-[2,3-d]-pyrimidine yields 2-(pryazol-1-yl)-6-methyl-4-(3,4-methylenedioxybenzylamino)-thieno-[2,3-d]-pyrimidine.

EXAMPLE 193

Following the procedure of Example 97, the reaction of pyrazole with 2-chloro-5-methyl-4-(3,4-methylenedioxybenzylamino)-thieno-[2,3-d]-pyrimidine gives 2-(pyrazol-1-yl)-5-methyl-4-(3,4-methylenedioxybenzylamino)-thieno-[2,3-d]-pyrimidine.

EXAMPLE 194

Following the procedure of Example 97, the reaction of pyrazole with 2-chloro-5,6,7,8-tetrahydro-4-(3,4-methylenedioxybenzylamino)-[1]-benzothieno-[2,3-d]-pyrimidine gives 2-(pyrazol-1-yl)-5,6,7,8-tetrahydro-4-(3,4-methylenedioxybenzylamino)-[1]-benzothieno-[2,3-d]-pyrimidine.

EXAMPLE 195

Following the procedure of Example 97, the reaction of pyrazole with 2-chloro-5,6-cyclopenteno-4-(3,4-methylenedioxybenzylamino)-[1]-benzothieno-[2,3-d]-pyrimidine gives 2-(pyrazol-1-yl)-5,6-cyclopenteno-4-(3,4-methylenedioxybenzylamino)-[1]-benzothieno-[2,3-d]-pyrimidine.

EXAMPLE 196

Following the procedure of Example 97, the reaction of pyrazole with 2-chloro-5,6-cyclohepteno-4-93,4-methylenedioxybenzylamino)-[1]-benzothieno-[2,3-d]-pyrimidine gives 2-(pyrazol-1-yl)-5,6-cyclohepteno-4-93,4-methylenedioxybenzylamino)-[1]-benzothieno-[2,3-d]-pyrimidine.

EXAMPLE 197

Following the procedure of Example 97, the reaction of pyrazole with 2-chloro-6-ethyl-4-(3,4-methylenedioxybenzylamino)-thieno-[2,3-d]-pyrimidine gives 2-(pyrazol-1-yl)-6-ethyl-4-(3,4-methylenedioxybenzylamino)-thieno-[2,3-d]-pyrimidine.

EXAMPLE 198

Following the procedure of Example 97, the reaction of pyrazole with 2,6-dichloro-4-(3,4-methylenedioxybenzylamino)-thieno-[2,3-d]-pyrimidine gives 2-(pyrazol-1-yl)-6-chloro-4-(3,4-methylenedioxybenzylamino)-thieno-[2,3-d]-pyrimidine.

EXAMPLE 199

Following the procedure of Example 97, the reaction pyrazole with 2,5-dichloro-6-methyl-4-93,4-methylenedioxybenzylamino)-thieno-[2,3-d]-pyrimidine gives 2-(pyrazol-1-yl)-5-chloro-6-methyl-4-93,4-methylenedioxybenzylamino)-thieno-[2,3-d]-pyrimidine.

EXAMPLE 200

Following the procedure of Example 97, the reaction of pyrazole with 2-chloro-6-nitro-4-(3,4-methylenedioxybenzylamino)-thieno-[2,3-d]-pyrimidine gives 2-(pyrazol-1-yl)-6-nitro-4-(3,4-methylenedioxybenzylamino)-thieno-[2,3-d]-pyrimidine.

EXAMPLE 201

Following the procedure of Example 97, the reaction of pyrazole with 2-chloro-5,6-dimethyl-4-(3,4-methylenedioxybenzylamino)-thieno-[2,3-d]-pyrimidine gives 2-(pyrazol-1-yl)-5,6-dimethyl-4-(3,4-methylenedioxybenzylamino)-thieno-[2,3-d]-pyrimidine.

EXAMPLE 202

Following the procedure of Example 97, the reaction of pyrazole with 2-chloro-6-trifluoromethyl-4-(3,4-methylenedioxybenzylamino)-thieno-[2,3-d]-pyrimidine gives 2-(pyrazol-1-yl)-6-trifluoromethyl-4-(3,4-methylenedioxybenzylamino)-thieno-[2,3-d]-pyrimidine.

EXAMPLE 203

Following the procedure of Example 97, the reaction of pyrazole with 2-chloro-6-methyl-4-(3-chloro-4-methoxybenzylamino)-thieno-[2,3-d]-pyrimidine gives 2-(pyrazol-1-yl)-6-methyl-4-(3-chloro-4-methoxybenzylamino)-thieno-[2,3-d]-pyrimidine.

EXAMPLE 204

Following the procedure of Example 97, the reaction of pyrazole with 2-chloro-5-methyl-4-(3-chloro-4-methoxybenzylamino)-thieno-[2,3-d]-pyrimidine gives 2-(pyrazol-1-yl)-5-methyl-4-(3-chloro-4-methoxybenzylamino)-thieno-[2,3-d]-pyrimidine.

EXAMPLE 205

Following the procedure of Example 97, the reaction of pyrazole with 2-chloro-5,6,7,8-tetrahydro-4-(3-chloro-4-methoxybenzylamino)-[1]-[1]-benzothieno-[2,3-d]-pyrimidine gives 2-(pyrazol-1-yl)-5,6,7,8-tetrahydro-4-(3-chloro-4-methoxybenzylamino)-[1]-[1]-benzothieno-[2,3-d]-pyrimidine.

EXAMPLE 206

Following the procedure of Example 97, the reaction of pyrazole with 2-chloro-5,6-cyclopenteno-4-(3-chloro-4-methoybenzylamino)-[1]-benzothieno-[2,3-d]-pyrimidine gives 2-(pyrazol-1-yl)-5,6-cyclopenteno-4-(3-chloro-4-methoybenzylamino)-[1]-benzothieno-[2,3-d]-pyrimidine.

EXAMPLE 207

Following the procedure of Example 97, the reaction of pyrazole with 2-chloro-5,6-cyclohepteno-4-(3-chloro-4-methoxybenzylamino)-[1]-benzothieno-[2,3-d]-pyrimidine gives 2-(pyrazol-1-yl)-5,6-cyclohepteno-4-(3-chloro-4-methoxybenzylamino)-[1]-benzothieno-[2,3-d]-pyrimidine.

EXAMPLE 208

Following the procedure of Example 97, the reaction of pyrazole with 2-chloro-6-ethyl-4-(3-chloro-4-methoxybenzylamino)-thieno-[2,3-d]-pyrimidine gives 2-(pyrazol-1-yl)-6-ethyl-4-(3-chloro-4-methoxybenzylamino)-thieno-[2,3-d]-pyrimidine.

EXAMPLE 209

Following the procedure of Example 97, the reaction of pyrazole with 2,6-dichloro-4-(3-chloro-4-methoxybenzylamino)-thieno-[2,3-d]-pyrimidine gives 2-(pyrazol-1-yl)-6-chloro-4-(3-chloro-4-methoxybenzylamino)-thieno-[2,3-d]-pyrimidine.

EXAMPLE 210

Following the procedure of Example 97, the reaction of pyrazole with 2,5-dichloro-6-methyl-4-(3-chloro-4-methoxybenzylamino)-thieno-[2,3-d]-pyrimidine gives 2-(pyrazol-1-yl)-5-chloro-6-methyl-4-(3-chloro-4-methoxybenzylamino)-thieno-[2,3-d]-pyrimidine.

EXAMPLE 211

Following the procedure of Example 97, the reaction of pyrazole with 2-chloro-6-nitro-4-(3-chloro-4-methoxybenzylamino)-thieno-[2,3-d]-pyrimidine gives 2-(pyrazol-1-yl)-6-nitro-4-(3-chloro-4-methoxybenzylamino)-thieno-[2,3-d]-pyrimidine.

EXAMPLE 212

Following the procedure of Example 97, the reaction of pyrazole with 2-chloro-5,6-dimethyl-4-(3-chloro-4-methoxybenzylamino)-thieno-[2,3-d]-pyrimidine gives 2-(pyrazol-1-yl)-5,6-dimethyl-4-(3-chloro-4-methoxybenzylamino)-thieno-[2,3-d]-pyrimidine.

EXAMPLE 213

Following the procedure of Example 97, the reaction of pyrazole with 2-chloro-6-trifluoromethyl-4-(3-chloro-4-methoxybenzylamino0-thieno-[2,3-d]-pyrimidine gives 2-(pyrazol-1-yl)-6-trifluoromethyl-4-(3-chloro-4-methoxybenzylamino0-thieno-[2,3-d]-pyrimidine.

EXAMPLE 214

Following the procedure of Example 97, the reaction of pyrazole with 2-chloro-6-methyl-4-(3,4-dimethoxybenzylamino)-thieno-[2,3-d]-pyrimidine gives 2-(pyrazol-1-yl)-6-methyl-4-(3,4-dimethoxybenzylamino)-thieno-[2,3-d]-pyrimidine.

EXAMPLE 215

Following the procedure of Example 97, the reaction of pyrazole with 2-chloro-5-methyl-4-(3,4- dimethoxybenzylamino)-thieno-[2,3-d]-pyrimidine gives 2-(pyrazol-1-yl)-5-methyl-4-(3,4-dimethoxybenzylamino)-thieno-[2,3-d]-pyrimidine.

EXAMPLE 216

Following the procedure of Example 97, the reaction of pyrazole with 2-chloro-5,6,7,8-tetrahydro-4-(3,4-dimethoxybenzylamino)-[1]-[1]-benzothieno-[2,3-d]pyrimidine gives 2-(pyrazol-1-yl)-5,6,7,8-tetrahydro-4-(3,4-dimethoxybenzylamino)-[1]-[1]-benzothieno-[2,3-d]-pyrimidine.

EXAMPLE 217

Following the procedure of Example 97, the reaction of pyrazole with 2-chloro-5,6-cyclopenteno-4-(3,4-dimethoxybenzylamino)-[1]-benzothieno-[2,3-d]-pyrimidine gives 2-(pyrazol-1-yl)-5,6-cyclopenteno-4-(3,4-dimethoxybenzylamino)-[1]-benzothieno-[2,3-d]-pyrimidine.

EXAMPLE 218

Following the procedure of Example 97, the reaction of pyrazole with 2-chloro-5,6-cyclopenteno-4-(3,4-dimethoxybenzylamino)-[1]-benzothieno-[2,3-d]-pyrimidine gives 2-(pyrazol-1-yl)-5,6-cyclopenteno-4-(3,4-dimethoxybenzylamino)-[1]-benzothieno-[2,3-d]-pyrimidine.

EXAMPLE 219

Following the procedure of Example 97, the reaction of pyrazole with 2-chloro-6-ethyl-4-(3,4-dimethoxybenzylamino)-thieno-[2,3-d]-pyrimidine gives 2-(pyrazol-1-yl)-6-ethyl-4-(3,4-dimethoxybenzylamino)-thieno-[2,3-d]-pyrimidine.

EXAMPLE 220

Following the procedure of Example 97, the reaction of pyrazole with 2,6-dichloro-4-(3,4-dimethoxybenzylamino)-thieno-[2,3-d]-pyrimidine gives 2-(pyrazol-1-yl)-6-chloro-4-(3,4-dimethoxybenzylamino)-thieno-[2,3-d]-pyrimidine.

EXAMPLE 221

Following the procedure of Example 97, the reaction of pyrazole with 2,5-dichloro-6-methyl-4-(3,4-dimethoxybenzylamino)-thieno-[2,3-d]-pyrimidine gives 2-(pyrazol-1-yl)-5-chloro-6-methyl-4-(3,4-dimethoxybenzylamino)-thieno-[2,3-d]-pyrimidine.

EXAMPLE 222

Following the procedure of Example 97, the reaction of pyrazole with 2-chloro-6-nitro-4-(3,4-dimethoxybenzylamino)-thieno-[2,3-d]-pyrimidine gives 2-(pyrazol-1-yl)-6-nitro-4-(3,4-dimethoxybenzylamino)-thieno-[2,3-d]-pyrimidine.

EXAMPLE 223

Following the procedure of Example 97, the reaction of pyrazole with 2-chloro-5,6-dimethyl-4-(3,4-dimethoxybenzylamino)-thieno-[2,3-d]-pyrimidine gives 2-(pyrazol-1-yl)-5,6-dimethyl-4-(3,4-dimethoxybenzylamino)-thieno-[2,3-d]-pyrimidine.

EXAMPLE 224

Following the procedure of Example 97, the reaction of pyrazole with yields 2-chloro-6-trifluoromethyl-4-(3,4-dimethoxybenzylamino)-thieno-[2,3-d]-pyrimidine gives 2-(pyrazol-1-yl)-6-trifluoromethyl-4-(3,4-dimethoxybenzylamino)-thieno-[2,3-d]-pyrimidine.

EXAMPLE 225

Following the procedure of Example 97, the reaction of pyrazole with 2-chloro-6-methyl-4-benzylamino-thieno-[2,3-d]-pyrimidine gives 2-(pyrazol-1-yl)-6-methyl-4-benzylamino-thieno-[2,3-d]-pyrimidine.

EXAMPLE 226

Following the procedure of Example 97, the reaction of pyrazole with 2-chloro-5-methyl-4-benzylamino-thieno-[2,3-d]-pyrimidine gives 2-(pyrazol-1-yl)-5-methyl-4-benzylamino-thieno-[2,3-d]-pyrimidine.

EXAMPLE 227

Following the procedure of Example 97, the reaction of pyrazole with 2-chloro-5,6,7,8-tetrahydro-4-benzylamino-thieno-[1]-[1]-benzothieno-[2,3-d]-pyrimidine gives 2-(pyrazol-1-yl)-5,6,7,8-tetrahydro-4-benzylamino-thieno-[1]-[1]-benzothieno-[2,3-d]-pyrimidine.

EXAMPLE 228

Following the procedure of Example 97, the reaction of pyrazole with 2-chloro-5,6-cyclopenteno-4-benzylamino-[2,3-d]-pyrimidine gives 2-(pyrazol-1-yl)-5,6-cyclopenteno-4-benzylamino-[2,3-d]-pyrimidine.

EXAMPLE 229

Following the procedure of Example 97, the reaction of pyrazole with 2-chloro-5,6-cyclopenteno-4-benzylamino-[1]-benzothieno-[2,3-d]-pyrimidine gives 2-(pyrazol-1-yl)-5,6-cyclopenteno-4-benzylamino-[1]-benzothieno-[2,3-d]-pyrimidine.

EXAMPLE 230

Following the procedure of Example 97, the reaction of pyrazole with 2-chloro-6-ethyl-4-benzylamino-thieno-[2,3-d]-pyrimidine gives 2-(pyrazol-1-yl)-6-ethyl-4-benzylamino-thieno-[2,3-d]-pyrimidine.

EXAMPLE 231

Following the procedure of Example 97, the reaction of pyrazole with 2,6-dichloro-6-4-benzylamino-thieno-[2,3-d]-pyrimidine gives 2-(pyrazol-1-yl)-6-chloro-6-4-benzylamino-thieno-[2,3-d]-pyrimidine.

EXAMPLE 232

Following the procedure of Example 97, the reaction of pyrazole with 2,5-dichloro-6-methyl-4-benzylamino-thieno-[2,3-d]-pyrimidine gives 2-(pyrazol-1-yl)-5-chloro-6-methyl-4-benzylamino-thieno-[2,3-d]-pyrimidine.

EXAMPLE 233

Following the procedure of Example 97, the reaction of pyrazole with 2-chloro-6-nitro-4-benzylamino-thieno-[2,3-d]-pyrimidine gives 2-pyrazol-1-yl)-6-nitro-4-benzylamino-thieno-[2,3-d]-pyrimidine. 57-

EXAMPLE 234

Following the procedure of Example 97, the reaction of pyrazole with 2-chloro-5,6-dimethyl-4-benzylamino-thieno-

[2,3-d]-pyrimidine gives 2-(pyrazol-1-yl)-5,6-dimethyl-4-benzylamino-thieno-[2,3-d]-pyrimidine.

EXAMPLE 235

Following the procedure of Example 97, the reaction of pyrazole with 2-chloro-6-trifluoromethyl-4-benzylamino-thieno-[2,3-d]-pyrimidine gives 2-(pyrazol-1-yl)-6-triufloromethyl-4-benylamino-thieno-[2,3-d]-pyrimidine.

EXAMPLE 236

Following the procedure of Example 97, the reaction of pyrazole with 2-chloro-6-methyl-4-(4-fluorobenzylamino)-thieno-[2,3-d]-pyrimidine gives 2-(pyrazol-1-yl)-6-methyl-4-(4-fluorobenzylamino)-thieno-[2,3-d]-pyrimidine.

EXAMPLE 237

Following the procedure of Example 97, the reaction of pyrazole with 2-chloro-5,6,7,8-tetrahydro-4-(4-fluorobenzylamino)-[1]-benzothieno-[2,3-d]-pyrimidine gives 2-(pyrazol-1-yl)-5,6,7,8-tetrahydro-4-(4-fluorobenzylamino)-[1]-benzothieno-[2,3-d]-pyrimidine.

EXAMPLE 238

Following the procedure of Example 97, the reaction of pyrazole with 2-chloro-5,6-cyclopenteno-4-(4-fluorobenzylamino)-[1]-benzothieno-[2,3-d]-pyrimidine gives 2-(pyrazol-1-yl)-5,6-cyclopenteno-4-(4-fluorobenzylamino)-[1]-benzothieno-[2,3-d]-pyrimidine.

EXAMPLE 239

Following the procedure of Example 97, the reaction of pyrazole with 2-chloro-5,6-cyclohepteno-4-(4-fluorobenzylamino)-[1]-benzothieno-[2,3-d]-pyrimidine gives 2-(pyrazol-1-yl)-5,6-cyclohepteno-4-(4-fluorobenzylamino)-[1]-benzothieno-[2,3-d]-pyrimidine.

EXAMPLE 240

Following the procedure of Example 97, the reaction of pyrazole with 2-chloro-6-ethyl-4-(4-fluorobenzylamino)-thieno-[2,3-d]-pyrimidine gives 2-(pyrazol-1-yl)-6-ethyl-4-(4-fluorobenzylamino)-thieno-[2,3-d]-pyrimidine.

EXAMPLE 241

Following the procedure of Example 97, the reaction of pyrazole with 2,6-dichloro-4-(4-fluorobenzylamino)-thieno-[2,3-d]-pyrimidine gives 2-(pyrazol-1-yl)-6-dichloro-4-(4-fluorobenzylamino)-thieno-[2,3-d]-pyrimidine.

EXAMPLE 242

Following the procedure of Example 97, the reaction of pyrazole with 2,5-dichloro-6-methyl-4-(4-fluorobenzylamino)-thieno-[2,3-d]-pyrimidine gives 2-(pyrazol-1-yl)-5-chloro-6-methyl-4-(4-fluorobenzylamino)-thieno-[2,3-d]-pyrimidine.

EXAMPLE 243

Following the procedure of Example 97, the reaction of pyrazole with 2-chloro-6-nitro-4-(4-fluorobenzylamino)-thieno-[2,3-d]-pyrimidine gives 2-(pyrazol-1-yl)-6-nitro-4-(4-fluorobenzylamino)-thieno-[2,3-d]-pyrimidine.

EXAMPLE 244

Following the procedure of Example 97, the reaction of pyrazole with 2-chloro-5,6-dimethyl-4-(4-fluorobenzylamino)-thieno-[2,3-d]-pyrimidine gives 2-(pyrazol-1-yl)-5,6-dimethyl-4-(4-fluorobenzylamino)-thieno-[2,3-d]-pyrimidine.

EXAMPLE 245

Following the procedure of Example 97, the reaction of pyrazole with 2-(pyrazol-1-yl)-6-trifluoromethyl-4-(4-fluorobenzylamino)-thieno-[2,3-d]-pyrimidine.

EXAMPLE 246

Following the procedure of Example 97, the reaction of pyrazole with 2-chloro-6-methyl-4-(3,4-dichlorobenzylamino)-thieno-[2,3-d]-pyrimidine gives 2-(pyrazol-1-yl)-6-methyl-4-(3,4-dichlorobenzylamino)-thieno-[2,3-d]-pyrimidine.

EXAMPLE 247

Following the procedure of Example 97, the reaction of pyrazole with 2-chloro-5-methyl-4-(3,4-dichlorobenzylamino)-thieno-[2,3-d]-pyrimidine gives 2-(pyrazol-1-yl)-5-methyl-4-(3,4-dichlorobenzylamino)-thieno-[2,3-d]-pyrimidine.

EXAMPLE 248

Following the procedure of Example 97, the reaction of pyrazole with 2-chloro-5,6,7,8-tetrahydro-4-(3,4-dichlorobenzylamino)-[1]-benzothieno-[2,3-d]-pyrimidine gives 2-(pyrazol-1-yl)-5,6,7,8-tetrahydro-4-(3,4-dichlorobenzylamino)-[1]-benzothieno-[2,3-d]-pyrimidine.

EXAMPLE 249

Following the procedure of Example 97, the reaction of pyrazole with 2-chloro-5,6-cyclopenteno-4-(3,4-dichlorobenzylamino)-[1]-benzothieno-[2,3-d]-pyrimidine gives 2-(pyrazol-1-yl)-5,6-cyclopenteno-4-(3,4-dichlorobenzylamino)-[1]-benzothieno-[2,3-d]-pyrimidine.

EXAMPLE 250

Following the procedure of Example 97, the reaction of pyrazole with 2-chloro-5,6-cyclopenteno-4-(3,4-dichlorobenzylamino)-[1]-benzothieno-[2,3-d]-pyrimidine gives 2-(pyrazol-1-yl)-5,6-cyclopenteno-4-(3,4-dichlorobenzylamino)-[1]-benzothieno-[2,3-d]-pyrimidine.

EXAMPLE 251

Following the procedure of Example 97, the reaction of pyrazole with 2-chloro-6-ethyl-4-(3,4-dichlorobenzylamino)-thieno-[2,3-d]-pyrimidine gives 2-(pyrazol-1-yl)-6-ethyl-4-(3,4-dichlorobenzylamino)-thieno-[2,3-d]-pyrimidine. P-157

EXAMPLE 252

Following the procedure of Example 97, the reaction of pyrazole with 2-6-dichloro-4-(3,4-dichlorobenzylamino)-thieno-[2,3-d]-pyrimidine gives 2-(pyrazol-1-yl)-6-chloro-4-(3,4-dichlorobenzylamino)-thieno-[2,3-d]-pyrimidine.

EXAMPLE 253

Following the procedure of Example 97, the reaction of pyrazole with 2,5-dichloro-6-methyl-4-(3,4-dichlorobenzylamino)-thieno-[2,3-d]-pyrimidine gives 2-(pyrazol-1-yl)-5-chloro-6-methyl-4-(3,4-dichlorobenzylamino)-thieno-[2,3-d]-pyrimidine.

EXAMPLE 254

Following the procedure of Example 97, the reaction of pyrazole with 2-chloro-6-nitro-4-(3,4-dichlorobenzylamino)-thieno-[2,3-d]-pyrimidine gives 2-(pyrazol-1-yl)-6-nitro-4-(3,4-dichlorobenzylamino)-thieno-[2,3-d]-pyrimidine.

EXAMPLE 255

Following the procedure of Example 97, the reaction of pyrazole with 2-chloro-5,6-dimethyl-4-(3,4-dichlorobenzylamino)-thieno-[2,3-d]-pyrimidine gives 2-(pyrazol-1-yl)-5,6-dimethyl-4-(3,4-dichlorobenzylamino)-thieno-[2,3-d]-pyrimidine.

EXAMPLE 256

Following the procedure of Example 97, the reaction of pyrazole with 2-chloro-6-trifluoromethyl-4-(3,4-dichlorobenzylamino)-thieno-[2,3-d]-pyrimidine gives 2-(pyrazol-1-yl)-6-trifluoromethyl-4-(3,4-dichlorobenzylamino)-thieno-[2,3-d]-pyrimidine.

EXAMPLE 257

Following the procedure of Example 97, the reaction of pyrazole with 2-chloro-6-methyl-4-(3-nitrobenzylamino)-thieno-[2,3-d]-pyrimidine gives 2-(pyrazol-1-yl)-6-methyl-4-(3-nitrobenzylamino)-thieno-[2,3-d]-pyrimidine.

EXAMPLE 258

Following the procedure of Example 97, the reaction of pyrazole with 2-chloro-5-methyl-4-(3-nitrobenzylamino)-thieno-[2,3-d]-pyrimidine gives 2-(pyrazol-1-yl)-5-methyl-4-(3-nitrobenzylamino)-thieno-[2,3-d]-pyrimidine.

EXAMPLE 259

Following the procedure of Example 97, the reaction of pyrazole with 2-chloro-5,6,7,8-tetrahydro-4-(3-nitrobenzylamino)-[1]-benzothieno-[2,3-d]-pyrimidine gives 2-(pyrazol-1-yl)-5,6,7,8-tetrahydro-4-(3-nitrobenzylamino)-[1]-benzothieno-[2,3-d]-pyrimidine.

EXAMPLE 260

Following the procedure of Example 97, the reaction of pyrazole with 2-chloro-5,6-cyclopenteno-4-(3-nitrobenzylamino)-[1]-benzothieno-[2,3-d]-pyrimidine gives 2-(pyrazol-1-yl)-5,6-cyclopenteno-4-(3-nitrobenzylamino)-[1]-benzothieno-[2,3-d]-pyrimidine.

EXAMPLE 261

Following the procedure of Example 97, the reaction of pyrazole with 2-chloro-5,6-cyclopenteno-4-(3-nitrobenzylamino)-[1]-benzothieno-[2,3-d]-pyrimidine gives 2-(pyrazol-1-yl)-5,6-cyclopenteno-4-(3-nitrobenzylamino)-[ 1 ]-benzothieno-[2,3-d]-pyrimidine.

EXAMPLE 262

Following the procedure of Example 97, the reaction of pyrazole with 2-chloro-6-ethyl-4-(3-nitrobenzylamino)-thieno-[2,3-d]-pyrimidine gives 2-(pyrazol-1-yl)-6-ethyl-4-(3-nitrobenzylamino)-thieno-[2,3-d]-pyrimidine.

EXAMPLE 263

Following the procedure of Example 97, the reaction of pyrazole with 6-chloro-4-(3-nitrobenzylamino)-thieno-[2,3-d]-pyrimidine gives 2-(pyrazol-1-yl)-4-(3-nitrobenzylamino)-thieno-[2,3-d]-pyrimidine.

EXAMPLE 264

Following the procedure of Example 97, the reaction of pyrazole with 5-chloro-6-methyl-4-(3-nitrobenzylamino)-thieno-[2,3-d]-pyrimidine gives 2-(pyrazol-1-yl)-6-methyl-4-(3-nitrobenzylamino)-thieno-[2,3-d]-pyrimidine.

EXAMPLE 265

Following the procedure of Example 97, the reaction of pyrazole with 2-chloro-6-nitro-4-(3-nitrobenzylamino)-thieno-[2,3-d]-pyrimidine gives 2-(pyrazol-1-yl)-6-nitro-4-(3-nitrobenzylamino)-thieno-[2,3-d]-pyrimidine.

EXAMPLE 266

Following the procedure of Example 97, the reaction of pyrazole with 2-chloro-5,6-dimethyl-4-(3-nitrobenzylamino)-thieno-[2,3-d]-pyrimidine gives 2-(pyrazol-1-yl)-5,6-dimethyl-4-(3-nitrobenzylamino)-thieno-[2,3-d]-pyrimidine.

EXAMPLE 267

Following the procedure of Example 97, the reaction of pyrazole with 2-chloro-6-trifluoromethyl-4-(3-nitrobenzylamino)-thieno-[2,3-d]-pyrimidine gives 2-(pyrazol-1-yl)-6-trifluoromethyl-4-(3-nitrobenzylamino)-thieno-[2,3-d]-pyrimidine.

EXAMPLE 268

Following the procedure of Example 97, the reaction of pyrazole with 2-chloro-6-methyl-4-(3-nitrobenzylamino)-thieno-[2,3-d]-pyrimidine gives 2-(pyrazol-1-yl)-6-methyl-4-(3-nitrobenzylamino)-thieno-[2,3-d]-pyrimidine.

EXAMPLE 269

Following the procedure of Example 97, the reaction of pyrazole with 2-chloro-5-methyl-4-(3,4-methylenedioxyphenethylamino)-thieno-[2,3-d]-pyrimidine gives 2-(pyrazol-1-yl)-5-methyl-4-(3,4-methylenedioxyphenethylamino)-thieno-[2,3-d]-pyrimidine.

EXAMPLE 270

Following the procedure of Example 97, the reaction of pyrazole with 2-chloro-5,6,7,8-tetrahydro-4-(3,4-methylenedioxyphenethylamino)-[1]-benzothieno-[2,3-d]-pyrimidine gives 2-(pyrazol-1-yl)-5,6,7,8-tetrahydro-4-(3,4-methylenedioxyphenethylamino)-[1l]-benzothieno-[2,3-d]-pyrimidine.

EXAMPLE 271

Following the procedure of Example 97, the reaction of pyrazole with 2-chloro-5,6-cyclopenteno-4-(3,4-methylenedioxyphenethylamino)-[1]-benzothieno-[2,3-d]-pyrimidine gives 2-(pyrazol-1-yl)-5,6-cyclopenteno-4-(3,4-methylenedioxyphenethylamino)-[1]-benzothieno-[2,3-d]-pyrimidine.

EXAMPLE 272

Following the procedure of Example 97, the reaction of pyrazole with 2-chloro-6-ethyl-4-(3,4-methylenedioxyphenethylamino)-thieno-[2,3-d]-pyrimidine gives 2-(pyrazol-1-yl)-6-ethyl-4-(3,4-methylenedioxyphenethylamino)-thieno-[2,3-d]-pyrimidine.

EXAMPLE 273

Following the procedure of Example 97, the reaction of pyrazole with 6-chloro-4-(3,4-methylenedioxyphenethylamino)-thieno-[2,3-d]-pyrimidine gives 2-(pyrazol-1-yl)-4-(3,4-methylenedioxyphenethylamino)-thieno-[2,3-d]-pyrimidine.

EXAMPLE 274

Following the procedure of Example 97, the reaction of pyrazole with 5-chloro-6-methyl-4-(3,4-methylenedioxyphenethylamino)-thieno-[2,3-d]-pyrimidine gives 2-(pyrazol-1-yl)-6-methyl-4-(3,4-methylenedioxyphenethylamino)-thieno-[2,3-d]-pyrimidine.

EXAMPLE 275

Following the procedure of Example 97, the reaction of pyrazole with 2-chloro-6-nitro-4-(3,4-methylenedioxyphenethylamino)-thieno-[2,3-d]-pyrimidine gives 2-(pyrazol-1-yl)-6-nitro-4-(3,4-methylenedioxyphenethylamino)-thieno-[2,3-d]-pyrimidine.

EXAMPLE 276

Following the procedure of Example 97, the reaction of pyrazole with 2-chloro-5,6-dimethyl-4-(3,4-methylenedioxyphenethylamino)-thieno-[2,3-d]-pyrimidine gives 2-(pyrazol-1-yl)-5,6-dimethyl-4-(3,4-methylenedioxyphenethylamino)-thieno-[2,3-d]-pyrimidine.

EXAMPLE 277

Following the procedure of Example 97, the reaction of pyrazole with 2-chloro-6-trifluoromethyl-4-(3,4-methylenedioxyphenethylamino)-thieno-[2,3-d]-pyrimidine gives 2-(pyrazol-1-yl)-6-trifluoromethyl-4-(3,4-methylenedioxyphenethylamino)-thieno-[2,3-d]-pyrimidine.

EXAMPLE 278

Following the procedure of Example 97, the reaction of pyrazole with 2-chloro-6-methyl-4-(3,4-ethylendioxybenzylamino)-thieno-[2,3-d]-pyrimidine gives 2-(pyrazol-1-yl)-6-methyl-4-(3,4-ethylendioxybenzylamino)-thieno-[2,3-d]-pyrimidine.

EXAMPLE 279

Following the procedure of Example 97, the reaction of pyrazole with 2-chloro-5-methyl-4-(3,4-ethylendioxybenzylamino)-thieno-[2,3-d]-pyrimidine gives 2-(pyrazol-1-yl)-5-methyl-4-(3,4-ethylendioxybenzylamino)-thieno-[2,3-d]-pyrimidine.

EXAMPLE 280

Following the procedure of Example 97, the reaction of pyrazole with 2-chloro-5,6,7,8-tetrahydro-4-(3,4-ethylendioxybenzylamino)-[1]-benzothieno-[2,3-d]-pyrimidine gives 2-(pyrazol-1-yl)-5,6,7,8-tetrahydro-4-(3,4-ethylendioxybenzylamino)-[1]-benzothieno-[2,3-d]-pyrimidine.

EXAMPLE 281

Following the procedure of Example 97, the reaction of pyrazole with 2-chloro-6-ethyl-4-(3,4-ethylendioxybenzylamino)-thieno-[2,3-d]-pyrimidine gives 2-(pyrazol-1-yl)-6-ethyl-4-(3,4-ethylendioxybenzylamino)-thieno-[2,3-d]-pyrimidine.

EXAMPLE 282

Following the procedure of Example 97, the reaction of pyrazole with 2,6-dichloro-4-(3,4-ethylendioxybenzylamino)-thieno-[2,3-d]-pyrimidine gives 2-(pyrazol-1-yl)-6-chloro-4-(3,4-ethylendioxybenzylamino)-thieno-[2,3-d]-pyrimidine.

EXAMPLE 283

Following the procedure of Example 97, the reaction of 2,5-dichloro-6-methyl-4-(3,4-ethylendioxybenzylamino)-thieno-[2,3-d]-pyrimidine gives 2-(pyrazol-1-yl)-5-chloro-6-methyl-4-(3,4-ethylendioxybenzylamino)-thieno-[2,3-d]-pyrimidine.

EXAMPLE 284

Following the procedure of Example 97, the reaction of pyrazole with 2-chloro-6-nitro-4-(3,4-ethylendioxybenzylamino)-thieno-[2,3-d]-pyrimidin e gives 2-(pyrazol-1-yl)-6-nitro-4-(3,4-ethylendioxybenzylamino)-thieno-[2,3-d]-pyrimidine.

EXAMPLE 285

Following the procedure of Example 97, the reaction of pyrazole with 2-chloro-5,6-dimethyl-4-(3,4-ethylendioxybenzylamino)-thieno-[2,3-d]-pyrimidine gives 2-pyrazol-1-yl)-5,6-dimethyl-4-(3,4-ethylendioxybenzylamino)-thieno-[2,3-d]-pyrimidine.

EXAMPLE 286

Following the procedure of Example 97, the reaction of pyrazole with 2-chloro-6-trifluoromethyl-4-(3,4-ethylendioxybenzylamino)-thieno-[2,3-d]-pyrimidine gives 2-(pyrazol-1-yl)-6-trifluoromethyl-4-(3,4-ethylendioxybenzylamino)-thieno-[2,3-d]-pyrimidine.

EXAMPLE 287

Following the procedure of Example 97, the reaction of 1,2,4-triazole with 2-chloro-6-methyl-4-(3,4-methylene dioxybenzylamino)-thieno-[2,3-d]-pyrimidine yields 2-(pryazol-1-yl)-6-methyl-4-(3,4-methylenedioxybenzylamino)-thieno-[2,3-d]-pyrimidine.

EXAMPLE 288

Following the procedure of Example 97, the reaction of 1,2,4-triazole with 2-chloro-5-methyl-4-(3,4-methylenedioxybenzylamino)-thieno-[2,3-d]-pyrimidine gives 2-(1,2,4-triazol-1-yl)-5-methyl-4-(3,4-methylenedioxybenzylamino)-thieno-[2,3-d]-pyrimidine.

EXAMPLE 289

Following the procedure of Example 97, the reaction of 1,2,4-triazole with 2-chloro-5,6,7,8-tetrahydro-4-(3,4-methylenedioxybenzylamino)-[1]-benzothieno-[2,3-d]-pyrimidine gives 2-(1,2,4-triazol-1-yl)-5,6,7,8-tetrahydro-4-(3,4-methylenedioxybenzylamino)-[1]-benzothieno-[2,3-d]-pyrimidine.

EXAMPLE 290

Following the procedure of Example 97, the reaction of 1,2,4-triazole with 2-chloro-5,6-cyclopenteno-4-(3,4-methylenedioxybenzylamino)-[1]-benzothieno-[2,3-d]-pyrimidine gives 2-(1,2,4-triazol-1-yl)-5,6-cyclopenteno-4-(3,4-methylenedioxybenzylamino)-[1]-benzothieno-[2,3-d]-pyrimidine.

EXAMPLE 291

Following the procedure of Example 97, the reaction of 1,2,4-triazole with 2-chloro-5,6-cyclohepteno-4-93,4-methylenedioxybenzylamino)-[1]-benzothieno-[2,3-d]-pyrimidine gives 2-(1,2,4-triazol-1-yl)-5,6-cyclohepteno-4-93,4-methylenedioxybenzylamino)-[1]-benzothieno-[2,3-d]-pyrimidine.

EXAMPLE 292

Following the procedure of Example 97, the reaction of 1,2,4-triazole with 2-chloro-6-ethyl-4-(3,4-methylenedioxybenzylamino)-thieno-[2,3-d]-pyrimidine gives 2-(1,2,4-triazol-1-yl)-6-ethyl-4-(3,4-methylenedioxybenzylamino)-thieno-[2,3-d]-pyrimidine.

EXAMPLE 293

Following the procedure of Example 97, the reaction of 1,2,4-triazole with 2,6-dichloro-4-(3,4-methylenedioxybenzylamino)-thieno-[2,3-d]-pyrimidine gives 2-(1,2,4-triazol-1-yl)-6-chloro-4-(3,4-methylenedioxybenzylamino)-thieno-[2,3-d]-pyrimidine.

EXAMPLE 294

Following the procedure of Example 97, the reaction 1,2,4-triazole with 2,5-dichloro-6-methyl-4-93,4-methylenedioxybenzylamino)-thieno-[2,3-d]-pyrimidine gives 2-(1,2,4-triazol-1-yl)-5-chloro-6-methyl-4-93,4-methylenedioxybenzylamino)-thieno-[2,3-d]-pyrimidine.

EXAMPLE 295

Following the procedure of Example 97, the reaction of 1,2,4-triazole with 2-chloro-6-nitro-4-(3,4-methylenedioxybenzylamino)-thieno-[2,3-d]-pyrimidine gives 2-(1,2,4-triazol-1-yl)-6-nitro-4-(3,4-methylenedioxybenzylamino)-thieno-[2,3-d]-pyrimidine.

EXAMPLE 296

Following the procedure of Example 97, the reaction of 1,2,4-triazole with 2-chloro-5,6-dimethyl-4-(3,4-methylenedioxybenzylamino)-thieno-[2,3-d]-pyrimidine gives 2-(1,2,4-triazol-1-yl)-5,6-dimethyl-4-(3,4-methylenedioxybenzylamino)-thieno-[2,3-d]-pyrimidine.

EXAMPLE 297

Following the procedure of Example 97, the reaction of 1,2,4-triazole with 2-chloro-6-trifluoromethyl-4-(3,4-methylenedioxybenzylamino)-thieno-[2,3-d]-pyrimidine gives 2-(1,2,4-triazol-1-yl)-6-trifluoromethyl-4-(3,4-methylenedioxybenzylamino)-thieno-[2,3-d]-pyrimidine.

EXAMPLE 298

Following the procedure of Example 97, the reaction of 1,2,4-triazole with 2-chloro-6-methyl-4-(3-chloro-4-methoxybenzylamino)-thieno-[2,3-d]-pyrimidine gives 2-(1,2,4-triazol-1-yl)-6-methyl-4-(3-chloro-4-methoxybenzylamino)-thieno-[2,3-d]-pyrimidine.

EXAMPLE 299

Following the procedure of Example 97, the reaction of 1,2,4-triazole with 2-chloro-5-methyl-4-(3-chloro-4-methoxybenzylamino)-thieno-[2,3-d]-pyrimidine gives 2-(1,2,4-triazol-1-yl)-5-methyl-4-(3-chloro-4-methoxybenzylamino)-thieno-[2,3-d]-pyrimidine.

EXAMPLE 300

Following the procedure of Example 97, the reaction of 1,2,4-triazole with 2-chloro-5,6,7,8-tetrahydro-4-(3-chloro-4-methoxybenzylamino)-[1]-[1]-benzothieno-[2,3-d]-pyrimidine gives 2-(1,2,4-triazol-1-yl)-5,6,7,8-tetrahydro-4-(3-chloro-4-methoxybenzylamino)-[1]-[1]-benzothieno-[2,3-d]-pyrimidine.

EXAMPLE 301

Following the procedure of Example 97, the reaction of 1,2,4-triazole with 2-chloro-5,6-cyclopenteno-4-(3-chloro-4-methoybenzylamino)-[1]-benzothieno-[2,3-d]-pyrimidine gives 2-(1,2,4-triazol-1-yl)-5,6-cyclopenteno-4-(3-chloro-4-methoybenzylamino)-[1]-benzothieno-[2,3-d]-pyrimidine.

EXAMPLE 302

Following the procedure of Example 97, the reaction of 1,2,4-triazole with 2-chloro-5,6-cyclohepteno-4-(3-chloro-4-methoxybenzylamino)-[1]-benzothieno-[2,3-d]-pyrimidine gives 2-(1,2,4-triazol-1-yl)-5,6-cyclohepteno-4-(3-chloro-4-methoxybenzylamino)-[1]-benzothieno-[2,3-d]-pyrimidine.

EXAMPLE 303

Following the procedure of Example 97, the reaction of 1,2,4-triazole with 2-chloro-6-ethyl-4-(3-chloro-4-methoxybenzylamino)-thieno-[2,3-d]-pyrimidine gives 2-(1,2,4-triazol-1-yl)-6-ethyl-4-(3-chloro-4-methoxybenzylamino)-thieno-[2,3-d]-pyrimidine.

EXAMPLE 304

Following the procedure of Example 97, the reaction of 1,2,4-triazole with 2,6-dichloro-4-(3-chloro-4-methoxybenzylamino)-thieno-[2,3-d]-pyrimidine gives 2-(1,2,4-triazol-1-yl)-6-chloro-4-(3-chloro-4-methoxybenzylamino)-thieno-[2,3-d]-pyrimidine.

EXAMPLE 305

Following the procedure of Example 97, the reaction of 1,2,4-triazole with 2,5-dichloro-6-methyl-4-(3-chloro-4-methoxybenzylamino)-thieno-[2,3-d]-pyrimidine gives 2-(1,2,4-triazol-1-yl)-5-chloro-6-methyl-4-(3-chloro-4-methoxybenzylamino)-thieno-[2,3-d]-pyrimidine.

EXAMPLE 306

Following the procedure of Example 97, the reaction of 1,2,4-triazole with 2-chloro-6-nitro-4-(3-chloro-4-methoxybenzylamino)-thieno-[2,3-d]-pyrimidine gives 2-(1,2,4-triazol-1-yl)-6-nitro-4-(3-chloro-4-methoxybenzylamino)-thieno-[2,3-d]-pyrimidine.

EXAMPLE 307

Following the procedure of Example 97, the reaction of 1,2,4-triazole with 2-chloro-5,6-dimethyl-4-(3-chloro-4-methoxybenzylamino)-thieno-[2,3-d]-pyrimidine gives 2-(1,2,4-triazol-1-yl)-5,6-dimethyl-4-(3-chloro-4-methoxybenzylamino)-thieno-[2,3-d]-pyrimidine.

EXAMPLE 308

Following the procedure of Example 97, the reaction of 1,2,4-triazole with 2-chloro-6-trifluoromethyl-4-(3-chloro-4-methoxybenzylamino0-thieno-[2,3-d]-pyrimidine gives 2-(1,2,4-triazol-1-yl)-6-trifluoromethyl-4-(3-chloro-4-methoxybenzylamino0-thieno-[2,3-d]-pyrimidine.

EXAMPLE 309

Following the procedure of Example 97, the reaction of 1,2,4-triazole with 2-chloro-6-methyl-4-(3,4-dimethoxybenzylamino)-thieno-[2,3-d]-pyrimidine gives 2-(1,2,4-triazol-1-yl)-6-methyl-4-(3,4-dimethoxybenzylamino)-thieno-[2,3-d]-pyrimidine.

EXAMPLE 310

Following the procedure of Example 97, the reaction of 1,2,4-triazole with 2-chloro-5-methyl-4-(3,4-dimethoxybenzylamino)-thieno-[2,3-d]-pyrimidine gives 2-(1,2,4-triazol-1-yl)-5-methyl-4-(3,4-dimethoxybenzylamino)-thieno-[2,3-d]-pyrimidine.

EXAMPLE 311

Following the procedure of Example 97, the reaction of 1,2,4-triazole with 2-chloro-5,6,7,8-tetrahydro-4-(3,4-dimethoxybenzylamino)-[1]-[1]-benzothieno-[2,3-d]-pyrimidine gives 2-(1,2,4-triazol-1-yl)-5,6,7,8-tetrahydro-4-(3,4-dimethoxybenzylamino)-[1]-[1]-benzothieno-[2,3-d]-pyrimidine.

EXAMPLE 312

Following the procedure of Example 97, the reaction of 1,2,4-triazole with 2-chloro-5,6-cyclopenteno-4-(3,4-dimethoxybenzylamino)-[1]-benzothieno-[2,3-d]-pyrimidine gives 2-(1,2,4-triazol-1-yl)-5,6-cyclopenteno-4-(3,4-dimethoxybenzylamino)-[1]-benzothieno-[2,3-d]-pyrimidine.

EXAMPLE 313

Following the procedure of Example 97, the reaction of 1,2,4-triazole with 2-chloro-5,6-cyclopenteno-4-(3,4-dimethoxybenzylamino)-[1]-benzothieno-[2,3-d]-pyrimidine gives 2-(1,2,4-triazol-1-yl)-5,6-cyclopenteno-4-(3,4-dimethoxybenzylamino)-[1]-benzothieno-[2,3-d]-pyrimidine.

EXAMPLE 314

Following the procedure of Example 97, the reaction of 1,2,4-triazole with 2-chloro-6-ethyl-4-(3,4-dimethoxybenzylamino)-thieno-[2,3-d]-pyrimidine gives 2-(1,2,4-triazol-1-yl)-6-ethyl-4-(3,4-dimethoxybenzylamino)-thieno-[2,3-d]-pyrimidine.

EXAMPLE 315

Following the procedure of Example 97, the reaction of 1,2,4-triazole with 2,6-dichloro-4-(3,4-dimethoxybenzylamino)-thieno-[2,3-d]-pyrimidine gives 2-(1,2,4-triazol-1-yl)-6-chloro-4-(3,4-dimethoxybenzylamino)-thieno-[2,3-d]-pyrimidine.

EXAMPLE 316

Following the procedure of Example 97, the reaction of 1,2,4-triazole with 2,5-dichloro-6-methyl-4-(3,4-dimethoxybenzylamino)-thieno-[2,3-d]-pyrimidine gives 2-(1,2,4-triazol-1-yl)-5-chloro-6-methyl-4-(3,4-dimethoxybenzylamino)-thieno-[2,3-d]-pyrimidine.

EXAMPLE 317

Following the procedure of Example 97, the reaction of 1,2,4-triazole with 2-chloro-6-nitro-4-(3,4-dimethoxybenzylamino)-thieno-[2,3-d]-pyrimidine gives 2-(1,2,4-triazol-1-yl)-6-nitro-4-(3,4-dimethoxybenzylamino)-thieno-[2,3-d]-pyrimidine.

EXAMPLE 318

Following the procedure of Example 97, the reaction of 1,2,4-triazole with 2-chloro-5,6-dimethyl-4-(3,4-dimethoxybenzylamino)-thieno-[2,3-d]-pyrimidine gives 2-(1,2,4-triazol-1-yl)-5,6-dimethyl-4-(3,4-dimethoxybenzylamino)-thieno-[2,3-d]-pyrimidine.

EXAMPLE 319

Following the procedure of Example 97, the reaction of 1,2,4-triazole with yields 2-chloro-6-trifluoromethyl-4-(3,4-dimethoxybenzylamino)-thieno-[2,3-d]-pyrimidine gives 2-(1,2,4-triazol-1-yl)-6-trifluoromethyl-4-(3,4-dimethoxybenzylamino)-thieno-[2,3-d]-pyrimidine.

EXAMPLE 320

Following the procedure of Example 97, the reaction of 1,2,4-triazole with 2-chloro-6-methyl-4-benzylamino-thieno-[2,3-d]-pyrimidine gives 2-(1,2,4-triazol-1-yl)-6-methyl-4-benzylamino-thieno-[2,3-d]-pyrimidine.

EXAMPLE 321

Following the procedure of Example 97, the reaction of 1,2,4-triazole with 2-chloro-5-methyl-4-benzylamino-thieno-[2,3-d]-pyrimidine gives 2-(1,2,4-triazol-1-yl)-5-methyl-4-benzylamino-thieno-[2,3-d]-pyrimidine.

EXAMPLE 322

Following the procedure of Example 97, the reaction of 1,2,4-triazole with 2-chloro-5,6,7,8-tetrahydro-4-benzylamino-thieno-[1]-[1]-benzothieno-[2,3-d]-pyrimidine gives 2-(1,2,4-triazol-1-yl)-5,6,7,8-tetrahydro-4-benzylamino-thieno-[1]-[1]-benzothieno-[2,3-d]-pyrimidine.

EXAMPLE 323

Following the procedure of Example 97, the reaction of 1,2,4-triazole with 2-chloro-5,6-cyclopenteno-4-benzylamino-[2,3-d]-pyrimidine gives 2-(1,2,4-triazol-1-yl)-5,6-cyclopenteno-4-benzylamino-[2,3-d]-pyrimidine.

EXAMPLE 324

Following the procedure of Example 97, the reaction of 1,2,4-triazole with 2-chloro-5,6-cyclopenteno-4-benzylamino-[1]-benzothieno-[2,3-d]-pyrimidine gives 2-(1,2,4-triazol-1-yl)-5,6-cyclopenteno-4-benzylamino-[1]-benzothieno-[2,3-d]-pyrimidine.

EXAMPLE 325

Following the procedure of Example 97, the reaction of 1,2,4-triazole with 2-chloro-6-ethyl-4-benzylamino-thieno-[2,3-d]-pyrimidine gives 2-(1,2,4-triazol-1-yl) -6-ethyl-4-benzylamino-thieno-[2,3-d]-pyrimidine.

EXAMPLE 326

Following the procedure of Example 97, the reaction of 1,2,4-triazole with 2,6-dichloro-6-4-benzylamino-thieno-[2, 3-d]-pyrimidine gives 2-(1,2,4-triazol-1-yl)-thieno-6-chloro-6-4-benzylamino-thieno-[2,3-d]-pyrimidine.

EXAMPLE 327

Following the procedure of Example 97, the reaction of 1,2,4-triazole with 2,5-dichloro-6-methyl-4-benzylamino-thieno-[2,3-d]-pyrimidine gives 2-(1,2,4-triazol-1-yl)-5-chloro-6-methyl-4-benzylamino-thieno-[2,3-d]-pyrimidine.

EXAMPLE 328

Following the procedure of Example 97, the reaction of 1,2,4-triazole with 2-chloro-6-nitro-4-benzylamino-thieno-[2,3-d]-pyrimidine gives 2-(1,2,4-triazol-1-yl) -6-nitro-4-benzylamino-thieno-[2,3-d]-pyrimidine.

EXAMPLE 329

Following the procedure of Example 97, the reaction of 1,2,4-triazole with 2-chloro-5,6-dimethyl-4-benzylamino-thieno-[2,3-d]-pyrimidine gives 2-(1,2,4-triazol-1-yl)-5,6-dimethyl-4-benzylamino-thieno-[2,3-d]-pyrimidine.

EXAMPLE 330

Following the procedure of Example 97, the reaction of 1,2,4-triazole with 2-chloro-6-trifluoromethyl-4-benzylamino-thieno-[2,3-d]-pyrimidine gives 2-(1,2,4-triazol-1-yl)-6-trifluoromethyl-4-benzylamino-thieno-[2,3-d]-pyrimidine.

EXAMPLE 331

Following the procedure of Example 97, the reaction of 1,2,4-triazole with 2-chloro-6-methyl-4-(4-fluorobenzylamino)-thieno-[2,3-d]-pyrimidine gives 2-(1,2,4-triazol-1-yl)-6-methyl-4-(4-fluorobenzylamino)-thieno-[2,3-d]-pyrimidine.

EXAMPLE 332

Following the procedure of Example 97, the reaction of 1,2,4-triazole with 2-chloro-5,6,7,8-tetrahydro-4-(4-fluorobenzylamino)-[1]-benzothieno-[2,3-d]-pyrimidine gives 2-(1,2,4-triazol-1-yl)-5,6,7,8-tetrahydro-4-(4-fluorobenzylamino)-thieno-[1]-benzothieno-[2,3-d]-pyrimidine.

EXAMPLE 333

Following the procedure of Example 97, the reaction of 1,2,4-triazole with 2-chloro-5,6-cyclopenteno-4-(4-fluorobenzylamino)-[1]-benzothieno-[2,3-d]-pyrimidine gives 2-(1,2,4-triazol-1-yl)-5,6-cyclopenteno-4-(4-fluorobenzylamino)-[1]-benzothieno-[2,3-d]-pyrimidine.

EXAMPLE 334

Following the procedure of Example 97, the reaction of 1,2,4-triazole with 2-chloro-5,6-cyclohepteno-4-(4-fluorobenzylamino)-[1]-benzothieno-[2,3-d]-pyrimidine gives 2-(1,2,4-triazol-1-yl)-5,6-cyclohepteno-4-(4-fluorobenzylamino)-[1]-benzothieno-[2,3-d]-pyrimidine.

EXAMPLE 335

Following the procedure of Example 97, the reaction of 1,2,4-triazole with 2-chloro-6-ethyl-4-(4-fluorobenzylamino)-thieno-[2,3-d]-pyrimidine gives 2-(1,2,4-triazol-1-yl)-6-ethyl-4-(4-fluorobenzylamino)-thieno-[2,3-d]-pyrimidine.

EXAMPLE 336

Following the procedure of Example 97, the reaction of 1,2,4-triazole with 2,6-dichloro-4-(4-fluorobenzylamino)-thieno-[2,3-d]-pyrimidine gives 2-(1,2,4-triazol-1-yl)-6-dichloro-4-(4-fluorobenzylamino)-thieno-[2,3-d]-pyrimidine.

EXAMPLE 337

Following the procedure of Example 97, the reaction of 1,2,4-triazole with 2,5-dichloro-6-methyl-4-(4-fluorobenzylamino)-thieno-[2,3-d]-pyrimidine gives 2-(1,2,4-triazol-1-yl)-5-chloro-6-methyl-4-(4-fluorobenzylamino)-thieno-[2,3-d]-pyrimidine.

EXAMPLE 338

Following the procedure of Example 97, the reaction of 1,2,4-triazole with 2-chloro-6-nitro-4-(4-fluorobenzylamino)-thieno-[2,3-d]-pyrimidine gives 2-(1,2,4-triazol-1-yl)-6-nitro-4-(4-fluorobenzylamino)-thieno-[2,3-d]-pyrimidine.

EXAMPLE 339

Following the procedure of Example 97, the reaction of 1,2,4-triazole with 2-chloro-5,6-dimethyl-4-(4-fluorobenzylamino)-thieno-[2,3-d]-pyrimidine gives 2-(1,2,4-triazol-1-yl)-5,6-dimethyl-4-(4-fluorobenzylamino)-thieno-[2,3-d]-pyrimidine.

EXAMPLE 340

Following the procedure of Example 97, the reaction of 1,2,4-triazole with 2-chloro-6-trifluoromethyl-4-(4-fluorobenzylamino)-thieno-[2,3-d]-pyrimidine gives 2-(1,2,4-triazol-1-yl)-6-trifluoromethyl-4-(4-fluorobenzylamino)-thieno-[2,3-d]-pyrimidine.

EXAMPLE 341

Following the procedure of Example 97, the reaction of 1,2,4-triazole with 2-chloro-6-methyl-4-(3,4-dichlorobenzylamino)-thieno-[2,3-d]-pyrimidine gives 2-(1,2,4-triazol-1-yl)-6-methyl-4-(3,4-dichlorobenzylamino)-thieno-[2,3-d]-pyrimidine.

EXAMPLE 342

Following the procedure of Example 97, the reaction of 1,2,4-triazole with 2-chloro-5-methyl-4-(3,4-dichlorobenzylamino)-thieno-[2,3-d]-pyrimidine gives 2-(1,2,4-triazol-1-yl)-5-methyl-4-(3,4-dichlorobenzylamino)-thieno-[2,3-d]-pyrimidine.

EXAMPLE 343

Following the procedure of Example 97, the reaction of 1,2,4-triazole with 2-chloro-5,6,7,8-tetrahydro-4-(3,4-dichlorobenzylamino)-[1]-benzothieno-[2,3-d]-pyrimidine gives 2-(1,2,4-triazol-1-yl)-5,6,7,8-tetrahydro-4-(3,4-dichlorobenzylamino)-[1]-benzothieno-[2,3-d]-pyrimidine.

EXAMPLE 344

Following the procedure of Example 97, the reaction of 1,2,4-triazole with 2-chloro-5,6-cyclopenteno-4-(3,4-dichlorobenzylamino)-[1]-benzothieno-[2,3-d]-pyrimidine gives 2-(1,2,4-triazol-1-yl)-5,6-cyclopenteno-4-(3,4-dichlorobenzylamino)-[1]-benzothieno-[2,3-d]-pyrimidine.

EXAMPLE 345

Following the procedure of Example 97, the reaction of 1,2,4-triazole with 2-chloro-5,6-cyclopenteno-4-(3,4- dichlorobenzylamino)-[1]-benzothieno-[2,3-d]-pyrimidine gives 2-(1,2,4-triazol-1-yl)-5,6-cyclopenteno-4-(3,4-dichlorobenzylamino)-[1]-benzothieno-[2,3-d]-pyrimidine.

EXAMPLE 346

Following the procedure of Example 97, the reaction of 1,2,4-triazole with 2-chloro-6-ethyl-4-(3,4-dichlorobenzylamino)-thieno-[2,3-d]-pyrimidine gives 2-(1,2,4-triazol-1-yl)-6-ethyl-4-(3,4-dichlorobenzylamino)-thieno-[2,3-d]-pyrimidine.

EXAMPLE 347

Following the procedure of Example 97, the reaction of 1,2,4-triazole with 2-6-dichloro-4-(3,4-dichlorobenzylamino)-thieno-[2,3-d]-pyrimidine gives 2-(1,2,4-triazol-1-yl)-6-chloro-4-(3,4-dichlorobenzylamino)-thieno-[2,3-d]-pyrimidine.

EXAMPLE 348

Following the procedure of Example 97, the reaction of 1,2,4-triazole with 2,5-dichloro-6-methyl-4-(3,4-dichlorobenzylamino)-thieno-[2,3-d]-pyrimidine gives 2-(1,2,4-triazol-1-yl)-5-chloro-6-methyl-4-(3,4-dichlorobenzylamino)-thieno-[2,3-d]-pyrimidine.

EXAMPLE 349

Following the procedure of Example 97, the reaction of 1,2,4-triazole with 2-chloro-6-nitro-4-(3,4-dichlorobenzylamino)-thieno-[2,3-d]-pyrimidine gives 2-(1,2,4-triazol-1-yl)-6-nitro-4-(3,4-dichlorobenzylamino)-thieno-[2,3-d]-pyrimidine.

EXAMPLE 350

Following the procedure of Example 97, the reaction of 1,2,4-triazole with 2-chloro-5,6-dimethyl-4-(3,4-dichlorobenzylamino)-thieno-[2,3-d]-pyrimidine gives 2-(1,2,4-triazol-1-yl)-5,6-dimethyl-4-(3,4-dichlorobenzylamino)-thieno-[2,3-d]-pyrimidine.

EXAMPLE 351

Following the procedure of Example 97, the reaction of 1,2,4-triazole with 2-chloro-6-trifluoromethyl-4-(3,4-dichlorobenzylamino)-thieno-[2,3-d]-pyrimidine gives 2-(1,2,4-triazol-1-yl)-6-trifluoromethyl-4-(3,4-dichlorobenzylamino)-thieno-[2,3-d]-pyrimidine.

EXAMPLE 352

Following the procedure of Example 97, the reaction of 1,2,4-triazole with 2-chloro-6-methyl-4-(3-nitrobenzylamino)-thieno-[2,3-d]-pyrimidine gives 2-(1,2,4-triazol-1-yl)-6-methyl-4-(3-nitrobenzylamino)-thieno-[2,3-d]-pyrimidine.

EXAMPLE 353

Following the procedure of Example 97, the reaction of 1,2,4-triazole with 2-chloro-5-methyl-4-(3-nitrobenzylamino)-thieno-[2,3-d]-pyrimidine gives 2-(1,2,4-triazol-1-yl)-5-methyl-4-(3-nitrobenzylamino)-thieno-[2,3-d]-pyrimidine.

EXAMPLE 354

Following the procedure of Example 97, the reaction of 1,2,4-triazole with 2-chloro-5,6,7,8-tetrahydro-4-(3-nitrobenzylamino)-[1]-benzothieno-[2,3-d]-pyrimidine gives 2-(1,2,4-triazol-1-yl)-5,6,7,8-tetrahydro-4-(3-nitrobenzylamino)-[1]-benzothieno-[2,3-d]-pyrimidine.

EXAMPLE 355

Following the procedure of Example 97, the reaction of 1,2,4-triazole with 2-chloro-5,6-cyclopenteno-4-(3-nitrobenzylamino)-[1]-benzothieno-[2,3-d]-pyrimidine gives 2-(1,2,4-triazol-1-yl)-5,6-cyclopenteno-4-(3-nitrobenzylamino)-[1]-benzothieno-[2,3-d]-pyrimidine.

EXAMPLE 356

Following the procedure of Example 97, the reaction of 1,2,4-triazole with 2-chloro-5,6-cyclopenteno-4-(3-nitrobenzylamino)-[1]-benzothieno-[2,3-d]-pyrimidine gives 2-(1,2,4-triazol-1-yl)-5,6-cyclopenteno-4-(3-nitrobenzylamino)-[1]-benzothieno-[2,3-d]-pyrimidine.

EXAMPLE 357

Following the procedure of Example 97, the reaction of 1,2,4-triazole with 2-chloro-6-ethyl-4-(3-nitrobenzylamino)-thieno-[2,3-d]-pyrimidine gives 2-(1,2,4-triazol-1-yl)-6-ethyl-4-(3-nitrobenzylamino)-thieno-[2,3-d]-pyrimidine.

EXAMPLE 358

Following the procedure of Example 97, the reaction of 1,2,4-triazole with 6-chloro-4-(3-nitrobenzylamino)-thieno-[2,3-d]-pyrimidine gives 2-(1,2,4-triazol-1-yl)-4-(3-nitrobenzylamino)-thieno-[2,3-d]-pyrimidine.

EXAMPLE 359

Following the procedure of Example 97, the reaction of 1,2,4-triazole with 5-chloro-6-methyl-4-(3-nitrobenzylamino)-thieno-[2,3-d]-pyrimidine gives 2-(1,2,4-triazol-1-yl)-6-methyl-4-(3-nitrobenzylamino)-thieno-[2,3-d]-pyrimidine.

EXAMPLE 360

Following the procedure of Example 97, the reaction of 1,2,4-triazole with 2-chloro-6-nitro-4-(3-nitrobenzylamino)-thieno-[2,3-d]-pyrimidine gives 2-(1,2,4-triazol-1-yl)-6-nitro-4-(3-nitrobenzylamino)-thieno-[2,3-d]-pyrimidine.

EXAMPLE 361

Following the procedure of Example 97, the reaction of 1,2,4-triazole with 2-chloro-5,6-dimethyl-4-(3-nitrobenzylamino)-thieno-[2,3-d]-pyrimidine gives 2-(1,2,4-triazol-1-yl)-5,6-dimethyl-4-(3-nitrobenzylamino)-thieno-[2,3-d]-pyrimidine.

EXAMPLE 362

Following the procedure of Example 97, the reaction of 1,2,4-triazole with 2-chloro-6-trifluoromethyl-4-(3-nitrobenzylamino)-thieno-[2,3-d]-pyrimidine gives 2-(1,2,4-triazol-1-yl)-6-trifluoromethyl-4-(3-nitrobenzylamino)-thieno-[2,3-d]-pyrimidine.

EXAMPLE 363

Following the procedure of Example 97, the reaction of 1,2,4-triazole with 2-chloro-6-methyl-4-(3-nitrobenzylamino)-thieno-[2,3-d]-pyrimidine gives 2-(1,2,4-triazol-1-yl)-6-methyl-4-(3-nitrobenzylamino)-thieno-[2,3-d]-pyrimidine.

EXAMPLE 364

Following the procedure of Example 97, the reaction of 1,2,4-triazole with 2-chloro-5-methyl-4-(3,4-methylenedioxyphenethylamino)-thieno-[2,3-d]-pyrimidine gives 2-(1,2,4-triazol-1-yl)-5-methyl-4-(3,4-methylenedioxyphenethylamino)-thieno-[2,3-d]-pyrimidine.

EXAMPLE 365

Following the procedure of Example 97, the reaction of 1,2,4-triazole with 2-chloro-5,6,7,8-tetrahydro-4-(3,4-methylenedioxyphenethylamino)-[1]-benzothieno-[2,3-d]-pyrimidine gives 2-(1,2,4-triazol-1-yl)-5,6,7,8-tetrahydro-4-(3,4-methylenedioxyphenethylamino)-[1]-benzothieno-[2,3-d]-pyrimidine.

EXAMPLE 366

Following the procedure of Example 97, the reaction of 1,2,4-triazole with 2-chloro-5,6-cyclopenteno-4-(3,4-methylenedioxyphenethylamino)-[1]-benzothieno-[2,3-d]-pyrimidine gives 2-(1,2,4-triazol-1-yl)-5,6-cyclopenteno-4-(3,4-methylenedioxyphenethylamino)-[1]-benzothieno-[2,3-d]-pyrimidine.

EXAMPLE 367

Following the procedure of Example 97, the reaction of 1,2,4-triazole with 2-chloro-6-ethyl-4-(3,4-methylenedioxyphenethylamino)-thieno-[2,3-d]-pyrimidine gives 2-(1,2,4-triazol-1-yl)-6-ethyl-4-(3,4-methylenedioxyphenethylamino)-thieno-[2,3-d]-pyrimidine.

EXAMPLE 368

Following the procedure of Example 97, the reaction of 1,2,4-triazole with 6-chloro-4-(3,4-methylenedioxyphenethylamino)-thieno-[2,3-d]-pyrimidine gives 2-(1,2,4-triazol-1-yl)-4-(3,4-methylenedioxyphenethylamino)-thieno-[2,3-d]-pyrimidine.

EXAMPLE 369

Following the procedure of Example 97, the reaction of 1,2,4-triazole with 5-chloro-6-methyl-4-(3,4-methylenedioxyphenethylamino)-thieno-[2,3-d]-pyrimidine gives 2-(1,2,4-triazol-1-yl)-6-methyl-4-(3,4-methylenedioxyphenethylamino)-thieno-[2,3-d]-pyrimidine.

EXAMPLE 370

Following the procedure of Example 97, the reaction of 1,2,4-triazole with 2-chloro-6-nitro-4-(3,4-methylenedioxyphenethylamino)-thieno-[2,3-d]-pyrimidine gives 2-(1,2,4-triazol-1-yl)-6-nitro-4-(3,4-methylenedioxyphenethylamino)-thieno-[2,3-d]-pyrimidine.

EXAMPLE 371

Following the procedure of Example 97, the reaction of 1,2,4-triazole with 2-chloro-5,6-dimethyl-4-(3,4-methylenedioxyphenethylamino)-thieno-[2,3-d]-pyrimidine gives 2-(1,2,4-triazol-1-yl)-5,6-dimethyl-4-(3,4-methylenedioxyphenethylamino)-thieno-[2,3-d]-pyrimidine.

EXAMPLE 372

Following the procedure of Example 97, the reaction of 1,2,4-triazole with 2-chloro-6-trifluoromethyl-4-(3,4-methylenedioxyphenethylamino)-thieno-[2,3-d]-pyrimidine gives 2-(1,2,4-triazol-1-yl)-6-trifluoromethyl-4-(3,4-methylenedioxyphenethylamino)-thieno-[2,3-d]-pyrimidine.

EXAMPLE 373

Following the procedure of Example 97, the reaction of 1,2,4-triazole with 2-chloro-6-methyl-4-(3,4-ethylendioxybenzylamino)-thieno-[2,3-d]-pyrimidine gives 2-(1,2,4-triazol-1-yl)-6-methyl-4-(3,4-ethylendioxybenzylamino)-thieno-[2,3-d]-pyrimidine.

EXAMPLE 374

Following the procedure of Example 97, the reaction of 1,2,4-triazole with 2-chloro-5-methyl-4-(3,4-ethylendioxybenzylamino)-thieno-[2,3-d]-pyrimidine gives 2-(1,2,4-triazol-1-yl)-5-methyl-4-(3,4-ethylendioxybenzylamino)-thieno-[2,3-d]-pyrimidine.

EXAMPLE 375

Following the procedure of Example 97, the reaction of 1,2,4-triazole with 2-chloro-5,6,7,8-tetrahydro-4-(3,4-ethylendioxybenzylamino)-[1]-benzothieno-[2,3-d]-pyrimidine gives 2-(1,2,4-triazol-1-yl)-5,6,7,8-tetrahydro-4-(3,4-ethylendioxybenzylamino)-[1]-benzothieno-[2,3-d]-pyrimidine.

EXAMPLE 376

Following the procedure of Example 97, the reaction of 1,2,4-triazole with 2-chloro-6-ethyl-4-(3,4-ethylendioxybenzylamino)-thieno-[2,3-d]-pyrimidine gives 2-(1,2,4-triazol-1-yl)-6-ethyl-4-(3,4-ethylendioxybenzylamino)-thieno-[2,3-d]-pyrimidine.

EXAMPLE 377

Following the procedure of Example 97, the reaction of 1,2,4-triazole with 2,6-dichloro-4-(3,4-ethylendioxybenzylamino)-thieno-[2,3-d]-pyrimidine gives 2-(1,2,4-triazol-1-yl)-6-chloro-4-(3,4-ethylendioxybenzylamino)-thieno-[2,3-d]-pyrimidine.

EXAMPLE 378

Following the procedure of Example 97, the reaction of 2,5-dichloro-6-methyl-4-(3,4-ethylendioxybenzylamino)-thieno-[2,3-d]-pyrimidine gives 2-(1,2,4-triazol-1-yl)-5-chloro-6-methyl-4-(3,4-ethylendioxybenzylamino)-thieno-[2,3-d]-pyrimidine.

EXAMPLE 379

Following the procedure of Example 97, the reaction of 1,2,4-triazole with 2-chloro-6-nitro-4-(3,4-ethylendioxybenzylamino)-thieno-[2,3-d]-pyrimidine gives 2-(1,2,4-triazol-1-yl)-6-nitro-4-(3,4-ethylendioxybenzylamino)-thieno-[2,3-d]-pyrimidine.

EXAMPLE 380

Following the procedure of Example 97, the reaction of 1,2,4-triazole with 2-chloro-5,6-dimethyl-4-(3,4-ethylendioxybenzylamino)-thieno-[2,3-d]-pyrimidine gives 2-(1,2,4-triazol-1-yl)-5,6-dimethyl-4-(3,4-ethylendioxybenzylamino)-thieno-[2,3-d]-pyrimidine.

EXAMPLE 381

Following the procedure of Example 97, the reaction of 1,2,4-triazole with 2-chloro-6-trifluoromethyl-4-(3,4-ethylendioxybenzylamino)-thieno-[2,3-d]-pyrimidine gives 2-(1,2,4-triazol-1-yl)-6-trifluoromethyl-4-(3,4-ethylendioxybenzylamino)-thieno-[2,3-d]-pyrimidine.

EXAMPLE 382

Following the procedure of Example 97, the reaction of 2-methylimidazole with 2-chloro-6-methyl-4-(3,4-methylene dioxybenzylamino)-thieno-[2,3-d]-pyrimidine yields 2-(2-methylimidazol-1-yl)-6-methyl-4-(3,4-methylenedioxybenzylamino)-thieno-[2,3-d]-pyrimidine.

EXAMPLE 383

Following the procedure of Example 97, the reaction of 2-methylimidazole with 2-chloro-5-methyl-4-(3,4-methylenedioxybenzylamino)-thieno-[2,3-d]-pyrimidine gives 2-(2-methylimidazol-1-yl)-5-methyl-4-(3,4-methylenedioxybenzylamino)-thieno-[2,3-d]-pyrimidine.

EXAMPLE 384

Following the procedure of Example 97, the reaction of 2-methylimidazole with 2-chloro-5,6,7,8-tetrahydro-4-(3,4-methylenedioxybenzylamino)-[1]-benzothieno-[2,3-d]-pyrimidine gives 2-(2-methylimidazol-1-yl)-5,6,7,8-tetrahydro-4-(3,4-methylenedioxybenzylamino)-[1]-benzothieno-[2,3-d]-pyrimidine.

EXAMPLE 385

Following the procedure of Example 97, the reaction of 2-methylimidazole with 2-chloro-5,6-cyclopenteno-4-(3,4-methylenedioxybenzylamino)-[1]-benzothieno-[2,3-d]-pyrimidine gives 2-(2-methylimidazol-1-yl)-5,6-cyclopenteno-4-(3,4-methylenedioxybenzylamino)-[1]-benzothieno-[2,3-d]-pyrimidine.

EXAMPLE 386

Following the procedure of Example 97, the reaction of 2-methylimidazole with 2-chloro-5,6-cyclohepteno-4-93,4-methylenedioxybenzylamino)-[1]-benzothieno-[2,3-d]-pyrimidine gives 2-(2-methylimidazol-1-yl)-5,6-cyclohepteno-4-93,4-methylenedioxybenzylamino)-[1]-benzothieno-[2,3-d]-pyrimidine.

EXAMPLE 387

Following the procedure of Example 97, the reaction of 2-methylimidazole with 2-chloro-6-ethyl-4-(3,4-methylenedioxybenzylamino)-thieno-[2,3-d]-pyrimidine gives 2-(2-methylimidazol-1-yl)-6-ethyl-4-(3,4-methylenedioxybenzylamino)-thieno-[2,3-d]-pyrimidine.

EXAMPLE 388

Following the procedure of Example 97, the reaction of 2-methylimidazole with 2,6-dichloro-4-(3,4-methylenedioxybenzylamino)-thieno-[2,3-d]-pyrimidine gives 2-(2-methylimidazol-1-yl)-6-chloro-4-(3,4-methylenedioxybenzylamino)-thieno-[2,3-d]-pyrimidine.

EXAMPLE 389

Following the procedure of Example 97, the reaction 2-methylimidazole with 2,5-dichloro-6-methyl-4-93,4-methylenedioxybenzylamino)-thieno-[2,3-d]-pyrimidine gives 2-(2-methylimidazol-1-yl)-5-chloro-6-methyl-4-93,4-methylenedioxybenzylamino)-thieno-[2,3-d]-pyrimidine.

EXAMPLE 390

Following the procedure of Example 97, the reaction of 2-methylimidazole with 2-chloro-6-nitro-4-(3,4-methylenedioxybenzylamino)-thieno-[2,3-d]-pyrimidine gives 2-(2-methylimidazol-1-yl)-6-nitro-4-(3,4-methylenedioxybenzylamino)-thieno-[2,3-d]-pyrimidine.

EXAMPLE 391

Following the procedure of Example 97, the reaction of 2-methylimidazole with 2-chloro-5,6-dimethyl-4-(3,4-methylenedioxybenzylamino)-thieno-[2,3-d]-pyrimidine gives 2-(2-methylimidazol-1-yl)-5,6-dimethyl-4-(3,4-methylenedioxybenzylamino)-thieno-[2,3-d]-pyrimidine.

EXAMPLE 392

Following the procedure of Example 97, the reaction of 2-methylimidazole with 2-chloro-6-trifluoromethyl-4-(3,4-methylenedioxybenzylamino)-thieno-[2,3-d]-pyrimidine gives 2-(2-methylimidazol-1-yl)-6-trifluoromethyl-4-(3,4-methylenedioxybenzylamino)-thieno-[2,3-d]-pyrimidine.

EXAMPLE 393

Following the procedure of Example 97, the reaction of 2-methylimidazole with 2-chloro-6-methyl-4-(3-chloro-4-methoxybenzylamino)-thieno-[2,3-d]-pyrimidine gives 2-(2-methylimidazol-1-yl)-6-methyl-4-(3-chloro-4-methoxybenzylamino)-thieno-[2,3-d]-pyrimidine.

EXAMPLE 394

Following the procedure of Example 97, the reaction of 2-methylimidazole with 2-chloro-5-methyl-4-(3-chloro-4-methoxybenzylamino)-thieno-[2,3-d]-pyrimidine gives 2-(2-methylimidazol-1-yl)-5-methyl-4-(3-chloro-4-methoxybenzylamino)-thieno-[2,3-d]-pyrimidine.

EXAMPLE 395

Following the procedure of Example 97, the reaction of 2-methylimidazole with 2-chloro-5,6,7,8-tetrahydro-4-(3-chloro-4-methoxybenzylamino)-[1]-[1]-benzothieno-[2,3-d]-pyrimidine gives 2-(2-methylimidazol-1-yl)-5,6,7,8-tetrahydro-4-(3-chloro-4-methoxybenzylamino)-[1]-[1]-benzothieno-[2,3-d]-pyrimidine.

EXAMPLE 396

Following the procedure of Example 97, the reaction of 2-methylimidazole with 2-chloro-5,6-cyclopenteno-4-(3-chloro-4-methoybenzylamino)-[1]-benzothieno-[2,3-d]-pyrimidine gives 2-(2-methylimidazol-1-yl)-5,6-cyclopenteno-4-(3-chloro-4-methoybenzylamino)-[1]-benzothieno-[2,3-d]-pyrimidine.

EXAMPLE 397

Following the procedure of Example 97, the reaction of 2-methylimidazole with 2-chloro-5,6-cyclohepteno-4-(3-chloro-4-methoxybenzylamino)-[1]-benzothieno-[2,3-d]-pyrimidine gives 2-(2-methylimidazol-1-yl)-5,6-cyclohepteno-4-(3-chloro-4-methoxybenzylamino)-[1]-benzothieno-[2,3-d]-pyrimidine.

EXAMPLE 398

Following the procedure of Example 97, the reaction of 2-methylimidazole with 2-chloro-6-ethyl-4-(3-chloro-4- methoxybenzylamino)-thieno-[2,3-d]-pyrimidine gives 2-(2-methylimidazol-1-yl)-6-ethyl-4-(3-chloro-4-methoxybenzylamino)-thieno-[2,3-d]-pyrimidine.

EXAMPLE 399

Following the procedure of Example 97, the reaction of 2-methylimidazole with 2,6-dichloro-4-(3-chloro-4-methoxybenzylamino)-thieno-[2,3-d]-pyrimidine gives 2-(2-methylimidazol-1-yl)-6-chloro-4-(3-chloro-4-methoxybenzylamino)-thieno-[2,3-d]-pyrimidine.

EXAMPLE 400

Following the procedure of Example 97, the reaction of 2-methylimidazole with 2,5-dichloro-6-methyl-4-(3-chloro-4-methoxybenzylamino)-thieno-[2,3-d]-pyrimidine gives 2-(2-methylimidazol-1-yl)-5-chloro-6-methyl-4-(3-chloro-4-methoxybenzylamino)-thieno-[2,3-d]-pyrimidine.

EXAMPLE 401

Following the procedure of Example 97, the reaction of 2-methylimidazole with 2-chloro-6-nitro-4-(3-chloro-4-methoxybenzylamino)-thieno-[2,3-d]-pyrimidine gives 2-(2-methylimidazol-1-yl)-6-nitro-4-(3-chloro-4-methoxybenzylamino)-thieno-[2,3-d]-pyrimidine.

EXAMPLE 402

Following the procedure of Example 97, the reaction of 2-methylimidazole with 2-chloro-5,6-dimethyl-4-(3-chloro-4-methoxybenzylamino)-thieno-[2,3-d]-pyrimidine gives 2-(2-methylimidazol-1-yl)-5,6-dimethyl-4-(3-chloro-4-methoxybenzylamino)-thieno-[2,3-d]-pyrimidine.

EXAMPLE 403

Following the procedure of Example 97, the reaction of 2-methylimidazole with 2-chloro-6-trifluoromethyl-4-(3-chloro-4-methoxybenzylamino0-thieno-[2,3-d]-pyrimidine gives 2-(2-methylimidazol-1-yl)-6-trifluoromethyl-4-(3-chloro-4-methoxybenzylamino0-thieno-[2,3-d]-pyrimidine.

EXAMPLE 404

Following the procedure of Example 97, the reaction of 2-methylimidazole with 2-chloro-6-methyl-4-(3,4-dimethoxybenzylamino)-thieno-[2,3-d]-pyrimidine gives 2-(2-methylimidazol-1-yl)-6-methyl-4-(3,4-dimethoxybenzylamino)-thieno-[2,3-d]-pyrimidine.

EXAMPLE 405

Following the procedure of Example 97, the reaction of 2-methylimidazole with 2-chloro-5-methyl-4-(3,4-dimethoxybenzylamino)-thieno-[2,3-d]-pyrimidine gives 2-(2-methylimidazol-1-yl)-5-methyl-4-(3,4-dimethoxybenzylamino)-thieno-[2,3-d]-pyrimidine.

EXAMPLE 406

Following the procedure of Example 97, the reaction of 2-methylimidazole with 2-chloro-5,6,7,8-tetrahydro-4-(3,4-dimethoxybenzylamino)-[1]-[1]-benzothieno-[2,3-d]-pyrimidine gives 2-(2-methylimidazol-1-yl)-5,6,7,8-tetrahydro-4-(3,4-dimethoxybenzylamino)-[1]-[1]-benzothieno-[2,3-d]-pyrimidine.

EXAMPLE 407

Following the procedure of Example 97, the reaction of 2-methylimidazole with 2-chloro-5,6-cyclopenteno-4-(3,4-dimethoxybenzylamino)-[1]-benzothieno-[2,3-d]-pyrimidine gives 2-(2-methylimidazol-1-yl)-5,6-cyclopenteno-4-(3,4-dimethoxybenzylamino)-[1]-benzothieno-[2,3-d]-pyrimidine.

EXAMPLE 408

Following the procedure of Example 97, the reaction of 2-methylimidazole with 2-chloro-5,6-cyclopenteno-4-(3,4-dimethoxybenzylamino)-[1]-benzothieno-[2,3-d]-pyrimidine gives 2-(2-methylimidazol-1-yl)-5,6-cyclopenteno-4-(3,4-dimethoxybenzylamino)-[1]-benzothieno-[2,3-d]-pyrimidine.

EXAMPLE 409

Following the procedure of Example 97, the reaction of 2-methylimidazole with 2-chloro-6-ethyl-4-(3,4-dimethoxybenzylamino)-thieno-[2,3-d]-pyrimidine gives 2-(2-methylimidazol-1-yl)-6-ethyl-4-(3,4-dimethoxybenzylamino)-thieno-[2,3-d]-pyrimidine.

EXAMPLE 410

Following the procedure of Example 97, the reaction of 2-methylimidazole with 2,6-dichloro-4-(3,4-dimethoxybenzylamino)-thieno-[2,3-d]-pyrimidine gives 2-(2-methylimidazol-1-yl)-6-chloro-4-(3,4-dimethoxybenzylamino)-thieno-[2,3-d]-pyrimidine.

EXAMPLE 411

Following the procedure of Example 97, the reaction of 2-methylimidazole with 2,5-dichloro-6-methyl-4-(3,4-dimethoxybenzylamino)-thieno-[2,3-d]-pyrimidine gives 2-(2-methylimidazol-1-yl)-5-chloro-6-methyl-4-(3,4-dimethoxybenzylamino)-thieno-[2,3-d]-pyrimidine.

EXAMPLE 412

Following the procedure of Example 97, the reaction of 2-methylimidazole with 2-chloro-6-nitro-4-(3,4-dimethoxybenzylamino)-thieno-[2,3-d]-pyrimidine gives 2-(2-methylimidazol-1-yl)-6-nitro-4-(3,4-dimethoxybenzylamino)-thieno-[2,3-d]-pyrimidine.

EXAMPLE 413

Following the procedure of Example 97, the reaction of 2-methylimidazole with 2-chloro-5,6-dimethyl-4-(3,4-dimethoxybenzylamino)-thieno-[2,3-d]-pyrimidine gives 2-(2-methylimidazol-1-yl)-5,6-dimethyl-4-(3,4-dimethoxybenzylamino)-thieno-[2,3-d]-pyrimidine.

EXAMPLE 414

Following the procedure of Example 97, the reaction of 2-methylimidazole with yields 2-chloro-6-trifluoromethyl-4-(3,4-dimethoxybenzylamino)-thieno-[2,3-d]-pyrimidine gives 2-(2-methylimidazol-1-yl)-6-trifluoromethyl-4-(3,4-dimethoxybenzylamino)-thieno-[2,3-d]-pyrimidine.

EXAMPLE 415

Following the procedure of Example 97, the reaction of 2-methylimidazole with 2-chloro-6-methyl-4-benzylamino-thieno-[2,3-d]-pyrimidine gives 2-(2-methylimidazol-1-yl)-6-methyl-4-benzylamino-thieno-[2,3-d]-pyrimidine.

EXAMPLE 416

Following the procedure of Example 97, the reaction of 2-methylimidazole with 2-chloro-5-methyl-4-benzylaminothieno-[2,3-d]-pyrimidine gives 2-(2-methylimidazol-1-yl)-5-methyl-4-benzylamino-thieno-[2,3-d]-pyrimidine.

EXAMPLE 417

Following the procedure of Example 97, the reaction of 2-methylimidazole with 2-chloro-5,6,7,8-tetrahydro-4-benzylamino-thieno-[1]-[1]-benzothieno-[2,3-d]-pyrimidine gives 2-(2-methylimidazol-1-yl)-5,6,7,8-tetrahydro-4-benzylamino-thieno-[1]-[1]-benzothieno-[2,3-d]-pyrimidine.

EXAMPLE 418

Following the procedure of Example 97, the reaction of 2-methylimidazole with 2-chloro-5,6-cyclopenteno-4-benzylamino-[2,3-d]-pyrimidine gives 2-(2-methylimidazol-1-yl)-5,6-cyclopenteno-4-benzylamino-[2,3-d]-pyrimidine.

EXAMPLE 419

Following the procedure of Example 97, the reaction of 2-methylimidazole with 2-chloro-5,6-cyclopenteno-4-benzylamino-[1]-benzothieno-[2,3-d]-pyrimidine gives 2-(2-methylimidazol-1-yl)-5,6-cyclopenteno-4-benzylamino-[1]-benzothieno-[2,3-d]-pyrimidine.

EXAMPLE 420

Following the procedure of Example 97, the reaction of 2-methylimidazole with 2-chloro-6-ethyl-4-benzylamino-thieno-[2,3-d]-pyrimidine gives 2-(2-methylimidazol-1-yl)-6-ethyl-4-benzylamino-thieno-[2,3-d]-pyrimidine.

EXAMPLE 421

Following the procedure of Example 97, the reaction of 2-methylimidazole with 2,6-dichloro-6-4-benzylamino-thieno-[2,3-d]-pyrimidine gives 2-(2-methylimidazol-1-yl)-6-chloro-6-4-benzylamino-thieno-[2,3-d]-pyrimidine.

EXAMPLE 422

Following the procedure of Example 97, the reaction of 2-methylimidazole with 2,5-dichloro-6-methyl-4-benzylamino-thieno-[2,3-d]-pyrimidine gives 2-(2-methylimidazol-1-yl)-5-chloro-6-methyl-4-benzylamino-thieno-[2,3-d]-pyrimidine.

EXAMPLE 423

Following the procedure of Example 97, the reaction of 2-methylimidazole with 2-chloro-6-nitro-4-benzylamino-thieno-[2,3-d]-pyrimidine gives 2-(2-methylimidazol-1-yl)-6-nitro-4-benzylamino-thieno-[2,3-d]-pyrimidine.

EXAMPLE 424

Following the procedure of Example 97, the reaction of 2-methylimidazole with 2-chloro-5,6-dimethyl-4-benzylamino-thieno-[2,3-d]-pyrimidine gives 2-(2-methylimidazol-1-yl)-5,6-dimethyl-4-benzylamino-thieno-[2,3-d]-pyrimidine.

EXAMPLE 425

Following the procedure of Example 97, the reaction of 2-methylimidazole with 2-chloro-6-trifluoromethyl-4-benzylamino-thieno-[2,3-d]-pyrimidine gives 2-(2-methylimidazol-1-yl)-6-trifluoromethyl-4-benzylamino-thieno-[2,3-d]-pyrimidine.

EXAMPLE 426

Following the procedure of Example 97, the reaction of 2-methylimidazole with 2-chloro-6-methyl-4-(4-fluorobenzylamino)-thieno-[2,3-d]-pyrimidine gives 2-(2-methylimidazol-1-yl)-6-methyl-4-(4-fluorobenzylamino)-thieno-[2,3-d]-pyrimidine.

EXAMPLE 427

Following the procedure of Example 97, the reaction of 2-methylimidazole with 2-chloro-5,6,7,8-tetrahydro-4-(4-fluorobenzylamino)-[1]-benzothieno-[2,3-d]-pyrimidine gives 2-(2-methylimidazol-1-yl)-5,6,7,8-tetrahydro-4-(4-fluorobenzylamino)-[1]-benzothieno-[2,3-d]-pyrimidine.

EXAMPLE 428

Following the procedure of Example 97, the reaction of 2-methylimidazole with 2-chloro-5,6-cyclopenteno-4-(4-fluorobenzylamino)-[1]-benzothieno-[2,3-d]-pyrimidine gives 2-(2-methylimidazol-1-yl)-5,6-cyclopenteno-4-(4-fluorobenzylamino)-[1]-benzothieno-[2,3-d]-pyrimidine.

EXAMPLE 429

Following the procedure of Example 97, the reaction of 2-methylimidazole with 2-chloro-5,6-cyclohepteno-4-(4-fluorobenzylamino)-[1]-benzothieno-[2,3-d]-pyrimidine gives 2-(2-methylimidazol-1-yl)-5,6-cyclohepteno-4-(4-fluorobenzylamino)-[1]-benzothieno-[2,3-d]-pyrimidine.

EXAMPLE 430

Following the procedure of Example 97, the reaction of 2-methylimidazole with 2-chloro-6-ethyl-4-(4-fluorobenzylamino)-thieno-[2,3-d]-pyrimidine gives 2-(2-methylimidazol-1-yl)-6-ethyl-4-(4-fluorobenzylamino)-thieno-[2,3-d]-pyrimidine.

EXAMPLE 431

Following the procedure of Example 97, the reaction of 2-methylimidazole with 2,6-dichloro-4-(4-fluorobenzylamino)-thieno-[2,3-d]-pyrimidine gives 2-(2-methylimidazol-1-yl)-6-dichloro-4-(4-fluorobenzylamino)-thieno-[2,3-d]-pyrimidine.

EXAMPLE 432

Following the procedure of Example 97, the reaction of 2-methylimidazole with 2,5-dichloro-6-methyl-4-(4-fluorobenzylamino)-thieno-[2,3-d]-pyrimidine gives 2-(2-methylimidazol-1-yl)-5-chloro-6-methyl-4-(4-fluorobenzylamino)-thieno-[2,3-d]-pyrimidine.

EXAMPLE 433

Following the procedure of Example 97, the reaction of 2-methylimidazole with 2-chloro-6-nitro-4-(4-fluorobenzylamino)-thieno-[2,3-d]-pyrimidine gives 2-(2-methylimidazol-1-yl)-6-nitro-4-(4-fluorobenzylamino)-thieno-[2,3-d]-pyrimidine.

EXAMPLE 434

Following the procedure of Example 97, the reaction of 2-methylimidazole with 2-chloro-5,6-dimethyl-4-(4-fluorobenzylamino)-thieno-[2,3-d]-pyrimidine gives 2-(2-methylimidazol-1-yl)-5,6-dimethyl-4-(4-fluorobenzylamino)-thieno-[2,3-d]-pyrimidine.

EXAMPLE 435

Following the procedure of Example 97, the reaction of 2-methylimidazole with 2-chloro-6-trifluoromethyl-4-(4- fluorobenzylamino)-thieno-[2,3-d]-pyrimidine gives 2-(2-methylimidazol-1-yl)-6-trifluoromethyl-4-(4-fluorobenzylamino)-thieno-[2,3-d]-pyrimidine.

EXAMPLE 436

Following the procedure of Example 97, the reaction of 2-methylimidazole with 2-chloro-6-methyl-4-(3,4-dichlorobenzylamino)-thieno-[2,3-d]-pyrimidine gives 2-(2-methylimidazol-1-yl)-6-methyl-4-(3,4-dichlorobenzylamino)-thieno-[2,3-d]-pyrimidine.

EXAMPLE 437

Following the procedure of Example 97, the reaction of 2-methylimidazole with 2-chloro-5-methyl-4-(3,4-dichlorobenzylamino)-thieno-[2,3-d]-pyrimidine gives 2-(2-methylimidazol-1-yl)-5-methyl-4-(3,4-dichlorobenzylamino)-thieno-[2,3-d]-pyrimidine.

EXAMPLE 438

Following the procedure of Example 97, the reaction of 2-methylimidazole with 2-chloro-5,6,7,8-tetrahydro-4-(3,4-dichlorobenzylamino)-[1]-benzothieno-[2,3-d]-pyrimidine gives 2-(2-methylimidazol-1-yl)-5,6,7,8-tetrahydro-4-(3,4-dichlorobenzylamino)-[1]-benzothieno-[2,3-d]-pyrimidine.

EXAMPLE 439

Following the procedure of Example 97, the reaction of 2-methylimidazole with 2-chloro-5,6-cyclopenteno-4-(3,4-dichlorobenzylamino)-[1]-benzothieno-[2,3-d]-pyrimidine gives 2-(2-methylimidazol-1-yl)-5,6-cyclopenteno-4-(3,4-dichlorobenzylamino)-[1]-benzothieno-[2,3-d]-pyrimidine.

EXAMPLE 440

Following the procedure of Example 97, the reaction of 2-methylimidazole with 2-chloro-5,6-cyclopenteno-4-(3,4-dichlorobenzylamino)-[1]-benzothieno-[2,3-d]-pyrimidine gives 2-(2-methylimidazol-1-yl)-5,6-cyclopenteno-4-(3,4-dichlorobenzylamino)-[1]-benzothieno-[2,3-d]-pyrimidine.

EXAMPLE 441

Following the procedure of Example 97, the reaction of 2-methylimidazole with 2-chloro-6-ethyl-4-(3,4-dichlorobenzylamino)-thieno-[2,3-d]-pyrimidine gives 2-(2-methylimidazol-1-yl)-6-ethyl-4-(3,4-dichlorobenzylamino)-thieno-[2,3-d]-pyrimidine.

EXAMPLE 442

Following the procedure of Example 97, the reaction of 2-methylimidazole with 2-6-dichloro-4-(3,4-dichlorobenzylamino)-thieno-[2,3-d]-pyrimidine gives 2-(2-methylimidazol-1-yl)-6-chloro-4-(3,4-dichlorobenzylamino)-thieno-[2,3-d]-pyrimidine.

EXAMPLE 443

Following the procedure of Example 97, the reaction of 2-methylimidazole with 2,5-dichloro-6-methyl-4-(3,4-dichlorobenzylamino)-thieno-[2,3-d]-pyrimidine gives 2-(2-methylimidazol-1-yl)-5-chloro-6-methyl-4-(3,4-dichlorobenzylamino)-thieno-[2,3-d]-pyrimidine.

EXAMPLE 444

Following the procedure of Example 97, the reaction of 2-methylimidazole with 2-chloro-6-nitro-4-(3,4-dichlorobenzylamino)-thieno-[2,3-d]-pyrimidine gives 2-(2-methylimidazol-1-yl)-6-nitro-4-(3,4-dichlorobenzylamino)-thieno-[2,3-d]-pyrimidine.

EXAMPLE 445

Following the procedure of Example 97, the reaction of 2-methylimidazole with 2-chloro-5,6-dimethyl-4-(3,4-dichlorobenzylamino)-thieno-[2,3-d]-pyrimidine gives 2-(2-methylimidazol-1-yl)-5,6-dimethyl-4-(3,4-dichlorobenzylamino)-thieno-[2,3-d]-pyrimidine.

EXAMPLE 446

Following the procedure of Example 97, the reaction of 2-methylimidazole with 2-chloro-6-trifluoromethyl-4-(3,4-dichlorobenzylamino)-thieno-[2,3-d]-pyrimidine gives 2-(2-methylimidazol-1-yl)-6-trifluoromethyl-4-(3,4-dichlorobenzylamino)-thieno-[2,3-d]-pyrimidine.

EXAMPLE 447

Following the procedure of Example 97, the reaction of 2-methylimidazole with 2-chloro-6-methyl-4-(3-nitrobenzylamino)-thieno-[2,3-d]-pyrimidine gives 2-(2-methylimidazol-1-yl)-6-methyl-4-(3-nitrobenzylamino)-thieno-[2,3-d]-pyrimidine.

EXAMPLE 448

Following the procedure of Example 97, the reaction of 2-methylimidazole with 2-chloro-5-methyl-4-(3-nitrobenzylamino)-thieno-[2,3-d]-pyrimidine gives 2-(2-methylimidazol-1-yl)-5-methyl-4-(3-nitrobenzylamino)-thieno-[2,3-d]-pyrimidine.

EXAMPLE 449

Following the procedure of Example 97, the reaction of 2-methylimidazole with 2-chloro-5,6,7,8-tetrahydro-4-(3-nitrobenzylamino)-[1]-benzothieno-[2,3-d]-pyrimidine gives 2-(2-methylimidazol-1-yl)-5,6,7,8-tetrahydro-4-(3-nitrobenzylamino)-[1]-benzothieno-[2,3-d]-pyrimidine.

EXAMPLE 450

Following the procedure of Example 97, the reaction of 2-methylimidazole with 2-chloro-5,6-cyclopenteno-4-(3-nitrobenzylamino)-[1]-benzothieno-[2,3-d]-pyrimidine gives 2-(2-methylimidazol-1-yl)-5,6-cyclopenteno-4-(3-nitrobenzylamino)-[1]-benzothieno-[2,3-d]-pyrimidine.

EXAMPLE 451

Following the procedure of Example 97, the reaction of 2-methylimidazole with 2-chloro-5,6-cyclopenteno-4-(3-nitrobenzylamino)-[1]-benzothieno-[2,3-d]-pyrimidine gives 2-(2-methylimidazol-1-yl)-5,6-cyclopenteno-4-(3-nitrobenzylamino)-[1]-benzothieno-[2,3-d]-pyrimidine.

EXAMPLE 452

Following the procedure of Example 97, the reaction of 2-methylimidazole with 2-chloro-6-ethyl-4-(3-nitrobenzylamino)-thieno-[2,3-d]-pyrimidine gives 2-(2-methylimidazol-1-yl)-6-ethyl-4-(3-nitrobenzylamino)-thieno-[2,3-d]-pyrimidine.

EXAMPLE 453

Following the procedure of Example 97, the reaction of 2-methylimidazole with 6-chloro-4-(3-nitrobenzylamino)- thieno-[2,3-d]-pyrimidine gives 2-(2-methylimidazol-1-yl)-4-(3-nitrobenzylamino)-thieno-[2,3-d]-pyrimidine.

EXAMPLE 454

Following the procedure of Example 97, the reaction of 2-methylimidazole with 5-chloro-6-methyl-4-(3-nitrobenzylamino)-thieno-[2,3-d]-pyrimidine gives 2-(2-methylimidazol-1-yl)-6-methyl-4-(3-nitrobenzylamino)-thieno-[2,3-d]-pyrimidine.

EXAMPLE 455

Following the procedure of Example 97, the reaction of 2-methylimidazole with 2-chloro-6-nitro-4-(3-nitrobenzylamino)-thieno-[2,3-d]-pyrimidine gives 2-(2-methylimidazol-1-yl)-6-nitro-4-(3-nitrobenzylamino)-thieno-[2,3-d]-pyrimidine.

EXAMPLE 456

Following the procedure of Example 97, the reaction of 2-methylimidazole with 2-chloro-5,6-dimethyl-4-(3-nitrobenzylamino)-thieno-[2,3-d]-pyrimidine gives 2-(2-methylimidazol-1-yl)-5,6-dimethyl-4-(3-nitrobenzylamino)-thieno-[2,3-d]-pyrimidine.

EXAMPLE 457

Following the procedure of Example 97, the reaction of 2-methylimidazole with 2-chloro-6-trifluoromethyl-4-(3-nitrobenzylamino)-thieno-[2,3-d]-pyrimidine gives 2-(2-methylimidazol-1-yl)-6-trifluoromethyl-4-(3-nitrobenzylamino)-thieno-[2,3-d]-pyrimidine.

EXAMPLE 458

Following the procedure of Example 97, the reaction of 2-methylimidazole with 2-chloro-6-methyl-4-(3-nitrobenzylamino)-thieno-[2,3-d]-pyrimidine gives 2-(2-methylimidazol-1-yl)-6-methyl-4-(3-nitrobenzylamino)-thieno-[2,3-d]-pyrimidine.

EXAMPLE 459

Following the procedure of Example 97, the reaction of 2-methylimidazole with 2-chloro-5-methyl-4-(3,4-methylenedioxyphenethylamino)-thieno-[2,3-d]-pyrimidine gives 2-(2-methylimidazol-1-yl)-5-methyl-4-(3,4-methylenedioxyphenethylamino)-thieno-[2,3-d]-pyrimidine.

EXAMPLE 460

Following the procedure of Example 97, the reaction of 2-methylimidazole with 2-chloro-5,6,7,8-tetrahydro-4-(3,4-methylenedioxyphenethylamino)-[1]-benzothieno-[2,3-d]-pyrimidine gives 2-(2-methylimidazol-1-yl)-5,6,7,8-tetrahydro-4-(3,4-methylenedioxyphenethylamino)-[1]-benzothieno-[2,3-d]-pyrimidine.

EXAMPLE 461

Following the procedure of Example 97, the reaction of 2-methylimidazole with 2-chloro-5,6-cyclopenteno-4-(3,4-methylenedioxyphenethylamino)-[1]-benzothieno-[2,3-d]-pyrimidine gives 2-(2-methylimidazol-1-yl)-5,6-cyclopenteno-4-(3,4-methylenedioxyphenethylamino)-[1]-benzothieno-[2,3-d]-pyrimidine.

EXAMPLE 462

Following the procedure of Example 97, the reaction of 2-methylimidazole with 2-chloro-6-ethyl-4-(3,4-methylenedioxyphenethylamino)-thieno-[2,3-d]-pyrimidine gives 2-(2-methylimidazol-1-yl)-6-ethyl-4-(3,4-methylenedioxyphenethylamino)-thieno-[2,3-d]-pyrimidine.

EXAMPLE 463

Following the procedure of Example 97, the reaction of 2-methylimidazole with 6-chloro-4-(3,4-methylenedioxyphenethylamino)-thieno-[2,3-d]-pyrimidine gives 2-(2-methylimidazol-1-yl)-4-(3,4-methylenedioxyphenethylamino)-thieno-[2,3-d]-pyrimidine.

EXAMPLE 464

Following the procedure of Example 97, the reaction of 2-methylimidazole with 5-chloro-6-methyl-4-(3,4-methylenedioxyphenethylamino)-thieno-[2,3-d]-pyrimidine gives 2-(2-methylimidazol-1-yl)-6-methyl-4-(3,4-methylenedioxyphenethylamino)-thieno-[2,3-d]-pyrimidine.

EXAMPLE 465

Following the procedure of Example 97, the reaction of 2-methylimidazole with 2-chloro-6-nitro-4-(3,4-methylenedioxyphenethylamino)-thieno-[2,3-d]-pyrimidine gives 2-(2-methylimidazol-1-yl)-6-nitro-4-(3,4-methylenedioxyphenethylamino)-thieno-[2,3-d]-pyrimidine.

EXAMPLE 466

Following the procedure of Example 97, the reaction of 2-methylimidazole with 2-chloro-5,6-dimethyl-4-(3,4-methylenedioxyphenethylamino)-thieno-[2,3-d]-pyrimidine gives 2-(2-methylimidazol-1-yl)-5,6-dimethyl-4-(3,4-methylenedioxyphenethylamino)-thieno-[2,3-d]-pyrimidine.

EXAMPLE 467

Following the procedure of Example 97, the reaction of 2-methylimidazole with 2-chloro-6-trifluoromethyl-4-(3,4-methylenedioxyphenethylamino)-thieno-[2,3-d]-pyrimidine gives 2-(2-methylimidazol-1-yl)-6-trifluoromethyl-4-(3,4-methylenedioxyphenethylamino)-thieno-[2,3-d]-pyrimidine.

EXAMPLE 468

Following the procedure of Example 97, the reaction of 2-methylimidazole with 2-chloro-6-methyl-4-(3,4-ethylendioxybenzylamino)-thieno-[2,3-d]-pyrimidine gives 2-(2-methylimidazol-1-yl)-6-methyl-4-(3,4-ethylendioxybenzylamino)-thieno-[2,3-d]-pyrimidine.

EXAMPLE 469

Following the procedure of Example 97, the reaction of 2-methylimidazole with 2-chloro-5-methyl-4-(3,4-ethylendioxybenzylamino)-thieno-[2,3-d]-pyrimidine gives 2-(2-methylimidazol-1-yl)-5-methyl-4-(3,4-ethylendioxybenzylamino)-thieno-[2,3-d]-pyrimidine.

EXAMPLE 470

Following the procedure of Example 97, the reaction of 2-methylimidazole with 2-chloro-5,6,7,8-tetrahydro-4-(3,4-ethylendioxybenzylamino)-[1]-benzothieno-[2,3-d]- pyrimidine gives 2-(2-methylimidazol-1-yl)-5,6,7,8-tetrahydro-4-(3,4-ethylendioxybenzylamino)-[1]-benzothieno-[2,3-d]-pyrimidine.

EXAMPLE 471

Following the procedure of Example 97, the reaction of 2-methylimidazole with 2-chloro-6-ethyl-4-(3,4-ethylendioxybenzylamino)-thieno-[2,3-d]-pyrimidine gives 2-(2-methylimidazol-1-yl)-6-ethyl-4-(3,4-ethylendioxybenzylamino)-thieno-[2,3-d]-pyrimidine.

EXAMPLE 472

Following the procedure of Example 97, the reaction of 2-methylimidazole with 2,6-dichloro-4-(3,4-ethylendioxybenzylamino)-thieno-[2,3-d]-pyrimidine gives 2-(2-methylimidazol-1-yl)-6-chloro-4-(3,4-ethylendioxybenzylamino)-thieno-[2,3-d]-pyrimidine.

EXAMPLE 473

Following the procedure of Example 97, the reaction of 2,5-dichloro-6-methyl-4-(3,4-ethylendioxybenzylamino)-thieno-[2,3-d]-pyrimidine gives 2-(2-methylimidazol-1-yl)-5-chloro-6-methyl-4-(3,4-ethylendioxybenzylamino)-thieno-[2,3-d]-pyrimidine.

EXAMPLE 474

Following the procedure of Example 97, the reaction of 2-methylimidazole with 2-chloro-6-nitro-4-(3,4-ethylendioxybenzylamino)-thieno-[2,3-d]-pyrimidine gives 2-(2-methylimidazol-1-yl)-6-nitro-4-(3,4-ethylendioxybenzylamino)-thieno-[2,3-d]-pyrimidine.

EXAMPLE 475

Following the procedure of Example 97, the reaction of 2-methylimidazole with 2-chloro-5,6-dimethyl-4-(3,4-ethylendioxybenzylamino)-thieno-[2,3-d]-pyrimidine gives 2-(2-methylimidazol-1-yl)-5,6-dimethyl-4-(3,4-ethylendioxybenzylamino)-thieno-[2,3-d]-pyrimidine.

EXAMPLE 476

Following the procedure of Example 97, the reaction of 2-methylimidazole with 2-chloro-6-trifluoromethyl-4-(3,4-ethylendioxybenzylamino)-thieno-[2,3-d]-pyrimidine gives 2-(2-methylimidazol-1-yl)-6-trifluoromethyl-4-(3,4-ethylendioxybenzylamino)-thieno-[2,3-d]-pyrimidine.

EXAMPLE 477

2-Amino-5-methyl-3-ethoxycarbonyl-thiophene (5 g) is solved with 3-cyanopyrimidine (2.7 g) in dioxane (40 ml). Then gaseous HCl is conducted through the solution for 5 hours. The usual workup yields 3,4-dihydro-4-oxo-2-(pyridin-3-yl)-6-methyl-thieno-[2,3-d]-pyrimidine (6 g).

The replacement of the keto group by Cl under the formation of the aromatic pyrimidine ring takes place under standard conditions. A mixture of $POCl_3$ (18 ml) with 3,4-dihydro-4-oxo-2-(pyridin-3-yl)-6-methyl-thieno-[2,3-d]-pyrimidine (6 g) is refluxed for 4 hours under the addition of N,N-dimethylaniline (1,8 m). The usual workup yields 4-chloro-2-(pyridin-3-yl)-6-methyl-thieno-[2,3-d]-pyrimidine (5 g)

EXAMPLE 478

With the procedure of Example 477, the reaction of 3-cyanopyridine and 2-amino-4-methyl-3-ethoxycarbonyl-thiophene, and the subsequent reaction with $POCl_3$ yields 4-chloro-2-(pyridin-3-yl)-5-methyl-thieno-[2,3-d]-pyrimidine.

EXAMPLE 479

With the procedure of Example 477, the reaction of 3-cyanopyridine and 2-amino-4,5,6,7-tetrahydro-3-ethoxycarbonyl-thiophene, and the subsequent reaction with $POCl_3$ yields 4-chloro-2-(pyridin-3-yl)-5,6,7,8-tetrahydro-[1]-benzothieno-[2,3-d]-pyrimidine m.p. 143° C.

EXAMPLE 480

With the procedure of Example 477, the reaction of 3-cyanopyridine and 2-amino-4,5-cyclopenteno-3-ethoxycarbonyl-thiophene, and the subsequent reaction with $POCl_3$ yields 4-chloro-2-(pyridin-3-yl)-5,6-cyclopenteno-thieno-[2,3-d]-pyrimidine

EXAMPLE 481

With the procedure of Example 477, the reaction of 3-cyanopyridine and 2-amino-4,5-cyclopenteno-3-ethoxycarbonyl-thiophene, and the subsequent reaction with $POCl_3$ yields 4-chloro-2-(pyridin-3-yl)-5,6-cyclopenteno-thieno-[2,3-d]-pyrimidine

EXAMPLE 482

With the procedure of Example 477, the reaction of 3-cyanopyridine and 2-amino-4,5-cholohepteno-3-ethoxycarbonyl-thiophene, and the subsequent reaction with $POCl_3$ yields 4-chloro-2-(pyridin-3-yl)-5,6-cyclohepteno-thieno-[2,3-d]-pyrimidine

EXAMPLE 483

With the procedure of Example 477, the reaction of 3-cyanopyridine and 2-amino-5-ethyl-3-ethoxycarbonyl-thiophene, and the subsequent reaction with $POCl_3$ yields 4-chloro-2-(pyridin-3-yl)-6-ethyl-thieno-[2,3-d]-pyrimidine

EXAMPLE 484

With the procedure of Example 477, the reaction of 3-cyanopyridine and 2-amino-5-clhoro-3-ethoxycarbonyl-thiophene, and the subsequent reaction with $POCl_3$ yields 4-chloro-2-(pyridin-3-yl)-6-chloro-thieno-[2,3-d]-pyrimidine

EXAMPLE 485

With the procedure of Example 477, the reaction of 3-cyanopyridine and 2-amino-4-chloro-5-methyl-3-ethoxycarbonyl-thiophene, and the subsequent reaction with $POCl_3$ yields 4-chloro-2-(pyridin-3-yl)-5-chloro-6-methyl-thieno-[2,3-d]-pyrimidine

EXAMPLE 486

With the procedure of Example 477, the reaction of 3-cyanopyridine and 2-amino-5-nitro-3-ethoxycarbonyl-thiophene, and the subsequent reaction with $POCl_3$ yields 4-chloro-2-(pyridin-3-yl)-6-nitro-thieno-[2,3-d]-pyrimidine

EXAMPLE 487

With the procedure of Example 477, the reaction of 3-cyanopyridine and 2-amino-5-trifluoromethyl-3-ethoxycarbonyl-thiophene, and the subsequent reaction with $POCl_3$ yields 4-chloro-2-(pyridin-3-yl)-6-trifluoromethyl-thieno-[2,3-d]-pyrimidine

EXAMPLE 488

With the procedure of Example 477, the reaction of 5-cyanoisoxazole and 2-amino-5-methyl-3-ethoxycarbonyl-thiophene, and the subsequent reaction with $POCl_3$ yields 4-chloro-2-(isoxazol-5-yl)-6-methyl-thieno-[2,3-d]-pyrimidine

EXAMPLE 489

With the procedure of Example 477, the reaction of 5-cyanoisoxazole and 2-amino-4-methyl-3-ethoxycarbonyl-thiophene, and the subsequent reaction with $POCl_3$ yields 4-chloro-2-(isoxazol-5-yl)-5-methyl-thieno-[2,3-d]-pyrimidine

EXAMPLE 490

With the procedure of Example 477, the reaction of 5-cyanoisoxazole and 2-amino-4,5,6,7-tetrahydro-3-ethoxycarbonyl-thiophene, and the subsequent reaction with $POCl_3$ yields 4-chloro-2-(isoxazol-5-yl)-5,6,7,8-tetrahydro-[1]-benzothieno-[2,3-d]-pyrimidine

EXAMPLE 491

With the procedure of Example 477, the reaction of 5-cyanoisoxazole and 2-amino-4,5-cyclopenteno-3-ethoxycarbonyl-thiophene, and the subsequent reaction with $POCl_3$ yields 4-chloro-2-(isoxazol-5-yl)-5,6-cyclopenteno-thieno-[2,3-d]-pyrimidine

EXAMPLE 492

With the procedure of Example 477, the reaction of 5-cyanoisoxazole and 2-amino-4,5-cyclohepteno-3-ethoxycarbonyl-thiophene, and the subsequent reaction with $POCl_3$ yields 4-chloro-2-(isoxazol-5-yl)-5,6-cyclohepteno-thieno-[2,3-d]-pyrimidine

EXAMPLE 493

With the procedure of Example 477, the reaction of 5-cyanoisoxazole and 2-amino-5-ethyl-3-ethoxycarbonyl-thiophene, and the subsequent reaction with $POCl_3$ yields 4-chloro-2-(isoxazol-5-yl)-6-ethyl-thieno-[2,3-d]-pyrimidine

EXAMPLE 494

With the procedure of Example 477, the reaction of 5-cyanoisoxazole and 2-amino-5-chloro-3-ethoxycarbonyl-thiophene, and the subsequent reaction with $POCl_3$ yields 4-chloro-2-(isoxazol-5-yl)-6-chloro-thieno-[2,3-d]-pyrimidine

EXAMPLE 495

With the procedure of Example 477, the reaction of 5-cyanoisoxazole and 2-amino-4-chloro-3-ethoxycarbonyl-thiophene, and the subsequent reaction with $POCl_3$ yields 4-chloro-2-(isoxazol-5-yl)-5-chloro-6-methyl-thieno-[2,3-d]-pyrimidine

EXAMPLE 496

With the procedure of Example 477, the reaction of 5-cyanoisoxazole and 2-amino-5-nitro-3-ethoxycarbonyl-thiophene, and the subsequent reaction with $POCl_3$ yields 4-chloro-2-(isoxazol-5-yl)-6-nitro-thieno-[2,3-d]-pyrimidine

EXAMPLE 497

With the procedure of Example 477, the reaction of 5-cyanoisoxazole and 2-amino-4,5-dimethyl-3-ethoxycarbonyl-thiophene, and the subsequent reaction with $POCl_3$ yields 4-chloro-2-(isoxazol-5-yl)-5,6-dimethyl-thieno-[2,3-d]-pyrimidine

EXAMPLE 498

With the procedure of Example 477, the reaction of 5-cyanoisoxazole and 2-amino-5-trifluoromethyl-3-ethoxycarbonyl-thiophene, and the subsequent reaction with $POCl_3$ yields 4-chloro-2-(isoxazol-5-yl)-6-trifluoromethyl-thieno-[2,3-d]-pyrimidine

EXAMPLE 499

With the procedure of Example 477, the reaction of 2-cyanopyrazine and 2-amino-5-methyl-3-ethoxycarbonyl-thiophene, and the subsequent reaction with $POCl_3$ yields 4-chloro-2-(pyrazin-2-yl)-6-methyl-thieno-[2,3-d]-pyrimidine

EXAMPLE 500

With the procedure of Example 477, the reaction of 2-cyanopyrazine and 2-amino-4-methyl-3-ethoxycarbonyl-thiophene, and the subsequent reaction with $POCl_3$ yields 4-chloro-2-(pyrazin-2-yl)-5-methyl-thieno-[2,3-d]-pyrimidine

EXAMPLE 501

With the procedure of Example 477, the reaction of 2-cyanopyrazine and 2-amino-4,5,6,7-tetrahydro-3-ethoxycarbonyl-thiophene, and the subsequent reaction with $POCl_3$ yields 4-chloro-2-(pyrazin-2-yl)-5,6,7,8-tetrahydro-[1]-benzothieno-[2,3-d]-pyrimidine

EXAMPLE 502

With the procedure of Example 477, the reaction of 2-cyanopyrazine and 2-amino-4,5-cyclopenteno-3-ethoxycarbonyl-thiophene, and the subsequent reaction with $POCl_3$ yields 4-chloro-2-(pyrazin-2-yl)-5,6-cyclopenteno-thieno-[2,3-d]-pyrimidine

EXAMPLE 503

With the procedure of Example 477, the reaction of 2-cyanopyrazine and 2-amino-4,5-cyclohepteno-3-ethoxycarbonyl-thiophene, and the subsequent reaction with $POCl_3$ yields 4-chloro-2-(pyrazin-2-yl)-5,6-cyclohepteno-thieno-[2,3-d]-pyrimidine

EXAMPLE 504

With the procedure of Example 477, the reaction of 2-cyanopyrazine and 2-amino-5-ethyl-3-ethoxycarbonyl-thiophene, and the subsequent reaction with $POCl_3$ yields 4-chloro-2-(pyrazin-2-yl)-6-ethyl-thieno-[2,3-d]-pyrimidine

EXAMPLE 505

With the procedure of Example 477, the reaction of 2-cyanopyrazine and 2-amino-5-chloro-3-ethoxycarbonyl-thiophene, and the subsequent reaction with $POCl_3$ yields 4-chloro-2-(pyrazin-2-yl)-6-chloro-thieno-[2,3-d]-pyrimidine

EXAMPLE 506

With the procedure of Example 477, the reaction of 2-cyanopyrazine and 2-amino-4-chloro-3-ethoxycarbonyl-thiophene, and the subsequent reaction with $POCl_3$ yields 4-chloro-2-(pyrazin-2-yl)-5-chloro-6-thieno-[2,3-d]-pyrimidine

EXAMPLE 507

With the procedure of Example 477, the reaction of 2-cyanopyrazine and 2-amino-5-nitro-3-ethoxycarbonyl-thiophene, and the subsequent reaction with POCl$_3$ yields 4-chloro-2-(pyrazin-2-yl)-6-nitro-thieno-[2,3-d]-pyrimidine

EXAMPLE 508

With the procedure of Example 477, the reaction of 2-cyanopyrazine and 2-amino-4,5-dimethyl-3-ethoxycarbonyl-thiophene, and the subsequent reaction with POCl$_3$ yields 4-chloro-2-(pyrazin-2-yl)-5,6-dimethyl-thieno-[2,3-d]-pyrimidine

EXAMPLE 509

With the procedure of Example 477, the reaction of 2-cyanopyrazine and 2-amino-5-trifluoromethyl-3-ethoxycarbonyl-thiophene, and the subsequent reaction with POCl$_3$ yields 4-chloro-2-(pyrazin-2-yl)-6-trifluoromethyl-thieno-[2,3-d]-pyrimidine

EXAMPLE 510

With the procedure of Example 477, the reaction of 2-cyanopyridine and 2-amino-5-methyl-3-ethoxycarbonyl-thiophene, and the subsequent reaction with POCl$_3$ yields 4-chloro-2-(pyridin-2-yl)-6-methyl-thieno-[2,3-d]-pyrimidine

EXAMPLE 511

With the procedure of Example 477, the reaction of 2-cyanopyridine and 2-amino-4-methyl-3-ethoxycarbonyl-thiophene, and the subsequent reaction with POCl$_3$ yields 4-chloro-2-(pyridin-2-yl)-5-methyl-thieno-[2,3-d]-pyrimidine

EXAMPLE 512

With the procedure of Example 477, the reaction of 2-cyanopyridine and 2-amino-4,5,6,7-tetrahydro-3-ethoxycarbonyl-thiophene, and the subsequent reaction with POCl$_3$ yields 4-chloro-2-(pyridin-2-yl)-5,6,7,8-tetrahydro-[1]-benzothieno-[2,3-d]-pyrimidine

EXAMPLE 513

With the procedure of Example 477, the reaction of 2-cyanopyridine and 2-amino-4,5-cyclopenteno-3-ethoxycarbonyl-thiophene, and the subsequent reaction with POCl$_3$ yields 4-chloro-2-(pyridin-2-yl)-5,6-cyclopenteno-hieno-[2,3-d]-pyrimidine

EXAMPLE 514

With the procedure of Example 477, the reaction of 2-cyanopyridine and 2-amino-4,5-cyclohepteno-3-ethoxycarbonyl-thiophene, and the subsequent reaction with POCl$_3$ yields 4-chloro-2-(pyridin-2-yl)-5,6-cyclohepteno-thieno-[2,3-d]-pyrimidine

EXAMPLE 515

With the procedure of Example 477, the reaction of 2-cyanopyridine and 2-amino-5-ethyl-3-ethoxycarbonyl-thiophene, and the subsequent reaction With POCl$_3$ yields 4-chloro-2-(pyridin-2-yl)-6-ethyl-thieno-[2,3-d]-pyrimidine

EXAMPLE 516

With the procedure of Example 477, the reaction of 2-cyanopyridine and 2-amino-5-chloro-3-ethoxycarbonyl-thiophene, and the subsequent reaction with POCl$_3$ yields 4-chloro-2-(pyridin-2-yl)-6-chloro-thieno-[2,3-d]-pyrimidine

EXAMPLE 517

With the procedure of Example 477, the reaction of 2-cyanopyridine and 2-amino-4-chloro-3-ethoxycarbonyl-thiophene, and the subsequent reaction with POCl$_3$ yields 4-chloro-2-(pyridin-2-yl)-5-chloro-6-methyl-thieno-[2,3-d]-pyrimidine

EXAMPLE 518

With the procedure of Example 477, the reaction of 2-cyanopyridine and 2-amino-4,5-dimethyl-3-ethoxycarbonyl-thiophene, and the subsequent reaction with POCl$_3$ yields 4-chloro-2-(pyridin-2-yl)-5,6-dimethyl-thieno-[2,3-d]-pyrimidine

EXAMPLE 519

With the procedure of Example 477, the reaction of 2-cyanopyridine and 2-amino-5-trifluoromethyl-3-ethoxycarbonyl-thiophene, and the subsequent reaction with POCl$_3$ yields 4-chloro-2-(pyridin-2-yl)-6-trifluoromethyl-thieno-[2,3-d]-pyrimidine

EXAMPLE 520

With the procedure of Example 477, the reaction of 4-cyanopyridine and 2-amino-5-methyl-3-ethoxycarbonyl-thiophene, and the subsequent reaction with POCl$_3$ yields 4-chloro-2-(pyridin-4-yl)-6-methyl-thieno-[2,3-d]-pyrimidine

EXAMPLE 521

With the procedure of Example qq, the reaction of 4-cyanopyridine and 2-amino-4-methyl-3-ethoxycarbonyl-thiophene, and the subsequent reaction with POCl$_3$ yields 4-chloro-2-(pyridin-4-yl)-5-methyl-thieno-[2,3-d]-pyrimidine

EXAMPLE 522

With the procedure of Example qq, the reaction of 4-cyanopyridine and 2-amino-4,5,6,7-tetrahydro-3-ethoxycarbonyl-thiophene, and the subsequent reaction with POCl$_3$ yields 4-chloro-2-(pyridin-4-yl)-5,6,7,8-tetrahydro-[1]-benzothieno-[2,3-d]-pyrimidine

EXAMPLE 523

With the procedure of Example qq, the reaction of 4-cyanopyridine and 2-amino-4,5-cyclopenteno-3-ethoxycarbonyl-thiophene, and the subsequent reaction with POCl$_3$ yields 4-chloro-2-(pyridin-4-yl)-5,6-cyclopenteno-thieno-[2,3-d]-pyrimidine

EXAMPLE 524

With the procedure of Example 477, the reaction of 4-cyanopyridine and 2-amino-4,5-cyclohepteno-3-ethoxycarbonyl-thiophene, and the subsequent reaction with POCl$_3$ yields 4-chloro-2-(pyridin-4-yl)-5,6-cyclohepteno-thieno-[2,3-d]-pyrimidine

EXAMPLE 525

With the procedure of Example 477, the reaction of 4-cyanopyridine and 2-amino-5-ethyl-3-ethoxycarbonylthiophene, and the subsequent reaction with POCl₃ yields 4-chloro-2-(pyridin-4-yl)-6-ethyl-thieno-[2,3-d]-pyrimidine

EXAMPLE 526

With the procedure of Example 477, the reaction of 4-cyanopyridine and 2-amino-5-chloro-3-ethoxycarbonyl-thiophene, and the subsequent reaction with POCl₃ yields 4-chloro-2-(pyridin-4-yl)-6-chloro-thieno-[2,3-d]-pyrimidine

EXAMPLE 527

With the procedure of Example 477, the reaction of 4-cyanopyridine and 2-amino-4-chloro-5-methyl-3-ethoxycarbonyl-thiophene, and the subsequent reaction with POCl₃ yields 4-chloro-2-(pyridin-4-yl)-5-chloro-6-methyl-thieno-[2,3-d]-pyrimidine

EXAMPLE 528

With the procedure of Example 477, the reaction of 4-cyanopyridine and 2-amino-6-nitro-3-ethoxycarbonyl-thiophene, and the subsequent reaction with POCl₃ yields 4-chloro-2-(pyridin-4-yl)-6-nitro-thieno-[2,3-d]-pyrimidine

EXAMPLE 529

With the procedure of Example 477, the reaction of 4-cyanopyridine and 2-amino-4,5-dimethyl-3-ethoxycarbonyl-thiophene, and the subsequent reaction with POCl₃ yields 4-chloro-2-(pyridin-4-yl)-5,6-dimethyl-thieno-[2,3-d]-pyrimidine

EXAMPLE 530

With the procedure of Example 477, the reaction of 4-cyanopyridine and 2-amino-5-trifluoromethyl-3-ethoxycarbonyl-thiophene, and the subsequent reaction with POCl₃ yields 4-chloro-2-(pyridin-4-yl)-6-trifluoromethyl-thieno-[2,3-d]-pyrimidine

EXAMPLE 531

With the procedure of Example 1, the reaction of 3,4-methylenedioxybenzylamine with 4-chloro-2-(pyridin-3-yl)-6-methyl-thieno-[2,3-d]-pyrimidine yields yields 2-(pyridin-3-yl)-4-(3,4-methylenedioxybenzylamino-6-methyl-thieno-[2,3-d]-pyrimidine.

EXAMPLE 532

With the procedure of Example 1, the reaction of 3,4-methylenedioxybenzylamine with 4-chloro-2-(pyridin-3-yl)-5-methyl-thieno-[2,3-d]-pyrimidine yields yields 2-(pyridin-3-yl)-4-(3,4-methylenedioxybenzylamino-5-methyl-thieno-[2,3-d]-pyrimidine.

EXAMPLE 533

With the procedure of Example 1, the reaction of 3,4-methylenedioxybenzylamine with 4-chloro-2-(pyridin-3-yl)-5,6,7,8-tetrahydro-[1]-benzothieno-[2,3-d]-pyrimidine yields 2-(pyridin-3-yl)-4-(3,4-methylenedioxybenzylamino-5,6,7,8-tetrahydro-thieno-[2,3-d]-pyrimidine.

EXAMPLE 534

With the procedure of Example 1, the reaction of 3,4-methylenedioxybenzylamine with 4-chloro-2-(pyridin-3-yl)-5,6-cyclopenteno-thieno-[2,3-d]-pyrimidine yields 2-(pyridin-3-yl)-4-(3,4-methylenedioxybenzylamino-5,6-cyclopenteno-thieno-[2,3-d]-pyrimidine.

EXAMPLE 535

With the procedure of Example 1, the reaction of 3,4-methylenedioxybenzylamine with 4-chloro-2-(pyridin-3-yl)-5,6-cyclohepteno-thieno-[2,3-d]-pyrimidine yields 2-(pyridin-3-yl)-4-(3,4-methylenedioxybenzylamino-5,6-cyclohepteno-thieno-[2,3-d]-pyrimidine.

EXAMPLE 536

With the procedure of Example 1, the reaction of 3,4-methylenedioxybenzylamine with 4-chloro-2-(pyridin-3-yl)-6-ethyl-thieno-[2,3-d]-pyrimidine yields 2-(pyridin-3-yl)-4-(3,4-methylenedioxybenzylamino-6-ethyl-thieno-[2,3-d]-pyrimidine.

EXAMPLE 537

With the procedure of Example 1, the reaction of 3,4-methylenedioxybenzylamine with 4-chloro-2-(pyridin-3-yl)-6-chloro-thieno-[2,3-d]-pyrimidine yields 2-(pyridin-3-yl)-4-(3,4-methylenedioxybenzylamino-6-chloro-thieno-[2,3-d]-pyrimidine.

EXAMPLE 538

With the procedure of Example 1, the reaction of 3,4-methylenedioxybenzylamine with 4-chloro-2-(pyridin-3-yl)-5-chloro-6-methyl-thieno-[2,3-d]-pyrimidine yields 2-(pyridin-3-yl)-4-(3,4-methylenedioxybenzylamino-5-chloro-6-methyl-thieno-[2,3-d]-pyrimidine.

EXAMPLE 539

With the procedure of Example 1, the reaction of 3,4-methylenedioxybenzylamine with 4-chloro-2-(pyridin-3-yl)-6-nitro-thieno-[2,3-d]-pyrimidine yields 2-(pyridin-3-yl)-4-(3,4-methylenedioxybenzylamino-6-nitro-thieno-[2,3-d]-pyrimidine.

EXAMPLE 540

With the procedure of Example 1, the reaction of 3,4-methylenedioxybenzylamine with 4-chloro-2-(pyridin-3-yl)-6-trifluormethyl-thieno-[2,3-d]-pyrimidine yields 2-(pyridin-3-yl)-4-(3,4-methylenedioxybenzylamino-6-trifluoromethyl-thieno-[2,3-d]-pyrimidine.

EXAMPLE 541

With the procedure of Example 1, the reaction of 3,4-methylenedioxybenzylamine with 4-chloro-2-(isoxazol-5-yl)-6-methyl-thieno-[2,3-d]-pyrimidine yields 2-(isoxasol-5-yl)-4-(3,4-methylenedioxybenzylamino-6-methyl-thieno-[2,3-d]-pyrimidine.

EXAMPLE 542

With the procedure of Example 1, the reaction of 3,4-methylenedioxybenzylamine with 4-chloro-2-(isoxazol-5-yl)-5-methyl-thieno-[2,3-d]-pyrimidine yields 2-(isoxasol-5-yl)-4-(3,4-methylenedioxybenzylamino-5-methyl-thieno-[2,3-d]-pyrimidine.

EXAMPLE 543

With the procedure of Example 1, the reaction of 3,4-methylenedioxybenzylamine with 4-chloro-2-(isoxazol-5-yl)-5,6,7,8-tetrahydro-[1]-benzothieno-[2,3-d]-pyrimidine yields 2-(isoxasol-5-yl)-4-(3,4-methylenedioxybenzylamino-5,6,7,8-tetrahydro-thieno-[2,3-d]-pyrimidine.

EXAMPLE 544

With the procedure of Example 1, the reaction of 3,4-methylenedioxybenzylamine with 4-chloro-2-(isoxazol-5-yl)-5,6-cyclopenteno-thieno-[2,3-d]-pyrimidine yields 2-(isoxasol-5-yl)-4-(3,4-methylenedioxybenzylamino-5,6-cyclopenteno-thieno-[2,3-d]-pyrimidine.

EXAMPLE 545

With the procedure of Example 1, the reaction of 3,4-methylenedioxybenzylamine with 4-chloro-2-(isoxazol-5-yl)-5,6-cyclohepteno-thieno-[2,3-d]-pyrimidine yields 2-(isoxasol-5-yl)-4-(3,4-methylenedioxybenzylamino-5,6-cyclohepteno-thieno-[2,3-d]-pyrimidine.

EXAMPLE 546

With the procedure of Example 1, the reaction of 3,4-methylenedioxybenzylamine with 4-chloro-2-(isoxazol-5-yl)-6-ethyl-thieno-[2,3-d]-pyrimidine yields 2-(isoxasol-5-yl)-4-(3,4-methylenedioxybenzylamino-6-ethyl-thieno-[2,3-d]-pyrimidine.

EXAMPLE 547

With the procedure of Example 1, the reaction of 3,4-methylenedioxybenzylamine with 4-chloro-2-(isoxazol-5-yl)-6-chloro-thieno-[2,3-d]-pyrimidine yields 2-(isoxasol-5-yl)-4-(3,4-methylenedioxybenzylamino-6-chloro-thieno-[2,3-d]-pyrimidine.

EXAMPLE 548

With the procedure of Example 1, the reaction of 3,4-methylenedioxybenzylamine with 4-chloro-2-(isoxazol-5-yl)-5-chloro-6-methyl-thieno-[2,3-d]-pyrimidine yields 2-(isoxasol-5-yl)-4-(3,4-methylenedioxybenzylamino-5-chlror-6-methyl-thieno-[2,3-d]-pyrimidine.

EXAMPLE 549

With the procedure of Example 1, the reaction of 3,4-methylenedioxybenzylamine with 4-chloro-2-(isoxazol-5-yl)-6-nitro-thieno-[2,3-d]-pyrimidine yields 2-(isoxasol-5-yl)-4-(3,4-methylenedioxybenzylamino-6-nitro-thieno-[2,3-d]-pyrimidine.

EXAMPLE 550

With the procedure of Example 1, the reaction of 3,4-methylenedioxybenzylamine with 4-chloro-2-(isoxazol-5-yl)-5,6-dimethyl-thieno-[2,3-d]-pyrimidine yields 2-(isoxasol-5-yl)-4-(3,4-methylenedioxybenzylamino-5,6-dimethyl-thieno-[2,3-d]-pyrimidine.

EXAMPLE 551

With the procedure of Example 1, the reaction of 3,4-methylenedioxybenzylamine with 4-chloro-2-(isoxazol-5-yl)-6-trifluormethyl-thieno-[2,3-d]-pyrimidine yields 2-(isoxasol-5-yl)-4-(3,4-methylenedioxybenzylamino-6-trifluoromethyl-thieno-[2,3-d]-pyrimidine.

EXAMPLE 552

With the procedure of Example 1, the reaction of 3,4-methylenedioxybenzylamine with 4-chloro-2-(pyrazin-2-yl)-6-methyl-thieno-[2,3-d]-pyrimidine yields 2-(pyrazin-2-yl)-4-(3,4-methylenedioxybenzylamino-6-methyl-thieno-[2,3-d]-pyrimidine.

EXAMPLE 553

With the procedure of Example 1, the reaction of 3,4-methylenedioxybenzylamine with 4-chloro-2-(pyrazin-2-yl)-5-methyl-thieno-[2,3-d]-pyrimidine yields 2-(pyrazin-2-yl)-4-(3,4-methylenedioxybenzylamino-5-methyl-thieno-[2,3-d]-pyrimidine.

EXAMPLE 554

With the procedure of Example 1, the reaction of 3,4-methylenedioxybenzylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-methylenedioxybenzylamino-5,6,7,8-tetrahydro-thieno-[2,3-d]-pyrimidine.

EXAMPLE 555

With the procedure of Example 1, the reaction of 3,4-methylenedioxybenzylamine with 4-chloro-2-(pyrazin-2-yl)-5,6-cyclopenteno-thieno-[2,3-d]-pyrimidine yields 2-(pyrazin-2-yl)4-(3,4-methylenedioxybenzylamino-5,6-cyclopenteno-thieno-[2,3-d]-pyrimidine.

EXAMPLE 556

With the procedure of Example 1, the reaction of 3,4-methylenedioxybenzylamine with 4-chloro-2-(pyrazin-2-yl)-5,6-cyclohepteno-thieno-[2,3-d]-pyrimidine yields 2-(pyrazin-2-yl)-4-(3,4-methylenedioxybenzylamino-5,6-cyclohepteno-thieno-[2,3-d]-pyrimidine.

EXAMPLE 557

With the procedure of Example 1, the reaction of 3,4-methylenedioxybenzylamine with 4-chloro-2-(pyrazin-2-yl)-6-ethyl-thieno-[2,3-d]-pyrimidine yields 2-(pyrazin-2-yl)-4-(3,4-methylenedioxybenzylamino-6-ethyl-thieno-[2,3-d]-pyrimidine.

EXAMPLE 558

With the procedure of Example 1, the reaction of 3,4-methylenedioxybenzylamine with 4-chloro-2-(pyrazin-2-yl)-6-chloro-thieno-[2,3-d]-pyrimidine yields 2-(pyrazin-2-yl)-4-(3,4-methylenedioxybenzylamino-6-chloro-thieno-[2,3-d]-pyrimidine.

EXAMPLE 559

With the procedure of Example 1, the reaction of 3,4-methylenedioxybenzylamine with 4-chloro-2-(pyrazin-2-yl)-5-chloro-6-thieno-[2,3-d]-pyrimidine yields 2-(pyrazin-2-yl)-4-(3,4-methylenedioxybenzylamino-5-chloro-thieno-[2,3-d]-pyrimidine.

EXAMPLE 560

With the procedure of Example 1, the reaction of 3,4-methylenedioxybenzylamine with 4-chloro-2-(pyrazin-2-yl)-6-nitro-thieno-[2,3-d]-pyrimidine yields 2-(pyrazin-2-yl)-4-(3,4-methylenedioxybenzylamino-6-nitro-thieno-[2,3-d]-pyrimidine.

EXAMPLE 561

With the procedure of Example 1, the reaction of 3,4-methylenedioxybenzylamine with 4-chloro-2-(pyrazin-2-yl)-5,6-dimethyl-thieno-[2,3-d]-pyrimidine yields 2-(pyrazin-2-yl)-4-(3,4-methylenedioxybenzylamino-5,6-dimethyl-thieno-[2,3-d]-pyrimidine.

EXAMPLE 562

With the procedure of Example 1, the reaction of 3,4-methylenedioxybenzylamine with 4-chloro-2-(pyrazin-2- yl)-6-trifluoromethyl-thieno-[2,3-d]-pyrimidine yields 2-(pyrazin-2-yl)-4-(3,4-methylenedioxybenzylamino-6-trifluoromethyl-thieno-[2,3-d]-pyrimidine.

EXAMPLE 563

With the procedure of Example 1, the reaction of 3,4-methylenedioxybenzylamine with 4-chloro-2-(pyridin-2-yl)-6-methyl-thieno-[2,3-d]-pyrimidine yields 2-(pyridin-2-yl)-4-(3,4-methylenedioxybenzylamino-6-methyl-thieno-[2,3-d]-pyrimidine.

EXAMPLE 564

With the procedure of Example 1, the reaction of 3,4-methylenedioxybenzylamine with 4-chloro-2-(pyridin-2-yl)-5-methyl-thieno-[2,3-d]-pyrimidine yields 2-(pyridin-2-yl)-4-(3,4-methylenedioxybenzylamino-5-methyl-thieno-[2,3-d]-pyrimidine.

EXAMPLE 565

With the procedure of Example 1, the reaction of 3,4-methylenedioxybenzylamine with 4-chloro-2-(pyridin-2-yl)-5,6,7,8-tetrahydro-[1]-benzothieno-[2,3-d]-pyrimidine yields 2-(pyridin-2-yl)-4-(3,4-methylenedioxybenzylamino-5,6,7,8-tetrahydro-thieno-[2,3-d]-pyrimidine.

EXAMPLE 566

With the procedure of Example 1, the reaction of 3,4-methylenedioxybenzylamine with 4-chloro-2-(pyridin-2-yl)-5,6-cyclopenteno-thieno-[2,3-d]-pyrimidine yields 2-(pyridin-2-yl)-4-(3,4-methylenedioxybenzylamino-5,6-cyclopenteno-thieno-[2,3-d]-pyrimidine.

EXAMPLE 567

With the procedure of Example 1, the reaction of 3,4-methylenedioxybenzylamine with 4-chloro-2-(pyridin-2-yl)-5,6-cyclohepteno-thieno-[2,3-d]-pyrimidine yields 2-(pyridin-2-yl)-4-(3,4-methylenedioxybenzylamino-5,6-cyclohepteno-thieno-[2,3-d]-pyrimidine.

EXAMPLE 568

With the procedure of Example 1, the reaction of 3,4-methylenedioxybenzylamine with 4-chloro-2-(pyridin-2-yl)-6-ethyl-thieno-[2,3-d]-pyrimidine yields 2-(pyridin-2-yl)-4-(3,4-methylenedioxybenzylamino-6-ethyl-thieno-[2,3-d]-pyrimidine.

EXAMPLE 569

With the procedure of Example 1, the reaction of 3,4-methylenedioxybenzylamine with 4-chloro-2-(pyridin-2-yl)-6-chloro-thieno-[2,3-d]-pyrimidine yields 2-(pyridin-2-yl)-4-(3,4-methylenedioxybenzylamino-6-chloro-thieno-[2,3-d]-pyrimidine.

EXAMPLE 570

With the procedure of Example 1, the reaction of 3,4-methylenedioxybenzylamine with 4-chloro-2-(pyridin-2-yl)-5-chloro-6-methyl-thieno-[2,3-d]-pyrimidine yields 2-(pyridin-2-yl)-4-(3,4-methylenedioxybenzylamino-5-chloro-thieno-[2,3-d]-pyrimidine.

EXAMPLE 571

With the procedure of Example 1, the reaction of 3,4-methylenedioxybenzylamine with 4-chloro-2-(pyridin-2-yl)-5,6-dimethyl-thieno-[2,3-d]-pyrimidine yields 2-(pyridin-2-yl)-4-(3,4-methylenedioxybenzylamino-5,6-dimethyl-thieno-[2,3-d]-pyrimidine.

EXAMPLE 572

With the procedure of Example 1, the reaction of 3,4-methylenedioxybenzylamine with 4-chloro-2-(pyridin-2-yl)-6-trifluoromethyl-thieno-[2,3-d]-pyrimidine yields 2-(pyridin-2-yl)-4-(3,4-methylenedioxybenzylamino-6-triflurormethyl-thieno-[2,3-d]-pyrimidine.

EXAMPLE 573

With the procedure of Example 1, the reaction of 3,4-methylenedioxybenzylamine with 4-chloro-2-(pyridin-4-yl)-6-methyl-thieno-[2,3-d]-pyrimidine yields 2-(pyridin-4-yl)-4-(3,4-methylenedioxybenzylamino-6-methyl-thieno-[2,3-d]-pyrimidine.

EXAMPLE 574

With the procedure of Example 1, the reaction of 3,4-methylenedioxybenzylamine with 4-chloro-2-(pyridin-4-yl)-5-methyl-thieno-[2,3-d]-pyrimidine yields 2-(pyridin-4-yl)-4-(3,4-methylenedioxybenzylamino-5-methyl-thieno-[2,3-d]-pyrimidine.

EXAMPLE 575

With the procedure of Example 1, the reaction of 3,4-methylenedioxybenzylamine with 4-chloro-2-(pyridin-4-yl)-5,6,7,8-tetrahydro-[1]-benzothieno-[2,3-d]-pyrimidine yields 2-(pyridin-4-yl)-4-(3,4-methylenedioxybenzylamino-5,6,7,8-tetrahydro-thieno-[2,3-d]-pyrimidine.

EXAMPLE 576

With the procedure of Example 1, the reaction of 3,4-methylenedioxybenzylamine with 4-chloro-2-(pyridin-4-yl)-5,6-cyclopenteno-thieno-[2,3-d]-pyrimidine yields 2-(pyridin-4-yl)-4-(3,4-methylenedioxybenzylamino-5,6-cyclopenteno-thieno-[2,3-d]-pyrimidine.

EXAMPLE 577

With the procedure of Example 1, the reaction of 3,4-methylenedioxybenzylamine with 4-chloro-2-(pyridin-4-yl)-5,6-cyclohepteno-thieno-[2,3-d]-pyrimidine yields 2-(pyridin-4-yl)-4-(3,4-methylenedioxybenzylamino-5,6-cyclohepteno-thieno-[2,3-d]-pyrimidine.

EXAMPLE 578

With the procedure of Example 1, the reaction of 3,4-methylenedioxybenzylamine with 4-chloro-2-(pyridin-4-yl)-6-ethyl-thieno-[2,3-d]-pyrimidine yields -4 []2-(pyridin-4-yl)-4-(3,4-methylenedioxybenzylamino-6-ethyl-thieno-[2,3-d]-pyrimidine.

EXAMPLE 579

With the procedure of Example 1, the reaction of 3,4-methylenedioxybenzylamine with 4-chloro-2-(pyridin-4-yl)-6-chloro-thieno-[2,3-d]-pyrimidine yields 2-(pyridin-4-yl)-4-(3,4-methylenedioxybenzylamino-6-chloro-thieno-[2,3-d]-pyrimidine.

EXAMPLE 580

With the procedure of Example 1, the reaction of 3,4-methylenedioxybenzylamine with 4-chloro-2-(pyridin-4- yl)-5-chloro-6-methyl-thieno-[2,3-d]-pyrimidine yields 2-(pyridin-4-yl)-4-(3,4-methylenedioxybenzylamino-5-chlror-6-methyl-thieno-[2,3-d]-pyrimidine.

EXAMPLE 581

With the procedure of Example 1, the reaction of 3,4-methylenedioxybenzylamine with 4-chloro-2-(pyridin-4-yl)-6-nitro-thieno-[2,3-d]-pyrimidine yields 2-(pyridin-4-yl)-4-(3,4-methylenedioxybenzylamino-6-nitro-thieno-[2,3-d]-pyrimidine.

EXAMPLE 582

With the procedure of Example 1, the reaction of 3,4-methylenedioxybenzylamine with 4-chloro-2-(pyridin-4-yl)-5,6-dimethyl-thieno-[2,3-d]-pyrimidine yields 2-(pyridin-4-yl)-4-(3,4-methylenedioxybenzylamino-5,6-dimethyl-thieno-[2,3-d]-pyrimidine.

EXAMPLE 583

With the procedure of Example 1, the reaction of 3,4-methylenedioxybenzylamine with 4-chloro-2-(pyridin-4-yl)-6-trifluoromethyl-thieno-[2,3-d]-pyrimidine yields 2-(pyridin-4-yl)-4-(3,4-methylenedioxybenzylamino-6-trifluoromethyl-thieno-[2,3-d]-pyrimidine.

EXAMPLE 584

With the procedure of Example 1, the reaction of 3,4-dimethoxy-benzylamine with 4-chloro-2-(pyridin-3-yl)-6-methyl-thieno-[2,3-d]-pyrimidine yields 2-(pyridin-3-yl)-4-(3,4-dimethoxybenzylamino-6-methyl-thieno-[2,3-d]-pyrimidine.

EXAMPLE 585

With the procedure of Example 1, the reaction of 3,4-dimethoxy-benzylamine with 4-chloro-2-(pyridin-3-yl)-5-methyl-thieno-[2,3-d]-pyrimidine yields 2-(pyridin-3-yl)-4-(3,4-dimethoxybenzylamino-5-methyl-thieno-[2,3-d]-pyrimidine.

EXAMPLE 586

With the procedure of Example 1, the reaction of 3,4-dimethoxy-benzylamine with 4-chloro-2-(pyridin-3-yl)-5,6,7,8-tetrahydro-[1]-benzothieno-[2,3-d]-pyrimidine yields 2-(pyridin-3-yl)-4-(3,4-dimethoxybenzylamino-5,6,7,8-tetrahydro-thieno-[2,3-d]-pyrimidine.

EXAMPLE 587

With the procedure of Example 1, the reaction of 3,4-dimethoxy-benzylamine with 4-chloro-2-(pyridin-3-yl)-5,6-cyclopenteno-thieno-[2,3-d]-pyrimidine yields 2-(pyridin-3-yl)-4-(3,4-dimethoxybenzylamino-5,6-cyclopenteno-thieno-[2,3-d]-pyrimidine.

EXAMPLE 588

With the procedure of Example 1, the reaction of 3,4-dimethoxy-benzylamine with 4-chloro-2-(pyridin-3-yl)-5,6-cyclohepteno-thieno-[2,3-d]-pyrimidine yields 2-(pyridin-3-yl)-4-(3,4-dimethoxybenzylamino-5,6-cyclohepteno-thieno-[2,3-d]-pyrimidine.

EXAMPLE 589

With the procedure of Example 1, the reaction of 3,4-dimethoxy-benzylamine with 4-chloro-2-(pyridin-3-yl)-6-ethyl-thieno-[2,3-d]-pyrimidine yields 2-(pyridin-3-yl)-4-(3,4-dimethoxybenzylamino-6-ethyl-thieno-[2,3-d]-pyrimidine.

EXAMPLE 590

With the procedure of Example 1, the reaction of 3,4-dimethoxy-benzylamine with 4-chloro-2-(pyridin-3-yl)-6-chloro-thieno-[2,3-d]-pyrimidine yields 2-(pyridin-3-yl)-4-(3,4-dimethoxybenzylamino-6-chloro-thieno-[2,3-d]-pyrimidine.

EXAMPLE 591

With the procedure of Example 1, the reaction of 3,4-dimethoxy-benzylamine with 4-chloro-2-(pyridin-3-yl)-5-chloro-6-methyl-thieno-[2,3-d]-pyrimidine yields 2-(pyridin-3-yl)-4-(3,4-dimethoxybenzylamino-5-chlror-6-methyl-thieno-[2,3-d]-pyrimidine.

EXAMPLE 592

With the procedure of Example 1, the reaction of 3,4-dimethoxy-benzylamine with 4-chloro-2-(pyridin-3-yl)-6-nitro-thieno-[2,3-d]-pyrimidine yields 2-(pyridin-3-yl)-4-(3,4-dimethoxybenzylamino-6-nitro-thieno-[2,3-d]-pyrimidine.

EXAMPLE 593

With the procedure of Example 1, the reaction of 3,4-dimethoxy-benzylamine with 4-chloro-2-(pyridin-3-yl)-5,6-dimethyl-thieno-[2,3-d]-pyrimidine yields 2-(pyridin-3-yl)-4-(3,4-dimethoxybenzylamino-5,6-dimethyl-thieno-[2,3-d]-pyrimidine.

EXAMPLE 594

With the procedure of Example 1, the reaction of 3,4-dimethoxy-benzylamine with 4-chloro-2-(pyridin-3-yl)-6-trifluoromethyl-thieno-[2,3-d]-pyrimidine yields 2-(pyridin-3-yl)-4-(3,4-dimethoxybenzylamino-6-trifluoromethyl-thieno-[2,3-d]-pyrimidine.

EXAMPLE 595

With the procedure of Example 1, the reaction of 3,4-dimethoxy-benzylamine with 4-chloro-2-(isoxazol-5-yl)-6-methyl-thieno-[2,3-d]-pyrimidine yields 2-(isoxazol-5-yl)-4-(3,4-dimethoxybenzylamino-6-methyl-thieno-[2,3-d]-pyrimidine.

EXAMPLE 596

With the procedure of Example 1, the reaction of 3,4-dimethoxy-benzylamine with 4-chloro-2-(isoxazol-5-yl)-5-methyl-thieno-[2,3-d]-pyrimidine yields 2-(isoxazol-5-yl)-4-(3,4-dimethoxybenzylamino-5-methyl-thieno-[2,3-d]-pyrimidine.

EXAMPLE 597

With the procedure of Example 1, the reaction of 3,4-dimethoxy-benzylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-dimethoxybenzylamino-5,6,7,8-tetrahydro-thieno-[2,3-d]-pyrimidine.

EXAMPLE 598

With the procedure of Example 1, the reaction of 3,4-dimethoxy-benzylamine with 4-chloro-2-(isoxazol-5-yl)-5, 6-cyclopenteno-thieno-[2,3-d]-pyrimidine yields 2-(isoxazol-5-yl)-4-(3,4-dimethoxybenzylamino-5,6-cyclopenteno-thieno-[2,3-d]-pyrimidine.

EXAMPLE 599

With the procedure of Example 1, the reaction of 3,4-dimethoxy-benzylamine with 4-chloro-2-(isoxazol-5-yl)-5,6-cyclohepteno-thieno-[2,3-d]-pyrimidine yields 2-(isoxazol-5-yl)-4-(3,4-dimethoxybenzylamino-5,6-cyclohepteno-thieno-[2,3-d]-pyrimidine.

EXAMPLE 600

With the procedure of Example 1, the reaction of 3,4-dimethoxy-benzylamine with 4-chloro-2-(isoxazol-5-yl)-6-ethyl-thieno-[2,3-d]-pyrimidine yields 2-(isoxazol-5-yl)-4-(3,4-dimethoxybenzylamino-6-ethyl-thieno-[2,3-d]-pyrimidine.

EXAMPLE 601

With the procedure of Example 1, the reaction of 3,4-dimethoxy-benzylamine with 4-chloro-2-(isoxazol-5-yl)-6-chloro-thieno-[2,3-d]-pyrimidine yields 2-(isoxazol-5-yl)-4-(3,4-dimethoxybenzylamino-6-chloro-thieno-[2,3-d]-pyrimidine.

EXAMPLE 602

With the procedure of Example 1, the reaction of 3,4-dimethoxy-benzylamine with 4-chloro-2-(isoxazol-5-yl)-5-chloro-6-methyl-thieno-[2,3-d]-pyrimidine yields 2-(isoxazol-5-yl)-4-(3,4-dimethoxybenzylamino-5-chlror-6-methyl-thieno-[2,3-d]-pyrimidine.

EXAMPLE 603

With the procedure of Example 1, the reaction of 3,4-dimethoxy-benzylamine with 4-chloro-2-(isoxazol-5-yl)-6-nitro-thieno-[2,3-d]-pyrimidine yields 2-(isoxazol-5-yl)-4-(3,4-dimethoxybenzylamino-6-nitro-thieno-[2,3-d]-pyrimidine.

EXAMPLE 604

With the procedure of Example 1, the reaction of 3,4-dimethoxy-benzylamine with 4-chloro-2-(isoxazol-5-yl)-5,6-dimethyl-thieno-[2,3-d]-pyrimidine yields 2-(isoxazol-5-yl)-4-(3,4-dimethoxybenzylamino-5,6-dimethyl-thieno-[2,3-d]-pyrimidine

EXAMPLE 605

With the procedure of Example 1, the reaction of 3,4-dimethoxy-benzylamine with 4-chloro-2-(isoxazol-5-yl)-6-trifluoromethyl-thieno-[2,3-d]-pyrimidine yields 2-(isoxazol-5-yl)-4-(3,4-dimethoxybenzylamino-6-trifluoromethyl-thieno-[2,3-d]-pyrimidine.

EXAMPLE 606

With the procedure of Example 1, the reaction of 3,4-dimethoxy-benzylamine with 4-chloro-2-(pyrazin-2-yl)-6-methyl-thieno-[2,3-d]-pyrimidine yields 2-(pyrazin-2-yl)-4-(3,4-dimethoxybenzylamino-6-methyl-thieno-[2,3-d]-pyrimidine.

EXAMPLE 607

With the procedure of Example 1, the reaction of 3,4-dimethoxy-benzylamine with 4-chloro-2-(pyrazin-2-yl)-5-methyl-thieno-[2,3-d]-pyrimidine yields 2-(pyrazin-2-yl)-4-(3,4-dimethoxybenzylamino-5-methyl-thieno-[2,3-d]-pyrimidine.

EXAMPLE 608

With the procedure of Example 1, the reaction of 3,4-dimethoxy-benzylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-dimethoxybenzylamino-5,6,7,8-tetrahydro-thieno-[2,3-d]-pyrimidine.

EXAMPLE 609

With the procedure of Example 1, the reaction of 3,4-dimethoxy-benzylamine with 4-chloro-2-(pyrazin-2-yl)-5,6-cyclopenteno-thieno-[2,3-d]-pyrimidine yields 2-(pyrazin-2-yl)-4-(3,4-dimethoxybenzylamino-5,6-cyclopenteno-thieno-[2,3-d]-pyrimidine.

EXAMPLE 610

With the procedure of Example 1, the reaction of 3,4-dimethoxy-benzylamine with 4-chloro-2-(pyrazin-2-yl)-5,6-cyclohepteno-thieno-[2,3-d]-pyrimidine yields 2-(pyrazin-2-yl)-4-(3,4-dimethoxybenzylamino-5,6-cyclohepteno-thieno-[2,3-d]-pyrimidine.

EXAMPLE 611

With the procedure of Example 1, the reaction of 3,4-dimethoxy-benzylamine with 4-chloro-2-(pyrazin-2-yl)-6-ethyl-thieno-[2,3-d]-pyrimidine yields 2-(pyrazin-2-yl)-4-(3,4-dimethoxybenzylamino-6-ethyl-thieno-[2,3-d]-pyrimidine.

EXAMPLE 612

With the procedure of Example 1, the reaction of 3,4-dimethoxy-benzylamine with 4-chloro-2-(pyrazin-2-yl)-6-chloro-thieno-[2,3-d]-pyrimidine yields Be. 2-(pyrazin-2-yl)-4-(3,4-dimethoxybenzylamino-6-chloro-thieno-[2,3-d]-pyrimidine.

EXAMPLE 613

With the procedure of Example 1, the reaction of 3,4-dimethoxy-benzylamine with 4-chloro-2-(pyrazin-2-yl)-5-chloro-6-methyl-thieno-[2,3-d]-pyrimidine yields 2-(pyrazin-2-yl)-4-(3,4-dimethoxybenzylamino-5-chlror-6-methyl-thieno-[2,3-d]-pyrimidine.

EXAMPLE 614

With the procedure of Example 1, the reaction of 3,4-dimethoxy-benzylamine with 4-chloro-2-(pyrazin-2-yl)-6-nitro-thieno-[2,3-d]-pyrimidine yields 2-(pyrazin-2-yl)-4-(3,4-dimethoxybenzylamino-6-nitro-thieno-[2,3-d]-pyrimidine.

EXAMPLE 615

With the procedure of Example 1, the reaction of 3,4-dimethoxy-benzylamine with 4-chloro-2-(pyrazin-2-yl)-5,6-dimethyl-thieno-[2,3-d]-pyrimidine yields 2-(pyrazin-2-yl)-4-(3,4-dimethoxybenzylamino-5,6-dimethyl-thieno-[2,3-d]-pyrimidine.

EXAMPLE 616

With the procedure of Example 1, the reaction of 3,4-dimethoxy-benzylamine with 4-chloro-2-(pyrazin-2-yl)-6- trifluoromethyl-thieno-[2,3-d]-pyrimidine yields 2-(pyrazin-2-yl)-4-(3,4-dimethoxybenzylamino-6-trifluoromethyl-thieno-[2,3-d]-pyrimidine.

EXAMPLE 617

With the procedure of Example 1, the reaction of 3,4-dimethoxy-benzylamine with 4-chloro-2-(pyridin-2-yl)-6-methyl-thieno-[2,3-d]-pyrimidine yields 2-(pyridin-2-yl)-4-(3,4-dimethoxybenzylamino-6-methyl-thieno-[2,3-d]-pyrimidine.

EXAMPLE 618

With the procedure of Example 1, the reaction of 3,4-dimethoxy-benzylamine with 4-chloro-2-(pyridin-2-yl)-5-methyl-thieno-[2,3-d]-pyrimidine yields 2-(pyridin-2-yl)-4-(3,4-dimethoxybenzylamino-5-methyl-thieno-[2,3-d]-pyrimidine.

EXAMPLE 619

With the procedure of Example 1, the reaction of 3,4-dimethoxy-benzylamine with 4-chloro-2-(pyridin-2-yl)-5,6,7,8-tetrahydro-[1]-benzothieno-[2,3-d]-pyrimidine yields 2-(pyridin-2-yl)-4-(3,4-dimethoxybenzylamino-5,6,7,8-tetrahydro-thieno-[2,3-d]-pyrimidine.

EXAMPLE 620

With the procedure of Example 1, the reaction of 3,4-dimethoxy-benzylamine with 4-chloro-2-(pyridin-2-yl)-5,6-cyclopenteno-thieno-[2,3-d]-pyrimidine yields 2-(pyridin-2-yl)-4-(3,4-dimethoxybenzylamino-5,6-cyclopenteno-thieno-[2,3-d]-pyrimidine.

EXAMPLE 621

With the procedure of Example 1, the reaction of 3,4-dimethoxy-benzylamine with 4-chloro-2-(pyridin-2-yl)-5,6-cyclohepteno-thieno-[2,3-d]-pyrimidine yields 2-(pyridin-2-yl)-4-(3,4-dimethoxybenzylamino-5,6-cyclohepteno-thieno-[2,3-d]-pyrimidine.

EXAMPLE 622

With the procedure of Example 1, the reaction of 3,4-dimethoxy-benzylamine with 4-chloro-2-(pyridin-2-yl)-6-ethyl-thieno-[2,3-d]-pyrimidine yields 2-(pyridin-2-yl)-4-(3,4-dimethoxybenzylamino-6-ethyl-thieno-[2,3-d]-pyrimidine.

EXAMPLE 623

With the procedure of Example 1, the reaction of 3,4-dimethoxy-benzylamine with 4-chloro-2-(pyridin-2-yl)-6-chloro-thieno-[2,3-d]-pyrimidine yields 2-(pyridin-2-yl)-4-(3,4-dimethoxybenzylamino-6-chloro-thieno-[2,3-d]-pyrimidine.

EXAMPLE 624

With the procedure of Example 1, the reaction of 3,4-dimethoxy-benzylamine with 4-chloro-2-(pyridin-2-yl)-5-chloro-6-methyl-thieno-[2,3-d]-pyrimidine yields 2-(pyridin-2-yl)-4-(3,4-dimethoxybenzylamino-5-chlror-6-methyl-thieno-[2,3-d]-pyrimidine.

EXAMPLE 625

With the procedure of Example 1, the reaction of 3,4-dimethoxy-benzylamine with 4-chloro-2-(pyridin-2-yl)-6-nitro-thieno-[2,3-d]-pyrimidine yields 2-(pyridin-2-yl)-4-(3,4-dimethoxybenzylamino-6-nitro-thieno-[2,3-d]-pyrimidine.

EXAMPLE 626

With the procedure of Example 1, the reaction of 3,4-dimethoxy-benzylamine with 4-chloro-2-(pyridin-2-yl)-5,6-dimethyl-thieno-[2,3-d]-pyrimidine yields 2-(pyridin-2-yl)-4-(3,4-dimethoxybenzylamino-5,6-dimethyl-thieno-[2,3-d]-pyrimidine.

EXAMPLE 627

With the procedure of Example 1, the reaction of 3,4-dimethoxy-benzylamine with 4-chloro-2-(pyridin-2-yl)-6-trifluoromethyl-thieno-[2,3-d]-pyrimidine yields 2-(pyridin-2-yl)-4-(3,4-dimethoxybenzylamino-6-trifluoromethyl-thieno-[2,3-d]-pyrimidine.

EXAMPLE 628

With the procedure of Example 1, the reaction of 3,4-dimethoxy-benzylamine with 4-chloro-2-(pyridin-4-yl)-6-methyl-thieno-[2,3-d]-pyrimidine yields 2-(pyridin-4-yl)-4-(3,4-dimethoxybenzylamino-6-methyl-thieno-[2,3-d]-pyrimidine.

EXAMPLE 629

With the procedure of Example 1, the reaction of 3,4-dimethoxy-benzylamine with 4-chloro-2-(pyridin-4-yl)-5-methyl-thieno-[2,3-d]-pyrimidine yields 2-(pyridin-4-yl)-4-(3,4-dimethoxybenzylamino-5-methyl-thieno-[2,3-d]-pyrimidine.

EXAMPLE 630

With the procedure of Example 1, the reaction of 3,4-dimethoxy-benzylamine with 4-chloro-2-(pyridin-4-yl)-5,6,7,8-tetrahydro-[1]-benzothieno-[2,3-d]-pyrimidine yields 2-(pyridin-4-yl)-4-(3,4-dimethoxybenzylamino-5,6,7,8-tetrahydro-thieno-[2,3-d]-pyrimidine.

EXAMPLE 631

With the procedure of Example 1, the reaction of 3,4-dimethoxy-benzylamine with 4-chloro-2-(pyridin-4-yl)-5,6-cyclopenteno-thieno-[2,3-d]-pyrimidine yields 2-(pyridin-4-yl)-4-(3,4-dimethoxybenzylamino-5,6-cyclopenteno-thieno-[2,3-d]-pyrimidine.

EXAMPLE 632

With the procedure of Example 1, the reaction of 3,4-dimethoxy-benzylamine with 4-chloro-2-(pyridin-4-yl)-5,6-cyclohepteno-thieno-[2,3-d]-pyrimidine yields 2-(pyridin-4-yl)-4-(3,4-dimethoxybenzylamino-5,6-cyclohepteno-thieno-[2,3-d]-pyrimidine.

EXAMPLE 633

With the procedure of Example 1, the reaction of 3,4-dimethoxy-benzylamine with 4-chloro-2-(pyridin-4-yl)-6-ethyl-thieno-[2,3-d]-pyrimidine yields 2-(pyridin-4-yl)-4-(3,4-dimethoxybenzylamino-6-ethyl-thieno-[2,3-d]-pyrimidine.

EXAMPLE 634

With the procedure of Example 1, the reaction of 3,4-dimethoxy-benzylamine with 4-chloro-2-(pyridin-4-yl)-6- chloro-thieno-[2,3-d]-pyrimidine yields 2-(pyridin-4-yl)-4-(3,4-dimethoxybenzylamino-6-chloro-thieno-[2,3-d]-pyrimidine.

EXAMPLE 635

With the procedure of Example 1, the reaction of 3,4-dimethoxy-benzylamine with 4-chloro-2-(pyridin-4-yl)-5-chloro-6-methyl-thieno-[2,3-d]-pyrimidine yields 2-(pyridin-4-yl)-4-(3,4-dimethoxybenzylamino-5-chlror-6-methyl-thieno-[2,3-d]-pyrimidine.

EXAMPLE 636

With the procedure of Example 1, the reaction of 3,4-dimethoxy-benzylamine with 4-chloro-2-(pyridin-4-yl)-6-nitro-thieno-[2,3-d]-pyrimidine yields 2-(pyridin-4-yl)-4-(3,4-dimethoxybenzylamino-6-nitro-thieno-[2,3-d]-pyrimidine.

EXAMPLE 637

With the procedure of Example 1, the reaction of 3,4-dimethoxy-benzylamine with 4-chloro-2-(pyridin-4-yl)-5,6-dimethyl-thieno-[2,3-d]-pyrimidine yields 2-(pyridin-4-yl)-4-(3,4-dimethoxybenzylamino-5,6-dimethyl-thieno-[2,3-d]-pyrimidine.

EXAMPLE 638

With the procedure of Example 1, the reaction of 3,4-dimethoxy-benzylamine with 4-chloro-2-(pyridin-4-yl)-6-trifluoromethyl-thieno-[2,3-d]-pyrimidine yields 2-(pyridin-4-yl)-4-(3,4-dimethoxybenzylamino-6-trifluoromethyl-thieno-[2,3-d]-pyrimidine.

EXAMPLE 639

With the procedure of Example 1, the reaction of 3,4-dimethoxy-benzylamine with 4-chloro-2-(pyridin-3-yl)-6-methyl-thieno-[2,3-d]-pyrimidine yields 2-(pyridin-3-yl)-4-(3,4-dimethoxybenzylamino-6-methyl-thieno-[2,3-d]-pyrimidine.

EXAMPLE 640

With the procedure of Example 1, the reaction of 3,4-dimethoxy-benzylamine with 4-chloro-2-(pyridin-3-yl)-5-methyl-thieno-[2,3-d]-pyrimidine yields 2-(pyridin-3-yl)-4-(3,4-dimethoxybenzylamino-5-methyl-thieno-[2,3-d]-pyrimidine.

EXAMPLE 641

With the procedure of Example 1, the reaction of 3,4-dimethoxy-benzylamine with 4-chloro-2-(pyridin-3-yl)-5,6,7,8-tetrahydro-[1]-benzothieno-[2,3-d]-pyrimidine yields 2-(pyridin-3-yl)-4-(3,4-dimethoxybenzylamino-5,6,7,8-tetrahydro-thieno-[2,3-d]-pyrimidine.

EXAMPLE 642

With the procedure of Example 1, the reaction of 3,4-dimethoxy-benzylamine with 4-chloro-2-(pyridin-3-yl)-5,6-cyclopenteno-thieno-[2,3-d]-pyrimidine yields 2-(pyridin-3-yl)-4-(3,4-dimethoxybenzylamino-5,6-cyclopenteno-thieno-[2,3-d]-pyrimidine.

EXAMPLE 643

With the procedure of Example 1, the reaction of 3,4-dimethoxy-benzylamine with 4-chloro-2-(pyridin-3-yl)-5,6-cyclohepteno-thieno-[2,3-d]-pyrimidine yields 2-(pyridin-3-yl)-4-(3,4-dimethoxybenzylamino-5,6-cyclohepteno-thieno-[2,3-d]-pyrimidine.

EXAMPLE 644

With the procedure of Example 1, the reaction of 3,4-dimethoxy-benzylamine with 4-chloro-2-(pyridin-3-yl)-6-ethyl-thieno-[2,3-d]-pyrimidine yields 2-(pyridin-3-yl)-4-(3,4-dimethoxybenzylamino-6-ethyl-thieno-[2,3-d]-pyrimidine.

EXAMPLE 645

With the procedure of Example 1, the reaction of 3,4-dimethoxy-benzylamine with 4-chloro-2-(pyridin-3-yl)-6-chloro-thieno-[2,3-d]-pyrimidine yields 2-(pyridin-3-yl)-4-(3,4-dimethoxybenzylamino-6-chloro-thieno-[2,3-d]-pyrimidine.

EXAMPLE 646

With the procedure of Example 1, the reaction of 3,4-dimethoxy-benzylamine with 4-chloro-2-(pyridin-3-yl)-5-chloro-6-methyl-thieno-[2,3-d]-pyrimidine yields 2-(pyridin-3-yl)-4-(3,4-dimethoxybenzylamino-5-chlror-6-methyl-thieno-[2,3-d]-pyrimidine.

EXAMPLE 647

With the procedure of Example 1, the reaction of 3,4-dimethoxy-benzylamine with 4-chloro-2-(pyridin-3-yl)-6-nitro-thieno-[2,3-d]-pyrimidine yields 2-(pyridin-3-yl)-4-(3,4-dimethoxybenzylamino-6-nitro-thieno-[2,3-d]-pyrimidine.

EXAMPLE 648

With the procedure of Example 1, the reaction of 3,4-dimethoxy-benzylamine with 4-chloro-2-(pyridin-3-yl)-5,6-dimethyl-thieno-[2,3-d]-pyrimidine yields 2-(pyridin-3-yl)-4-(3,4-dimethoxybenzylamino-5,6-dimethyl-thieno-[2,3-d]-pyrimidine.

EXAMPLE 649

With the procedure of Example 1, the reaction of 3,4-dimethoxy-benzylamine with 4-chloro-2-(pyridin-3-yl)-6-trifluoromethyl-thieno-[2,3-d]-pyrimidine yields 2 (pyridin-3-yl)-4-(3,4-dimethoxybenzylamino-6-trifluoromethyl-thieno-[2,3-d]-pyrimidine.

EXAMPLE 650

With the procedure of Example 1, the reaction of 3,4-dimethoxy-benzylamine with 4-chloro-2-(isoxazol-5-yl)-6-methyl-thieno-[2,3-d]-pyrimidine yields 2-(isoxazol-5-yl)-4-(3,4-dimethoxybenzylamino-6-methyl-thieno-[2,3-d]-pyrimidine.

EXAMPLE 651

With the procedure of Example 1, the reaction of 3,4-dimethoxy-benzylamine with 4-chloro-2-(isoxazol-5-yl)-5-methyl-thieno-[2,3-d]-pyrimidine yields 2-(isoxazol-5-yl)-4-(3,4-dimethoxybenzylamino-5-methyl-thieno-[2,3-d]-pyrimidine.

EXAMPLE 652

With the procedure of Example 1, the reaction of 3,4-dimethoxy-benzylamine with 4-chloro-2-(isoxazol-5-yl)-5,

EXAMPLE 653

With the procedure of Example 1, the reaction of 3,4-dimethoxy-benzylamine with 4-chloro-2-(isoxazol-5-yl)-5,6-cyclopenteno-thieno-[2,3-d]-pyrimidine yields 2-(isoxazol-5-yl)-4-(3,4-dimethoxybenzylamino-5,6-cyclopenteno-thieno-[2,3-d]-pyrimidine.

EXAMPLE 654

With the procedure of Example 1, the reaction of 3,4-dimethoxy-benzylamine with 4-chloro-2-(isoxazol-5-yl)-5,6-cyclohepteno-thieno-[2,3-d]-pyrimidine yields 2-(isoxazol-5-yl)-4-(3,4-dimethoxybenzylamino-5,6-cyclohepteno-thieno-[2,3-d]-pyrimidine.

EXAMPLE 655

With the procedure of Example 1, the reaction of 3,4-dimethoxy-benzylamine with 4-chloro-2-(isoxazol-5-yl)-6-ethyl-thieno-[2,3-d]-pyrimidine yields 2-(isoxazol-5-yl)-4-(3,4-dimethoxybenzylamino-6-ethyl-thieno-[2,3-d]-pyrimidine.

EXAMPLE 656

With the procedure of Example 1, the reaction of 3,4-dimethoxy-benzylamine with 4-chloro-2-(isoxazol-5-yl)-6-chloro-thieno-[2,3-d]-pyrimidine yields 2-(isoxazol-5-yl)-4-(3,4-dimethoxybenzylamino-6-chloro-thieno-[2,3-d]-pyrimidine.

EXAMPLE 657

With the procedure of Example 1, the reaction of 3,4-dimethoxy-benzylamine with 4 yields 2-(isoxazol-5-yl)-4-(3,4-dimethoxybenzylamino-5-chlror-6-methyl-thieno-[2,3-d]-pyrimidine.

EXAMPLE 658

With the procedure of Example 1, the reaction of 3,4-dimethoxy-benzylamine with 4-chloro-2-(isoxazol-5-yl)-6-nitro-thieno-[2,3-d]-pyrimidine yields 2-(isoxazol-5-yl)-4-(3,4-dimethoxybenzylamino-6-nitro-thieno-[2,3-d]-pyrimidine.

EXAMPLE 659

With the procedure of Example 1, the reaction of 3,4-dimethoxy-benzylamine with 4-chloro-2-(isoxazol-5-yl)-5,6-dimethyl-thieno-[2,3-d]-pyrimidine yields 2-(isoxazol-5-yl)-4-(3,4-dimethoxybenzylamino-5,6-dimethyl-thieno-[2,3-d]-pyrimidine.

EXAMPLE 660

With the procedure of Example 1, the reaction of 3,4-dimethoxy-benzylamine with 4-chloro-2-(isoxazol-5-yl)-6-trifluoromethyl-thieno-[2,3-d]-pyrimidine yields 2-(isoxazol-5-yl)-4-(3,4-dimethoxybenzylamino-6-trifluoromethyl-thieno-[2,3-d]-pyrimidine.

EXAMPLE 661

With the procedure of Example 1, the reaction of 3,4-dimethoxy-benzylamine with 4-chloro-2-(pyrazin-2-yl)-6-methyl-thieno-[2,3-d]-pyrimidine yields 2-(pyrazin-2-yl)-4-(3,4-dimethoxybenzylamino-6-methyl-thieno-[2,3-d]-pyrimidine.

EXAMPLE 662

With the procedure of Example 1, the reaction of 3,4-dimethoxy-benzylamine with 4-chloro-2-(pyrazin-2-yl)-5-methyl-thieno-[2,3-d]-pyrimidine yields 2-(pyrazin-2-yl)-4-(3,4-dimethoxybenzylamino-5-methyl-thieno-[2,3-d]-pyrimidine.

EXAMPLE 663

With the procedure of Example 1, the reaction of 3,4-dimethoxy-benzylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-dimethoxybenzylamino-5,6,7,8-tetrahydro-thieno-[2,3-d]-pyrimidine.

EXAMPLE 664

With the procedure of Example 1, the reaction of 3,4-dimethoxy-benzylamine with 4-chloro-2-(pyrazin-2-yl)-5,6-cyclopenteno-thieno-[2,3-d]-pyrimidine yields 2-(pyrazin-2-yl)-4-(3,4-dimethoxybenzylamino-5,6-cyclopenteno-thieno-[2,3-d]-pyrimidine.

EXAMPLE 665

With the procedure of Example 1, the reaction of 3,4-dimethoxy-benzylamine with 4-chloro-2-(pyrazin-2-yl)-5,6-cyclohepteno-thieno-[2,3-d]-pyrimidine yields 2-(pyrazin-2-yl)-4-(3,4-dimethoxybenzylamino-5,6-cyclohepteno-thieno-[2,3-d]-pyrimidine.

EXAMPLE 666

With the procedure of Example 1, the reaction of 3,4-dimethoxy-benzylamine with 4-chloro-2-(pyrazin-2-yl)-6-ethyl-thieno-[2,3-d]-pyrimidine yields 2-(pyrazin-2-yl)-4-(3,4-dimethoxybenzylamino-6-ethyl-thieno-[2,3-d]-pyrimidine.

EXAMPLE 667

With the procedure of Example 1, the reaction of 3,4-dimethoxy-benzylamine with 4-chloro-2-(pyrazin-2-yl)-6-chloro-thieno-[2,3-d]-pyrimidine yields 2-(pyrazin-2-yl)-4-(3,4-dimethoxybenzylamino-6-chloro-thieno-[2,3-d]-pyrimidine.

EXAMPLE 668

With the procedure of Example 1, the reaction of 3,4-dimethoxy-benzylamine with 4-chloro-2-(pyrazin-2-yl)-5-chloro-6-methyl-thieno-[2,3-d]-pyrimidine yields 2-(pyrazin-2-yl)-4-(3,4-dimethoxybenzylamino-5-chlror-6-methyl-thieno-[2,3-d]-pyrimidine.

EXAMPLE 669

With the procedure of Example 1, the reaction of 3,4-dimethoxy-benzylamine with 4-chloro-2-(pyrazin-2-yl)-6-nitro-thieno-[2,3-d]-pyrimidine yields 2-(pyrazin-2-yl)-4-(3,4-dimethoxybenzylamino-6-nitro-thieno-[2,3-d]-pyrimidine.

EXAMPLE 670

With the procedure of Example 1, the reaction of 3,4-dimethoxy-benzylamine with 4-chloro-2-(pyrazin-2-yl)-5,6-dimethyl-thieno-[2,3-d]-pyrimidine yields 2-(pyrazin-2-yl)-4-(3,4-dimethoxybenzylamino-5,6-dimethyl-thieno-[2,3-d]-pyrimidine.

EXAMPLE 671

With the procedure of Example 1, the reaction of 3,4-dimethoxy-benzylamine with 4-chloro-2-(pyrazin-2-yl)-6-

(continued from previous page: 6,7,8-tetrahydro-[1]-benzothieno-[2,3-d]-pyrimidine yields 2-(isoxazol-5-yl)-4-(3,4-dimethoxybenzylamino-5,6,7,8-tetrahydro-thieno-[2,3-d]-pyrimidine.)

trifluoromethyl-thieno-[2,3-d]-pyrimidine yields 2-(pyrazin-2-yl)-4-(3,4-dimethoxybenzylamino-6-trifluoromethyl-thieno-[2,3-d]-pyrimidine.

EXAMPLE 672

With the procedure of Example 1, the reaction of 3,4-dimethoxy-benzylamine with 4-chloro-2-(pyridin-2-yl)-6-methyl-thieno-[2,3-d]-pyrimidine yields 2-(pyridin-2-yl)-4-(3,4-dimethoxybenzylamino-6-methyl-thieno-[2,3-d]-pyrimidine.

EXAMPLE 673

With the procedure of Example 1, the reaction of 3,4-dimethoxy-benzylamine with 4-chloro-2-(pyridin-2-yl)-5-methyl-thieno-[2,3-d]-pyrimidine yields 2-(pyridin-2-yl)-4-(3,4-dimethoxybenzylamino-5-m ethyl-thieno-[2,3-d]-pyrimidine.

EXAMPLE 674

With the procedure of Example 1, the reaction of 3,4-dimethoxy-benzylamine with 4-chloro-2-(pyridin-2-yl)-5,6,7,8-tetrahydro-[1]-benzothieno-[2,3-d ]-pyrimidine yl (pyridin-2-yl)-4-(3,4-dimethoxybenzylamino-5,6,7,8-tetrahydro-thieno-[2,3-d]-pyrimidine.

EXAMPLE 675

With the procedure of Example 1, the reaction of 3,4-dimethoxy-benzylamine with 4-chloro-2-(pyridin-2-yl)-5,6-cyclopenteno-thieno-[2,3-d]-pyrimidine yields 2-(pyridin-2-yl)-4-(3,4-dimethoxybenzylamino-5,6-cyclopenteno-thieno-[2,3-d]-pyrimidine.

EXAMPLE 676

With the procedure of Example 1, the reaction of 3,4-dimethoxy-benzylamine with 4-chloro-2-(pyridin-2-yl)-5,6-cyclohepteno-thieno-[2,3-d]-pyrimidine yields 2-(pyridin-2-yl)-4-(3,4-dimethoxybenzylamino-5,6-cyclohepteno-thieno-[2,3-d]-pyrimidine.

EXAMPLE 677

With the procedure of Example 1, the reaction of 3,4-dimethoxy-benzylamine with 4-chloro-2-(pyridin-2-yl)-6-ethyl-thieno-[2,3-d]-pyrimidine yields 2-(pyridin-2-yl)-4-(3,4-dimethoxybenzylamino-6-ethyl-thieno-[2,3-d]-pyrimidine.

EXAMPLE 678

With the procedure of Example 1, the reaction of 3,4-dimethoxy-benzylamine with 4-chloro-2-(pyridin-2-yl)-6-chloro-thieno-[2,3-d]-pyrimidine yields 2-(pyridin-2-yl)-4-(3,4-dimethoxybenzylamino-6-chloro-thieno-[2,3-d]-pyrimidine.

EXAMPLE 679

With the procedure of Example 1, the reaction of 3,4-dimethoxy-benzylamine with 4-chloro-2-(pyridin-2-yl)-5-chloro-6-methyl-thieno-[2,3-d]-pyrimidine yields 2-(pyridin-2-yl)-4-(3,4-dimethoxybenzylamino-5-chlror-6-methyl-thieno-[2,3-d]-pyrimidine.

EXAMPLE 680

With the procedure of Example 1, the reaction of 3,4-dimethoxy-benzylamine with 4-chloro-2-(pyridin-2-yl)-6-nitro-thieno-[2,3-d]-pyrimidine yields 2-(pyridin-2-yl)-4-(3,4-dimethoxybenzylamino-6-nitro-thieno-[2,3-d]-pyrimidine.

EXAMPLE 681

With the procedure of Example 1, the reaction of 3,4-dimethoxy-benzylamine with 4-chloro-2-(pyridin-2-yl)-5,6-dimethyl-thieno-[2,3-d]-pyrimidine yields 2-(pyridin-2-yl)-4-(3,4-dimethoxybenzylamino-5,6-dimethyl-thieno-[2,3-d]-pyrimidine.

EXAMPLE 682

With the procedure of Example 1, the reaction of 3,4-dimethoxy-benzylamine with 4-chloro-2-(pyridin-2-yl)-6-trifluoromethyl-thieno-[2,3-d]-pyrimidine yields 2-(pyridin-2-yl)-4-(3,4-dimethoxybenzylamino-6-trifluoromethyl-thieno-[2,3-d]-pyrimidine.

EXAMPLE 683

With the procedure of Example 1, the reaction of 3,4-dimethoxy-benzylamine with 4-chloro-2-(pyridin-4-yl)-6-methyl-thieno-[2,3-d]-pyrimidine yields 2-(pyridin-4-yl)-4-(3,4-dimethoxybenzylamino-6-methyl-thieno-[2,3-d]-pyrimidine.

EXAMPLE 684

With the procedure of Example 1, the reaction of 3,4-dimethoxy-benzylamine with 4-chloro-2-(pyridin-4-yl)-5-methyl-thieno-[2,3-d]-pyrimidine yields 2-(pyridin-4-yl)-4-(3,4-dimethoxybenzylamino-5-methyl-thieno-[2,3-d]-pyrimidine.

EXAMPLE 685

With the procedure of Example 1, the reaction of 3,4-dimethoxy-benzylamine with 4-chloro-2-(pyridin-4-yl)-5,6,7,8-tetrahydro-[1]-benzothieno-[2,3-d]-pyrimidine yields 2-(pyridin-4-yl)-4-(3,4-dimethoxybenzylamino-5,6,7,8-tetrahydro-thieno-[2,3-d]-pyrimidine.

EXAMPLE 686

With the procedure of Example 1, the reaction of 3,4-dimethoxy-benzylamine with 4-chloro-2-(pyridin-4-yl)-5,6-cyclopenteno-thieno-[2,3-d]-pyrimidine yields 2-(pyridin-4-yl)-4-(3,4-dimethoxybenzylamino-5,6-cyclopenteno-thieno-[2,3-d]-pyrimidine.

EXAMPLE 687

With the procedure of Example 1, the reaction of 3,4-dimethoxy-benzylamine with 4-chloro-2-(pyridin-4-yl)-5,6-cyclohepteno-thieno-[2,3-d]-pyrimidine yields 2-(pyridin-4-yl)-4-(3,4-dimethoxybenzylamino-5,6-cyclohepteno-thieno-[2,3-d]-pyrimidine.

EXAMPLE 688

With the procedure of Example 1, the reaction of 3,4-dimethoxy-benzylamine with 4-chloro-2-(pyridin-4-yl)-6-ethyl-thieno-[2,3-d]-pyrimidine yields 2-(pyridin-4-yl)-4-(3,4-dimethoxybenzylamino-6-ethyl-thieno-[2,3-d]-pyrimidine.

EXAMPLE 689

With the procedure of Example 1, the reaction of 3,4-dimethoxy-benzylamine with 4-chloro-2-(pyridin-4-yl)-6- chloro-thieno-[2,3-d]-pyrimidine yields 2-(pyridin-4-yl)-4-(3,4-dimethoxybenzylamino-6-chloro-thieno-[2,3-d]-pyrimidine.

EXAMPLE 690

With the procedure of Example 1, the reaction of 3,4-dimethoxy-benzylamine with 4-chloro-2-(pyridin-4-yl)-5-chloro-6-methyl-thieno-[2,3-d]-pyrimidine yields 2 (pyridin-4-yl)-4-(3,4-dimethoxybenzylamino-5-chlror-6-methyl-thieno-[2,3-d]-pyrimidine.

EXAMPLE 691

With the procedure of Example 1, the reaction of 3,4-dimethoxy-benzylamine with 4-chloro-2-(pyridin-4-yl)-6-nitro-thieno-[2,3-d]-pyrimidine yields 2-(pyridin-4-yl)-4-(3,4-dimethoxybenzylamino-6-nitro-thieno-[2,3-d]-pyrimidine.

EXAMPLE 692

With the procedure of Example 1, the reaction of 3,4-dimethoxy-benzylamine with 4-chloro-2-(pyridin-4-yl)-5,6-dimethyl-thieno-[2,3-d]-pyrimidine yields 2-(pyridin-4-yl)-4-(3,4-dimethoxybenzylamino-5,6-dimethyl-thieno-[2,3-d]-pyrimidine.

EXAMPLE 693

With the procedure of Example 1, the reaction of 3,4-dimethoxy-benzylamine with 4-chloro-2-(pyridin-4-yl)-6-trifluoromethyl-thieno-[2,3-d]-pyrimidine yields 2-(pyridin-4-yl)-4-(3,4-dimethoxybenzylamino-6-trifluoromethyl-thieno-[2,3-d]-pyrimidine.

EXAMPLE 694

With the procedure of Example 1, the reaction of benzylamine with 4-chloro-2-(pyridin-3-yl)-6-methyl-thieno-[2,3-d]-pyrimidine yields 2-(pyridin-3-yl)-4-benzylamino-6-methyl-thieno-[2,3-d]-pyrimidine.

EXAMPLE 695

With the procedure of Example 1, the reaction of benzylamine with 4-chloro-2-(pyridin-3-yl)-5-methyl-thieno-[2,3-d]-pyrimidine yields 2-(pyridin-3-yl)-4-benzylamino-5-methyl-thieno-[2,3-d]-pyrimidine.

EXAMPLE 696

With the procedure of Example 1, the reaction of benzylamine with 4-chloro-2-(pyridin-3-yl)-5,6,7,8-tetrahydro-[1]-benzothieno-[2,3-d]-pyrimidine yields 2-(pyridin-3-yl)-4-benzylamino-5,6,7,8-tetrahydro-thieno-[2,3-d]-pyrimidine.

EXAMPLE 697

With the procedure of Example 1, the reaction of benzylamine with 4-chloro-2-(pyridin-3-yl)-5,6-cyclopenteno-thieno-[2,3-d]-pyrimidine yields 2-(pyridin-3-yl)-4-benzylamino-5,6-cyclopenteno-thieno-[2,3-d]-pyrimidine.

EXAMPLE 698

With the procedure of Example 1, the reaction of benzylamine with 4-chloro-2-(pyridin-3-yl)-5,6-cyclohepteno-thieno-[2,3-d]-pyrimidine yields 2-(pyridin-3-yl)-4-benzylamino-5,6-cyclohepteno-thieno-[2,3-d]-pyrimidine.

EXAMPLE 699

With the procedure of Example 1, the reaction of benzylamine with 4-chloro-2-(pyridin-3-yl)-6-ethyl-thieno-[2,3-d]-pyrimidine yields 2-(pyridin-3-yl)-4-benzylamino-6-ethyl-thieno-[2,3-d]-pyrimidine.

EXAMPLE 700

With the procedure of Example 1, the reaction of benzylamine with 4-chloro-2-(pyridin-3-yl)-6-chloro-thieno-[2,3-d]-pyrimidine yields 2-(pyridin-3-yl)-4-benzylamino-6-chloro-thieno-[2,3-d]-pyrimidine.

EXAMPLE 701

With the procedure of Example 1, the reaction of benzylamine with 4-chloro-2-(pyridin-3-yl)-5-chloro-6-methyl-thieno-[2,3-d]-pyrimidine yields 2-(pyridin-3-yl)-4-benzylamino-5-chlror-6-methyl-thieno-[2,3-d]-pyrimidine.

EXAMPLE 702

With the procedure of Example 1, the reaction of benzylamine with 4-chloro-2-(pyridin-3-yl)-6-nitro-thieno-[2,3-d]-pyrimidine yields 2-(pyridin-3-yl)-4-benzylamino-6-nitro-thieno-[2,3-d]-pyrimidine.

EXAMPLE 703

With the procedure of Example 1, the reaction of benzylamine with 4-chloro-2-(pyridin-3-yl)-5,6-dimethyl-thieno-[2,3-d]-pyrimidine yields 2-(pyridin-3-yl)-4-benzylamino-5,6-dimethyl-thieno-[2,3-d]-pyrimidine.

EXAMPLE 704

With the procedure of Example 1, the reaction of benzylamine with 4-chloro-2-(pyridin-3-yl)-6-trifluoromethyl-thieno-[2,3-d]-pyrimidine yields 2-(pyridin-3-yl)-4-benzylamino-6-trifluoromethyl-thieno-[2,3-d]-pyrimidine.

EXAMPLE 705

With the procedure of Example 1, the reaction of benzylamine with 4-chloro-2-(isoxazol-5-yl)-6-methyl-thieno-[2,3-d]-pyrimidine yields 2-(isoxazol-5-yl)-4-benzylamino-6-methyl-thieno-[2,3-d]-pyrimidine.

EXAMPLE 706

With the procedure of Example 1, the reaction of benzylamine with 4-chloro-2-(isoxazol-5-yl)-5-methyl-thieno-[2,3-d]-pyrimidine yields 2-(isoxazol-5-yl)-4-benzylamino-5-methyl-thieno-[2,3-d]-pyrimidine.

EXAMPLE 707

With the procedure of Example 1, the reaction of benzylamine with 4-chloro-2-(isoxazol-5-yl)-5,6,7,8-tetrahydro-[1]-benzothieno-[2,3-d]-pyrimidine yields 2-(isoxazol-5-yl)-4-benzylamino-5,6,7,8-tetrahydro-thieno-[2,3-d]-pyrimidine.

EXAMPLE 708

With the procedure of Example 1, the reaction of benzylamine with 4-chloro-2-(isoxazol-5-yl)-5,6-cyclopenteno-thieno-[2,3-d]-pyrimidine yields 2-(isoxazol-5-yl)-4-benzylamino-5,6-cyclopenteno-thieno-[2,3-d]-pyrimidine.

EXAMPLE 709

With the procedure of Example 1, the reaction of benzylamine with 4-chloro-2-(isoxazol-5-yl)-5,6-cyclohepteno-thieno-[2,3-d]-pyrimidine yields 2-(isoxazol-5-yl)-4-benzylamino-5,6-cyclohepteno-thieno-[2,3-d]-pyrimidine.

EXAMPLE 710

With the procedure of Example 1, the reaction of benzylamine with 4-chloro-2-(isoxazol-5-yl)-6-ethyl-thieno-[2,3-d]-pyrimidine yields 2-(isoxazol-5-yl)-4-benzylamino-6-ethyl-thieno-[2,3-d]-pyrimidine.

EXAMPLE 711

With the procedure of Example 1, the reaction of benzylamine with 4-chloro-2-(isoxazol-5-yl)-6-chloro-thieno-[2,3-d]-pyrimidine yields 2-(isoxazol-5-yl)-4-benzylamino-6-chloro-thieno-[2,3-d]-pyrimidine.

EXAMPLE 712

With the procedure of Example 1, the reaction of benzylamine with 4-chloro-2-(isoxazol-5-yl)-5-chloro-6-methyl-thieno-[2,3-d]-pyrimidine yields 2-(isoxazol-5-yl)-4-benzylamino-5-chlror-6-methyl-thieno-[2,3-d]-pyrimidine.

EXAMPLE 713

With the procedure of Example 1, the reaction of benzylamine with 4-chloro-2-(isoxazol-5-yl)-6-nitro-thieno-[2,3-d]-pyrimidine yields 2-(isoxazol-5-yl)-4-benzylamino-6-nitro-thieno-[2,3-d]-pyrimidine.

EXAMPLE 714

With the procedure of Example 1, the reaction of benzylamine with 4-chloro-2-(isoxazol-5-yl)-5,6-dimethyl-thieno-[2,3-d]-pyrimidine yields 2-(isoxazol-5-yl)-4-benzylamino-5,6-dimethyl-thieno-[2,3-d]-pyrimidine.

EXAMPLE 715

With the procedure of Example 1, the reaction of benzylamine with 4-chloro-2-(isoxazol-5-yl)-6-trifluoromethyl-thieno-[2,3-d]-pyrimidine yields 2-(isoxazol-5-yl)-4-benzylamino-6-trifluoromethyl-thieno-[2,3-d]-pyrimidine.

EXAMPLE 716

With the procedure of Example 1, the reaction of benzylamine with 4-chloro-2-(pyrazin-2-yl)-6-methyl-thieno-[2,3-d]-pyrimidine yields 2-(pyrazin-2-yl)-4-benzylamino-6-methyl-thieno-[2,3-d]-pyrimidine.

EXAMPLE 717

With the procedure of Example 1, the reaction of benzylamine with 4-chloro-2-(pyrazin-2-yl)-5-methyl-thieno-[2,3-d]-pyrimidine yields 2-(pyrazin-2-yl)-4-benzylamino-5-methyl-thieno-[2,3-d]-pyrimidine.

EXAMPLE 718

With the procedure of Example 1, the reaction of benzylamine with 4-chloro-2-(pyrazin-2-yl)-5,6,7,8-tetrahydro-[1]-benzothieno-[2,3-d]-pyrimidine yields 2-(pyrazin-2-yl)-4-benzylamino-5,6,7,8-tetrahydro-thieno-[2,3-d]-pyrimidine.

EXAMPLE 719

With the procedure of Example 1, the reaction of benzylamine with 4-chloro-2-(pyrazin-2-yl)-5,6-cyclopenteno-thieno-[2,3-d]-pyrimidine yields 2-(pyrazin-2-yl)-4-benzylamino-5,6-cyclopenteno-thieno-[2,3-d]-pyrimidine.

EXAMPLE 720

With the procedure of Example 1, the reaction of benzylamine with 4-chloro-2-(pyrazin-2-yl)-5,6-cyclohepteno-thieno-[2,3-d]-pyrimidine yields 2-(pyrazin-2-yl)-4-benzylamino-5,6-cyclohepteno-thieno-[2,3-d]-pyrimidine.

EXAMPLE 721

With the procedure of Example 1, the reaction of benzylamine with 4-chloro-2-(pyrazin-2-yl)-6-ethyl-thieno-[2,3-d]-pyrimidine yields 2-(pyrazin-2-yl)-4-benzylamino-6-ethyl-thieno-[2,3-d]-pyrimidine.

EXAMPLE 722

With the procedure of Example 1, the reaction of benzylamine with 4-chloro-2-(pyrazin-2-yl)-6-chloro-thieno-[2,3-d]-pyrimidine yields 2-(pyrazin-2-yl)-4-benzylamino-6-chloro-thieno-[2,3-d]-pyrimidine.

EXAMPLE 723

With the procedure of Example 1, the reaction of benzylamine with 4-chloro-2-(pyrazin-2-yl)-5-chloro-6-methyl-thieno-[2,3-d]-pyrimidine yields 2-(pyrazin-2-yl)-4-benzylamino-5-chlror-6-methyl-thieno-[2,3-d]-pyrimidine.

EXAMPLE 724

With the procedure of Example 1, the reaction of benzylamine with 4-chloro-2-(pyrazin-2-yl)-6-nitro-thieno-[2,3-d]-pyrimidine yields 2-(pyrazin-2-yl)-4-benzylamino-6-nitro-thieno-[2,3-d]-pyrimidine.

EXAMPLE 725

With the procedure of Example 1, the reaction of benzylamine with 4-chloro-2-(pyrazin-2-yl)-5,6-dimethyl-thieno-[2,3-d]-pyrimidine yields 2-(pyrazin-2-yl)-4-benzylamino-5,6-dimethyl-thieno-[2,3-d]-pyrimidine.

EXAMPLE 726

With the procedure of Example 1, the reaction of benzylamine with 4-chloro-2-(pyrazin-2-yl)-6-trifluoromethyl-thieno-[2,3-d]-pyrimidine yields 2-(pyrazin-2-y)-4-benzylamino-6-trifluoromethyl-thieno-[2,3-d]-pyrimidine.

EXAMPLE 727

With the procedure of Example 1, the reaction of benzylamine with 4-chloro-2-(pyridin-2-yl)-6-methyl-thieno-[2,3-d]-pyrimidine yields 2-(pyridin-2-yl)-4-benzylamino-6-methyl-thieno-[2,3-d]-pyrimidine.

EXAMPLE 728

With the procedure of Example 1, the reaction of benzylamine with 4-chloro-2-(pyridin-2-yl)-5-methyl-thieno-[2,3-d]-pyrimidine yields 2-(pyridin-2-yl)-4-benzylamino-5-methyl-thieno-[2,3-d]-pyrimidine.

EXAMPLE 729

With the procedure of Example 1, the reaction of benzylamine with 4-chloro-2-(pyridin-2-yl)-5,6,7,8-tetrahydro-[1]-benzothieno-[2,3-d]-pyrimidine yields 2-(pyridin-2-yl)-4-benzylamino-5,6,7,8-tetrahydro-thieno-[2,3-d]-pyrimidine.

EXAMPLE 730

With the procedure of Example 1, the reaction of benzylamine with 4-chloro-2-(pyridin-2-yl)-5,6-cyclopenteno-thieno-[2,3-d]-pyrimidine yields 2-(pyridin-2-yl)-4-benzylamino-5,6-cyclopenteno-thieno-[2,3-d]-pyrimidine.

EXAMPLE 731

With the procedure of Example 1, the reaction of benzylamine with 4-chloro-2-(pyridin-2-yl)-5,6-cyclohepteno-thieno-[2,3-d]-pyrimidine yields 2-(pyridin-2-yl)-4-benzylamino-5,6-cyclohepteno-thieno-[2,3-d]-pyrimidine.

EXAMPLE 732

With the procedure of Example 1, the reaction of benzylamine with 4-chloro-2-(pyridin-2-yl)-6-ethyl-thieno-[2,3-d]-pyrimidine yields 2-(pyridin-2-yl)-4-benzylamino-6-ethyl-thieno-[2,3-d]-pyrimidine.

EXAMPLE 733

With the procedure of Example 1, the reaction of benzylamine with 4-chloro-2-(pyridin-2-yl)-6-chloro-thieno-[2,3-d]-pyrimidine yields 2-(pyridin-2-yl)-4-benzylamino-6-chloro-thieno-[2,3-d]-pyrimidine.

EXAMPLE 734

With the procedure of Example 1, the reaction of benzylamine with 4-chloro-2-(pyridin-2-yl)-5-chloro-6-methyl-thieno-[2,3-d]-pyrimidine yields 2-(pyridin-2-yl)-4-benzylamino-5-chlror-6-methyl-thieno-[2,3-d]-pyrimidine.

EXAMPLE 735

With the procedure of Example 1, the reaction of benzylamine with 4-chloro-2-(pyridin-2-yl)-6-nitro-thieno-[2,3-d]-pyrimidine yields 2-(pyridin-2-yl)-4-benzylamino-6-nitro-thieno-[2,3-d]-pyrimidine.

EXAMPLE 736

With the procedure of Example 1, the reaction of benzylamine with 4-chloro-2-(pyridin-2-yl)-5,6-dimethyl-thieno-[2,3-d]-pyrimidine yields 2-(pyridin-2-yl)-4-benzylamino-5,6-dimethyl-thieno-[2,3-d]-pyrimidine.

EXAMPLE 737

With the procedure of Example 1, the reaction of benzylamine with 4-chloro-2-(pyridin-2-yl)-6-trifluoromethyl-thieno-[2,3-d]-pyrimidine yields 2-(pyridin-2-yl)-4-benzylamino-6-trifluoromethyl-thieno-[2,3-d]-pyrimidine.

EXAMPLE 738

With the procedure of Example 1, the reaction of benzylamine with 4-chloro-2-(pyridin-4-yl)-6-methyl-thieno-[2,3-d]-pyrimidine yields 2-(pyridin-4-yl)-4-benzylamino-6-methyl-thieno-[2,3-d]-pyrimidine.

EXAMPLE 739

With the procedure of Example 1, the reaction of benzylamine with 4-chloro-2-(pyridin-4-yl)-5-methyl-thieno-[2,3-d]-pyrimidine yields 2-(pyridin-4-yl)-4-benzylamino-5-methyl-thieno-[2,3-d]-pyrimidine.

EXAMPLE 740

With the procedure of Example 1, the reaction of benzylamine with 4-chloro-2-(pyridin-4-yl)-5,6,7,8-tetrahydro-[1]-benzothieno-[2,3-d]-pyrimidine yields 2-(pyridin-4-yl)-4-benzylamino-5,6,7,8-tetrahydro-thieno-[2,3-d]-pyrimidine.

EXAMPLE 741

With the procedure of Example 1, the reaction of benzylamine with 4-chloro-2-(pyridin-4-yl)-5,6-cyclopenteno-thieno-[2,3-d]-pyrimidine yields 2-(pyridin-4-yl)-4-benzylamino-5,6-cyclopenteno-thieno-[2,3-d]-pyrimidine.

EXAMPLE 742

With the procedure of Example 1, the reaction of benzylamine with 4-chloro-2-(pyridin-4-yl)-5,6-cyclohepteno-thieno-[2,3-d]-pyrimidine yields 2-(pyridin-4-yl)-4-benzylamino-5,6-cyclohepteno-thieno-[2,3-d]-pyrimidine.

EXAMPLE 743

With the procedure of Example 1, the reaction of benzylamine with 4-chloro-2-(pyridin-4-yl)-6-ethyl-thieno-[2,3-d]-pyrimidine yields 2-(pyridin-4-yl)-4-benzylamino-6-ethyl-thieno-[2,3-d]-pyrimidine.

EXAMPLE 744

With the procedure of Example 1, the reaction of benzylamine with 4-chloro-2-(pyridin-4-yl)-6-chloro-thieno-[2,3-d]-pyrimidine yields 2-(pyridin-4-yl)-4-benzylamino-6-chloro-thieno-[2,3-d]-pyrimidine.

EXAMPLE 745

With the procedure of Example 1, the reaction of benzylamine with 4-chloro-2-(pyridin-3-yl)-5-chloro-6-methyl-thieno-[2,3-d]-pyrimidine yields 2-pyridin-4-yl)-4-benzylamino-5-chlror-6-methyl-thieno-[2,3-d]-pyrimidine.

EXAMPLE 746

With the procedure of Example 1, the reaction of benzylamine with 4-chloro-2-(pyridin-4-yl)-6-nitro-thieno-[2,3-d]-pyrimidine yields 2-(pyridin-4-yl)-4-benzylamino-6-nitro-thieno-[2,3-d]-pyrimidine.

EXAMPLE 747

With the procedure of Example 1, the reaction of benzylamine with 4-chloro-2-(pyridin-4-yl)-5,6-dimethyl-thieno-[2,3-d]-pyrimidine yields 2-(pyridin-4-yl)-4-benzylamino-5,6-dimethyl-thieno-[2,3-d]-pyrimidine.

EXAMPLE 748

With the procedure of Example 1, the reaction of benzylamine with 4-chloro-2-(pyridin-4-yl)-6-trifluoromethyl-thieno-[2,3-d]-pyrimidine yields 2-(pyridin-4-yl)-4-benzylamino-6-trifluoromethyl-thieno-[2,3-d]-pyrimidine.

EXAMPLE 749

With the procedure of Example 1, the reaction of benzylamine with 4-chloro-2-(pyridin-3-yl)-6-methyl-thieno-[2,3-d]-pyrimidine yields 2-(pyridin-3-yl)-4-benzylamino-6-methyl-thieno-[2,3-d]-pyrimidine.

EXAMPLE 750

With the procedure of Example 1, the reaction of benzylamine with 4-chloro-2-(pyridin-3-yl)-5-methyl-thieno-[2,3-d]-pyrimidine yields 2-(pyridin-3-yl)-4-benzylamino-5-methyl-thieno-[2,3-d]-pyrimidine.

EXAMPLE 751

With the procedure of Example 1, the reaction of benzylamine with 4-chloro-2-(pyridin-3-yl)-5,6,7,8-tetrahydro-[1]-benzothieno-[2,3-d]-pyrimidine yields 2-(pyridin-3-yl)-4-benzylamino-5,6,7,8-tetrahydro-thieno-[2,3-d]-pyrimidine.

EXAMPLE 752

With the procedure of Example 1, the reaction of benzylamine with 4-chloro-2-(pyridin-3-yl)-5,6-cyclopenteno-thieno-[2,3-d]-pyrimidine yields 2-(pyridin-3-yl)-4-benzylamino-5,6-cyclopenteno-thieno-[2,3-d]-pyrimidine.

EXAMPLE 753

With the procedure of Example 1, the reaction of benzylamine with 4-chloro-2-(pyridin-3-yl)-5,6-cyclohepteno-thieno-[2,3-d]-pyrimidine yields 2-(pyridin-3-yl)-4-benzylamino-5,6-cyclohepteno-thieno-[2,3-d]-pyrimidine,

EXAMPLE 754

With the procedure of Example 1, the reaction of benzylamine with 4-chloro-2-(pyridin-3-yl)-6-ethyl-thieno-[2,3-d]-pyrimidine yields 2-(pyridin-3-yl)-4-benzylamino-6-ethyl-thieno-[2,3-d]-pyrimidine.

EXAMPLE 755

With the procedure of Example 1, the reaction of benzylamine with 4-chloro-2-(pyridin-3-yl)-6-chloro-thieno-[2,3-d]-pyrimidine yields 2-(pyridin-3-yl)-4-benzylamino-6-chloro-thieno-[2,3-d]-pyrimidine.

EXAMPLE 756

With the procedure of Example 1, the reaction of benzylamine with 4-chloro-2-(pyridin-3-yl)-5-chloro-6-methyl-thieno-[2,3-d]-pyrimidine yields 2-(pyridin-3-yl)-4-benzylamino-5-chlror-6-methyl-thieno-[2,3-d]-pyrimidine.

EXAMPLE 757

With the procedure of Example 1, the reaction of benzylamine with 4-chloro-2-(pyridin-3-yl)-6-nitro-thieno-[2,3-d]-pyrimidine yields 2-(pyridin-3-yl)-4-benzylamino-6-nitro-thieno-[2,3-d]-pyrimidine.

EXAMPLE 758

With the procedure of Example 1, the reaction of benzylamine with 4-chloro-2-(pyridin-3-yl)-5,6-dimethyl-thieno-[2,3-d]-pyrimidine yields 2-(pyridin-3-yl)-4-benzylamino-5,6-dimethyl-thieno-[2,3-d]-pyrimidine.

EXAMPLE 759

With the procedure of Example 1, the reaction of benzylamine with 4-chloro-2-(pyridin-3-yl)-6-trifluoromethyl-thieno-[2,3-d]-pyrimidine yields 2-(pyridin-3-yl)-4-benzylamino-6-trifluoromethyl-thieno-[2,3-d]-pyrimidine.

EXAMPLE 760

With the procedure of Example 1, the reaction of benzylamine with 4-chloro-2-(isoxazol-5-yl)-6-methyl-thieno-[2,3-d]-pyrimidine yields 2-(isoxazol-5-yl)-4-benzylamino-6-methyl-thieno-[2,3-d]-pyrimidine.

EXAMPLE 761

With the procedure of Example 1, the reaction of benzylamine with 4-chloro-2-(isoxazol-5-yl)-5-methyl-thieno-[2,3-d]-pyrimidine yields 2-(isoxazol-5-yl)-4-benzylamino-5-methyl-thieno-[2,3-d]-pyrimidine.

EXAMPLE 762

With the procedure of Example 1, the reaction of benzylamine with 4-chloro-2-(isoxazol-5-yl)-5,6,7,8-tetrahydro-[1]-benzothieno-[2,3-d]-pyrimidine yields 2-(isoxazol-5-yl)-4-benzylamino-5,6,7,8-tetrahydro-thieno-[2,3-d]-pyrimidine.

EXAMPLE 763

With the procedure of Example 1, the reaction of benzylamine with 4-chloro-2-(isoxazol-5-yl)-5,6-cyclopenteno-thieno-[2,3-d]-pyrimidine yields 2-(isoxazol-5-yl)-4-benzylamino-5,6-cyclopenteno-thieno-[2,3-d]-pyrimidine.

EXAMPLE 764

With the procedure of Example 1, the reaction of benzylamine with 4-chloro-2-(isoxazol-5-yl)-5,6-cyclohepteno-thieno-[2,3-d]-pyrimidine yields 2-(isoxazol-5-yl)-4-benzylamino-5,6-cyclohepteno-thieno-[2,3-d]-pyrimidine.

EXAMPLE 765

With the procedure of Example 1, the reaction of benzylamine with 4-chloro-2-(isoxazol-5-yl)-6-ethyl-thieno-[2,3-d]-pyrimidine yields 2-(isoxazol-5-yl)-4-benzylamino-6-ethyl-thieno-[2,3-d]-pyrimidine.

EXAMPLE 766

With the procedure of Example 1, the reaction of benzylamine with 4-chloro-2-(isoxazol-5-yl)-6-chloro-thieno-[2,3-d]-pyrimidine yields 2-(isoxazol-5-yl)-4-benzylamino-6-chloro-thieno-[2,3-d]-pyrimidine.

EXAMPLE 767

With the procedure of Example 1, the reaction of benzylamine with 4-chloro-2-(isoxazol-5-yl)-5-chloro-6-methyl-thieno-[2,3-d]-pyrimidine yields 2-(isoxazol-5-yl)-4-benzylamino-5-chlror-6-methyl-thieno-[2,3-d]-pyrimidine.

EXAMPLE 768

With the procedure of Example 1, the reaction of benzylamine with 4-chloro-2-(isoxazol-5-yl)-6-nitro-thieno-[2,3-d]-pyrimidine yields 2-(isoxazol-5-yl)-4-benzylamino-6-nitro-thieno-[2,3-d]-pyrimidine.

EXAMPLE 769

With the procedure of Example 1, the reaction of benzylamine with 4-chloro-2-(isoxazol-5-yl)-5,6-dimethyl-thieno-[2,3-d]-pyrimidine yields 2-(isoxazol-5-yl)-4-benzylamino-5,6-dimethyl-thieno-[2,3-d]-pyrimidine.

EXAMPLE 770

With the procedure of Example 1, the reaction of benzylamine with 4-chloro-2-(isoxazol-5-yl)-6-trifluoromethyl-thieno-[2,3-d]-pyrimidine yields 2-(isoxazol-5-yl)-4-benzylamino-6-trifluoromethyl-thieno-[2,3-d]-pyrimidine.

EXAMPLE 771

With the procedure of Example 1, the reaction of benzylamine with 4-chloro-2-(pyrazin-2-yl)-6-methyl-thieno-[2,3-d]-pyrimidine yields 2-(pyrazin-2-yl)-4-benzylamino-6-methyl-thieno-[2,3-d]-pyrimidine.

EXAMPLE 772

With the procedure of Example 1, the reaction of benzylamine with 4-chloro-2-(pyrazin-2-yl)-5-methyl-thieno-[2,3-d]-pyrimidine yields 2-(pyrazin-2-yl)-4-benzylamino-5-methyl-thieno-[2,3-d]-pyrimidine.

EXAMPLE 773

With the procedure of Example 1, the reaction of benzylamine with 4-chloro-2-(pyrazin-2-yl)-5,6,7,8-tetrahydro-[1]-benzothieno-[2,3-d]-pyrimidine yields 2-(pyrazin-2-yl)-4-benzylamino-5,6,7,8-tetrahydro-thieno-[2,3-d]-pyrimidine.

EXAMPLE 774

With the procedure of Example 1, the reaction of benzylamine with 4-chloro-2-(pyrazin-2-yl)-5,6-cyclopenteno-thieno-[2,3-d]-pyrimidine yields 2-(pyrazin-2-yl)-4-benzylamino-5,6-cyclopenteno-thieno-[2,3-d]-pyrimidine.

EXAMPLE 775

With the procedure of Example 1, the reaction of benzylamine with 4-chloro-2-(pyrazin-2-yl)-5,6-cyclohepteno-thieno-[2,3-d]-pyrimidine yields 2-(pyrazin-2-yl)-4-benzylamino-5,6-cyclohepteno-thieno-[2,3-d]-pyrimidine.

EXAMPLE 776

With the procedure of Example 1, the reaction of benzylamine with 4-chloro-2-(pyrazin-2-yl)-6-ethyl-thieno-[2,3-d]-pyrimidine yields 2-(pyrazin-2-yl)-4-benzylamino-6-ethyl-thieno-[2,3-d]-pyrimidine.

EXAMPLE 777

With the procedure of Example 1, the reaction of benzylamine with 4-chloro-2-(pyrazin-2-yl)-6-chloro-thieno-[2,3-d]-pyrimidine yields 2-(pyrazin-2-yl)-4-benzylamino-6-chloro-thieno-[2,3-d]-pyrimidine.

EXAMPLE 778

With the procedure of Example 1, the reaction of benzylamine with 4-chloro-2-(pyrazin-2-yl)-5-chloro-6-methyl-thieno-[2,3-d]-pyrimidine yields 2-(pyrazin-2-yl)-4-benzylamino-5-chlror-6-methyl-thieno-[2,3-d]-pyrimidine.

EXAMPLE 779

With the procedure of Example 1, the reaction of benzylamine with 4-chloro-2-(pyrazin-2-yl)-6-nitro-thieno-[2,3-d]-pyrimidine yields 2-(pyrazin-2-yl)-4-benzylamino-6-nitro-thieno-[2,3-d]-pyrimidine.

EXAMPLE 780

With the procedure of Example 1, the reaction of benzylamine with 4-chloro-2-(pyrazin-2-yl)-5,6-dimethyl-thieno-[2,3-d]-pyrimidine yields 2-(pyrazin-2-yl)-4-benzylamino-5,6-dimethyl-thieno-[2,3-d]-pyrimidine.

EXAMPLE 781

With the procedure of Example 1, the reaction of benzylamine with 4-chloro-2-(pyrazin-2-yl)-6-trifluoromethyl-thieno-[2,3-d]-pyrimidine yields 2-(pyrazin-2-yl)-4-benzylamino-6-trifluoromethyl-thieno-[2,3-d]-pyrimidine.

EXAMPLE 782

With the procedure of Example 1, the reaction of benzylamine with 4-chloro-2-(pyridin-2-yl)-6-methyl-thieno-[2,3-d]-pyrimidine yields 2-(pyridin-2-yl)-4-benzylamino-6-methyl-thieno-[2,3-d]-pyrimidine.

EXAMPLE 783

With the procedure of Example 1, the reaction of benzylamine with 4-chloro-2-(pyridin-2-yl)-5-methyl-thieno-[2,3-d]-pyrimidine yields 2-(pyridin-2-yl)-4-benzylamino-5-methyl-thieno-[2,3-d]-pyrimidine.

EXAMPLE 784

With the procedure of Example 1, the reaction of benzylamine with 4-chloro-2-(pyridin-2-yl)-5,6,7,8-tetrahydro-[1]-benzothieno-[2,3-d]-pyrimidine yields 2-(pyridin-2-yl)-4-benzylamino-5,6,7,8-tetrahydro-thieno-[2,3-d]-pyrimidine.

EXAMPLE 785

With the procedure of Example 1, the reaction of benzylamine with 4-chloro-2-(pyridin-2-yl)-5,6-cyclopenteno-thieno-[2,3-d]-pyrimidine yields 2-(pyridin-2-yl)-4-benzylamino-5,6-cyclopenteno-thieno-[2,3-d]-pyrimidine.

EXAMPLE 786

With the procedure of Example 1, the reaction of benzylamine with 4-chloro-2-(pyridin-2-yl)-5,6-cyclohepteno-thieno-[2,3-d]-pyrimidine yields 2-(pyridin-2-yl)-4-benzylamino-5,6-cyclohepteno-thieno-[2,3-d]-pyrimidine.

EXAMPLE 787

With the procedure of Example 1, the reaction of benzylamine with 4-chloro-2-(pyridin-2-yl)-6-ethyl-thieno-[2,3-d]-pyrimidine yields 2-(pyridin-2-yl)-4-benzylamino-6-ethyl-thieno-[2,3-d]-pyrimidine.

EXAMPLE 788

With the procedure of Example 1, the reaction of benzylamine with 4-chloro-2-(pyridin-2-yl)-6-chloro-thieno-[2,3-d]-pyrimidine yields 2-(pyridin-2-yl)-4-benzylamino-6-chloro-thieno-[2,3-d]-pyrimidine.

EXAMPLE 789

With the procedure of Example 1, the reaction of benzylamine with 4-chloro-2-(pyridin-2-yl)-5-chloro-6-methyl-thieno-[2,3-d]-pyrimidine yields 2-(pyridin-2-yl)-4-benzylamino-5-chlror-6-methyl-thieno-[2,3-d]-pyrimidine.

EXAMPLE 790

With the procedure of Example 1, the reaction of benzylamine with 4-chloro-2-(pyridin-2-yl)-6-nitro-thieno-[2,3-d]-pyrimidine yields 2-(pyridin-2-yl)-4-benzylamino-6-nitro-thieno-[2,3-d]-pyrimidine.

EXAMPLE 791

With the procedure of Example 1, the reaction of benzylamine with 4-chloro-2-(pyridin-2-yl)-5,6-dimethyl-thieno-[2,3-d]-pyrimidine yields 2-(pyridin-2-yl)-4-benzylamino-5,6-dimethyl-thieno-[2,3-d]-pyrimidine.

EXAMPLE 792

With the procedure of Example 1, the reaction of benzylamine with 4-chloro-2-(pyridin-2-yl)-6-trifluoromethyl-thieno-[2,3-d]-pyrimidine yields 2-(pyridin-2-yl)-4-benzylamino-6-trifluoromethyl-thieno-[2,3-d]-pyrimidine.

EXAMPLE 793

With the procedure of Example 1, the reaction of benzylamine with 4-chloro-2-(pyridin-4-yl)-6-methyl-thieno-[2,3-d]-pyrimidine yields 2-(pyridin-4-yl)-4-benzylamino-6-methyl-thieno-[2,3-d]-pyrimidine.

EXAMPLE 794

With the procedure of Example 1, the reaction of benzylamine with 4-chloro-2-(pyridin-4-yl)-5-methyl-thieno-[2,3-d]-pyrimidine yields 2-(pyridin-4-yl)-4-benzylamino-5-methyl-thieno-[2,3-d]-pyrimidine.

EXAMPLE 795

With the procedure of Example 1, the reaction of benzylamine with 4-chloro-2-(pyridin-4-yl)-5,6,7,8-tetrahydro-[1]-benzothieno-[2,3-d]-pyrimidine yields 2-(pyridin-4-yl)-4-benzylamino-5,6,7,8-tetrahydro-thieno-[2,3-d]-pyrimidine.

EXAMPLE 796

With the procedure of Example 1, the reaction of benzylamine with 4-chloro-2-(pyridin-4-yl)-5,6-cyclopenteno-thieno-[2,3-d]-pyrimidine yields 2-(pyridin-4-yl)-4-benzylamino-5,6-cyclopenteno-thieno-[2,3-d]-pyrimidine.

EXAMPLE 797

With the procedure of Example 1, the reaction of benzylamine with 4-chloro-2-(pyridin-4-yl)-5,6-cyclohepteno-thieno-[2,3-d]-pyrimidine yields 2-(pyridin-4-yl)-4-benzylamino-5,6-cyclohepteno-thieno-[2,3-d]-pyrimidine.

EXAMPLE 798

With the procedure of Example 1, the reaction of benzylamine with 4-chloro-2-(pyridin-4-yl)-6-ethyl-thieno-[2,3-d]-pyrimidine yields 2-(pyridin-4-yl)-4-benzylamino-6-ethyl-thieno-[2,3-d]-pyrimidine.

EXAMPLE 799

With the procedure of Example 1, the reaction of benzylamine with 4-chloro-2-(pyridin-4-yl)-6-chloro-thieno-[2,3-d]-pyrimidine yields 2-(pyridin-4-yl)-4-benzylamino-6-chloro-thieno-[2,3-d]-pyrimidine.

EXAMPLE 800

With the procedure of Example 1, the reaction of benzylamine with 4-chloro-2-(pyridin-4-yl)-5-chloro-6-methyl-thieno-[2,3-d]-pyrimidine yields 2-(pyridin-4-yl)-4-benzylamino-5-chlror-6-methyl-thieno-[2,3-d]-pyrimidine.

EXAMPLE 801

With the procedure of Example 1, the reaction of benzylamine with 4-chloro-2-(pyridin-4-yl)-6-nitro-thieno-[2,3-d]-pyrimidine yields 2-(pyridin-4-yl)-4-benzylamino-6-nitro-thieno-[2,3-d]-pyrimidine.

EXAMPLE 802

With the procedure of Example 1, the reaction of benzylamine with 4-chloro-2-(pyridin-4-yl)-5,6-dimethyl-thieno-[2,3-d]-pyrimidine yields 2-(pyridin-4-yl)-4-benzylamino-5,6-dimethyl-thieno-[2,3-d]-pyrimidine.

EXAMPLE 803

With the procedure of Example 1, the reaction of benzylamine with 4-chloro-2-(pyridin-4-yl)-6-trifluoromethyl-thieno-[2,3-d]-pyrimidine yields 2-(pyridin-4-yl)-4-benzylamino-6-trifluoromethyl-thieno-[2,3-d]-pyrimidine.

EXAMPLE 804

With the procedure of Example 1, the reaction of 4-fluorobenzylamine with 4-chloro-2-(pyridin-3-yl)-6-methyl-thieno-[2,3-d]-pyrimidine yields 2-(pyridin-3-yl)-4-(4-fluoro(4-fluorobenzylamino))-6-methyl-thieno-[2,3-d]-pyrimidine.

EXAMPLE 805

With the procedure of Example 1, the reaction of 4-fluoro-4-fluorobenzylamine with 4-chloro-2-(pyridin-3-yl)-5-methyl-thieno-[2,3-d]-pyrimidine yields 2-(pyridin-3-yl)-4-(4-fluorobenzylamino)-5-methyl-thieno-[2,3-d]-pyrimidine.

EXAMPLE 806

With the procedure of Example 1, the reaction of 4-fluoro-4-fluorobenzylamine with 4-chloro-2-(pyridin-3-yl)-5,6,7,8-tetrahydro-[1]-benzothieno-[2,3-d]-pyrimidine yields 2-(pyridin-3-yl)-4-(4-fluorobenzylamino)-5,6,7,8-tetrahydro-thieno-[2,3-d]-pyrimidine.

EXAMPLE 807

With the procedure of Example 1, the reaction of 4-fluorobenzylamine with 4-chloro-2-(pyridin-3-yl)-5,6-cyclopenteno-thieno-[2,3-d]-pyrimidine yields 2-(pyridin-3-yl)-4-(4-fluorobenzylamino)-5,6-cyclopenteno-thieno-[2,3-d]-pyrimidine.

EXAMPLE 808

With the procedure of Example 1, the reaction of 4-fluorobenzylamine with 4-chloro-2-(pyridin-3-yl)-5,6-cyclohepteno-thieno-[2,3-d]-pyrimidine yields 2-(pyridin-3-yl)-4-(4-fluorobenzylamino)-5,6-cyclohepteno-thieno-[2,3-d]-pyrimidine.

EXAMPLE 809

With the procedure of Example 1, the reaction of 4-fluorobenzylamine with 4-chloro-2-(pyridin-3-yl)-6-ethyl-thieno-[2,3-d]-pyrimidine yields 2-(pyridin-3-yl)-4-(4-fluorobenzylamino)-6-ethyl-thieno-[2,3-d]-pyrimidine.

EXAMPLE 810

With the procedure of Example 1, the reaction of 4-fluorobenzylamine with 4-chloro-2-(pyridin-3-yl)-6-chloro-thieno-[2,3-d]-pyrimidine yields 2-(pyridin-3-yl)-4-(4-fluorobenzylamino)-6-chloro-thieno-[2,3-d]-pyrimidine.

EXAMPLE 811

With the procedure of Example 1, the reaction of 4-fluorobenzylamine with 4-chloro-2-(pyridin-3-yl)-5-chloro-6-methyl-thieno-[2,3-d]-pyrimidine yields 2-(pyridin-3-yl)-4-(4-fluorobenzylamino)-5-chlror-6-methyl-thieno-[2,3-d]-pyrimidine.

EXAMPLE 812

With the procedure of Example 1, the reaction of 4-fluorobenzylamine with 4-chloro-2-(pyridin-3-yl)-6-nitro-thieno-[2,3-d]-pyrimidine yields 2-(pyridin-3-yl)-4-(4-fluorobenzylamino)-6-nitro-thieno-[2,3-d]-pyrimidine.

EXAMPLE 813

With the procedure of Example 1, the reaction of 4-fluorobenzylamine with 4-chloro-2-(pyridin-3-yl)-5,6-dimethyl-thieno-[2,3-d]-pyrimidine yields 2-(pyridin-3-yl)-4-(4-fluorobenzylamino)-5,6-dimethyl-thieno-[2,3-d]-pyrimidine.

EXAMPLE 814

With the procedure of Example 1, the reaction of 4-fluorobenzylamine with 4-chloro-2-(pyridin-3-yl)-6- trifluoromethyl-thieno-[2,3-d]-pyrimidine yields 2-(pyridin-3-yl)-4-(4-fluorobenzylamino)-6-trifluoromethyl-thieno-[2,3-d]-pyrimidine.

EXAMPLE 815

With the procedure of Example 1, the reaction of 4-fluorobenzylamine with 4-chloro-2-(isoxazol-5-yl)-6-methyl-thieno-[2,3-d]-pyrimidine yields 2-(isoxazol-5-yl)-4-(4-fluorobenzylamino)-6-methyl-thieno-[2,3-d]-pyrimidine.

EXAMPLE 816

With the procedure of Example 1, the reaction of 4-fluorobenzylamine with 4-chloro-2-(isoxazol-5-yl)-5-methyl-thieno-[2,3-d]-pyrimidine yields 2-(isoxazol-5-yl) 4-(4-fluorobenzylamino)-5-methyl-thieno-[2,3 d]-pyrimidine.

EXAMPLE 817

With the procedure of Example 1, the reaction of 4-fluorobenzylamine with 4-chloro-2-(isoxazol-5-yl)-5,6,7,8-tetrahydro-[i]-benzothieno-[2,3-d]-pyrimidine yields 2(isoxazol-5-yl)-4-(4-fluorobenzylamino)-5,6,7,8-tetrahydro-thieno-[2,3-d]-pyrimidine pyrimidine.

EXAMPLE 818

With the procedure of Example 1, the reaction of 4-fluorobenzylamine with 4-chloro-2-(isoxazol-5-yl)-5,6-cyclopenteno-thieno-[2,3-d]-pyrimidine yields 2-(isoxazol-5-yl)-4-(4-fluorobenzylamino)-5,6-cyclopenteno-hieno-[2,3-d]-pyrimidine.

EXAMPLE 819

With the procedure of Example 1, the reaction of 4-fluorobenzylamine with 4-chloro-2-(isoxazol-5-yl)-5,6-cyclohepteno-thieno-[2,3-d]-pyrimidine yields 2-(isoxazol-5-yl)-4-(4-fluorobenzylamino)-5,6-cyclohepteno-thieno-[2,3-d]-pyrimidine.

EXAMPLE 820

With the procedure of Example 1, the reaction of 4-fluorobenzylamine with 4-chloro-2-(isoxazol-5-yl)-6-ethyl-thieno-[2,3-d]-pyrimidine yields 2-(isoxazol-5-yl)-4-(4-fluorobenzylamino)-6-ethyl-thieno-[2,3-d]-pyrimidine.

EXAMPLE 821

With the procedure of Example 1, the reaction of 4-fluorobenzylamine with 4-chloro-2-(isoxazol-5-yl)-6-chloro-thieno-[2,3-d]-pyrimidine yields 2-(isoxazol-5-yl)-4-(4-fluorobenzylamino)-6-chloro-thieno-[2,3-d]-pyrimidine.

EXAMPLE 822

With the procedure of Example 1, the reaction of 4-fluorobenzylamine with 4-chloro-2-(isoxazol-5-yl)-5-chloro-6-methyl-thieno-[2,3-d]-pyrimidine yields 2-(isoxazol-5-yl)-4-(4-fluorobenzylamino)4-5-chiror-6-methyl-thieno-[2,3-d]-pyrimidine.

EXAMPLE 823

With the procedure of Example 1, the reaction of 4-fluorobenzylamine with 4-chloro-2-(isoxazol-5-yl)-6-nitro-thieno-[2,3-d]-pyrimidine yields 2-(isoxazol-5-yl)-4-(4-fluorobenzylamino)-6-nitro-thieno-[2,3-d]-pyrimidine.

EXAMPLE 824

With the procedure of Example 1, the reaction of 4-fluorobenzylamine with 4-chloro-2-(isoxazol-5-yl)-5,6-dimethyl-thieno-[2,3-d]-pyrimidine yields 2-(isoxazol-5-yl)-4-(4-fluorobenzylamino)-5,6-dimethyl-thieno-[2,3-d]-pyrimidine.

EXAMPLE 825

With the procedure of Example 1, the reaction of 4-fluorobenzylamine with 4-chloro-2-(isoxazol-5-yl)-6-trifluoromethyl-thieno-[2,3-d]-pyrimidine yields 2-(isoxazol-5-yl)4-(4-fluorobenzylamino)-6-trifluoromethyl-thieno-[2,3-d]-pyrimidine.

EXAMPLE 826

With the procedure of Example 1, the reaction of 4-fluorobenzylamine with 4-chloro-2-(pyrazin-2-yl)-6-methyl-thieno-[2,3-d]-pyrimidine yields 2-(pyrazin-2-yl)-4-(4-fluorobenzylamino)-6-methyl-thieno-[2,3-d]-pyrimidine.

EXAMPLE 827

With the procedure of Example 1, the reaction of 4-fluorobenzylamine with 4-chloro-2-(pyrazin-2-yl)-5-methyl-thieno-[2,3-d]-pyrimidine yields 2-(pyrazin-2-yl)-4-(4-fluorobenzylamino)-5-methyl-thieno-[2,3-d]-pyrimidine.

EXAMPLE 828

With the procedure of Example 1, the reaction of 4-fluorobenzylamine with 4-chloro-2-(pyrazin-2-yl)-5,6,7,8-tetrahydro-[1]-benzothieno-[2,3-d]-pyrimidine yields 2-(pyrazin-2-yl)-4-(4-fluorobenzylamino)-5,6,7,8-tetrahydro-thieno-[2,3-d]-pyrimidine.

EXAMPLE 829

With the procedure of Example 1, the reaction of 4-fluorobenzylamine with 4-chloro-2-(pyrazin-2-yl)-5,6-cyclopenteno-thieno-[2,3-d]-pyrimidine yields 2-(pyrazin-2-yl)-4-(4-fluorobenzylamino)-5,6-cyclopenteno-thieno-[2,3-d]-pyrimidine.

EXAMPLE 830

With the procedure of Example 1, the reaction of 4-fluorobenzylamine with 4-chloro-2-(pyrazin-2-yl)-5,6-cyclohepteno-thieno-[2,3-d]-pyrimidine yields 2-(pyrazin-2-yl)-4-(4-fluorobenzylamino)-5,6-cyclohepteno-thieno-[2,3-d]-pyrimidine.

EXAMPLE 831

With the procedure of Example 1, the reaction of 4-fluorobenzylamine with 4-chloro-2-(pyrazin-2-yl)-6-ethyl-thieno-[2,3-d]-pyrimidine yields 2-(pyrazin-2-yl)-4-(4-fluorobenzylamino)-6-ethyl-thieno-[2,3-d]-pyrimidine.

EXAMPLE 832

With the procedure of Example 1, the reaction of 4-fluorobenzylamine with 4-chloro-2-(pyrazin-2-yl)-6-chloro-thieno-[2,3-d]-pyrimidine yields 2-(pyrazin-2-yl)-4-(4-fluorobenzylamino)-6-chloro-thieno-[2,3-d]-pyrimidine.

EXAMPLE 833

With the procedure of Example 1, the reaction of 4-fluorobenzylamine with 4-chloro-2-(pyrazin-2-yl)-5- chloro-6-methyl-thieno-[2,3-d]-pyrimidine yields 2-(pyrazin-2-yl)-4-(4-fluorobenzylamino)-5-chlror-6-methyl-thieno-[2,3-d]-pyrimidine.

EXAMPLE 834

With the procedure of Example 1, the reaction of 4-fluorobenzylamine with 4-chloro-2-(pyrazin-2-yl)-6-nitro-thieno-[2,3-d]-pyrimidine yields 2-(pyrazin-2-yl)-4-(4-fluorobenzylamino)-6-nitro-thieno-[2,3-d]-pyrimidine.

EXAMPLE 835

With the procedure of Example 1, the reaction of 4-fluorobenzylamine with 4-chloro-2-(pyrazin-2-yl)-5,6-dimethyl-thieno-[2,3-d]-pyrimidine yields 2-(pyrazin-2-yl)-4-(4-fluorobenzylamino)-5,6-dimethyl-thieno-[2,3-d]-pyrimidine.

EXAMPLE 836

With the procedure of Example 1, the reaction of 4-fluorobenzylamine with 4-chloro-2-(pyrazin-2-yl)-6-trifluoromethyl-thieno-[2,3-d]-pyrimidine yields 2(pyrazin-2-yl)-4-(4-fluorobenzylamino)-6-trifluoromethyl-thieno-[2,3-d]-pyrimidine.

EXAMPLE 837

With the procedure of Example 1, the reaction of 4-fluorobenzylamine with 4-chloro-2-(pyridin-2-yl)-6-methyl-thieno-[2,3-d]-pyrimidine yields 2-(pyridin-2-yl)-4-(4-fluorobenzylamino)-6-methyl-thieno-[2,3-d]-pyrimidine.

EXAMPLE 838

With the procedure of Example 1, the reaction of 4-fluorobenzylamine with 4-chloro-2-(pyridin-2-yl)-5-methyl-thieno-[2,3-d]-pyrimidine yields 2-(pyridin-2-yl)-4-(4-fluorobenzylamino)-5-methyl-thieno-[2,3-d]-pyrimidine.

EXAMPLE 839

With the procedure of Example 1, the reaction of 4-fluorobenzylamine with 4-chloro-2-(pyridin-2-yl)-5,6,7,8-tetrahydro-[1]-benzothieno-[2,3-d]-pyrimidine yields 2-(pyridin-2-yl)-4-(4-fluorobenzylamino)-5,6,7,8-tetrahydro-thieno-[2,3-d]-pyrimidine.

EXAMPLE 840

With the procedure of Example 1, the reaction of 4-fluorobenzylamine with 4-chloro-2-(pyridin-2-yl)-5,6-cyclopenteno-thieno-[2,3-d]-pyrimidine yields 2-(pyridin-2-yl)4-(4-fluorobenzylamino)-5,6-cyclopenteno-thieno-[2,3-d]-pyrimidine.

EXAMPLE 841

With the procedure of Example 1, the reaction of 4-fluorobenzylamine with 4-chloro-2-(pyridin-2-yl)-5,6-cyclohepteno-thieno-[2,3-d]-pyrimidine yields 2-(pyradin-2-yl)-4-(4-fluorobenzylamino)-5,6-cyclohepteno-thieno-[2,3-d]-pyrimidine.

EXAMPLE 842

With the procedure of Example 1, the reaction of 4-fluorobenzylamine with 4-chloro-2-(pyridin-2-yl)-6-ethyl-thieno-[2,3-d]-pyrimidine yields 2-(pyridin-2-yl)-4-(4-fluorobenzylamino)-6-ethyl-thieno-[2,3-d]-pyrimidine.

EXAMPLE 843

With the procedure of Example 1, the reaction of 4-fluorobenzylamine with 4-chloro-2-(pyridin-2-yl)-6-chloro-thieno-[2,3-d]-pyrimidine yields 2-(pyridin-2-yl)-4-(4-fluorobenzylamino)-6-chloro-thieno-[2,3-d]-pyrimidine.

EXAMPLE 844

With the procedure of Example 1, the reaction of 4-fluorobenzylamine with 4-chloro-2-(pyridin-2-yl)-5-chloro-6-methyl-thieno-[2,3-d]-pyrimidine yields 2-(pyridin-2-yl)-4-(4-fluorobenzylamino)-5-chlror-6-methyl-thieno-[2,3-d]-pyrimidine.

EXAMPLE 845

With the procedure of Example 1, the reaction of 4-fluorobenzylamine with 4-chloro-2-(pyridin-2-yl)-6-nitro-thieno-[2,3-d]-pyrimidine yields 2-(pyridin-2-yl)-4-(4-fluorobenzylamino)-6-nitro-thieno-[2,3-d]-pyrimidine.

EXAMPLE 846

With the procedure of Example 1, the reaction of 4-fluorobenzylamine with 4-chloro-2-(pyridin-2-yl)-5,6-dimethyl-thieno-[2,3-d]-pyrimidine yields 2-(pyridin-2-yl)-4-(4-fluorobenzylamino)-5,6-dimethyl-thieno-[2,3-d]-pyrimidine.

EXAMPLE 847

With the procedure of Example 1, the reaction of 4-fluorobenzylamine with 4-chloro-2-(pyridin-2-yl)-6-trifluoromethyl-thieno-[2,3-d]-pyrimidine yields 2-(pyradin-2-yl)-4-(4-fluorobenzylamino)-6-trifluoromethyl-thieno-[2,3-d]-pyrimidine.

EXAMPLE 848

With the procedure of Example 1, the reaction of 4-fluorobenzylamine with 4-chloro-2-(pyridin-4-yl)-6-methyl-thieno-[2,3-d]-pyrimidine yields 2-(pyridin-4-yl)-4-(4-fluorobenzylamino)-6-methyl-thieno-[2,3-d]-pyrimidine.

EXAMPLE 849

With the procedure of Example 1, the reaction of 4-fluorobenzylamine with 4-chloro-2-(pyridin-4-yl)-5-methyl-thieno-[2,3-d]-pyrimidine yields 2-(pyridin-4-yl)-4-(4-fluorobenzylamino)-5-methyl-thieno-[2,3-d]-pyrimidine.

EXAMPLE 850

With the procedure of Example 1, the reaction of 4-fluorobenzylamine with 4-chloro-2-(pyridin-4-yl)-5,6,7,8-tetrahydro-[1]-benzothieno-[2,3-d]-pyrimidine yields 2-(pyridin-4-yl)-4-(4-fluorobenzylamino)-5,6,7,8-tetrahydro-thieno-[2,3-d]-pyrimidine.

EXAMPLE 851

With the procedure of Example 1, the reaction of 4-fluorobenzylamine with 4-chloro-2-(pyridin-4-yl)-5,6-cyclopenteno-thieno-[2,3-d]-pyrimidine yields 2-(pyridin-4-yl)-4-(4-fluorobenzylamino)-5,6-cyclopenteno-thieno-[2,3-d]-pyrimidine.

EXAMPLE 852

With the procedure of Example 1, the reaction of 4-fluorobenzylamine with 4-chloro-2-(pyridin-4-yl)-5,6-cyclohepteno-thieno-[2,3-d]-pyrimidine yields 2-(pyridin-4-yl)-4-(4-fluorobenzylamino)-5,6-cyclohepteno-thieno-[2,3-d]-pyrimidine.

EXAMPLE 853

With the procedure of Example 1, the reaction of 4-fluorobenzylamine with 4-chloro-2-(pyridin-4-yl)-6- ethyl-thieno-[2,3-d]-pyrimidine yields 2-(pyridin-4-yl)-4-(4-fluorobenzylamino)-6-ethyl-thieno-[2,3-d]-pyrimidine.

EXAMPLE 854

With the procedure of Example 1, the reaction of 4-fluorobenzylamine with 4-chloro-2-(pyridin-4-yl)-6-chloro-thieno-[2,3-d]-pyrimidine yields 2-(pyridin-4-yl)-4-(4-fluorobenzylamino)-6-chloro-thieno-[2,3-d]-pyrimidine.

EXAMPLE 855

With the procedure of Example 1, the reaction of 4-fluorobenzylamine with 4-chloro-2-(pyridin-4-yl)-5-chloro-6-methyl-thieno-[2,3-d]-pyrimidine yields 2-(pyridin-4-yl)-4-(4-fluorobenzylamino)-5-chlror-6-methyl-thieno-[2,3-d]-pyrimidine.

EXAMPLE 856

With the procedure of Example 1, the reaction of 4-fluorobenzylamine with 4-chloro-2-(pyridin-4-yl)-6-nitro-thieno-[2,3-d]-pyrimidine yields 2-(pyridin-4-yl)-4-(4-fluorobenzylamino)-6-nitro-thieno-[2,3-d]-pyrimidine.

EXAMPLE 857

With the procedure of Example 1, the reaction of 4-fluorobenzylamine with 4-chloro-2-(pyridin-4-yl)-5,6-dimethyl-thieno-[2,3-d]-pyrimidine yields 2-(pyridin-4-yl)-4-(4-fluorobenzylamino)-5,6-dimethyl-thieno-[2,3-d]-pyrimidine.

EXAMPLE 858

With the procedure of Example 1, the reaction of 4-fluorobenzylamine with 4-chloro-2-(pyridin-4-yl)-6-trifluoromethyl-thieno-[2,3-d]-pyrimidine yields 2-(pyridin-4-yl)-4-(4-fluorobenzylamino)-6-trifluoromethyl-thieno-[2,3-d]-pyrimidine.

EXAMPLE 859

With the procedure of Example 1, the reaction of 4-fluorobenzylamine with 4-chloro-2-(pyridin-3-yl)-6-methyl-thieno-[2,3-d]-pyrimidine yields 2-(pyridin-3-yl)-4-(4-fluorobenzylamino)-6-methyl-thieno-[2,3-d]-pyrimidine.

EXAMPLE 860

With the procedure of Example 1, the reaction of 4-fluorobenzylamine with 4-chloro-2-(pyridin-3-yl)-5-methyl-thieno-[2,3-d]-pyrimidine yields 2-(pyridin-3-yl)-4-(4-fluorobenzylamino)-5-methyl-thieno-[2,3-d]-pyrimidine.

EXAMPLE 861

With the procedure of Example 1, the reaction of 4-fluorobenzylamine with 4-chloro-2-(pyridin-3-yl)-5,6,7,8-tetrahydro-[1]-benzothieno-[2,3-d]-pyrimidine yields 2-(pyridin-3-yl)-4-(4-fluorobenzylamino)-5,6,7,8-tetrahydro-thieno-[2,3-d]-pyrimidine.

EXAMPLE 862

With the procedure of Example 1, the reaction of 4-fluorobenzylamine with 4-chloro-2-(pyridin-3-yl)-5,6-cyclopenteno-thieno-[2,3-d]-pyrimidine yields 2-(pyridin-3-yl)-4-(4-fluorobenzylamino)-5,6-cyclopenteno-thieno-[2,3-d]-pyrimidine.

EXAMPLE 863

With the procedure of Example 1, the reaction of 4-fluorobenzylamine with 4-chloro-2-(pyridin-3-yl)-5,6-cyclohepteno-thieno-[2,3-d]-pyrimidine yields 2-(pyridin-3-yl)-4-(4-fluorobenzylamino)-5,6-cyclohepteno-thieno-[2,3-d]-pyrimidine.

EXAMPLE 864

With the procedure of Example 1, the reaction of 4-fluorobenzylamine with 4-chloro-2-(pyridin-3-yl)-6-ethyl-thieno-[2,3-d]-pyrimidine yields 2-(pyridin-3-yl)-4-(4-fluorobenzylamino)-6-ethyl-thieno-[2,3-d]-pyrimidine.

EXAMPLE 865

With the procedure of Example 1, the reaction of 4-fluorobenzylamine with 4-chloro-2-(pyridin-3-yl)-6-chloro-thieno-[2,3-d]-pyrimidine yields 2-(pyridin-3-yl)-4-(4-fluorobenzylamino)-6-chloro-thieno-[2,3-d]-pyrimidine.

EXAMPLE 866

With the procedure of Example 1, the reaction of 4-fluorobenzylamine with 4-chloro-2-(pyridin-3-yl)-5-chloro-6-methyl-thieno-[2,3-d]-pyrimidine yields 2-(pyridin-3-yl)-4-(4-fluorobenzylamino)-5-chloro-6-methyl-thieno-[2,3-d]-pyrimidine.

EXAMPLE 867

With the procedure of Example 1, the reaction of 4-fluorobenzylamine with 4-chloro-2-(pyridin-3-yl)-6-nitro-thieno-[2,3-d]-pyrimidine yields 2-(pyridin-3-yl)-4-(4-fluorobenzylamino)-6-nitro-thieno-[2,3-d]-pyrimidine.

EXAMPLE 868

With the procedure of Example 1, the reaction of 4-fluorobenzylamine with 4-chloro-2-(pyridin-3-yl)-5,6-dimethyl-thieno-[2,3-d]-pyrimidine yields 2-(pyridin-3-yl)-4-(4-fluorobenzylamino)-5,6-dimethyl-thieno-[2,3-d]-pyrimidine.

EXAMPLE 869

With the procedure of Example 1, the reaction of 4-fluorobenzylamine with 4-chloro-2-(pyridin-3-yl)-6-trifluoromethyl-thieno-[2,3-d]-pyrimidine yields 2-(pyridin-3-yl)-4-(4-fluorobenzylamino)-6-trifluoromethyl-thieno-[2,3-d]-pyrimidine.

EXAMPLE 870

With the procedure of Example 1, the reaction of 4-fluorobenzylamine with 4-chloro-2-(isoxazol-5-yl)-6-methyl-thieno-[2,3-d]-pyrimidine yields 2-(isoxazol-5-yl)-4-(4-fluorobenzylamino)-6-methyl-thieno-[2,3-d]-pyrimidine.

EXAMPLE 871

With the procedure of Example 1, the reaction of 4-fluorobenzylamine with 4-chloro-2-(isoxazol-5-yl)-5-methyl-thieno-[2,3-d]-pyrimidine yields 2-(isoxazol-5-yl)-4-(4-fluorobenzylamino)-5-methyl-thieno-[2,3-d]-pyrimidine.

EXAMPLE 872

With the procedure of Example 1, the reaction of 4-fluorobenzylamine with 4-chloro-2-(isoxazol-5-yl)-5,6,7,8-tetrahydro-[1]-benzothieno-[2,3-d]-pyrimidine yields 2-(isoxazol-5-yl)-4-(4-fluorobenzylamino)-5,6,7,8-tetrahydro-thieno-[2,3-d]-pyrimidine.

EXAMPLE 873

With the procedure of Example 1, the reaction of 4-fluorobenzylamine with 4-chloro-2-(isoxazol-5-yl)-5,6-cyclopenteno-thieno-[2,3-d]-pyrimidine yields 2-(isoxazol-5-yl)-4-(4-fluorobenzylamino)-5,6-cyclopenteno-thieno-[2,3-d]-pyrimidine.

EXAMPLE 874

With the procedure of Example 1, the reaction of 4-fluorobenzylamine with 4-chloro-2-(isoxazol-5-yl)-5,6-cyclohepteno-thieno-[2,3-d]-pyrimidine yields 2-(isoxazol-5-yl)-4-(4-fluorobenzylamino)-5,6-cyclohepteno-thieno-[2,3-d]-pyrimidine.

EXAMPLE 875

With the procedure of Example 1, the reaction of 4-fluorobenzylamine with 4-chloro-2-(isoxazol-5-yl)-6-ethyl-thieno-[2,3-d]-pyrimidine yields 2-(isoxazol-5-yl)-4-(4-fluorobenzylamino)-6-ethyl-thieno-[2,3-d]-pyrimidine.

EXAMPLE 876

With the procedure of Example 1, the reaction of 4-fluorobenzylamine with 4-chloro-2-(isoxazol-5-yl)-6-chloro-thieno-[2,3-d]-pyrimidine yields 2-(isoxazol-5-yl)-4-(4-fluorobenzylamino)-6-chloro-thieno-[2,3-d]-pyrimidine.

EXAMPLE 877

With the procedure of Example 1, the reaction of 4-fluorobenzylamine with 4-chloro-2-(isoxazol-5-yl)-5-chloro-6-methyl-thieno-[2,3-d]-pyrimidine yields 2-(isoxazol-5-yl)-4-(4-fluorobenzylamino)-5-chlror-6-methyl-thieno-[2,3-d]-pyrimidine.

EXAMPLE 878

With the procedure of Example 1, the reaction of 4-fluorobenzylamine with 4-chloro-2-(isoxazol-5-yl)-6-nitro-thieno-[2,3-d]-pyrimidine yields 2-(isoxazol-5-yl)-4-(4-fluorobenzylamino)-6-nitro-thieno-[2,3-d]-pyrimidine.

EXAMPLE 879

With the procedure of Example 1, the reaction of 4-fluorobenzylamine with 4-chloro-2-(isoxazol-5-yl)-5,6-dimethyl-thieno-[2,3-d]-pyrimidine yields 2-(isoxazol-5-yl)-4-(4-fluorobenzylamino)-5,6-dimethyl-thieno-[2,3-d]-pyrimidine.

EXAMPLE 880

With the procedure of Example 1, the reaction of 4-fluorobenzylamine with 4-chloro-2-(isoxazol-5-yl)-6-trifluoromethyl-thieno-[2,3-d]-pyrimidine yields 2-(isoxazol-5-yl)-4-(4-fluorobenzylamino)-6-trifluoromethyl-thieno-[2,3-d]-pyrimidine.

EXAMPLE 881

With the procedure of Example 1, the reaction of 4-fluorobenzylamine with 4-chloro-2-(pyrazin-2-yl)-6-methyl-thieno-[2,3-d]-pyrimidine yields 2-(pyrazin-2-yl)-4-(4-fluorobenzylamino)-6-methyl-thieno-[2,3-d]-pyrimidine.

EXAMPLE 882

With the procedure of Example 1, the reaction of 4-fluorobenzylamine with 4-chloro-2-(pyrazin-2-yl)-5-methyl-thieno-[2,3-d]-pyrimidine yields 2-(pyrazin-2-yl)-4-(4-fluorobenzylamino)-5-methyl-thieno-[2,3-d]-pyrimidine.

EXAMPLE 883

With the procedure of Example 1, the reaction of 4-fluorobenzylamine with 4-chloro-2-(pyrazin-2-yl)-5,6,7,8-tetrahydro-[1]-benzothieno-[2,3-d]-pyrimidine yields 2-(pyrazin-2-yl)-4-(4-fluorobenzylamino)-5,6,7,8-tetrahydro-thieno-[2,3-d]-pyrimidine.

EXAMPLE 884

With the procedure of Example 1, the reaction of 4-fluorobenzylamine with 4-chloro-2-(pyrazin-2-yl)-5,6-cyclopenteno-thieno-[2,3-d]-pyrimidine yields 2-(pyrazin-2-yl)-4-(4-fluorobenzylamino)-5,6-cyclopenteno-thieno-[2,3-d]-pyrimidine.

EXAMPLE 885

With the procedure of Example 1, the reaction of 4-fluorobenzylamine with 4-chloro-2-(pyrazin-2-yl)-5,6-cyclohepteno-thieno-[2,3-d]-pyrimidine yields 2-(pyrazin-2-yl)-4-(4-fluorobenzylamino)-5,6-cyclohepteno-thieno-[2,3-d]-pyrimidine.

EXAMPLE 886

With the procedure of Example 1, the reaction of 4-fluorobenzylamine with 4-chloro-2-(pyrazin-2-yl)-6-ethyl-thieno-[2,3-d]-pyrimidine yields 2-(pyrazin-2-yl)-4-(4-fluorobenzylamino)-6-ethyl-thieno-[2,3-d]-pyrimidine.

EXAMPLE 887

With the procedure of Example 1, the reaction of 4-fluorobenzylamine with 4-chloro-2-(pyrazin-2-yl)-6-chloro-thieno-[2,3-d]-pyrimidine yields 2-(pyrazin-2-yl)-4-(4-fluorobenzylamino)-6-chloro-thieno-[2,3-d]-pyrimidine.

EXAMPLE 888

With the procedure of Example 1, the reaction of 4-fluorobenzylamine with 4-chloro-2-(pyrazin-2-yl)-5-chloro-6-methyl-thieno-[2,3-d]-pyrimidine yields 2-(pyrazin-2-yl)-4-(4-fluorobenzylamino)-5-chlror-6-methyl-thieno-[2,3-d]-pyrimidine.

EXAMPLE 889

With the procedure of Example 1, the reaction of 4-fluorobenzylamine with 4-chloro-2-(pyrazin-2-yl)-6-nitro-thieno-[2,3-d]-pyrimidine yields 2-(pyrazin-2-yl)-4-(4-fluorobenzylamino)-6-nitro-thieno-[2,3-d]-pyrimidine.

EXAMPLE 890

With the procedure of Example 1, the reaction of 4-fluorobenzylamine with 4-chloro-2-(pyrazin-2-yl)-5,6-dimethyl-thieno-[2,3-d]-pyrimidine yields 2-(pyrazin-2-yl)-4-(4-fluorobenzylamino)-5,6-dimethyl-thieno-[2,3-d]-pyrimidine.

EXAMPLE 891

With the procedure of Example 1, the reaction of 4-fluorobenzylamine with 4-chloro-2-(pyrazin-2-yl)-6-trifluoromethyl-thieno-[2,3-d]-pyrimidine yields 2-(pyrazin-2-yl)-4-(4-fluorobenzylamino)-6-trifluoromethyl-thieno-[2,3-d]-pyrimidine.

EXAMPLE 892

With the procedure of Example 1, the reaction of 4-fluorobenzylamine with 4-chloro-2-(pyridin-2-yl)-6- methyl-thieno-[2,3-d]-pyrimidine yields 2-(pyridin-2-yl)-4-(4-fluorobenzylamino)-6-methyl-thieno-[2,3-d]-pyrimidine.

EXAMPLE 893

With the procedure of Example 1, the reaction of 4-fluorobenzylamine with 4-chloro-2-(pyridin-2-yl)-5-methyl-thieno-[2,3-d]-pyrimidine yields 2-(pyridin-2-yl)-4-(4-fluorobenzylamino)-5-methyl-thieno-[2,3-d]-pyrimidine.

EXAMPLE 894

With the procedure of Example 1, the reaction of 4-fluorobenzylamine with 4-chloro-2-(pyridin-2-yl)-5,6,7,8-tetrahydro-[1]-benzothieno-[2,3-d]-pyrimidine yields 2-(pyridin-2-yl)-4-(4-fluorobenzylamino)-5,6,7,8-tetrahydro-thieno-[2,3-d]-pyrimidine.

EXAMPLE 895

With the procedure of Example 1, the reaction of 4-fluorobenzylamine with 4-chloro-2-(pyridin-2-yl)-5,6-cyclopenteno-thieno-[2,3-d]-pyrimidine yields 2-(pyradin-2-yl)-4-(4-fluorobenzylamino)-5,6-cyclopenteno-thieno-[2,3-d]-pyrimidine.

EXAMPLE 896

With the procedure of Example 1, the reaction of 4-fluorobenzylamine with 4-chloro-2-(pyridin-2-yl)-5,6-cyclohepteno-thieno-[2,3-d]-pyrimidine yields 2-(pyradin-2-yl)-4-(4-fluorobenzylamino)-5,6-cyclohepteno-thieno-[2,3-d]-pyrimidine.

EXAMPLE 897

With the procedure of Example 1, the reaction of 4-fluorobenzylamine with 4-chloro-2-(pyridin-2-yl)-6-ethyl-thieno-[2,3-d]-pyrimidine yields 2-(pyridin-2-yl)4-(4-fluorobenzylamino)-6-ethyl-thieno-[2,3-d]-pyrimidine.

EXAMPLE 898

With the procedure of Example 1, the reaction of 4-fluorobenzylamine with 4-chloro-2-(pyridin-2-yl)-6-chloro-thieno-[2,3-d]-pyrimidine yields 2-(pyridin-2-yl)-4-(4-fluorobenzylamino)-6-chloro-thieno-[2,3-d]-pyrimidine.

EXAMPLE 899

With the procedure of Example 1, the reaction of 4-fluorobenzylamine with 4-chloro-2-(pyridin-2-yl)-5-chloro-6-methyl-thieno-[2,3-d]-pyrimidine yields 2-(pyridin-2-yl)-4-(4-fluorobenzylamino)-5-chlror-6-methyl-thieno-[2,3-d]-pyrimidine.

EXAMPLE 900

With the procedure of Example 1, the reaction of 4-fluorobenzylamine with 4-chloro-2-(pyridin-2-yl)-6-nitro-thieno-[2,3-d]-pyrimidine yields 2-(pyridin-2-yl)-4-(4-fluorobenzylamino)-6-nitro-thieno-[2,3-d]-pyrimidine.

EXAMPLE 901

With the procedure of Example 1, the reaction of 4-fluorobenzylamine with 4-chloro-2-(pyridin-2-yl)-5,6-dimethyl-thieno-[2,3-d]-pyrimidine yields 2-(pyridin-2-yl)-4-(4-fluorobenzylamino)-5,6-dimethyl-thieno-[2,3-d]-pyrimidine.

EXAMPLE 902

With the procedure of Example 1, the reaction of 4-fluorobenzylamine with 4-chloro-2-(pyridin-2-yl)-6-trifluoromethyl-thieno-[2,3-d]-pyrimidine yields 2-(pyradin-2-yl)-4-(4-fluorobenzylamino)-6-trifluoromethyl-thieno-[2,3-d]-pyrimidine.

EXAMPLE 903

With the procedure of Example 1, the reaction of 4-fluorobenzylamine with 4-chloro-2-(pyridin-4-yl)-6-methyl-thieno-[2,3-d]-pyrimidine yields 2-(pyridin-4-yl)-4-(4-fluorobenzylamino)-6-methyl-thieno-[2,3-d]-pyrimidine.

EXAMPLE 904

With the procedure of Example 1, the reaction of 4-fluorobenzylamine with 4-chloro-2-(pyridin-4-yl)-5-methyl-thieno-[2,3-d]-pyrimidine yields 2-(pyridin-4-yl)-4-(4-fluorobenzylamino)-5-methyl-thieno-[2,3-d]-pyrimidine.

EXAMPLE 905

With the procedure of Example 1, the reaction of 4-fluorobenzylamine with 4-chloro-2-(pyridin-4-yl)-5,6,7,8-tetrahydro-[1]-benzothieno-[2,3-d]-pyrimidine yields 2-(pyridin-4-yl)-4-(4-fluorobenzylamino)-5,6,7,8-tetrahydro-thieno-[2,3-d]-pyrimidine.

EXAMPLE 906

With the procedure of Example 1, the reaction of 4-fluorobenzylamine with 4-chloro-2-(pyridin-4-yl)-5,6-cyclopenteno-thieno-[2,3-d]-pyrimidine yields 2-(pyridin-4-yl)-4-(4-fluorobenzylamino)-5,6-cyclopenteno-thieno-[2,3-d]-pyrimidine.

EXAMPLE 907

With the procedure of Example 1, the reaction of 4-fluorobenzylamine with 4-chloro-2-(pyridin-4-yl)-5,6-cyclohepteno-thieno-[2,3-d]-pyrimidine yields 2-(pyridin-4-yl)-4-(4-fluorobenzylamino)-5,6-cyclohepteno-thieno-[2,3-d]-pyrimidine.

EXAMPLE 908

With the procedure of Example 1, the reaction of 4-fluorobenzylamine with 4-chloro-2-(pyridin-4-yl)-6-ethyl-thieno-[2,3-d]-pyrimidine yields 2-(pyridin-4-yl)-4-(4-fluorobenzylamino)-6-ethyl-thieno-[2,3-d]-pyrimidine.

EXAMPLE 909

With the procedure of Example 1, the reaction of 4-fluorobenzylamine with 4-chloro-2-(pyridin-4-yl)-6-chloro-thieno-[2,3-d]-pyrimidine yields 2-(pyridin-4-yl)-4-(4-fluorobenzylamino)-6-chloro-thieno-[2,3-d]-pyrimidine.

EXAMPLE 910

With the procedure of Example 1, the reaction of 4-fluorobenzylamine with 4-chloro-2-(pyridin-4-yl)-5-chloro-6-methyl-thieno-[2,3-d]-pyrimidine yields 2-(pyridin-4-yl)-4-(4-fluorobenzylamino)-5-chlror-6-methyl-thieno-[2,3-d]-pyrimidine.

EXAMPLE 911

With the procedure of Example 1, the reaction of 4-fluorobenzylamine with 4-chloro-2-(pyridin-4-yl)-6-nitro-thieno-[2,3-d]-pyrimidine yields 2-(pyridin-4-yl)-4-(4-fluorobenzylamino)-6-nitro-thieno-[2,3-d]-pyrimidine.

EXAMPLE 912

With the procedure of Example 1, the reaction of 4-fluorobenzylamine with 4-chloro-2-(pyridin-4-yl)-5,6- dimethyl-thieno-[2,3-d]-pyrimidine yields 2-(pyridin-4-yl)-4-(4-fluorobenzylamino)-5,6-dimethyl-thieno-[2,3-d]-pyrimidine.

EXAMPLE 913

With the procedure of Example 1, the reaction of 4-fluorobenzylamine with 4-chloro-2-(pyridin-4-yl)-6-trifluoromethyl-thieno-[2,3-d]-pyrimidine yields 2-(pyridin-4-yl)-4-(4-fluorobenzylamino)-6-trifluoromethyl-thieno-[2,3-d]-pyrimidine.

EXAMPLE 914

With the procedure of Example 1, the reaction of 3,4-dichlorobenzylamine with 4-chloro-2-(pyridin-3-yl)-6-methyl-thieno-[2,3-d]-pyrimidine yields 2-(pyridin-3-yl)-4-(3,4-dichlorobenzylamino)-6-methyl-thieno-[2,3-d]-pyrimidine.

EXAMPLE 915

With the procedure of Example 1, the reaction of 4-fluoro-3,4-dichlorobenzylamine with 4-chloro-2-(pyridin-3-yl)-5-methyl-thieno-[2,3-d]-pyrimidine yields 2-(pyridin-3-yl)-4-(3,4-dichlorobenzylamino)-5-methyl-thieno-[2,3-d]-pyrimidine.

EXAMPLE 916

With the procedure of Example 1, the reaction of 4-fluoro-3,4-dichlorobenzylamine with 4-chloro-2-(pyridin-3-yl)-5,6,7,8-tetrahydro-[1]-benzothieno-[2,3-d]-pyrimidine yields 2-(pyridin-3-yl)-4-(3,4-dichlorobenzylamino)-5,6,7,8-tetrahydro-thieno-[2,3-d]-pyrimidine.

EXAMPLE 917

With the procedure of Example 1, the reaction of 3,4-dichlorobenzylamine with 4-chloro-2-(pyridin-3-yl)-5,6-cyclopenteno-thieno-[2,3-d]-pyrimidine yields 2-(pyridin-3-yl)-4-(3,4-dichlorobenzylamino)-5,6-cyclopenteno-thieno-[2,3-d]-pyrimidine.

EXAMPLE 918

With the procedure of Example 1, the reaction of 3,4-dichlorobenzylamine with 4-chloro-2-(pyridin-3-yl)-5,6-cyclohepteno-thieno-[2,3-d]-pyrimidine yields 2-(pyridin-3-yl)-4-(3,4-dichlorobenzylamino)-5,6-cyclohepteno-thieno-[2,3-d]-pyrimidine.

EXAMPLE 919

With the procedure of Example 1, the reaction of 3,4-dichlorobenzylamine with 4-chloro-2-(pyridin-3-yl)-6-ethyl-thieno-[2,3-d]-pyrimidine yields 2-(pyridin-3-yl)-4-(3,4-dichlorobenzylamino)-6-ethyl-thieno-[2,3-d]-pyrimidine.

EXAMPLE 920

With the procedure of Example 1, the reaction of 3,4-dichlorobenzylamine with 4-chloro-2-(pyridin-3-yl)-6-chloro-thieno-[2,3-d]-pyrimidine yields 2-(pyridin-3-yl)-4-(3,4-dichlorobenzylamino)-6-chloro-thieno-[2,3-d]-pyrimidine.

EXAMPLE 921

With the procedure of Example 1, the reaction of 3,4-dichlorobenzylamine with 4-chloro-2-(pyridin-3-yl)-5-chloro-6-methyl-thieno-[2,3-d]-pyrimidine yields 2-(pyridin-3-yl)-4-(3,4-dichlorobenzylamino)-5-chlror-6-methyl-thieno-[2,3-d]-pyrimidine.

EXAMPLE 922

With the procedure of Example 1, the reaction of 3,4-dichlorobenzylamine with 4-chloro-2-(pyridin-3-yl)-6-nitro-thieno-[2,3-d]-pyrimidine yields 2-(pyridin-3-yl)-4-(3,4-dichlorobenzylamino)-6-nitro-thieno-[2,3-d]-pyrimidine.

EXAMPLE 923

With the procedure of Example 1, the reaction of 3,4-dichlorobenzylamine with 4-chloro-2-(pyridin-3-yl)-5,6-dimethyl-thieno-[2,3-d]-pyrimidine yields 2-(pyridin-3-yl)-4-(3,4-dichlorobenzylamino)-5,6-dimethyl-thieno-[2,3-d]-pyrimidine.

EXAMPLE 924

With the procedure of Example 1, the reaction of 3,4-dichlorobenzylamine with 4-chloro-2-(pyridin-3-yl)-6-trifluoromethyl-thieno-[2,3-d]-pyrimidine yields 2-(pyridin-3-yl)-4-(3,4-dichlorobenzylamino)-6-trifluoromethyl-thieno-[2,3-d]-pyrimidine.

EXAMPLE 925

With the procedure of Example 1, the reaction of 3,4-dichlorobenzylamine with 4-chloro-2-(isoxazol-5-yl)-6-methyl-thieno-[2,3-d]-pyrimidine yields 2-(isoxazol-5-yl)-4-(3,4-dichlorobenzylamino)-6-methyl-thieno-[2,3-d]-pyrimidine.

EXAMPLE 926

With the procedure of Example 1, the reaction of 3,4-dichlorobenzylamine with 4-chloro-2-(isoxazol-5-yl)-5-methyl-thieno-[2,3-d]-pyrimidine yields 2-(isoxazol-5-yl)-4-(3,4-dichlorobenzylamino)-5-methyl-thieno-[2,3-d]-pyrimidine.

EXAMPLE 927

With the procedure of Example 1, the reaction of 3,4-dichlorobenzylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-dichlorobenzylamino)-5,6,7,8-tetrahydro-thieno-[2,3-d]-pyrimidine.

EXAMPLE 928

With the procedure of Example 1, the reaction of 3,4-dichlorobenzylamine with 4-chloro-2-(isoxazol-5-yl)-5,6-cyclopenteno-thieno-[2,3-d]-pyrimidine yields 2-(isoxazol-5-yl)-4-(3,4-dichlorobenzylamino)-5,6-cyclopenteno-thieno-[2,3-d]-pyrimidine.

EXAMPLE 929

With the procedure of Example 1, the reaction of 3,4-dichlorobenzylamine with 4-chloro-2-(isoxazol-5-yl)-5,6-cyclohepteno-thieno-[2,3-d]-pyrimidine yields 2 (isoxazol-5-yl)-4-(3,4-dichlorobenzylamino)-5,6-cyclohepteno-thieno-[2,3-d]-pyrimidine.

EXAMPLE 930

With the procedure of Example 1, the reaction of 3,4-dichlorobenzylamine with 4-chloro-2-(isoxazol-5-yl)-6-ethyl-thieno-[2,3-d]-pyrimidine yields 2-(isoxazol-5-yl)-4-(3,4-dichlorobenzylamino)-6-ethyl-thieno-[2,3-d]-pyrimidine.

EXAMPLE 931

With the procedure of Example 1, the reaction of 3,4-dichlorobenzylamine with 4-chloro-2-(isoxazol-5-yl)-6-chloro-thieno-[2,3-d]-pyrimidine yields 2-(isoxazol-5-yl)-4-(3,4-dichlorobenzylamino)-6-chloro-thieno-[2,3-d]-pyrimidine.

EXAMPLE 932

With the procedure of Example 1, the reaction of 3,4-dichlorobenzylamine with 4-chloro-2-(isoxazol-5-yl)-5-chloro-6-methyl-thieno-[2,3-d]-pyrimidine yields 2-(isoxazol-5-yl)-4-(3,4-dichlorobenzylamino)-5-chlror-6-methyl-thieno-[2,3-d]-pyrimidine.

EXAMPLE 933

With the procedure of Example 1, the reaction of 3,4-dichlorobenzylamine with 4-chloro-2-(isoxazol-5-yl)-6-nitro-thieno-[2,3-d]-pyrimidine yields 2-(isoxazol-5-yl)-4-(3,4-dichlorobenzylamino)-6-nitro-thieno-[2,3-d]-pyrimidine.

EXAMPLE 934

With the procedure of Example 1, the reaction of 3,4-dichlorobenzylamine with 4-chloro-2-(isoxazol-5-yl)-5,6-dimethyl-thieno-[2,3-d]-pyrimidine yields 2-(isoxazol-5-yl)-4-(3,4-dichlorobenzylamino)-5,6-dimethyl-thieno-[2,3-d]-pyrimidine.

EXAMPLE 935

With the procedure of Example 1, the reaction of 3,4-dichlorobenzylamine with 4-chloro-2-(isoxazol-5-yl)-6-trifluoromethyl-thieno-[2,3-d]-pyrimidine yields 2 (isoxazol-5-yl)-4-(3,4-dichlorobenzylamino)-6-trifluoromethyl-thieno-[2,3-d]-pyrimidine.

EXAMPLE 936

With the procedure of Example 1, the reaction of 3,4-dichlorobenzylamine with 4-chloro-2-(pyrazin-2-yl)-6-methyl-thieno-[2,3-d]-pyrimidine yields 2-(pyrazin-2-yl)-4-(3,4-dichlorobenzylamino)-6-methyl-thieno-[2,3-d]-pyrimidine.

EXAMPLE 937

With the procedure of Example 1, the reaction of 3,4-dichlorobenzylamine with 4-chloro-2-(pyrazin-2-yl)-5-methyl-thieno-[2,3-d]-pyrimidine yields 2-(pyrazin-2-yl)-4-(3,4-dichlorobenzylamino)-5-methyl-thieno-[2,3-d]-pyrimidine.

EXAMPLE 938

With the procedure of Example 1, the reaction of 3,4-dichlorobenzylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-dichlorobenzylamino)-5,6,7,8-tetrahydro-thieno-[2,3-d]-pyrimidine.

EXAMPLE 939

With the procedure of Example 1, the reaction of 3,4-dichlorobenzylamine with 4-chloro-2-(pyrazin-2-yl)-5,6-cyclopenteno-thieno-[2,3-d]-pyrimidine yields 2-(pyrazin-2-yl)-4-(3,4-dichlorobenzylamino)-5,6-cyclopenteno-thieno-[2,3-d]-pyrimidine.

EXAMPLE 940

With the procedure of Example 1, the reaction of 3,4-dichlorobenzylamine with 4-chloro-2-(pyrazin-2-yl)-5,6-cyclohepteno-thieno-[2,3-d]-pyrimidine yields 2-(pyrazin-2-yl)-4-(3,4-dichlorobenzylamino)-5,6-cyclohepteno-thieno-[2,3-d]-pyrimidine.

EXAMPLE 941

With the procedure of Example 1, the reaction of 3,4-dichlorobenzylamine with 4-chloro-2-(pyrazin-2-yl)-6-ethyl-thieno-[2,3-d]-pyrimidine yields 2-(pyrazin-2-yl)-4-(3,4-dichlorobenzylamino)-6-ethyl-thieno-[2,3-d]-pyrimidine.

EXAMPLE 942

With the procedure of Example 1, the reaction of 3,4-dichlorobenzylamine with 4-chloro-2-(pyrazin-2-yl)-6-chloro-thieno-[2,3-d]-pyrimidine yields 2-(pyrazin-2-yl)-4-(3,4-dichlorobenzylamino)-6-chloro-thieno-[2,3-d]-pyrimidine.

EXAMPLE 943

With the procedure of Example 1, the reaction of 3,4-dichlorobenzylamine with 4-chloro-2-(pyrazin-2-yl)-5-chloro-6-methyl-thieno-[2,3-d]-pyrimidine yields 2-(pyrazin-2-yl)-4-(3,4-dichlorobenzylamino)-5-chlror-6-methyl-thieno-[2,3-d]-pyrimidine.

EXAMPLE 944

With the procedure of Example 1, the reaction of 3,4-dichlorobenzylamine with 4-chloro-2-(pyrazin-2-yl)-6-nitro-thieno-[2,3-d]-pyrimidine yields 2-(pyrazin-2-yl)-4-(3,4-dichlorobenzylamino)-6-nitro-thieno-[2,3-d]-pyrimidine.

EXAMPLE 945

With the procedure of Example 1, the reaction of 3,4-dichlorobenzylamine with 4-chloro-2-(pyrazin-2-yl)-5,6-dimethyl-thieno-[2,3-d]-pyrimidine yields 2-(pyrazin-2-yl)-4-(3,4-dichlorobenzylamino)-5,6-dimethyl-thieno-[2,3-d]-pyrimidine.

EXAMPLE 946

With the procedure of Example 1, the reaction of 3,4-dichlorobenzylamine with 4-chloro-2-(pyrazin-2-yl)-6-trifluoromethyl-thieno-[2,3-d]-pyrimidine yields 2-(pyrazin-2-yl)-4-(3,4-dichlorobenzylamino)-6-trifluoromethyl-thieno-[2,3-d]-pyrimidine.

EXAMPLE 947

With the procedure of Example 1, the reaction of 3,4-dichlorobenzylamine with 4-chloro-2-(pyridin-2-yl)-6-methyl-thieno-[2,3-d]-pyrimidine yields 2-(pyradin-2-yl)-4-(3,4-dichlorobenzylamino)-6-methyl-thieno-[2,3-d]-pyrimidine.

EXAMPLE 948

With the procedure of Example 1, the reaction of 3,4-dichlorobenzylamine with 4-chloro-2-(pyridin-2-yl)-5-methyl-thieno-[2,3-d]-pyrimidine yields 2-(pyradin-2-yl)-4-(3,4-dichlorobenzylamino)-5-methyl-thieno-[2,3-d]-pyrimidine.

EXAMPLE 949

With the procedure of Example 1, the reaction of 3,4-dichlorobenzylamine with 4-chloro-2-(pyridin-2-yl)-5,6,7,8-tetrahydro-[1]-benzothieno-[2,3-d]-pyrimidine yields 2-(pyridin-2-yl)-4-(3,4-dichlorobenzylamino)-5,6,7,8-tetrahydro-thieno-[2,3-d]-pyrimidine.

EXAMPLE 950

With the procedure of Example 1, the reaction of 3,4-dichlorobenzylamine with 4-chloro-2-(pyridin-2-yl)-5,6-cyclopenteno-thieno-[2,3-d]-pyrimidine yields 2-(pyridin-2-yl)-4-(3,4-dichlorobenzylamino)-5,6-cyclopenteno-thieno-[2,3-d]-pyrimidine.

EXAMPLE 951

With the procedure of Example 1, the reaction of 3,4-dichlorobenzylamine with 4-chloro-2-(pyridin-2-yl)-5,6-cyclohepteno-thieno-[2,3-d]-pyrimidine yields 2-(pyridin-2-yl)-4-(3,4-dichlorobenzylamino)-5,6-cyclohepteno-thieno-[2,3-d]-pyrimidine.

EXAMPLE 952

With the procedure of Example 1, the reaction of 3,4-dichlorobenzylamine with 4-chloro-2-(pyridin-2-yl)-6-ethyl-thieno-[2,3-d]-pyrimidine yields 2-(pyridin-2-yl)-4-(3,4-dichlorobenzylamino)-6-ethyl-thieno-[2,3-d]-pyrimidine.

EXAMPLE 953

With the procedure of Example 1, the reaction of 3,4-dichlorobenzylamine with 4-chloro-2-(pyridin-2-yl)-6-chloro-thieno-[2,3-d]-pyrimidine yields 2-(pyridin-2-yl)-4-(3,4-dichlorobenzylamino)-6-chloro-thieno-[2,3-d]-pyrimidine.

EXAMPLE 954

With the procedure of Example 1, the reaction of 3,4-dichlorobenzylamine with 4-chloro-2-(pyridin-2-yl)-5-chloro-6-methyl-thieno-[2,3-d]-pyrimidine yields 2-(pyridin-2-yl)-4-(3,4-dichlorobenzylamino)-5-chlror-6-methyl-thieno-[2,3-d]-pyrimidine.

EXAMPLE 955

With the procedure of Example 1, the reaction of 3,4-dichlorobenzylamine with 4-chloro-2-(pyridin-2-yl)-6-nitro-thieno-[2,3-d]-pyrimidine yields 2-(pyridin-2-yl)-4-(3,4-dichlorobenzylamino)-6-nitro-thieno-[2,3-d]-pyrimidine.

EXAMPLE 956

With the procedure of Example 1, the reaction of 3,4-dichlorobenzylamine with 4-chloro-2-(pyridin-2-yl)-5,6-dimethyl-thieno-[2,3-d]-pyrimidine yields 2-(pyridin-2-yl)-4-(3,4-dichlorobenzylamino)-5,6-dimethyl-thieno-[2,3-d]-pyrimidine.

EXAMPLE 957

With the procedure of Example 1, the reaction of 3,4-dichlorobenzylamine with 4-chloro-2-(pyridin-2-yl)-6-trifluoromethyl-thieno-[2,3-d]-pyrimidine yields 2-(pyridin-2-yl)-4-(3,4-dichlorobenzylamino)-6-trifluoromethyl-thieno-[2,3-d]-pyrimidine.

EXAMPLE 958

With the procedure of Example 1, the reaction of 3,4-dichlorobenzylamine with 4-chloro-2-(pyridin-4-yl)-6-methyl-thieno-[2,3-d]-pyrimidine yields 2-(pyridin-4-yl)-4-(3,4-dichlorobenzylamino)-6-methyl-thieno-[2,3-d]-pyrimidine.

EXAMPLE 959

With the procedure of Example 1, the reaction of 3,4-dichlorobenzylamine with 4-chloro-2-(pyridin-4-yl)-5-methyl-thieno-[2,3-d]-pyrimidine yields 2-(pyridin-4-yl)-4-(3,4-dichlorobenzylamino)-5-methyl-thieno-[2,3-d]-pyrimidine.

EXAMPLE 960

With the procedure of Example 1, the reaction of 3,4-dichlorobenzylamine with 4-chloro-2-(pyridin-4-yl)-5,6,7,8-tetrahydro-[1]-benzothieno-[2,3-d]-pyrimidine yields 2-(pyridin-4-yl)-4-(3,4-dichlorobenzylamino)-5,6,7,8-tetrahydro-thieno-[2,3-d]-pyrimidine.

EXAMPLE 961

With the procedure of Example 1, the reaction of 3,4-dichlorobenzylamine with 4-chloro-2-(pyridin-4-yl)-5,6-cyclopenteno-thieno-[2,3-d]-pyrimidine yields 2-(pyridin-4-yl)-4-(3,4-dichlorobenzylamino)-5,6-cyclopenteno-thieno-[2,3-d]-pyrimidine.

EXAMPLE 962

With the procedure of Example 1, the reaction of 3,4-dichlorobenzylamine with 4-chloro-2-(pyridin-4-yl)-5,6-cyclohepteno-thieno-[2,3-d]-pyrimidine yields 2-(pyridin-4-yl)-4-(3,4-dichlorobenzylamino)-5,6-cyclohepteno-thieno-[2,3-d]-pyrimidine.

EXAMPLE 963

With the procedure of Example 1, the reaction of 3,4-dichlorobenzylamine with 4-chloro-2-(pyridin-4-yl)-6-ethyl-thieno-[2,3-d]-pyrimidine yields 2-(pyridin-4-yl)-4-(3,4-dichlorobenzylamino)-6-ethyl-thieno-[2,3-d]-pyrimidine.

EXAMPLE 964

With the procedure of Example 1, the reaction of 3,4-dichlorobenzylamine with 4-chloro-2-(pyridin-4-yl)-6-chloro-thieno-[2,3-d]-pyrimidine yields 2-(pyridin-4-yl)-4-(3,4-dichlorobenzylamino)-6-chloro-thieno-[2,3-d]-pyrimidine.

EXAMPLE 965

With the procedure of Example 1, the reaction of 3,4-dichlorobenzylamine with 4-chloro-2-(pyridin-4-yl)-5-chloro-6-methyl-thieno-[2,3-d]-pyrimidine yields 2-(pyridin-4-yl)-4-(3,4-dichlorobenzylamino)-5-chlror-6-methyl-thieno-[2,3-d]-pyrimidine.

EXAMPLE 966

With the procedure of Example 1, the reaction of 3,4-dichlorobenzylamine with 4-chloro-2-(pyridin-4-yl)-6-nitro-thieno-[2,3-d]-pyrimidine yields 2-(pyridin-4-yl)-4-(3,4-dichlorobenzylamino)-6-nitro-thieno-[2,3-d]-pyrimidine.

EXAMPLE 967

With the procedure of Example 1, the reaction of 3,4-dichlorobenzylamine with 4-chloro-2-(pyridin-4-yl)-5,6-dimethyl-thieno-[2,3-d]-pyrimidine yields 2-(pyridin-4-yl)-4-(3,4-dichlorobenzylamino)-5,6-dimethyl-thieno-[2,3-d]-pyrimidine.

EXAMPLE 968

With the procedure of Example 1, the reaction of 3,4-dichlorobenzylamine with 4-chloro-2-(pyridin-4-yl)-6- trifluoromethyl-thieno-[2,3-d]-pyrimidine yields 2-(pyridin-4-yl)-4-(3,4-dichlorobenzylamino)-6-trifluoromethyl-thieno-[2,3-d]-pyrimidine.

EXAMPLE 969

With the procedure of Example 1, the reaction of 3,4-dichlorobenzylamine with 4-chloro-2-(pyridin-3-yl)-6-methyl-thieno-[2,3-d]-pyrimidine yields 2-(pyridin-3-yl)-4-(3,4-dichlorobenzylamino)-6-methyl-thieno-[2,3-d]-pyrimidine.

EXAMPLE 970

With the procedure of Example 1, the reaction of 3,4-dichlorobenzylamine with 4-chloro-2-(pyridin-3-yl)-5-methyl-thieno-[2,3-d]-pyrimidine yields 2-(pyridin-3-yl)-4-(3,4-dichlorobenzylamino)-5-methyl-thieno-[2,3-d]-pyrimidine.

EXAMPLE 971

With the procedure of Example 1, the reaction of 3,4-dichlorobenzylamine with 4-chloro-2-(pyridin-3-yl)-5,6,7,8-tetrahydro-[1]-benzothieno-[2,3-d]-pyrimidine yields 2-(pyridin-3-yl)-4-(3,4-dichlorobenzylamino)-5,6,7,8-tetrahydro-thieno-[2,3-d]-pyrimidine.

EXAMPLE 972

With the procedure of Example 1, the reaction of 3,4-dichlorobenzylamine with 4-chloro-2-(pyridin-3-yl)-5,6-cyclopenteno-thieno-[2,3-d]-pyrimidine yields 2-(pyridin-3-yl)-4-(3,4-dichlorobenzylamino)-5,6-cyclopenteno-thieno-[2,3-d]-pyrimidine.

EXAMPLE 973

With the procedure of Example 1, the reaction of 3,4-dichlorobenzylamine with 4-chloro-2-(pyridin-3-yl)-5,6-cyclohepteno-thieno-[2,3-d]-pyrimidine yields 2-(pyridin-3-yl)-4-(3,4-dichlorobenzylamino)-5,6-cyclohepteno-thieno-[2,3-d]-pyrimidine.

EXAMPLE 974

With the procedure of Example 1, the reaction of 3,4-dichlorobenzylamine with 4-chloro-2-(pyridin-3-yl)-6-ethyl-thieno-[2,3-d]-pyrimidine yields 2-(pyridin-3-yl)-4-(3,4-dichlorobenzylamino)-6-ethyl-thieno-[2,3-d]-pyrimidine.

EXAMPLE 975

With the procedure of Example 1, the reaction of 3,4-dichlorobenzylamine with 4-chloro-2-(pyridin-3-yl)-6-chloro-thieno-[2,3-d]-pyrimidine yields 2-(pyridin-3-yl)-4-(3,4-dichlorobenzylamino)-6-chloro-thieno-[2,3-d]-pyrimidine.

EXAMPLE 976

With the procedure of Example 1, the reaction of 3,4-dichlorobenzylamine with 4-chloro-2-(pyridin-3-yl)-5-chloro-6-methyl-thieno-[2,3-d]-pyrimidine yields 2 (pyridin-3-yl)-4-(3,4-dichlorobenzylamino)-5-chlror-6-methyl-thieno-[2,3-d]-pyrimidine.

EXAMPLE 977

With the procedure of Example 1, the reaction of 3,4-dichlorobenzylamine with 4-chloro-2-(pyridin-3-yl)-6-nitro-thieno-[2,3-d]-pyrimidine yields 2-(pyridin-3-yl)-4-(3,4-dichlorobenzylamino)-6-nitro-thieno-[2,3-d]-pyrimidine.

EXAMPLE 978

With the procedure of Example 1, the reaction of 3,4-dichlorobenzylamine with 4-chloro-2-(pyridin-3-yl)-5,6-dimethyl-thieno-[2,3-d]-pyrimidine yields 2-(pyridin-3-yl)-4-(3,4-dichlorobenzylamino)-5,6-dimethyl-thieno-[2,3-d]-pyrimidine.

EXAMPLE 979

With the procedure of Example 1, the reaction of 3,4-dichlorobenzylamine with 4-chloro-2-(pyridin-3-yl)-6-trifluoromethyl-thieno-[2,3-d]-pyrimidine yields 2-(pyridin-3-yl)-4-(3,4-dichlorobenzylamino)-6-trifluoromethyl-thieno-[2,3-d]-pyrimidine.

EXAMPLE 980

With the procedure of Example 1, the reaction of 3,4-dichlorobenzylamine with 4-chloro-2-(isoxazol-5-yl)-6-methyl-thieno-[2,3-d]-pyrimidine yields 2-(isoxazol-5-yl)-4-(3,4-dichlorobenzylamino)-6-methyl-thieno-[2,3-d]-pyrimidine.

EXAMPLE 981

With the procedure of Example 1, the reaction of 3,4-dichlorobenzylamine with 4-chloro-2-(isoxazol-5-yl)-5-methyl-thieno-[2,3-d]-pyrimidine yields 2-(isoxazol-5-yl)-4-(3,4-dichlorobenzylamino)-5-methyl-thieno-[2,3-d]-pyrimidine.

EXAMPLE 982

With the procedure of Example 1, the reaction of 3,4-dichlorobenzylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-dichlorobenzylamino)-5,6,7,8-tetrahydro-thieno-[2,3-d]-pyrimidine.

EXAMPLE 983

With the procedure of Example 1, the reaction of 3,4-dichlorobenzylamine with 4-chloro-2-(isoxazol-5-yl)-5,6-cyclopenteno-thieno-[2,3-d]-pyrimidine yields 2-(isoxazol-5-yl)-4-(3,4-dichlorobenzylamino)-5,6-cyclopenteno-thieno-[2,3-d]-pyrimidine.

EXAMPLE 984

With the procedure of Example 1, the reaction of 3,4-dichlorobenzylamine with 4-chloro-2-(isoxazol-5-yl)-5,6-cyclohepteno-thieno-[2,3-d]-pyrimidine yields 2-(isoxazol-5-yl)-4-(3,4-dichlorobenzylamino)-5,6-cyclohepteno-thieno-[2,3-d]-pyrimidine.

EXAMPLE 985

With the procedure of Example 1, the reaction of 3,4-dichlorobenzylamine with 4-chloro-2-(isoxazol-5-yl)-6-ethyl-thieno-[2,3-d]-pyrimidine yields 2-(isoxazol-5-yl)-4-(3,4-dichlorobenzylamino)-6-ethyl-thieno-[2,3-d]-pyrimidine.

EXAMPLE 986

With the procedure of Example 1, the reaction of 3,4-dichlorobenzylamine with 4-chloro-2-(isoxazol-5-yl)-6-chloro-thieno-[2,3-d]-pyrimidine yields 2-(isoxazol-5-yl)-4-(3,4-dichlorobenzylamino)-6-chloro-thieno-[2,3-d]-pyrimidine.

EXAMPLE 987

With the procedure of Example 1, the reaction of 3,4-dichlorobenzylamine with 4-chloro-2-(isoxazol-5-yl)-5- chloro-6-methyl-thieno-[2,3-d]-pyrimidine yields 2-(isoxazol-5-yl)-4-(3,4-dichlorobenzylamino)-5-chlror-6-methyl-thieno-[2,3-d]-pyrimidine.

EXAMPLE 988

With the procedure of Example 1, the reaction of 3,4-dichlorobenzylamine with 4-chloro-2-(isoxazol-5-yl)-6-nitro-thieno-[2,3-d]-pyrimidine yields 2-(isoxazol-5-yl)-4-(3,4-dichlorobenzylamino)-6-nitro-thieno-[2,3-d]-pyrimidine.

EXAMPLE 989

With the procedure of Example 1, the reaction of 3,4-dichlorobenzylamine with 4-chloro-2-(isoxazol-5-yl)-5,6-dimethyl-thieno-[2,3-d]-pyrimidine yields 2-(isoxazol-5-yl)-4-(3,4-dichlorobenzylamino)-5,6-dimethyl-thieno-[2,3-d]-pyrimidine.

EXAMPLE 990

With the procedure of Example 1, the reaction of 3,4-dichlorobenzylamine with 4-chloro-2-(isoxazol-5-yl)-6-trifluoromethyl-thieno-[2,3-d]-pyrimidine yields 2-(isoxazol-5-yl)-4-(3,4-dichlorobenzylamino)-6-trifluoromethyl-thieno-[2,3-d]-pyrimidine.

EXAMPLE 991

With the procedure of Example 1, the reaction of 3,4-dichlorobenzylamine with 4-chloro-2-(pyrazin-2-yl)-6-methyl-thieno-[2,3-d]-pyrimidine yields 2-(pyrazin-2-yl)-4-(3,4-dichlorobenzylamino)-6-methyl-thieno-[2,3-d]-pyrimidine.

EXAMPLE 992

With the procedure of Example 1, the reaction of 3,4-dichlorobenzylamine with 4-chloro-2-(pyrazin-2-yl)-5-methyl-thieno-[2,3-d]-pyrimidine yields 2-(pyrazin-2-yl)-4-(3,4-dichlorobenzylamino)-5-methyl-thieno-[2,3-d]-pyrimidine.

EXAMPLE 992

With the procedure of Example 1, the reaction of 3,4-dichlorobenzylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-dichlorobenzylamino)-5,6,7,8-tetrahydro-thieno-[2,3-d]-pyrimidine.

EXAMPLE 993

With the procedure of Example 1, the reaction of 3,4-dichlorobenzylamine with 4-chloro-2-(pyrazin-2-yl)-5,6-cyclopenteno-thieno-[2,3-d]-pyrimidine yields 2-(pyrazin-2-yl)-4-(3,4-dichlorobenzylamino)-5,6-cyclopenteno-thieno-[2,3-d]-pyrimidine.

EXAMPLE 994

With the procedure of Example 1, the reaction of 3,4-dichlorobenzylamine with 4-chloro-2-(pyrazin-2-yl)-5,6-cyclohepteno-thieno-[2,3-d]-pyrimidine yields 2-(pyrazin-2-yl)-4-(3,4-dichlorobenzylamino)-5,6-cyclohepteno-thieno-[2,3-d]-pyrimidine.

EXAMPLE 995

With the procedure of Example 1, the reaction of 3,4-dichlorobenzylamine with 4-chloro-2-(pyrazin-2-yl)-6-ethyl-thieno-[2,3-d]-pyrimidine yields 2-(pyrazin-2-yl)-4-(3,4-dichlorobenzylamino)-6-ethyl-thieno-[2,3-d]-pyrimidine.

EXAMPLE 996

With the procedure of Example 1, the reaction of 3,4-dichlorobenzylamine with 4-chloro-2-(pyrazin-2-yl)-6-chloro-thieno-[2,3-d]-pyrimidine yields 2-(pyrazin-2-yl)-4-(3,4-dichlorobenzylamino)-6-chloro-thieno-[2,3-d]-pyrimidine.

EXAMPLE 997

With the procedure of Example 1, the reaction of 3,4-dichlorobenzylamine with 4-chloro-2-(pyrazin-2-yl)-5-chloro-6-methyl-thieno-[2,3-d]-pyrimidine yields 2-(pyrazin-2-yl)-4-(3,4-dichlorobenzylamino)-5-chlror-6-methyl-thieno-[2,3-d]-pyrimidine.

EXAMPLE 998

With the procedure of Example 1, the reaction of 3,4-dichlorobenzylamine with 4-chloro-2-(pyrazin-2-yl)-6-nitro-thieno-[2,3-d]-pyrimidine yields 2-(pyrazin-2-yl)-4-(3,4-dichlorobenzylamino)-6-nitro-thieno-[2,3-d]-pyrimidine.

EXAMPLE 999

With the procedure of Example 1, the reaction of 3,4-dichlorobenzylamine with 4-chloro-2-(pyrazin-2-yl)-5,6-dimethyl-thieno-[2,3-d]-pyrimidine yields 2-(pyrazin-2-yl)-4-(3,4-dichlorobenzylamino)-5,6-dimethyl-thieno-[2,3-d]-pyrimidine.

EXAMPLE 1000

With the procedure of Example 1, the reaction of 3,4-dichlorobenzylamine with 4-chloro-2-(pyrazin-2-yl)-6-trifluoromethyl-thieno-[2,3-d]-pyrimidine yields 2-(pyrazin-2-yl)-4-(3,4-dichlorobenzylamino)-6-trifluoromethyl-thieno-[2,3-d]-pyrimidine.

EXAMPLE 1001

With the procedure of Example 1, the reaction of 3,4-dichlorobenzylamine with 4-chloro-2-(pyridin-2-yl)-6-methyl-thieno-[2,3-d]-pyrimidine yields 2-(pyradin-2-yl)-4-(3,4-dichlorobenzylamino)-6-methyl-thieno-[2,3-d]-pyrimidine.

EXAMPLE 1002

With the procedure of Example 1, the reaction of 3,4-dichlorobenzylamine with 4-chloro-2-(pyridin-2-yl)-5-methyl-thieno-[2,3-d]-pyrimidine yields 2-(pyradin-2-yl)-4-(3,4-dichlorobenzylamino)-5-methyl-thieno-[2,3-d]-pyrimidine.

EXAMPLE 1003

With the procedure of Example 1, the reaction of 3,4-dichlorobenzylamine with 4-chloro-2-(pyridin-2-yl)-5,6,7,8-tetrahydro-[1]-benzothieno-[2,3-d]-pyrimidine yields 2-(pyridin-2-yl)-4-(3,4-dichlorobenzylamino)-5,6,7,8-tetrahydro-thieno-[2,3-d]-pyrimidine.

EXAMPLE 1004

With the procedure of Example 1, the reaction of 3,4-dichlorobenzylamine with 4-chloro-2-(pyridin-2-yl)-5,6-cyclopenteno-thieno-[2,3-d]-pyrimidine yields 2-(pyridin-2- yl)-4-(3,4-dichlorobenzylamino)-5,6-cyclopenteno-thieno-[2,3-d]-pyrimidine.

EXAMPLE 1005

With the procedure of Example 1, the reaction of 3,4-dichlorobenzylamine with 4-chloro-2-(pyridin-2-yl)-5,6-cyclohepteno-thieno-[2,3-d]-pyrimidine yields 2-(pyridin-2-yl)-4-(3,4-dichlorobenzylamino)-5,6-cyclohepteno-thieno-[2,3-d]-pyrimidine.

EXAMPLE 1006

With the procedure of Example 1, the reaction of 3,4-dichlorobenzylamine with 4-chloro-2-(pyridin-2-yl)-6-ethyl-thieno-[2,3-d]-pyrimidine yields 2-(pyridin-2-yl)-4-(3,4-dichlorobenzylamino)-6-ethyl-thieno-[2,3-d]-pyrimidine.

EXAMPLE 1007

With the procedure of Example 1, the reaction of 3,4-dichlorobenzylamine with 4-chloro-2-(pyridin-2-yl)-6-chloro-thieno-[2,3-d]-pyrimidine yields 2-(pyridin-2-yl)-4-(3,4-dichlorobenzylamino)-6-chloro-thieno-[2,3-d]-pyrimidine.

EXAMPLE 1008

With the procedure of Example 1, the reaction of 3,4-dichlorobenzylamine with 4-chloro-2-(pyridin-2-yl)-5-chloro-6-methyl-thieno-[2,3-d]-pyrimidine yields 2-(pyridin-2-yl)-4-(3,4-dichlorobenzylamino)-5-chlror-6-methyl-thieno-[2,3-d]-pyrimidine.

EXAMPLE 1009

With the procedure of Example 1, the reaction of 3,4-dichlorobenzylamine with 4-chloro-2-(pyridin-2-yl)-6-nitro-thieno-[2,3-d]-pyrimidine yields 2-(pyridin-2-yl)-4-(3,4-dichlorobenzylamino)-6-nitro-thieno-[2,3-d]-pyrimidine.

EXAMPLE 1010

With the procedure of Example 1, the reaction of 3,4-dichlorobenzylamine with 4-chloro-2-(pyridin-2-yl)-5,6-dimethyl-thieno-[2,3-d]-pyrimidine yields 2-(pyridin-2-yl)-4-(3,4-dichlorobenzylamino)-5,6-dimethyl-thieno-[2,3-d]-pyrimidine.

EXAMPLE 1011

With the procedure of Example 1, the reaction of 3,4-dichlorobenzylamine with 4-chloro-2-(pyridin-2-yl)-6-trifluoromethyl-thieno-[2,3-d]-pyrimidine yields 2-(pyridin-2-yl)-4-(3,4-dichlorobenzylamino)-6-trifluoromethyl-thieno-[2,3-d]-pyrimidine.

EXAMPLE 1012

With the procedure of Example 1, the reaction of 3,4-dichlorobenzylamine with 4-chloro-2-(pyridin-4-yl)-6-methyl-thieno-[2,3-d]-pyrimidine yields 2-(pyridin-4-yl)-4-(3,4-dichlorobenzylamino)-6-methyl-thieno-[2,3-d]-pyrimidine.

EXAMPLE 1013

With the procedure of Example 1, the reaction of 3,4-dichlorobenzylamine with 4-chloro-2-(pyridin-4-yl)-5-methyl-thieno-[2,3-d]-pyrimidine yields 2-(pyridin-4-yl)-4-(3,4-dichlorobenzylamino)-5-methyl-thieno-[2,3-d]-pyrimidine.

EXAMPLE 1014

With the procedure of Example 1, the reaction of 3,4-dichlorobenzylamine with 4-chloro-2-(pyridin-4-yl)-5,6,7,8-tetrahydro-[1]-benzothieno-[2,3-d]-pyrimidine yields 2-(pyridin-4-yl)-4-(3,4-dichlorobenzylamino)-5,6,7,8-tetrahydro-thieno-[2,3-d]-pyrimidine.

EXAMPLE 1015

With the procedure of Example 1, the reaction of 3,4-dichlorobenzylamine with 4-chloro-2-(pyridin-4-yl)-5,6-cyclopenteno-thieno-[2,3-d]-pyrimidine yields 2-(pyridin-4-yl)-4-(3,4-dichlorobenzylamino)-5,6-cyclopenteno-thieno-[2,3-d]-pyrimidine.

EXAMPLE 1016

With the procedure of Example 1, the reaction of 3,4-dichlorobenzylamine with 4-chloro-2-(pyridin-4-yl)-5,6-cyclohepteno-thieno-[2,3-d]-pyrimidine yields 2-(pyridin-4-yl)-4-(3,4-dichlorobenzylamino)-5,6-cyclohepteno-thieno-[2,3-d]-pyrimidine.

EXAMPLE 1017

With the procedure of Example 1, the reaction of 3,4-dichlorobenzylamine with 4-chloro-2-(pyridin-4-yl)-6-ethyl-thieno-[2,3-d]-pyrimidine yields 2-(pyridin-4-yl)-4-(3,4-dichlorobenzylamino)-6-ethyl-thieno-[2,3-d]-pyrimidine.

EXAMPLE 1018

With the procedure of Example 1, the reaction of 3,4-dichlorobenzylamine with 4-chloro-2-(pyridin-4-yl)-6-chloro-thieno-[2,3-d]-pyrimidine yields 2-(pyridin-4-yl)-4-(3,4-dichlorobenzylamino)-6-chloro-thieno-[2,3-d]-pyrimidine.

EXAMPLE 1019

With the procedure of Example 1, the reaction of 3,4-dichlorobenzylamine with 4-chloro-2-(pyridin-4-yl)-5-chloro-6-methyl-thieno-[2,3-d]-pyrimidine yields 2-(pyridin-4-yl)-4-(3,4-dichlorobenzylamino)-5-chlror-6-methyl-thieno-[2,3-d]-pyrimidine.

EXAMPLE 1020

With the procedure of Example 1, the reaction of 3,4-dichlorobenzylamine with 4-chloro-2-(pyridin-4-yl)-6-nitro-thieno-[2,3-d]-pyrimidine yields 2-(pyridin-4-yl)-4-(3,4-dichlorobenzylamino)-6-nitro-thieno-[2,3-d]-pyrimidine.

EXAMPLE 1021

With the procedure of Example 1, the reaction of 3,4-dichlorobenzylamine with 4-chloro-2-(pyridin-4-yl)-5,6-dimethyl-thieno-[2,3-d]-pyrimidine yields 2-(pyridin-4-yl)-4-(3,4-dichlorobenzylamino)-5,6-dimethyl-thieno-[2,3-d]-pyrimidine.

EXAMPLE 1022

With the procedure of Example 1, the reaction of 3,4-dichlorobenzylamine with 4-chloro-2-(pyridin-4-yl)-6-trifluoromethyl-thieno-[2,3-d]-pyrimidine yields 2 (pyridin-4-yl)-4-(3,4-dichlorobenzylamino)-6-trifluoromethyl-thieno-[2,3-d]-pyrimidine.

EXAMPLE 1023

With the procedure of Example 1, the reaction of 3-nitrobenzylamine with 4-chloro-2-(pyridin-3-yl)-6- methyl-thieno-[2,3-d]-pyrimidine yields 2-(pyridin-3-yl)-4-(3-nitrobenzylamino)-6-methyl-thieno-[2,3-d]-pyrimidine.

EXAMPLE 1024

With the procedure of Example 1, the reaction of 4-fluoro-3-nitrobenzylamine with 4-chloro-2-(pyridin-3-yl)-5-methyl-thieno-[2,3-d]-pyrimidine yields 2-(pyridin-3-yl)-4-(3-nitrobenzylamino)-5-methyl-thieno-[2,3-d]-pyrimidine.

EXAMPLE 1025

With the procedure of Example 1, the reaction of 4-fluoro-3-nitrobenzylamine with 4-chloro-2-(pyridin-3-yl)-5,6,7,8-tetrahydro-[1]-benzothieno-[2,3-d]-pyrimidine yields 2-(pyridin-3-yl)-4-(3-nitrobenzylamino)-5,6,7,8-tetrahydro-thieno-[2,3-d]-pyrimidine.

EXAMPLE 1026

With the procedure of Example 1, the reaction of 3-nitrobenzylamine with 4-chloro-2-(pyridin-3-yl)-5,6-cyclopenteno-thieno-[2,3-d]-pyrimidine yields 2-(pyridin-3-yl)-4-(3-nitrobenzylamino)-5,6-cyclopenteno-thieno-[2,3-d]-pyrimidine.

EXAMPLE 1027

With the procedure of Example 1, the reaction of 3-nitrobenzylamine with 4-chloro-2-(pyridin-3-yl)-5,6-cyclohepteno-thieno-[2,3-d]-pyrimidine yields 2-(pyridin-3-yl)-4-(3-nitrobenzylamino)-5,6-cyclohepteno-thieno-[2,3-d]-pyrimidine.

EXAMPLE 1028

With the procedure of Example 1, the reaction of 3-nitrobenzylamine with 4-chloro-2-(pyridin-3-yl)-6-ethyl-thieno-[2,3-d]-pyrimidine yields 2-(pyridin-3-yl)-4-(3-nitrobenzylamino)-6-ethyl-thieno-[2,3-d]-pyrimidine.

EXAMPLE 1029

With the procedure of Example 1, the reaction of 3-nitrobenzylamine with 4-chloro-2-(pyridin-3-yl)-6-chloro-thieno-[2,3-d]-pyrimidine yields 2-(pyridin-3-yl)-4-(3-nitrobenzylamino)-6-chloro-thieno-[2,3-d]-pyrimidine.

EXAMPLE 1030

With the procedure of Example 1, the reaction of 3-nitrobenzylamine with 4-chloro-2-(pyridin-3-yl)-5-chloro-6-methyl-thieno-[2,3-d]-pyrimidine yields 2-(pyridin-3-yl)-4-(3-nitrobenzylamino)-5-chlror-6-methyl-thieno-[2,3-d]-pyrimidine.

EXAMPLE 1031

With the procedure of Example 1, the reaction of 3-nitrobenzylamine with 4-chloro-2-(pyridin-3-yl)-6-nitro-thieno-[2,3-d]-pyrimidine yields 2-(pyridin-3-yl)-4-(3-nitrobenzylamino)-6-nitro-thieno-[2,3-d]-pyrimidine.

EXAMPLE 1032

With the procedure of Example 1, the reaction of 3-nitrobenzylamine with 4-chloro-2-(pyridin-3-yl)-5,6-dimethyl-thieno-[2,3-d]-pyrimidine yields 2-(pyridin-3-yl)-4-(3-nitrobenzylamino)-5,6-dimethyl-thieno-[2,3-d]-pyrimidine.

EXAMPLE 1033

With the procedure of Example 1, the reaction of 3-nitrobenzylamine with 4-chloro-2-(pyridin-3-yl)-6-trifluoromethyl-thieno-[2,3-d]-pyrimidine yields 2-(pyridin-3-yl)-4-(3-nitrobenzylamino)-6-trifluoromethyl-thieno-[2,3-d]-pyrimidine.

EXAMPLE 1034

With the procedure of Example 1, the reaction of 3-nitrobenzylamine with 4-chloro-2-(isoxazol-5-yl)-6-methyl-thieno-[2,3-d]-pyrimidine yields 2-(isoxazol-5-yl)-4-(3-nitrobenzylamino)-6-methyl-thieno-[2,3-d]-pyrimidine.

EXAMPLE 1035

With the procedure of Example 1, the reaction of 3-nitrobenzylamine with 4-chloro-2-(isoxazol-5-yl)-5-methyl-thieno-[2,3-d]-pyrimidine yields 2-(isoxazol-5-yl)-4-(3-nitrobenzylamino)-5-methyl-thieno-[2,3-d]-pyrimidine.

EXAMPLE 1036

With the procedure of Example 1, the reaction of 3-nitrobenzylamine with 4-chloro-2-(isoxazol-5-yl)-5,6,7,8-tetrahydro-[1]-benzothieno-[2,3-d]-pyrimidine yields 2-(isoxazol-5-yl)-4-(3-nitrobenzylamino)-5,6,7,8-tetrahydro-thieno-[2,3-d]-pyrimidine.

EXAMPLE 1037

With the procedure of Example 1, the reaction of 3-nitrobenzylamine with 4-chloro-2-(isoxazol-5-yl)-5,6-cyclopenteno-thieno-[2,3-d]-pyrimidine yields 2-(isoxazol-5-yl)-4-(3-nitrobenzylamino)-5,6-cyclopenteno-thieno-[2,3-d]-pyrimidine.

EXAMPLE 1038

With the procedure of Example 1, the reaction of 3-nitrobenzylamine with 4-chloro-2-(isoxazol-5-yl)-5,6-cyclohepteno-thieno-[2,3-d]-pyrimidine yields 2-(isoxazol-5-yl)-4-(3-nitrobenzylamino)-5,6-cyclohepteno-thieno-[2,3-d]-pyrimidine.

EXAMPLE 1039

With the procedure of Example 1, the reaction of 3-nitrobenzylamine with 4-chloro-2-(isoxazol-5-yl)-6-ethyl-thieno-[2,3-d]-pyrimidine yields 2-(isoxazol-5-yl)-4-(3-nitrobenzylamino)-6-ethyl-thieno-[2,3-d]-pyrimidine.

EXAMPLE 1040

With the procedure of Example 1, the reaction of 3-nitrobenzylamine with 4-chloro-2-(isoxazol-5-yl)-6-chloro-thieno-[2,3-d]-pyrimidine yields 2-(isoxazol-5-yl)-4-(3-nitrobenzylamino)-6-chloro-thieno-[2,3-d]-pyrimidine.

EXAMPLE 1041

With the procedure of Example 1, the reaction of 3-nitrobenzylamine with 4-chloro-2-(isoxazol-5-yl)-5-chloro-6-methyl-thieno-[2,3-d]-pyrimidine yields 2-(isoxazol-5-yl)-4-(3-nitrobenzylamino)-5-chlror-6-methyl-thieno-[2,3-d]-pyrimidine.

EXAMPLE 1042

With the procedure of Example 1, the reaction of 3-nitrobenzylamine with 4-chloro-2-(isoxazol-5-yl)-6-nitro-thieno-[2,3-d]-pyrimidine yields 2-(isoxazol-5-yl)-4-(3-nitrobenzylamino)-6-nitro-thieno-[2,3-d]-pyrimidine.

EXAMPLE 1043

With the procedure of Example 1, the reaction of 3-nitrobenzylamine with 4-chloro-2-(isoxazol-5-yl)-5,6-dimethyl-thieno-[2,3-d]-pyrimidine yields 2-(isoxazol-5-yl)-4-(3-nitrobenzylamino)-5,6-dimethyl-thieno-[2,3-d]-pyrimidine.

EXAMPLE 1044

With the procedure of Example 1, the reaction of 3-nitrobenzylamine with 4-chloro-2-(isoxazol-5-yl)-6-trifluoromethyl-thieno-[2,3-d]-pyrimidine yields 2-(isoxazol-5-yl)-4-(3-nitrobenzylamino)-6-trifluoromethyl-thieno-[2,3-d]-pyrimidine.

EXAMPLE 1045

With the procedure of Example 1, the reaction of 3-nitrobenzylamine with 4-chloro-2-(pyrazin-2-yl)-6-methyl-thieno-[2,3-d]-pyrimidine yields 2-(pyrazin-2-yl)-4-(3-nitrobenzylamino)-6-methyl-thieno-[2,3-d]-pyrimidine.

EXAMPLE 1046

With the procedure of Example 1, the reaction of 3-nitrobenzylamine with 4-chloro-2-(pyrazin-2-yl)-5-methyl-thieno-[2,3-d]-pyrimidine yields 2-(pyrazin-2-yl)-4-(3-nitrobenzylamino)-5-methyl-thieno-[2,3-d]-pyrimidine.

EXAMPLE 1047

With the procedure of Example 1, the reaction of 3-nitrobenzylamine with 4-chloro-2-(pyrazin-2-yl)-5,6,7,8-tetrahydro-[1]-benzothieno-[2,3-d]-pyrimidine yields 2-(pyrazin-2-yl)-4-(3-nitrobenzylamino)-5,6,7,8-tetrahydro-thieno-[2,3-d]-pyrimidine.

EXAMPLE 1048

With the procedure of Example 1, the reaction of 3-nitrobenzylamine with 4-chloro-2-(pyrazin-2-yl)-5,6-cyclopenteno-thieno-[2,3-d]-pyrimidine yields 2-(pyrazin-2-yl)-4-(3-nitrobenzylamino)-5,6-cyclopenteno-thieno-[2,3-d]-pyrimidine.

EXAMPLE 1049

With the procedure of Example 1, the reaction of 3-nitrobenzylamine with 4-chloro-2-(pyrazin-2-yl)-5,6-cyclohepteno-thieno-[2,3-d]-pyrimidine yields 2-(pyrazin-2-yl)-4-(3-nitrobenzylamino)-5,6-cyclohepteno-thieno-[2,3-d]-pyrimidine.

EXAMPLE 1050

With the procedure of Example 1, the reaction of 3-nitrobenzylamine with 4-chloro-2-(pyrazin-2-yl)-6-ethyl-thieno-[2,3-d]-pyrimidine yields 2-(pyrazin-2-yl)-4-(3-nitrobenzylamino)-6-ethyl-thieno-[2,3-d]-pyrimidine.

EXAMPLE 1051

With the procedure of Example 1, the reaction of 3-nitrobenzylamine with 4-chloro-2-(pyrazin-2-yl)-6-chloro-thieno-[2,3-d]-pyrimidine yields 2-(pyrazin-2-yl)-4-(3-nitrobenzylamino)-6-chloro-thieno-[2,3-d]-pyrimidine.

EXAMPLE 1052

With the procedure of Example 1, the reaction of 3-nitrobenzylamine with 4-chloro-2-(pyrazin-2-yl)-5-chloro-6-methyl-thieno-[2,3-d]-pyrimidine yields 2-(pyrazin-2-yl)-4-(3-nitrobenzylamino)-5-chlror-6-methyl-thieno-[2,3-d]-pyrimidine.

EXAMPLE 1053

With the procedure of Example 1, the reaction of 3-nitrobenzylamine with 4-chloro-2-(pyrazin-2-yl)-6-nitro-thieno-[2,3-d]-pyrimidine yields 2-(pyrazin-2-yl)-4-(3-nitrobenzylamino)-6-nitro-thieno-[2,3-d]-pyrimidine.

EXAMPLE 1054

With the procedure of Example 1, the reaction of 3-nitrobenzylamine with 4-chloro-2-(pyrazin-2-yl)-5,6-dimethyl-thieno-[2,3-d]-pyrimidine yields 2-(pyrazin-2-yl)-4-(3-nitrobenzylamino)-5,6-dimethyl-thieno-[2,3-d]-pyrimidine.

EXAMPLE 1055

With the procedure of Example 1, the reaction of 3-nitrobenzylamine with 4-chloro-2-(pyrazin-2-yl)-6-trifluoromethyl-thieno-[2,3-d]-pyrimidine yields 2-(pyrazin-2-yl)-4-(3-nitrobenzylamino)-6-trifluoromethyl-thieno-[2,3-d]-pyrimidine.

EXAMPLE 1056

With the procedure of Example 1, the reaction of 3-nitrobenzylamine with 4-chloro-2-(pyridin-2-yl)-6-methyl-thieno-[2,3-d]-pyrimidine yields 2-(pyridin-2-yl)-4-(3-nitrobenzylamino)-6-methyl-thieno-[2,3-d]-pyrimidine.

EXAMPLE 1057

With the procedure of Example 1, the reaction of 3-nitrobenzylamine with 4-chloro-2-(pyridin-2-yl)-5-methyl-thieno-[2,3-d]-pyrimidine yields 2-(pyridin-2-yl)-4-(3-nitrobenzylamino)-5-methyl-thieno-[2,3-d]-pyrimidine.

EXAMPLE 1058

With the procedure of Example 1, the reaction of 3-nitrobenzylamine with 4-chloro-2-(pyridin-2-yl)-5,6,7,8-tetrahydro-[1]-benzothieno-[2,3-d]-pyrimidine yields 2-(pyridin-2-yl)-4-(3-nitrobenzylamino)-5,6,7,8-tetrahydro-thieno-[2,3-d]-pyrimidine.

EXAMPLE 1059

With the procedure of Example 1, the reaction of 3-nitrobenzylamine with 4-chloro-2-(pyridin-2-yl)-5,6-cyclopenteno-thieno-[2,3-d]-pyrimidine yields 2-(pyradin-2-yl)-4-(3-nitrobenzylamino)-5,6-cyclopenteno-thieno-[2,3-d]-pyrimidine.

EXAMPLE 1060

With the procedure of Example 1, the reaction of 3-nitrobenzylamine with 4-chloro-2-(pyridin-2-yl)-5,6-cyclohepteno-thieno-[2,3-d]-pyrimidine yields 2-(pyradin-2-yl)-4-(3-nitrobenzylamino)-5,6-cyclohepteno-thieno-[2,3-d]-pyrimidine.

EXAMPLE 1061

With the procedure of Example 1, the reaction of 3-nitrobenzylamine with 4-chloro-2-(pyridin-2-yl)-6-ethyl-thieno-[2,3-d]-pyrimidine yields 2-(pyridin-2-yl)-4-(3-nitrobenzylamino)-6-ethyl-thieno-[2,3-d]-pyrimidine.

EXAMPLE 1062

With the procedure of Example 1, the reaction of 3-nitrobenzylamine with 4-chloro-2-(pyridin-2-yl)-6- chloro-thieno-[2,3-d]-pyrimidine yields 2-(pyridin-2-yl)-4-(3-nitrobenzylamino)-6-chloro-thieno-[2,3-d]-pyrimidine.

EXAMPLE 1063

With the procedure of Example 1, the reaction of 3-nitrobenzylamine with 4-chloro-2-(pyridin-2-yl)-5-chloro-6-methyl-thieno-[2,3-d]-pyrimidine yields 2-(pyridin-2-yl)-4-(3-nitrobenzylamino)-5-chlror-6-methyl-thieno-[2,3-d]-pyrimidine.

EXAMPLE 1064

With the procedure of Example 1, the reaction of 3-nitrobenzylamine with 4-chloro-2-(pyridin-2-yl)-6-nitro-thieno-[2,3-d]-pyrimidine yields 2-(pyridin-2-yl)-4-(3-nitrobenzylamino)-6-nitro-thieno-[2,3-d]-pyrimidine.

EXAMPLE 1065

With the procedure of Example 1, the reaction of 3-nitrobenzylamine with 4-chloro-2-(pyridin-2-yl)-5,6-dimethyl-thieno-[2,3-d]-pyrimidine yields 2-(pyridin-2-yl)-4-(3-nitrobenzylamino)-5,6-dimethyl-thieno-[2,3-d]-pyrimidine.

EXAMPLE 1066

With the procedure of Example 1, the reaction of 3-nitrobenzylamine with 4-chloro-2-(pyridin-2-yl)-6-trifluoromethyl-thieno-[2,3-d]-pyrimidine yields 2-(pyradin-2-yl)-4-(3-nitrobenzylamino)-6-trifluoromethyl-thieno-[2,3-d]-pyrimidine.

EXAMPLE 1067

With the procedure of Example 1, the reaction of 3-nitrobenzylamine with 4-chloro-2-(pyridin-4-yl)-6-methyl-thieno-[2,3-d]-pyrimidine yields 2-(pyridin-4-yl)-4-(3-nitrobenzylamino)-6-methyl-thieno-[2,3-d]-pyrimidine.

EXAMPLE 1068

With the procedure of Example 1, the reaction of 3-nitrobenzylamine with 4-chloro-2-(pyridin-4-yl)-5-methyl-thieno-[2,3-d]-pyrimidine yields 2-(pyridin-4-yl)-4-(3-nitrobenzylamino)-5-methyl-thieno-[2,3-d]-pyrimidine.

EXAMPLE 1069

With the procedure of Example 1, the reaction of 3-nitrobenzylamine with 4-chloro-2-(pyridin-4-yl)-5,6,7,8-tetrahydro-[1]-benzothieno-[2,3-d]-pyrimidine yields 2-(pyridin-4-yl)-4-(3-nitrobenzylamino)-5,6,7,8-tetrahydro-thieno-[2,3-d]-pyrimidine.

EXAMPLE 1070

With the procedure of Example 1, the reaction of 3-nitrobenzylamine with 4-chloro-2-(pyridin-4-yl)-5,6-cyclopenteno-thieno-[2,3-d]-pyrimidine yields 2-(pyridin-4-yl)-4-(3-nitrobenzylamino)-5,6-cyclopenteno-thieno-[2,3-d]-pyrimidine.

EXAMPLE 1071

With the procedure of Example 1, the reaction of 3-nitrobenzylamine with 4-chloro-2-(pyridin-4-yl)-5,6-cyclohepteno-thieno-[2,3-d]-pyrimidine yields 2-(pyridin-4-yl)-4-(3-nitrobenzylamino)-5,6-cyclohepteno-thieno-[2,3-d]-pyrimidine.

EXAMPLE 1072

With the procedure of Example 1, the reaction of 3-nitrobenzylamine with 4-chloro-2-(pyridin-4-yl)-6-ethyl-thieno-[2,3-d]-pyrimidine yields 2-(pyridin-4-yl)-4-(3-nitrobenzylamino)-6-ethyl-thieno-[2,3-d]-pyrimidine.

EXAMPLE 1073

With the procedure of Example 1, the reaction of 3-nitrobenzylamine with 4-chloro-2-(pyridin-4-yl)-6-chloro-thieno-[2,3-d]-pyrimidine yields 2-(pyridin-4-yl)-4-(3-nitrobenzylamino)-6-chloro-thieno-[2,3-d]-pyrimidine.

EXAMPLE 1074

With the procedure of Example 1, the reaction of 3-nitrobenzylamine with 4-chloro-2-(pyridin-4-yl)-5-chloro-6-methyl-thieno-[2,3-d]-pyrimidine yields 2-(pyridin-4-yl)-4-(3-nitrobenzylamino)-5-chlror-6-methyl-thieno-[2,3-d]-pyrimidine.

EXAMPLE 1075

With the procedure of Example 1, the reaction of 3-nitrobenzylamine with 4-chloro-2-(pyridin-4-yl)-6-nitro-thieno-[2,3-d]-pyrimidine yields 2-(pyridin-4-yl)-4-(3-nitrobenzylamino)-6-nitro-thieno-[2,3-d]-pyrimidine.

EXAMPLE 1076

With the procedure of Example 1, the reaction of 3-nitrobenzylamine with 4-chloro-2-(pyridin-4-yl)-5,6-dimethyl-thieno-[2,3-d]-pyrimidine yields 2-(pyridin-4-yl)-4-(3-nitrobenzylamino)-5,6-dimethyl-thieno-[2,3-d]-pyrimidine.

EXAMPLE 1077

With the procedure of Example 1, the reaction of 3-nitrobenzylamine with 4-chloro-2-(pyridin-4-yl)-6-trifluoromethyl-thieno-[2,3-d]-pyrimidine yields 2-(pyridin-4-yl)-4-(3-nitrobenzylamino)-6-trifluoromethyl-thieno-[2,3-d]-pyrimidine.

EXAMPLE 1078

With the procedure of Example 1, the reaction of 3-nitrobenzylamine with 4-chloro-2-(pyridin-3-yl)-6-methyl-thieno-[2,3-d]-pyrimidine yields 2-(pyridin-3-yl)-4-(3-nitrobenzylamino)-6-methyl-thieno-[2,3-d]-pyrimidine.

EXAMPLE 1079

With the procedure of Example 1, the reaction of 3-nitrobenzylamine with 4-chloro-2-(pyridin-3-yl)-5-methyl-thieno-[2,3-d]-pyrimidine yields 2-(pyridin-3-yl)-4-(3-nitrobenzylamino)-5-methyl-thieno-[2,3-d]-pyrimidine.

EXAMPLE 1080

With the procedure of Example 1, the reaction of 3-nitrobenzylamine with 4-chloro-2-(pyridin-3-yl)-5,6,7,8-tetrahydro-[1]-benzothieno-[2,3-d]-pyrimidine yields 2-(pyridin-3-yl)-4-(3-nitrobenzylamino)-5,6,7,8-tetrahydro-thieno-[2,3-d]-pyrimidine.

EXAMPLE 1081

With the procedure of Example 1, the reaction of 3-nitrobenzylamine with 4-chloro-2-(pyridin-3-yl)-5,6-cyclopenteno-thieno-[2,3-d]-pyrimidine yields 2-(pyridin-3-yl)-4-(3-nitrobenzylamino)-5,6-cyclopenteno-thieno-[2,3-d]-pyrimidine.

EXAMPLE 1082

With the procedure of Example 1, the reaction of 3-nitrobenzylamine with 4-chloro-2-(pyridin-3-yl)-5,6- cyclohepteno-thieno-[2,3-d]-pyrimidine yields 2-(pyridin-3-yl)-4-(3-nitrobenzylamino)-5,6-cyclohepteno-thieno-[2,3-d]-pyrimidine.

EXAMPLE 1083

With the procedure of Example 1, the reaction of 3-nitrobenzylamine with 4-chloro-2-(pyridin-3-yl)-6-ethyl-thieno-[2,3-d]-pyrimidine yields 2-(pyridin-3-yl)-4-(3-nitrobenzylamino)-6-ethyl-thieno-[2,3-d]-pyrimidine.

EXAMPLE 1084

With the procedure of Example 1, the reaction of 3-nitrobenzylamine with 4-chloro-2-(pyridin-3-yl)-6-chloro-thieno-[2,3-d]-pyrimidine yields 2-(pyridin-3-yl)-4-(3-nitrobenzylamino)-6-chloro-thieno-[2,3-d]-pyrimidine.

EXAMPLE 1085

With the procedure of Example 1, the reaction of 3-nitrobenzylamine with 4-chloro-2-(pyridin-3-yl)-5-chloro-6-methyl-thieno-[2,3-d]-pyrimidine yields 2-(pyridin-3-yl)-4-(3-nitrobenzylamino)-5-chlror-6-methyl-thieno-[2,3-d]-pyrimidine.

EXAMPLE 1086

With the procedure of Example 1, the reaction of 3-nitrobenzylamine with 4-chloro-2-(pyridin-3-yl)-6-nitro-thieno-[2,3-d]-pyrimidine yields 2-(pyridin-3-yl)-4-(3-nitrobenzylamino)-6-nitro-thieno-[2,3-d]-pyrimidine.

EXAMPLE 1087

With the procedure of Example 1, the reaction of 3-nitrobenzylamine with 4-chloro-2-(pyridin-3-yl)-5,6-dimethyl-thieno-[2,3-d]-pyrimidine yields 2-(pyridin-3-yl)-4-(3-nitrobenzylamino)-5,6-dimethyl-thieno-[2,3-d]-pyrimidine.

EXAMPLE 1088

With the procedure of Example 1, the reaction of 3-nitrobenzylamine with 4-chloro-2-(pyridin-3-yl)-6-trifluoromethyl-thieno-[2,3-d]-pyrimidine yields 2-(pyridin-3-yl)-4-(3-nitrobenzylamino)-6-trifluoromethyl-thieno-[2,3-d]-pyrimidine.

EXAMPLE 1089

With the procedure of Example 1, the reaction of 3-nitrobenzylamine with 4-chloro-2-(isoxazol-5-yl)-6-methyl-thieno-[2,3-d]-pyrimidine yields 2-(isoxazol-5-yl)-4-(3-nitrobenzylamino)-6-methyl-thieno-[2,3-d]-pyrimidine.

EXAMPLE 1090

With the procedure of Example 1, the reaction of 3-nitrobenzylamine with 4-chloro-2-(isoxazol-5-yl)-5-methyl-thieno-[2,3-d]-pyrimidine yields 2-(isoxazol-5-yl)-4-(3-nitrobenzylamino)-5-methyl-thieno-[2,3-d]-pyrimidine.

EXAMPLE 1091

With the procedure of Example 1, the reaction of 3-nitrobenzylamine with 4-chloro-2-(isoxazol-5-yl)-5,6,7,8-tetrahydro-[1]-benzothieno-[2,3-d]-pyrimidine yields 2-(isoxazol-5-yl)-4-(3-nitrobenzylamino)-5,6,7,8-tetrahydro-thieno-[2,3-d]-pyrimidine.

EXAMPLE 1092

With the procedure of Example 1, the reaction of 3-nitrobenzylamine with 4-chloro-2-(isoxazol-5-yl)-5,6-cyclopenteno-thieno-[2,3-d]-pyrimidine yields 2-(isoxazol-5-yl)-4-(3-nitrobenzylamino)-5,6-cyclopenteno-thieno-[2,3-d]-pyrimidine.

EXAMPLE 1093

With the procedure of Example 1, the reaction of 3-nitrobenzylamine with 4-chloro-2-(isoxazol-5-yl)-5,6-cyclohepteno-thieno-[2,3-d]-pyrimidine yields 2-(isoxazol-5-yl)-4-(3-nitrobenzylamino)-5,6-cyclohepteno-thieno-[2,3-d]-pyrimidine.

EXAMPLE 1094

With the procedure of Example 1, the reaction of 3-nitrobenzylamine with 4-chloro-2-(isoxazol-5-yl)-6-ethyl-thieno-[2,3-d]-pyrimidine yields 2-(isoxazol-5-yl)-4-(3-nitrobenzylamino)-6-ethyl-thieno-[2,3-d]-pyrimidine.

EXAMPLE 1095

With the procedure of Example 1, the reaction of 3-nitrobenzylamine with 4-chloro-2-(isoxazol-5-yl)-6-chloro-thieno-[2,3-d]-pyrimidine yields 2-(isoxazol-5-yl)-4-(3-nitrobenzylamino)-6-chloro-thieno-[2,3-d]-pyrimidine.

EXAMPLE 1096

With the procedure of Example 1, the reaction of 3-nitrobenzylamine with 4-chloro-2-(isoxazol-5-yl)-5-chloro-6-methyl-thieno-[2,3-d]-pyrimidine yields 2-(isoxazol-5-yl)-4-(3-nitrobenzylamino)-5-chlror-6-methyl-thieno-[2,3-d]-pyrimidine.

EXAMPLE 1097

With the procedure of Example 1, the reaction of 3-nitrobenzylamine with 4-chloro-2-(isoxazol-5-yl)-6-nitro-thieno-[2,3-d]-pyrimidine yields 2-(isoxazol-5-yl)-4-(3-nitrobenzylamino)-6-nitro-thieno-[2,3-d]-pyrimidine.

EXAMPLE 1098

With the procedure of Example 1, the reaction of 3-nitrobenzylamine with 4-chloro-2-(isoxazol-5-yl)-5,6-dimethyl-thieno-[2,3-d]-pyrimidine yields 2-(isoxazol-5-yl)-4-(3-nitrobenzylamino)-5,6-dimethyl-thieno-[2,3-d]-pyrimidine.

EXAMPLE 1099

With the procedure of Example 1, the reaction of 3-nitrobenzylamine with 4-chloro-2-(isoxazol-5-yl)-6-trifluoromethyl-thieno-[2,3-d]-pyrimidine yields 2-(isoxazol-5-yl)-4-(3-nitrobenzylamino)-6-trifluoromethyl-thieno-[2,3-d]-pyrimidine.

EXAMPLE 1100

With the procedure of Example 1, the reaction of 3-nitrobenzylamine with 4-chloro-2-(pyrazin-2-yl)-6-methyl-thieno-[2,3-d]-pyrimidine yields 2-(pyrazin-2-yl)-4-(3-nitrobenzylamino)-6-methyl-thieno-[2,3-d]-pyrimidine.

EXAMPLE 1101

With the procedure of Example 1, the reaction of 3-nitrobenzylamine with 4-chloro-2-(pyrazin-2-yl)-5- methyl-thieno-[2,3-d]-pyrimidine yields 2-(pyrazin-2-yl)-4-(3-nitrobenzylamino)-5-methyl-thieno-[2,3-d]-pyrimidine.

EXAMPLE 1102

With the procedure of Example 1, the reaction of 3-nitrobenzylamine with 4-chloro-2-(pyrazin-2-yl)-5,6,7,8-tetrahydro-[1]-benzothieno-[2,3-d]-pyrimidine yields 2-(pyrazin-2-yl)-4-(3-nitrobenzylamino)-5,6,7,8-tetrahydro-thieno-[2,3-d]-pyrimidine.

EXAMPLE 1103

With the procedure of Example 1, the reaction of 3-nitrobenzylamine with 4-chloro-2-(pyrazin-2-yl)-5,6-cyclopenteno-thieno-[2,3-d]-pyrimidine yields 2-(pyrazin-2-yl)-4-(3-nitrobenzylamino)-5,6-cyclopenteno-thieno-[2,3-d]-pyrimidine.

EXAMPLE 1104

With the procedure of Example 1, the reaction of 3-nitrobenzylamine with 4-chloro-2-(pyrazin-2-yl)-5,6-cyclohepteno-thieno-[2,3-d]-pyrimidine yields 2-(pyrazin-2-yl)-4-(3-nitrobenzylamino)-5,6-cyclohepteno-thieno-[2,3-d]-pyrimidine.

EXAMPLE 1105

With the procedure of Example 1, the reaction of 3-nitrobenzylamine with 4-chloro-2-(pyrazin-2-yl)-6-ethyl-thieno-[2,3-d]-pyrimidine yields 2-(pyrazin-2-yl)-4-(3-nitrobenzylamino)-6-ethyl-thieno-[2,3-d]-pyrimidine.

EXAMPLE 1106

With the procedure of Example 1, the reaction of 3-nitrobenzylamine with 4-chloro-2-(pyrazin-2-yl)-6-chloro-thieno-[2,3-d]-pyrimidine yields 2-(pyrazin-2-yl)-4-(3-nitrobenzylamino)-6-chloro-thieno-[2,3-d]-pyrimidine.

EXAMPLE 1107

With the procedure of Example 1, the reaction of 3-nitrobenzylamine with 4-chloro-2-(pyrazin-2-yl)-5-chloro-6-methyl-thieno-[2,3-d]-pyrimidine yields 2-(pyrazin-2-yl)-4-(3-nitrobenzylamino)-5-chlror-6-methyl-thieno-[2,3-d]-pyrimidine.

EXAMPLE 1108

With the procedure of Example 1, the reaction of 3-nitrobenzylamine with 4-chloro-2-(pyrazin-2-yl)-6-nitro-thieno-[2,3-d]-pyrimidine yields 2-(pyrazin-2-yl)-4-(3-nitrobenzylamino)-6-nitro-thieno-[2,3-d]-pyrimidine.

EXAMPLE 1109

With the procedure of Example 1, the reaction of 3-nitrobenzylamine with 4-chloro-2-(pyrazin-2-yl)-5,6-dimethyl-thieno-[2,3-d]-pyrimidine yields 2-(pyrazin-2-yl)-4-(3-nitrobenzylamino)-5,6-dimethyl-thieno-[2,3-d]-pyrimidine.

EXAMPLE 1110

With the procedure of Example 1, the reaction of 3-nitrobenzylamine with 4-chloro-2-(pyrazin-2-yl)-6-trifluoromethyl-thieno-[2,3-d]-pyrimidine yields 2-(pyrazin-2-yl)-4-(3-nitrobenzylamino)-6-trifluoromethyl-thieno-[2,3-d]-pyrimidine.

EXAMPLE 1111

With the procedure of Example 1, the reaction of 3-nitrobenzylamine with 4-chloro-2-(pyridin-2-yl)-6-methyl-thieno-[2,3-d]-pyrimidine yields 2-(pyridin-2-yl)-4-(3-nitrobenzylamino)-6-methyl-thieno-[2,3-d]-pyrimidine.

EXAMPLE 1112

With the procedure of Example 1, the reaction of 3-nitrobenzylamine with 4-chloro-2-(pyridin-2-yl)-5-methyl-thieno-[2,3-d]-pyrimidine yields 2-(pyridin-2-yl)-4-(3-nitrobenzylamino)-5-methyl-thieno-[2,3-d]-pyrimidine.

EXAMPLE 1113

With the procedure of Example 1, the reaction of 3-nitrobenzylamine with 4-chloro-2-(pyridin-2-yl)-5,6,7,8-tetrahydro-[1]-benzothieno-[2,3-d]-pyrimidine yields 2-(pyridin-2-yl)-4-(3-nitrobenzylamino)-5,6,7,8-tetrahydro-thieno-[2,3-d]-pyrimidine.

EXAMPLE 1114

With the procedure of Example 1, the reaction of 3-nitrobenzylamine with 4-chloro-2-(pyridin-2-yl)-5,6-cyclopenteno-thieno-[2,3-d]-pyrimidine yields 2-(pyradin-2-yl)-4-(3-nitrobenzylamino)-5,6-cyclopenteno-thieno-[2,3-d]-pyrimidine.

EXAMPLE 1115

With the procedure of Example 1, the reaction of 3-nitrobenzylamine with 4-chloro-2-(pyridin-2-yl)-5,6-cyclohepteno-thieno-[2,3-d]-pyrimidine yields 2-(pyradin-2-yl)-4-(3-nitrobenzylamino)-5,6-cyclohepteno-thieno-[2,3-d]-pyrimidine.

EXAMPLE 1116

With the procedure of Example 1, the reaction of 3-nitrobenzylamine with 4-chloro-2-(pyridin-2-yl)-6-ethyl-thieno-[2,3-d]-pyrimidine yields 2-(pyridin-2-yl)-4-(3-nitrobenzylamino)-6-ethyl-thieno-[2,3-d]-pyrimidine.

EXAMPLE 1117

With the procedure of Example 1, the reaction of 3-nitrobenzylamine with 4-chloro-2-(pyridin-2-yl)-6-chloro-thieno-[2,3-d]-pyrimidine yields 2-(pyridin-2-yl)-4-(3-nitrobenzylamino)-6-chloro-thieno-[2,3-d]-pyrimidine.

EXAMPLE 1118

With the procedure of Example 1, the reaction of 3-nitrobenzylamine with 4-chloro-2-(pyridin-2-yl)-5-chloro-6-methyl-thieno-[2,3-d]-pyrimidine yields 2-(pyridin-2-yl)-4-(3-nitrobenzylamino)-5-chlror-6-methyl-thieno-[2,3-d]-pyrimidine.

EXAMPLE 1119

With the procedure of Example 1, the reaction of 3-nitrobenzylamine with 4-chloro-2-(pyridin-2-yl)-6-nitro-thieno-[2,3-d]-pyrimidine yields 2-(pyridin-2-yl)-4-(3-nitrobenzylamino)-6-nitro-thieno-[2,3-d]-pyrimidine.

EXAMPLE 1120

With the procedure of Example 1, the reaction of 3-nitrobenzylamine with 4-chloro-2-(pyridin-2-yl)-5,6-dimethyl-thieno-[2,3-d]-pyrimidine yields 2-(pyridin-2-yl)-4-(3-nitrobenzylamino)-5,6-dimethyl-thieno-[2,3-d]-pyrimidine.

EXAMPLE 1121

With the procedure of Example 1, the reaction of 3-nitrobenzylamine with 4-chloro-2-(pyridin-2-yl)-6- trifluoromethyl-thieno-[2,3-d]-pyrimidine yields 2-(pyradin-2-yl)-4-(3-nitrobenzylamino)-6-trifluoromethyl-thieno-[2,3-d]-pyrimidine.

EXAMPLE 1122

With the procedure of Example 1, the reaction of 3-nitrobenzylamine with 4-chloro-2-(pyridin-4-yl)-6-methyl-thieno-[2,3-d]-pyrimidine yields 2-(pyridin-4-yl)-4-(3-nitrobenzylamino)-6-methyl-thieno-[2,3-d]-pyrimidine.

EXAMPLE 1123

With the procedure of Example 1, the reaction of 3-nitrobenzylamine with 4-chloro-2-(pyridin-4-yl)-5-methyl-thieno-[2,3-d]-pyrimidine yields 2-(pyridin-4-yl)-4-(3-nitrobenzylamino)-5-methyl-thieno-[2,3-d]-pyrimidine.

EXAMPLE 1124

With the procedure of Example 1, the reaction of 3-nitrobenzylamine with 4-chloro-2-(pyridin-4-yl)-5,6,7,8-tetrahydro-[1]-benzothieno-[2,3-d]-pyrimidine yields 2-(pyridin-4-yl)-4-(3-nitrobenzylamino)-5,6,7,8-tetrahydro-thieno-[2,3-d]-pyrimidine.

EXAMPLE 1125

With the procedure of Example 1, the reaction of 3-nitrobenzylamine with 4-chloro-2-(pyridin-4-yl)-5,6-cyclopenteno-thieno-[2,3-d]-pyrimidine yields 2-(pyridin-4-yl)-4-(3-nitrobenzylamino)-5,6-cyclopenteno-thieno-[2,3-d]-pyrimidine.

EXAMPLE 1126

With the procedure of Example 1, the reaction of 3-nitrobenzylamine with 4-chloro-2-(pyridin-4-yl)-5,6-cyclohepteno-thieno-[2,3-d]-pyrimidine yields 2-(pyridin-4-yl)-4-(3-nitrobenzylamino)-5,6-cyclohepteno-thieno-[2,3-d]-pyrimidine.

EXAMPLE 1127

With the procedure of Example 1, the reaction of 3-nitrobenzylamine with 4-chloro-2-(pyridin-4-yl)-6-ethyl-thieno-[2,3-d]-pyrimidine yields 2-(pyridin-4-yl)-4-(3-nitrobenzylamino)-6-ethyl-thieno-[2,3-d]-pyrimidine.

EXAMPLE 1128

With the procedure of Example 1, the reaction of 3-nitrobenzylamine with 4-chloro-2-(pyridin-4-yl)-6-chloro-thieno-[2,3-d]-pyrimidine yields 2-(pyridin-4-yl)-4-(3-nitrobenzylamino)-6-chloro-thieno-[2,3-d]-pyrimidine.

EXAMPLE 1129

With the procedure of Example 1, the reaction of 3-nitrobenzylamine with 4-chloro-2-(pyridin-4-yl)-5-chloro-6-methyl-thieno-[2,3-d]-pyrimidine yields 2-(pyridin-4-yl)-4-(3-nitrobenzylamino)-5-chiror-6-methyl-thieno-[2,3-d]-pyrimidine.

EXAMPLE 1130

With the procedure of Example 1, the reaction of 3-nitrobenzylamine with 4-chloro-2-(pyridin-4-yl)-6-nitro-thieno-[2,3-d]-pyrimidine yields 2-(pyridin-4-yl-4-(3-nitrobenzylamino)-6-nitro-thieno-[2,3-d]-pyrimidine.

EXAMPLE 1131

With the procedure of Example 1, the reaction of 3-nitrobenzylamine with 4-chloro-2-(pyridin-4-yl)-5,6-dimethyl-thieno-[2,3-d]-pyrimidine yields 2-(pyridin-4-yl)-4-(3-nitrobenzylamino)-5,6-dimethyl-thieno-[2,3-d]-pyrimidine.

EXAMPLE 1132

With the procedure of Example 1, the reaction of 3-nitrobenzylamine with 4-chloro-2-(pyridin-4-yl)-6-trifluoromethyl-thieno-[2,3-d]-pyrimidine yields 2-(pyridin-4-yl)-4-(3-nitrobenzylamino)-6-trifluoromethyl-thieno-[2,3-d]-pyrimidine.

EXAMPLE 1133

With the procedure of Example 1, the reaction of 3,4-methylenedioxyphenethylamine with 4-chloro-2-(pyridin-3-yl)-6-methyl-thieno-[2,3-d]-pyrimidine yields 2-(pyridin-3-yl)-4-(3,4-methylenedioxyphenethylamino)-6-methyl-thieno-[2,3-d]-pyrimidine.

EXAMPLE 1134

With the procedure of Example 1, the reaction of 4-fluoro-3,4-methylenedioxyphenethylamine with 4-chloro-2-(pyridin-3-yl)-5-methyl-thieno-[2,3-d]-pyrimidine yields 2-(pyridin-3-yl)-4-(3,4-methylenedioxyphenethylamino)-5-methyl-thieno-[2,3-d]-pyrimidine.

EXAMPLE 1135

With the procedure of Example 1, the reaction of 4-fluoro-3,4-methylenedioxyphenethylamine with 4-chloro-2-(pyridin-3-yl)-5,6,7,8-tetrahydro-[1]-benzothieno-[2,3-d]-pyrimidine yields 2-(pyridin-3-yl)-4-(3,4-methylenedioxyphenethylamino)-5,6,7,8-tetrahydro-thieno-[2,3-d]-pyrimidine.

EXAMPLE 1136

With the procedure of Example 1, the reaction of 3,4-methylenedioxyphenethylamine with 4-chloro-2-(pyridin-3-yl)-5,6-cyclopenteno-thieno-[2,3-d]-pyrimidine yields 2-(pyridin-3-yl)-4-(3,4-methylenedioxyphenethylamino)-5,6-cyclopenteno-thieno-[2,3-d]-pyrimidine.

EXAMPLE 1137

With the procedure of Example 1, the reaction of 3,4-methylenedioxyphenethylamine with 4-chloro-2-(pyridin-3-yl)-5,6-cyclohepteno-thieno-[2,3-d]-pyrimidine yields 2-(pyridin-3-yl)-4-(3,4-methylenedioxyphenethylamino)-5,6-cyclohepteno-thieno-[2,3-d]-pyrimidine.

EXAMPLE 1138

With the procedure of Example 1, the reaction of 3,4-methylenedioxyphenethylamine with 4-chloro-2-(pyridin-3-yl)-6-ethyl-thieno-[2,3-d]-pyrimidine yields 2-(pyridin-3-yl)-4-(3,4-methylenedioxyphenethylamino)-6-ethyl-thieno-[2,3-d]-pyrimidine.

EXAMPLE 1139

With the procedure of Example 1, the reaction of 3,4-methylenedioxyphenethylamine with 4-chloro-2-(pyridin-3-yl)-6-chloro-thieno-[2,3-d]-pyrimidine yields 2-(pyridin-3-yl)-4-(3,4-methylenedioxyphenethylamino)-6-chloro-thieno-[2,3-d]-pyrimidine.

EXAMPLE 1140

With the procedure of Example 1, the reaction of 3,4-methylenedioxyphenethylamine with 4-chloro-2-(pyridin-3- yl)-5-chloro-6-methyl-thieno-[2,3-d]-pyrimidine yields 2-(pyridin-3-yl)-4-(3,4-methylenedioxyphenethylamino)-5-chlror-6-methyl-thieno-[2,3-d]-pyrimidine.

EXAMPLE 1141

With the procedure of Example 1, the reaction of 3,4-methylenedioxyphenethylamine with 4-chloro-2-(pyridin-3-yl)-6-nitro-thieno-[2,3-d]-pyrimidine yields 2-(pyridin-3-yl)-4-(3,4-methylenedioxyphenethylamino)-6-nitro-thieno-[2,3-d]-pyrimidine.

EXAMPLE 1142

With the procedure of Example 1, the reaction of 3,4-methylenedioxyphenethylamine with 4-chloro-2-(pyridin-3-yl)-5,6-dimethyl-thieno-[2,3-d]-pyrimidine yields 2-(pyridin-3-yl)-4-(3,4-methylenedioxyphenethylamino)-5,6-dimethyl-thieno-[2,3-d]-pyrimidine.

EXAMPLE 1143

With the procedure of Example 1, the reaction of 3,4-methylenedioxyphenethylamine with 4-chloro-2-(pyridin-3-yl)-6-trifluoromethyl-thieno-[2,3-d]-pyrimidine yields 2-(pyridin-3-yl)-4-(3,4-methylenedioxyphenethylamino)-6-trifluoromethyl-thieno-[2,3-d]-pyrimidine.

EXAMPLE 1144

With the procedure of Example 1, the reaction of 3,4-methylenedioxyphenethylamine with 4-chloro-2-(isoxazol-5-yl)-6-methyl-thieno-[2,3-d]-pyrimidine yields 2-(isoxazol-5-yl)-4-(3,4-methylenedioxyphenethylamino)-6-methyl-thieno-[2,3-d]-pyrimidine.

EXAMPLE 1145

With the procedure of Example 1, the reaction of 3,4-methylenedioxyphenethylamine with 4-chloro-2-(isoxazol-5-yl)-5-methyl-thieno-[2,3-d]-pyrimidine yields 2-(isoxazol-5-yl)-4-(3,4-methylenedioxyphenethylamino)-5-methyl-thieno-[2,3-d]-pyrimidine.

EXAMPLE 1146

With the procedure of Example 1, the reaction of 3,4-methylenedioxyphenethylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-methylenedioxyphenethylamino)-5,6,7,8-tetrahydro-thieno-[2,3-d]-pyrimidine.

EXAMPLE 1147

With the procedure of Example 1, the reaction of 3,4-methylenedioxyphenethylamine with 4-chloro-2-(isoxazol-5-yl)-5,6-cyclopenteno-thieno-[2,3-d]-pyrimidine yields 2-(isoxazol-5-yl)-4-(3,4-methylenedioxyphenethylamino)-5,6-cyclopenteno-thieno-[2,3-d]-pyrimidine.

EXAMPLE 1148

With the procedure of Example 1, the reaction of 3,4-methylenedioxyphenethylamine with 4-chloro-2-(isoxazol-5-yl)-5,6-cyclohepteno-thieno-[2,3-d]-pyrimidine yields 2-(isoxazol-5-yl)-4-(3,4-methylenedioxyphenethylamino)-5,6-cyclohepteno-thieno-[2,3-d]-pyrimidine.

EXAMPLE 1149

With the procedure of Example 1, the reaction of 3,4-methylenedioxyphenethylamine with 4-chloro-2-(isoxazol-5-yl)-6-ethyl-thieno-[2,3-d]-pyrimidine yields 2-(isoxazol-5-yl)-4-(3,4-methylenedioxyphenethylamino)-6-ethyl-thieno-[2,3-d]-pyrimidine.

EXAMPLE 1150

With the procedure of Example 1, the reaction of 3,4-methylenedioxyphenethylamine with 4-chloro-2-(isoxazol-5-yl)-6-chloro-thieno-[2,3-d]-pyrimidine yields 2-(isoxazol-5-yl)-4-(3,4-methylenedioxyphenethylamino)-6-chloro-thieno-[2,3-d]-pyrimidine.

EXAMPLE 1151

With the procedure of Example 1, the reaction of 3,4-methylenedioxyphenethylamine with 4-chloro-2-(isoxazol-5-yl)-5-chloro-6-methyl-thieno-[2,3-d]-pyrimidine yields 2-(isoxazol-5-yl)-4-(3,4-methylenedioxyphenethylamino)-5-chlror-6-methyl-thieno-[2,3-d]-pyrimidine.

EXAMPLE 1152

With the procedure of Example 1, the reaction of 3,4-methylenedioxyphenethylamine with 4-chloro-2-(isoxazol-5-yl)-6-nitro-thieno-[2,3-d]-pyrimidine yields 2-(isoxazol-5-yl)-4-(3,4-methylenedioxyphenethylamino)-6-nitro-thieno-[2,3-d]-pyrimidine.

EXAMPLE 1153

With the procedure of Example 1, the reaction of 3,4-methylenedioxyphenethylamine with 4-chloro-2-(isoxazol-5-yl)-5,6-dimethyl-thieno-[2,3-d]-pyrimidine yields 2-(isoxazol-5-yl)-4-(3,4-methylenedioxyphenethylamino)-5,6-dimethyl-thieno-[2,3-d]-pyrimidine.

EXAMPLE 1154

With the procedure of Example 1, the reaction of 3,4-methylenedioxyphenethylamine with 4-chloro-2-(isoxazol-5-yl)-6-trifluoromethyl-thieno-[2,3-d]-pyrimidine yields 2-(isoxazol-5-yl)-4-(3,4-methylenedioxyphenethylamino)-6-trifluoromethyl-thieno-[2,3-d]-pyrimidine.

EXAMPLE 1155

With the procedure of Example 1, the reaction of 3,4-methylenedioxyphenethylamine with 4-chloro-2-(pyrazin-2-yl)-6-methyl-thieno-[2,3-d]-pyrimidine yields 2-(pyrazin-2-yl)-4-(3,4-methylenedioxyphenethylamino)-6-methyl-thieno-[2,3-d]-pyrimidine.

EXAMPLE 1156

With the procedure of Example 1, the reaction of 3,4-methylenedioxyphenethylamine with 4-chloro-2-(pyrazin-2-yl)-5-methyl-thieno-[2,3-d]-pyrimidine yields 2-(pyrazin-2-yl)-4-(3,4-methylenedioxyphenethylamino)-5-methyl-thieno-[2,3-d]-pyrimidine.

EXAMPLE 1157

With the procedure of Example 1, the reaction of 3,4-methylenedioxyphenethylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-methylenedioxyphenethylamino)-5,6,7,8-tetrahydro-thieno-[2,3-d]-pyrimidine.

EXAMPLE 1158

With the procedure of Example 1, the reaction of 3,4-methylenedioxyphenethylamine with 4-chloro-2-(pyrazin- 2-yl)-5,6-cyclopenteno-thieno-[2,3-d]-pyrimidine yields 2-(pyrazin-2-yl)-4-(3,4-methylenedioxyphenethylamino)-5,6-cyclopenteno-thieno-[2,3-d]-pyrimidine.

EXAMPLE 1159

With the procedure of Example 1, the reaction of 3,4-methylenedioxyphenethylamine with 4-chloro-2-(pyrazin-2-yl)-5,6-cyclohepteno-thieno-[2,3-d]-pyrimidine yields 2-(pyrazin-2-yl)-4-(3,4-methylenedioxyphenethylamino)-5,6-cyclohepteno-thieno-[2,3-d]-pyrimidine.

EXAMPLE 1160

With the procedure of Example 1, the reaction of 3,4-methylenedioxyphenethylamine with 4-chloro-2-(pyrazin-2-yl)-6-ethyl-thieno-[2,3-d]-pyrimidine yields 2-(pyrazin-2-yl)-4-(3,4-methylenedioxyphenethylamino)-6-ethyl-thieno-[2,3-d]-pyrimidine.

EXAMPLE 1161

With the procedure of Example 1, the reaction of 3,4-methylenedioxyphenethylamine with 4-chloro-2-(pyrazin-2-yl)-6-chloro-thieno-[2,3-d]-pyrimidine yields 2-(pyrazin-2-yl)-4-(3,4-methylenedioxyphenethylamino)-6-chloro-thieno-[2,3-d]-pyrimidine.

EXAMPLE 1162

With the procedure of Example 1, the reaction of 3,4-methylenedioxyphenethylamine with 4-chloro-2-(pyrazin-2-yl)-5-chloro-6-methyl-thieno-[2,3-d]-pyrimidine yields 2-(pyrazin-2-yl)-4-(3,4-methylenedioxyphenethylamino)-5-chlror-6-methyl-thieno-[2,3-d]-pyrimidine.

EXAMPLE 1163

With the procedure of Example 1, the reaction of 3,4-methylenedioxyphenethylamine with 4-chloro-2-(pyrazin-2-yl)-6-nitro-thieno-[2,3-d]-pyrimidine yields 2-(pyrazin-2-yl)-4-(3,4-methylenedioxyphenethylamino)-6-nitro-thieno-[2,3-d]-pyrimidine.

EXAMPLE 1164

With the procedure of Example 1, the reaction of 3,4-methylenedioxyphenethylamine with 4-chloro-2-(pyrazin-2-yl)-5,6-dimethyl-thieno-[2,3-d]-pyrimidine yields 2-(pyrazin-2-yl)-4-(3,4-methylenedioxyphenethylamino)-5,6-dimethyl-thieno-[2,3-d]-pyrimidine.

EXAMPLE 1165

With the procedure of Example 1, the reaction of 3,4-methylenedioxyphenethylamine with 4-chloro-2-(pyrazin-2-yl)-6-trifluoromethyl-thieno-[2,3-d]-pyrimidine yields 2-(pyrazin-2-yl)-4-(3,4-methylenedioxyphenethylamino)-6-trifluoromethyl-thieno-[2,3-d]-pyrimidine.

EXAMPLE 1166

With the procedure of Example 1, the reaction of 3,4-methylenedioxyphenethylamine with 4-chloro-2-(pyridin-2-yl)-6-methyl-thieno-[2,3-d]-pyrimidine yields 2-(pyridin-2-yl)-4-(3,4-methylenedioxyphenethylamino)-6-methyl-thieno-[2,3-d]-pyrimidine.

EXAMPLE 1167

With the procedure of Example 1, the reaction of 3,4-methylenedioxyphenethylamine with 4-chloro-2-(pyridin-2-yl)-5-methyl-thieno-[2,3-d]-pyrimidine yields 2-(pyridin-2-yl)-4-(3,4-methylenedioxyphenethylamino)-5-methyl-thieno-[2,3-d]-pyrimidine.

EXAMPLE 1168

With the procedure of Example 1, the reaction of 3,4-methylenedioxyphenethylamine with 4-chloro-2-(pyridin-2-yl)-5,6,7,8-tetrahydro-[1]-benzothieno-[2,3-d]-pyrimidine yields 2-(pyridin-2-yl)-4-(3,4-methylenedioxyphenethylamino)-5,6,7,8-tetrahydro-thieno-[2,3-d]-pyrimidine.

EXAMPLE 1169

With the procedure of Example 1, the reaction of 3,4-methylenedioxyphenethylamine with 4-chloro-2-(pyridin-2-yl)-5,6-cyclopenteno-thieno-[2,3-d]-pyrimidine yields 2-(pyridin-2-yl)-4-(3,4-methylenedioxyphenethylamino)-5,6-cyclopenteno-thieno-[2,3-d]-pyrimidine.

EXAMPLE 1170

With the procedure of Example 1, the reaction of 3,4-methylenedioxyphenethylamine with 4-chloro-2-(pyridin-2-yl)-5,6-cyclohepteno-thieno-[2,3-d]-pyrimidine yields 2-(pyridin-2-yl)-4-(3,4-methylenedioxyphenethylamino)-5,6-cyclohepteno-thieno-[2,3-d]-pyrimidine.

EXAMPLE 1171

With the procedure of Example 1, the reaction of 3,4-methylenedioxyphenethylamine with 4-chloro-2-(pyridin-2-yl)-6-ethyl-thieno-[2,3-d]-pyrimidine yields 2-(pyridin-2-yl)-4-(3,4-methylenedioxyphenethylamino)-6-ethyl-thieno-[2,3-d]-pyrimidine.

EXAMPLE 1172

With the procedure of Example 1, the reaction of 3,4-methylenedioxyphenethylamine with 4-chloro-2-(pyridin-2-yl)-6-chloro-thieno-[2,3-d]-pyrimidine yields 2-(pyridin-2-yl)-4-(3,4-methylenedioxyphenethylamino)-6-chloro-thieno-[2,3-d]-pyrimidine.

EXAMPLE 1173

With the procedure of Example 1, the reaction of 3,4-methylenedioxyphenethylamine with 4-chloro-2-(pyridin-2-yl)-5-chloro-6-methyl-thieno-[2,3-d]-pyrimidine yields 2-(pyridin-2-yl)-4-(3,4-methylenedioxyphenethylamino)-5-chlror-6-methyl-thieno-[2,3-d]-pyrimidine.

EXAMPLE 1174

With the procedure of Example 1, the reaction of 3,4-methylenedioxyphenethylamine with 4-chloro-2-(pyridin-2-yl)-6-nitro-thieno-[2,3-d]-pyrimidine yields 2-(pyridin-2-yl)-4-(3,4-methylenedioxyphenethylamino)-6-nitro-thieno-[2,3-d]-pyrimidine.

EXAMPLE 1175

With the procedure of Example 1, the reaction of 3,4-methylenedioxyphenethylamine with 4-chloro-2-(pyridin-2-yl)-5,6-dimethyl-thieno-[2,3-d]-pyrimidine yields 2-(pyridin-2-yl)-4-(3,4-methylenedioxyphenethylamino)-5,6-dimethyl-thieno-[2,3-d]-pyrimidine.

EXAMPLE 1176

With the procedure of Example 1, the reaction of 3,4-methylenedioxyphenethylamine with 4-chloro-2-(pyridin-2- yl)-6-trifluoromethyl-thieno-[2,3-d]-pyrimidine yields 2-(pyridin-2-yl)-4-(3,4-methylenedioxyphenethylamino)-6-trifluoromethyl-thieno-[2,3-d]-pyrimidine.

EXAMPLE 1177

With the procedure of Example 1, the reaction of 3,4-methylenedioxyphenethylamine with 4-chloro-2-(pyridin-4-yl)-6-methyl-thieno-[2,3-d]-pyrimidine yields 2-(pyridin-4-yl)-4-(3,4-methylenedioxyphenethylamino)-6-methyl-thieno-[2,3-d]-pyrimidine.

EXAMPLE 1178

With the procedure of Example 1, the reaction of 3,4-methylenedioxyphenethylamine with 4-chloro-2-(pyridin-4-yl)-5-methyl-thieno-[2,3-d]-pyrimidine yields 2-(pyridin-4-yl)-4-(3,4-methylenedioxyphenethylamino)-5-methyl-thieno-[2,3-d]-pyrimidine.

EXAMPLE 1179

With the procedure of Example 1, the reaction of 3,4-methylenedioxyphenethylamine with 4-chloro-2-(pyridin-4-yl)-5,6,7,8-tetrahydro-[1]-benzothieno-[2,3-d]-pyrimidine yields 2-(pyridin-4-yl)-4-(3,4-methylenedioxyphenethylamino)-5,6,7,8-tetrahydro-thieno-[2,3-d]-pyrimidine.

EXAMPLE 1180

With the procedure of Example 1, the reaction of 3,4-methylenedioxyphenethylamine with 4-chloro-2-(pyridin-4-yl)-5,6-cyclopenteno-thieno-[2,3-d]-pyrimidine yields 2-(pyridin-4-yl)-4-(3,4-methylenedioxyphenethylamino)-5,6-cyclopenteno-thieno-[2,3-d]-pyrimidine.

EXAMPLE 1181

With the procedure of Example 1, the reaction of 3,4-methylenedioxyphenethylamine with 4-chloro-2-(pyridin-4-yl)-5,6-cyclohepteno-thieno-[2,3-d]-pyrimidine yields 2-(pyridin-4-yl)-4-(3,4-methylenedioxyphenethylamino)-5,6-cyclohepteno-thieno-[2,3-d]-pyrimidine.

EXAMPLE 1182

With the procedure of Example 1, the reaction of 3,4-methylenedioxyphenethylamine with 4-chloro-2-(pyridin-4-yl)-6-ethyl-thieno-[2,3-d]-pyrimidine yields 2-(pyridin-4-yl)-4-(3,4-methylenedioxyphenethylamino)-6-ethyl-thieno-[2,3-d]-pyrimidine.

EXAMPLE 1183

With the procedure of Example 1, the reaction of 3,4-methylenedioxyphenethylamine with 4-chloro-2-(pyridin-4-yl)-6-chloro-thieno-[2,3-d]-pyrimidine yields 2-(pyridin-4-yl)-4-(3,4-methylenedioxyphenethylamino)-6-chloro-thieno-[2,3-d]-pyrimidine.

EXAMPLE 1184

With the procedure of Example 1, the reaction of 3,4-methylenedioxyphenethylamine with 4-chloro-2-(pyridin-4-yl)-5-chloro-6-methyl-thieno-[2,3-d]-pyrimidine yields 2-(pyridin-4-yl)-4-(3,4-methylenedioxyphenethylamino)-5-chlror-6-methyl-thieno-[2,3-d]-pyrimidine.

EXAMPLE 1185

With the procedure of Example 1, the reaction of 3,4-methylenedioxyphenethylamine with 4-chloro-2-(pyridin-4-yl)-6-nitro-thieno-[2,3-d]-pyrimidine yields 2-(pyridin-4-yl)-4-(3,4-methylenedioxyphenethylamino)-6-nitro-thieno-[2,3-d]-pyrimidine.

EXAMPLE 1186

With the procedure of Example 1, the reaction of 3,4-methylenedioxyphenethylamine with 4-chloro-2-(pyridin-4-yl)-5,6-dimethyl-thieno-[2,3-d]-pyrimidine yields 2-(pyridin-4-yl)-4-(3,4-methylenedioxyphenethylamino)-5,6-dimethyl-thieno-[2,3-d]-pyrimidine.

EXAMPLE 1187

With the procedure of Example 1, the reaction of 3,4-methylenedioxyphenethylamine with 4-chloro-2-(pyridin-4-yl)-6-trifluoromethyl-thieno-[2,3-d]-pyrimidine yields 2-(pyridin-4-yl)-4-(3,4-methylenedioxyphenethylamino)-6-trifluoromethyl-thieno-[2,3-d]-pyrimidine.

EXAMPLE 1188

With the procedure of Example 1, the reaction of 3,4-methylenedioxyphenethylamine with 4-chloro-2-(pyridin-3-yl)-6-methyl-thieno-[2,3-d]-pyrimidine yields 2-(pyridin-3-yl)-4-(3,4-methylenedioxyphenethylamino)-6-methyl-thieno-[2,3-d]-pyrimidine.

EXAMPLE 1189

With the procedure of Example 1, the reaction of 3,4-methylenedioxyphenethylamine with 4-chloro-2-(pyridin-3-yl)-5-methyl-thieno-[2,3-d]-pyrimidine yields 2-(pyridin-3-yl)-4-(3,4-methylenedioxyphenethylamino)-5-methyl-thieno-[2,3-d]-pyrimidine.

EXAMPLE 1190

With the procedure of Example 1, the reaction of 3,4-methylenedioxyphenethylamine with 4-chloro-2-(pyridin-3-yl)-5,6,7,8-tetrahydro-[1]-benzothieno-[2,3-d]-pyrimidine yields 2-(pyridin-3-yl)-4-(3,4-methylenedioxyphenethylamino)-5,6,7,8-tetrahydro-thieno-[2,3-d]-pyrimidine.

EXAMPLE 1191

With the procedure of Example 1, the reaction of 3,4-methylenedioxyphenethylamine with 4-chloro-2-(pyridin-3-yl)-5,6-cyclopenteno-thieno-[2,3-d]-pyrimidine yields 2-(pyridin-3-yl)-4-(3,4-methylenedioxyphenethylamino)-5,6-cyclopenteno-thieno-[2,3-d]-pyrimidine.

EXAMPLE 1192

With the procedure of Example 1, the reaction of 3,4-methylenedioxyphenethylamine with 4-chloro-2-(pyridin-3-yl)-5,6-cyclohepteno-thieno-[2,3-d]-pyrimidine yields 2-(pyridin-3-yl)-4-(3,4-methylenedioxyphenethylamino)-5,6-cyclohepteno-thieno-[2,3-d]-pyrimidine.

EXAMPLE 1193

With the procedure of Example 1, the reaction of 3,4-methylenedioxyphenethylamine with 4-chloro-2-(pyridin-3-yl)-6-ethyl-thieno-[2,3-d]-pyrimidine yields 2-(pyridin-3-yl)-4-(3,4-methylenedioxyphenethylamino)-6-ethyl-thieno-[2,3-d]-pyrimidine.

EXAMPLE 1194

With the procedure of Example 1, the reaction of 3,4-methylenedioxyphenethylamine with 4-chloro-2-(pyridin-3- yl)-6-chloro-thieno-[2,3-d]-pyrimidine yields 2-(pyridin-3-yl)-4-(3,4-methylenedioxyphenethylamino)-6-chloro-thieno-[2,3-d]-pyrimidine.

EXAMPLE 1195

With the procedure of Example 1, the reaction of 3,4-methylenedioxyphenethylamine with 4-chloro-2-(pyridin-3-yl)-5-chloro-6-methyl-thieno-[2,3-d]-pyrimidine yields 2-(pyridin-3-yl)-4-(3,4-methylenedioxyphenethylamino)-5-chlror-6-methyl-thieno-[2,3-d]-pyrimidine.

EXAMPLE 1196

With the procedure of Example 1, the reaction of 3,4-methylenedioxyphenethylamine with 4-chloro-2-(pyridin-3-yl)-6-nitro-thieno-[2,3-d]-pyrimidine yields 2-(pyridin-3-yl)-4-(3,4-methylenedioxyphenethylamino)-6-nitro-thieno-[2,3-d]-pyrimidine.

EXAMPLE 1197

With the procedure of Example 1, the reaction of 3,4-methylenedioxyphenethylamine with 4-chloro-2-(pyridin-3-yl)-5,6-dimethyl-thieno-[2,3-d]-pyrimidine yields 2-(pyridin-3-yl)-4-(3,4-methylenedioxyphenethylamino)-5,6-dimethyl-thieno-[2,3-d]-pyrimidine.

EXAMPLE 1198

With the procedure of Example 1, the reaction of 3,4-methylenedioxyphenethylamine with 4-chloro-2-(pyridin-3-yl)-6-trifluoromethyl-thieno-[2,3-d]-pyrimidine yields 2-(pyridin-3-yl)-4-(3,4-methylenedioxyphenethylamino)-6-trifluoromethyl-thieno-[2,3-d]-pyrimidine.

EXAMPLE 1199

With the procedure of Example 1, the reaction of 3,4-methylenedioxyphenethylamine with 4-chloro-2-(isoxazol-5-yl)-6-methyl-thieno-[2,3-d]-pyrimidine yields 2-(isoxazol-5-yl)-4-(3,4-methylenedioxyphenethylamino)-6-methyl-thieno-[2,3-d]-pyrimidine.

EXAMPLE 1200

With the procedure of Example 1, the reaction of 3,4-methylenedioxyphenethylamine with 4-chloro-2-(isoxazol-5-yl)-5-methyl-thieno-[2,3-d]-pyrimidine yields 2-(isoxazol-5-yl)-4-(3,4-methylenedioxyphenethylamino)-5-methyl-thieno-[2,3-d]-pyrimidine.

EXAMPLE 1201

With the procedure of Example 1, the reaction of 3,4-methylenedioxyphenethylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-methylenedioxyphenethylamino)-5,6,7,8-tetrahydro-thieno-[2,3-d]-pyrimidine.

EXAMPLE 1202

With the procedure of Example 1, the reaction of 3,4-methylenedioxyphenethylamine with 4-chloro-2-(isoxazol-5-yl)-5,6-cyclopenteno-thieno-[2,3-d]-pyrimidine yields 2-(isoxazol-5-yl)-4-(3,4-methylenedioxyphenethylamino)-5,6-cyclopenteno-thieno-[2,3-d]-pyrimidine.

EXAMPLE 1203

With the procedure of Example 1, the reaction of 3,4-methylenedioxyphenethylamine with 4-chloro-2-(isoxazol-5-yl)-5,6-cyclohepteno-thieno-[2,3-d]-pyrimidine yields 2-(isoxazol-5-yl)-4-(3,4-methylenedioxyphenethylamino)-5,6-cyclohepteno-thieno-[2,3-d]-pyrimidine.

EXAMPLE 1204

With the procedure of Example 1, the reaction of 3,4-methylenedioxyphenethylamine with 4-chloro-2-(isoxazol-5-yl)-6-ethyl-thieno-[2,3-d]-pyrimidine yields 2-(isoxazol-5-yl)-4-(3,4-methylenedioxyphenethylamino)-6-ethyl-thieno-[2,3-d]-pyrimidine.

EXAMPLE 1205

With the procedure of Example 1, the reaction of 3,4-methylenedioxyphenethylamine with 4-chloro-2-(isoxazol-5-yl)-6-chloro-thieno-[2,3-d]-pyrimidine yields 2-(isoxazol-5-yl)-4-(3,4-methylenedioxyphenethylamino)-6-chloro-thieno-[2,3-d]-pyrimidine.

EXAMPLE 1206

With the procedure of Example 1, the reaction of 3,4-methylenedioxyphenethylamine with 4-chloro-2-(isoxazol-5-yl)-5-chloro-6-methyl-thieno-[2,3-d]-pyrimidine yields 2-(isoxazol-5-yl)-4-(3,4-methylenedioxyphenethylamino)-5-chlror-6-methyl-thieno-[2,3-d]-pyrimidine.

EXAMPLE 1207

With the procedure of Example 1, the reaction of 3,4-methylenedioxyphenethylamine with 4-chloro-2-(isoxazol-5-yl)-6-nitro-thieno-[2,3-d]-pyrimidine yields 2-(isoxazol-5-yl)-4-(3,4-methylenedioxyphenethylamino)-6-nitro-thieno-[2,3-d]-pyrimidine.

EXAMPLE 1208

With the procedure of Example 1, the reaction of 3,4-methylenedioxyphenethylamine with 4-chloro-2-(isoxazol-5-yl)-5,6-dimethyl-thieno-[2,3-d]-pyrimidine yields 2-(isoxazol-5-yl)-4-(3,4-methylenedioxyphenethylamino)-5,6-dimethyl-thieno-[2,3-d]-pyrimidine.

EXAMPLE 1209

With the procedure of Example 1, the reaction of 3,4-methylenedioxyphenethylamine with 4-chloro-2-(isoxazol-5-yl)-6-trifluoromethyl-thieno-[2,3-d]-pyrimidine yields 2-(isoxazol-5-yl)-4-(3,4-methylenedioxyphenethylamino)-6-trifluoromethyl-thieno-[2,3-d]-pyrimidine.

EXAMPLE 1210

With the procedure of Example 1, the reaction of 3,4-methylenedioxyphenethylamine with 4-chloro-2-(pyrazin-2-yl)-6-methyl-thieno-[2,3-d]-pyrimidine yields 2-(pyrazin-2-yl)-4-(3,4-methylenedioxyphenethylamino)-6-methyl-thieno-[2,3-d]-pyrimidine.

EXAMPLE 1211

With the procedure of Example 1, the reaction of 3,4-methylenedioxyphenethylamine with 4-chloro-2-(pyrazin-2-yl)-5-methyl-thieno-[2,3-d]-pyrimidine yields 2-(pyrazin-2-yl)-4-(3,4-methylenedioxyphenethylamino)-5-methyl-thieno-[2,3-d]-pyrimidine.

EXAMPLE 1212

With the procedure of Example 1, the reaction of 3,4-methylenedioxyphenethylamine with 4-chloro-2-(pyrazin- 2-yl)-5,6,7,8-tetrahydro-[1]-benzothieno-[2,3-d]-pyrimidine yields 2-(pyrazin-2-yl)-4-(3,4-methylenedioxyphenethylamino)-5,6,7,8-tetrahydro-thieno-[2,3-d]-pyrimidine.

EXAMPLE 1213

With the procedure of Example 1, the reaction of 3,4-methylenedioxyphenethylamine with 4-chloro-2-(pyrazin-2-yl)-5,6-cyclopenteno-thieno-[2,3-d]-pyrimidine yields 2-(pyrazin-2-yl)-4-(3,4-methylenedioxyphenethylamino)-5,6-cyclopenteno-thieno-[2,3-d]-pyrimidine.

EXAMPLE 1214

With the procedure of Example 1, the reaction of 3,4-methylenedioxyphenethylamine with 4-chloro-2-(pyrazin-2-yl)-5,6-cyclohepteno-thieno-[2,3-d]-pyrimidine yields 2-(pyrazin-2-yl)-4-(3,4-methylenedioxyphenethylamino)-5,6-cyclohepteno-thieno-[2,3-d]-pyrimidine.

EXAMPLE 1215

With the procedure of Example 1, the reaction of 3,4-methylenedioxyphenethylamine with 4-chloro-2-(pyrazin-2-yl)-6-ethyl-thieno-[2,3-d]-pyrimidine yields 2-(pyrazin-2-yl)-4-(3,4-methylenedioxyphenethylamino)-6-ethyl-thieno-[2,3-d]-pyrimidine.

EXAMPLE 1216

With the procedure of Example 1, the reaction of 3,4-methylenedioxyphenethylamine with 4-chloro-2-(pyrazin-2-yl)-6-chloro-thieno-[2,3-d]-pyrimidine yields 2-(pyrazin-2-yl)-4-(3,4-methylenedioxyphenethylamino)-6-chloro-thieno-[2,3-d]-pyrimidine.

EXAMPLE 1217

With the procedure of Example 1, the reaction of 3,4-methylenedioxyphenethylamine with 4-chloro-2-(pyrazin-2-yl)-5-chloro-6-methyl-thieno-[2,3-d]-pyrimidine yields 2-(pyrazin-2-yl)-4-(3,4-methylenedioxyphenethylamino)-5-chlror-6-methyl-thieno-[2,3-d]-pyrimidine.

EXAMPLE 1218

With the procedure of Example 1, the reaction of 3,4-methylenedioxyphenethylamine with 4-chloro-2-(pyrazin-2-yl)-6-nitro-thieno-[2,3-d]-pyrimidine yields 2-(pyrazin-2-yl)-4-(3,4-methylenedioxyphenethylamino)-6-nitro-thieno-[2,3-d]-pyrimidine.

EXAMPLE 1219

With the procedure of Example 1, the reaction of 3,4-methylenedioxyphenethylamine with 4-chloro-2-(pyrazin-2-yl)-5,6-dimethyl-thieno-[2,3-d]-pyrimidine yields 2-(pyrazin-2-yl)-4-(3,4-methylenedioxyphenethylamino)-5,6-dimethyl-thieno-[2,3-d]-pyrimidine.

EXAMPLE 1220

With the procedure of Example 1, the reaction of 3,4-methylenedioxyphenethylamine with 4-chloro-2-(pyrazin-2-yl)-6-trifluoromethyl-thieno-[2,3-d]-pyrimidine yields 2-(pyrazin-2-yl)-4-(3,4-methylenedioxyphenethylamino)-6-trifluoromethyl-thieno-[2,3-d]-pyrimidine.

EXAMPLE 1221

With the procedure of Example 1, the reaction of 3,4-methylenedioxyphenethylamine with 4-chloro-2-(pyridin-2-yl)-6-methyl-thieno-[2,3-d]-pyrimidine yields 2-(pyridin-2-yl)-4-(3,4-methylenedioxyphenethylamino)-6-methyl-thieno-[2,3-d]-pyrimidine.

EXAMPLE 1222

With the procedure of Example 1, the reaction of 3,4-methylenedioxyphenethylamine with 4-chloro-2-(pyridin-2-yl)-5-methyl-thieno-[2,3-d]-pyrimidine yields 2-(pyridin-2-yl)-4-(3,4-methylenedioxyphenethylamino)-5-methyl-thieno-[2,3-d]-pyrimidine.

EXAMPLE 1223

With the procedure of Example 1, the reaction of 3,4-methylenedioxyphenethylamine with 4-chloro-2-(pyridin-2-yl)-5,6,7,8-tetrahydro-[1]-benzothieno-[2,3-d]-pyrimidine yields 2-(pyridin-2-yl)-4-(3,4-methylenedioxyphenethylamino)-5,6,7,8-tetrahydro-thieno-[2,3-d]-pyrimidine.

EXAMPLE 1224

With the procedure of Example 1, the reaction of 3,4-methylenedioxyphenethylamine with 4-chloro-2-(pyridin-2-yl)-5,6-cyclopenteno-thieno-[2,3-d]-pyrimidine yields 2-(pyridin-2-yl)-4-(3,4-methylenedioxyphenethylamino)-5,6-cyclopenteno-thieno-[2,3-d]-pyrimidine.

EXAMPLE 1225

With the procedure of Example 1, the reaction of 3,4-methylenedioxyphenethylamine with 4-chloro-2-(pyridin-2-yl)-5,6-cyclohepteno-thieno-[2,3-d]-pyrimidine yields 2-(pyridin-2-yl)-4-(3,4-methylenedioxyphenethylamino)-5,6-cyclohepteno-thieno-[2,3-d]-pyrimidine.

EXAMPLE 1226

With the procedure of Example 1, the reaction of 3,4-methylenedioxyphenethylamine with 4-chloro-2-(pyridin-2-yl)-6-ethyl-thieno-[2,3-d]-pyrimidine yields 2-(pyridin-2-yl)-4-(3,4-methylenedioxyphenethylamino)-6-ethyl-thieno-[2,3-d]-pyrimidine.

EXAMPLE 1227

With the procedure of Example 1, the reaction of 3,4-methylenedioxyphenethylamine with 4-chloro-2-(pyridin-2-yl)-6-chloro-thieno-[2,3-d]-pyrimidine yields 2-(pyridin-2-yl)-4-(3,4-methylenedioxyphenethylamino)-6-chloro-thieno-[2,3-d]-pyrimidine.

EXAMPLE 1228

With the procedure of Example 1, the reaction of 3,4-methylenedioxyphenethylamine with 4-chloro-2-(pyridin-2-yl)-5-chloro-6-methyl-thieno-[2,3-d]-pyrimidine yields 2-(pyridin-2-yl)-4-(3,4-methylenedioxyphenethylamino)-5-chlror-6-methyl-thieno-[2,3-d]-pyrimidine.

EXAMPLE 1229

With the procedure of Example 1, the reaction of 3,4-methylenedioxyphenethylamine with 4-chloro-2-(pyridin-2-yl)-6-nitro-thieno-[2,3-d]-pyrimidine yields 2-(pyridin-2-yl)-4-(3,4-methylenedioxyphenethylamino)-6-nitro-thieno-[2,3-d]-pyrimidine.

EXAMPLE 1230

With the procedure of Example 1, the reaction of 3,4-methylenedioxyphenethylamine with 4-chloro-2-(pyridin-2- yl)-5,6-dimethyl-thieno-[2,3-d]-pyrimidine yields 2-(pyridin-2-yl)-4-(3,4-methylenedioxyphenethylamino)-5,6-dimethyl-thieno-[2,3-d]-pyrimidine.

EXAMPLE 1231

With the procedure of Example 1, the reaction of 3,4-methylenedioxyphenethylamine with 4-chloro-2-(pyridin-2-yl)-6-trifluoromethyl-thieno-[2,3-d]-pyrimidine yields 2-(pyridin-2-yl)-4-(3,4-methylenedioxyphenethylamino)-6-trifluoromethyl-thieno-[2,3-d]-pyrimidine.

EXAMPLE 1232

With the procedure of Example 1, the reaction of 3,4-methylenedioxyphenethylamine with 4-chloro-2-(pyridin-4-yl)-6-methyl-thieno-[2,3-d]-pyrimidine yields 2-(pyridin-4-yl)-4-(3,4-methylenedioxyphenethylamino)-6-methyl-thieno-[2,3-d]-pyrimidine.

EXAMPLE 1233

With the procedure of Example 1, the reaction of 3,4-methylenedioxyphenethylamine with 4-chloro-2-(pyridin-4-yl)-5-methyl-thieno-[2,3-d]-pyrimidine yields 2-(pyridin-4-yl)-4-(3,4-methylenedioxyphenethylamino)-5-methyl-thieno-[2,3-d]-pyrimidine.

EXAMPLE 1234

With the procedure of Example 1, the reaction of 3,4-methylenedioxyphenethylamine with 4-chloro-2-(pyridin-4-yl)-5,6,7,8-tetrahydro-[1]-benzothieno-[2,3-d]-pyrimidine yields 2-(pyridin-4-yl)-4-(3,4-methylenedioxyphenethylamino)-5,6,7,8-tetrahydro-thieno-[2,3-d]-pyrimidine.

EXAMPLE 1235

With the procedure of Example 1, the reaction of 3,4-methylenedioxyphenethylamine with 4-chloro-2-(pyridin-4-yl)-5,6-cyclopenteno-thieno-[2,3-d]-pyrimidine yields 2-(pyridin-4-yl)-4-(3,4-methylenedioxyphenethylamino)-5,6-cyclopenteno-thieno-[2,3-d]-pyrimidine.

EXAMPLE 1236

With the procedure of Example 1, the reaction of 3,4-methylenedioxyphenethylamine with 4-chloro-2-(pyridin-4-yl)-5,6-cyclohepteno-thieno-[2,3-d]-pyrimidine yields 2-(pyridin-4-yl)-4-(3,4-methylenedioxyphenethylamino)-5,6-cyclohepteno-thieno-[2,3-d]-pyrimidine.

EXAMPLE 1237

With the procedure of Example 1, the reaction of 3,4-methylenedioxyphenethylamine with 4-chloro-2-(pyridin-4-yl)-6-ethyl-thieno-[2,3-d]-pyrimidine yields 2-(pyridin-4-yl)-4-(3,4-methylenedioxyphenethylamino)-6-ethyl-thieno-[2,3-d]-pyrimidine.

EXAMPLE 1238

With the procedure of Example 1, the reaction of 3,4-methylenedioxyphenethylamine with 4-chloro-2-(pyridin-4-yl)-6-chloro-thieno-[2,3-d]-pyrimidine yields 2-(pyridin-4-yl)-4-(3,4-methylenedioxyphenethylamino)-6-chloro-thieno-[2,3-d]-pyrimidine.

EXAMPLE 1239

With the procedure of Example 1, the reaction of 3,4-methylenedioxyphenethylamine with 4-chloro-2-(pyridin-4-yl)-5-chloro-6-methyl-thieno-[2,3-d]-pyrimidine yields 2-(pyridin-4-yl)-4-(3,4-methylenedioxyphenethylamino)-5-chlror-6-methyl-thieno-[2,3-d]-pyrimidine.

EXAMPLE 1240

With the procedure of Example 1, the reaction of 3,4-methylenedioxyphenethylamine with 4-chloro-2-(pyridin-4-yl)-6-nitro-thieno-[2,3-d]-pyrimidine yields 2-(pyridin-4-yl)-4-(3,4-methylenedioxyphenethylamino)-6-nitro-thieno-[2,3-d]-pyrimidine.

EXAMPLE 1241

With the procedure of Example 1, the reaction of 3,4-methylenedioxyphenethylamine with 4-chloro-2-(pyridin-4-yl)-5,6-dimethyl-thieno-[2,3-d]-pyrimidine yields 2-(pyridin-4-yl)-4-(3,4-methylenedioxyphenethylamino)-5,6-dimethyl-thieno-[2,3-d]-pyrimidine.

EXAMPLE 1242

With the procedure of Example 1, the reaction of 3,4-methylenedioxyphenethylamine with 4-chloro-2-(pyridin-4-yl)-6-trifluoromethyl-thieno-[2,3-d]-pyrimidine yields 2-(pyridin-4-yl)-4-(3,4-methylenedioxyphenethylamino)-6-trifluoromethyl-thieno-[2,3-d]-pyrimidine.

EXAMPLE 1243

With the procedure of Example 1, the reaction of 3,4-ethylenedioxyphenethylamine with 4-chloro-2-(pyridin-3-yl)-6-methyl-thieno-[2,3-d]-pyrimidine yields 2-(pyridin-3-yl)-4-(3,4-ethylenedioxyphenethylamino)-6-methyl-thieno-[2,3-d]-pyrimidine.

EXAMPLE 1244

With the procedure of Example 1, the reaction of 4-fluoro-3,4-ethylenedioxyphenethylamine with 4-chloro-2-(pyridin-3-yl)-5-methyl-thieno-[2,3-d]-pyrimidine yields 2-(pyridin-3-yl)-4-(3,4-ethylenedioxyphenethylamino)-5-methyl-thieno-[2,3-d]-pyrimidine.

EXAMPLE 1245

With the procedure of Example 1, the reaction of 4-fluoro-3,4-ethylenedioxyphenethylamine with 4-chloro-2-(pyridin-3-yl)-5,6,7,8-tetrahydro-[1]-benzothieno-[2,3-d]-pyrimidine yields 2-(pyridin-3-yl)-4-(3,4-ethylenedioxyphenethylamino)-5,6,7,8-tetrahydro-thieno-[2,3-d]-pyrimidine.

EXAMPLE 1246

With the procedure of Example 1, the reaction of 3,4-ethylenedioxyphenethylamine with 4-chloro-2-(pyridin-3-yl)-5,6-cyclopenteno-thieno-[2,3-d]-pyrimidine yields 2-(pyridin-3-yl)-4-(3,4-ethylenedioxyphenethylamino)-5,6-cyclopenteno-thieno-[2,3-d]-pyrimidine.

EXAMPLE 1247

With the procedure of Example 1, the reaction of 3,4-ethylenedioxyphenethylamine with 4-chloro-2-(pyridin-3-yl)-5,6-cyclohepteno-thieno-[2,3-d]-pyrimidine yields 2-(pyridin-3-yl)-4-(3,4-ethylenedioxyphenethylamino)-5,6-cyclohepteno-thieno-[2,3-d]-pyrimidine.

EXAMPLE 1248

With the procedure of Example 1, the reaction of 3,4-ethylenedioxyphenethylamine with 4-chloro-2-(pyridin-3- yl)-6-ethyl-thieno-[2,3-d]-pyrimidine yields 2-(pyridin-3-yl)-4-(3,4-ethylenedioxyphenethylamino)-6-ethyl-thieno-[2,3-d]-pyrimidine.

EXAMPLE 1249

With the procedure of Example 1, the reaction of 3,4-ethylenedioxyphenethylamine with 4-chloro-2-(pyridin-3-yl)-6-chloro-thieno-[2,3-d]-pyrimidine yields 2-(pyridin-3-yl)-4-(3,4-ethylenedioxyphenethylamino)-6-chloro-thieno-[2,3-d]-pyrimidine.

EXAMPLE 1250

With the procedure of Example 1, the reaction of 3,4-ethylenedioxyphenethylamine with 4-chloro-2-(pyridin-3-yl)-5-chloro-6-methyl-thieno-[2,3-d]-pyrimidine yields 2-(pyridin-3-yl)-4-(3,4-ethylenedioxyphenethylamino)-5-chlror-6-methyl-thieno-[2,3-d]-pyrimidine.

EXAMPLE 1251

With the procedure of Example 1, the reaction of 3,4-ethylenedioxyphenethylamine with 4-chloro-2-(pyridin-3-yl)-6-nitro-thieno-[2,3-d]-pyrimidine yields 2-(pyridin-3-yl)-4-(3,4-ethylenedioxyphenethylamino)-6-nitro-thieno-[2,3-d]-pyrimidine.

EXAMPLE 1252

With the procedure of Example 1, the reaction of 3,4-ethylenedioxyphenethylamine with 4-chloro-2-(pyridin-3-yl)-5,6-dimethyl-thieno-[2,3-d]-pyrimidine yields 2-(pyridin-3-yl)-4-(3,4-ethylenedioxyphenethylamino)-5,6-dimethyl-thieno-[2,3-d]-pyrimidine.

EXAMPLE 1253

With the procedure of Example 1, the reaction of 3,4-ethylenedioxyphenethylamine with 4-chloro-2-(pyridin-3-yl)-6-trifluoromethyl-thieno-[2,3-d]-pyrimidine yields 2-(pyridin-3-yl)-4-(3,4-ethylenedioxyphenethylamino)-6-trifluoromethyl-thieno-[2,3-d]-pyrimidine.

EXAMPLE 1254

With the procedure of Example 1, the reaction of 3,4-ethylenedioxyphenethylamine with 4-chloro-2-(isoxazol-5-yl)-6-methyl-thieno-[2,3-d]-pyrimidine yields 2-(isoxazol-5-yl)-4-(3,4-ethylenedioxyphenethylamino)-6-methyl-thieno-[2,3-d]-pyrimidine.

EXAMPLE 1255

With the procedure of Example 1, the reaction of 3,4-ethylenedioxyphenethylamine with 4-chloro-2-(isoxazol-5-yl)-5-methyl-thieno-[2,3-d]-pyrimidine yields 2-(isoxazol-5-yl)-4-(3,4-ethylenedioxyphenethylamino)-5-methyl-thieno-[2,3-d]-pyrimidine.

EXAMPLE 1256

With the procedure of Example 1, the reaction of 3,4-ethylenedioxyphenethylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-ethylenedioxyphenethylamino)-5,6,7,8-tetrahydro-thieno-[2,3-d]-pyrimidine.

EXAMPLE 1257

With the procedure of Example 1, the reaction of 3,4-ethylenedioxyphenethylamine with 4-chloro-2-(isoxazol-5-yl)-5,6-cyclopenteno-thieno-[2,3-d]-pyrimidine yields 2-(isoxazol-5-yl)-4-(3,4-ethylenedioxyphenethylamino)-5,6-cyclopenteno-thieno-[2,3-d]-pyrimidine.

EXAMPLE 1258

With the procedure of Example 1, the reaction of 3,4-ethylenedioxyphenethylamine with 4-chloro-2-(isoxazol-5-yl)-5,6-cyclohepteno-thieno-[2,3-d]-pyrimidine yields 2-(isoxazol-5-yl)-4-(3,4-ethylenedioxyphenethylamino)-5,6-cyclohepteno-thieno-[2,3-d]-pyrimidine.

EXAMPLE 1259

With the procedure of Example 1, the reaction of 3,4-ethylenedioxyphenethylamine with 4-chloro-2-(isoxazol-5-yl)-6-ethyl-thieno-[2,3-d]-pyrimidine yields 2-(isoxazol-5-yl)-4-(3,4-ethylenedioxyphenethylamino)-6-ethyl-thieno-[2,3-d]-pyrimidine.

EXAMPLE 1260

With the procedure of Example 1, the reaction of 3,4-ethylenedioxyphenethylamine with 4-chloro-2-(isoxazol-5-yl)-6-chloro-thieno-[2,3-d]-pyrimidine yields 2-(isoxazol-5-yl)-4-(3,4-ethylenedioxyphenethylamino)-6-chloro-thieno-[2,3-d]-pyrimidine.

EXAMPLE 1261

With the procedure of Example 1, the reaction of 3,4-ethylenedioxyphenethylamine with 4-chloro-2-(isoxazol-5-yl)-5-chloro-6-methyl-thieno-[2,3-d]-pyrimidine yields 2-(isoxazol-5-yl)-4-(3,4-ethylenedioxyphenethylamino)-5-chlror-6-methyl-thieno-[2,3-d]-pyrimidine.

EXAMPLE 1262

With the procedure of Example 1, the reaction of 3,4-ethylenedioxyphenethylamine with 4-chloro-2-(isoxazol-5-yl)-6-nitro-thieno-[2,3-d]-pyrimidine yields 2-(isoxazol-5-yl)-4-(3,4-ethylenedioxyphenethylamino)-6-nitro-thieno-[2,3-d]-pyrimidine.

EXAMPLE 1263

With the procedure of Example 1, the reaction of 3,4-ethylenedioxyphenethylamine with 4-chloro-2-(isoxazol-5-yl)-5,6-dimethyl-thieno-[2,3-d]-pyrimidine yields 2-(isoxazol-5-yl)-4-(3,4-ethylenedioxyphenethylamino)-5,6-dimethyl-thieno-[2,3-d]-pyrimidine.

EXAMPLE 1264

With the procedure of Example 1, the reaction of 3,4-ethylenedioxyphenethylamine with 4-chloro-2-(isoxazol-5-yl)-6-trifluoromethyl-thieno-[2,3-d]-pyrimidine yields 2-(isoxazol-5-yl)-4-(3,4-ethylenedioxyphenethylamino)-6-trifluoromethyl-thieno-[2,3-d]-pyrimidine.

EXAMPLE 1265

With the procedure of Example 1, the reaction of 3,4-ethylenedioxyphenethylamine with 4-chloro-2-(pyrazin-2-yl)-6-methyl-thieno-[2,3-d]-pyrimidine yields 2-(pyrazin-2-yl)-4-(3,4-ethylenedioxyphenethylamino)-6-methyl-thieno-[2,3-d]-pyrimidine.

EXAMPLE 1266

With the procedure of Example 1, the reaction of 3,4-ethylenedioxyphenethylamine with 4-chloro-2-(pyrazin-2- yl)-5-methyl-thieno-[2,3-d]-pyrimidine yields 2-(pyrazin-2-yl)-4-(3,4-ethylenedioxyphenethylamino)-5-methyl-thieno-[2,3-d]-pyrimidine

EXAMPLE 1267

With the procedure of Example 1, the reaction of 3,4-ethylenedioxyphenethylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-ethylenedioxyphenethylamino)-5,6,7,8-tetrahydro-thieno-[2,3-d]-pyrimidine.

EXAMPLE 1268

With the procedure of Example 1, the reaction of 3,4-ethylenedioxyphenethylamine with 4-chloro-2-(pyrazin-2-yl)-5,6-cyclopenteno-thieno-[2,3-d]-pyrimidine yields 2-(pyrazin-2-yl)-4-(3,4-ethylenedioxyphenethylamino)-5,6-cyclopenteno-thieno-[2,3-d]-pyrimidine.

EXAMPLE 1269

With the procedure of Example 1, the reaction of 3,4-ethylenedioxyphenethylamine with 4-chloro-2-(pyrazin-2-yl)-5,6-cyclohepteno-thieno-[2,3-d]-pyrimidine yields 2-(pyrazin-2-yl)-4-(3,4-ethylenedioxyphenethylamino)-5,6-cyclohepteno-thieno-[2,3-d]-pyrimidine.

EXAMPLE 1270

With the procedure of Example 1, the reaction of 3,4-ethylenedioxyphenethylamine with 4-chloro-2-(pyrazin-2-yl)-6-ethyl-thieno-[2,3-d]-pyrimidine yields 2-(pyrazin-2-yl)-4-(3,4-ethylenedioxyphenethylamino)-6-ethyl-thieno-[2,3-d]-pyrimidine.

EXAMPLE 1271

With the procedure of Example 1, the reaction of 3,4-ethylenedioxyphenethylamine with 4-chloro-2-(pyrazin-2-yl)-6-chloro-thieno-[2,3-d]-pyrimidine yields 2-(pyrazin-2-yl)-4-(3,4-ethylenedioxyphenethylamino)-6-chloro-thieno-[2,3-d]-pyrimidine.

EXAMPLE 1272

With the procedure of Example 1, the reaction of 3,4-ethylenedioxyphenethylamine with 4-chloro-2-(pyrazin-2-yl)-5-chloro-6-methyl-thieno-[2,3-d]-pyrimidine yields 2-(pyrazin-2-yl)-4-(3,4-ethylenedioxyphenethylamino)-5-chlror-6-methyl-thieno-[2,3-d]-pyrimidine.

EXAMPLE 1273

With the procedure of Example 1, the reaction of 3,4-ethylenedioxyphenethylamine with 4-chloro-2-(pyrazin-2-yl)-6-nitro-thieno-[2,3-d]-pyrimidine yields 2-(pyrazin-2-yl)-4-(3,4-ethylenedioxyphenethylamino)-6-nitro-thieno-[2,3-d]-pyrimidine.

EXAMPLE 1274

With the procedure of Example 1, the reaction of 3,4-ethylenedioxyphenethylamine with 4-chloro-2-(pyrazin-2-yl)-5,6-dimethyl-thieno-[2,3-d]-pyrimidine yields 2-(pyrazin-2-yl)-4-(3,4-ethylenedioxyphenethylamino)-5,6-dimethyl-thieno-[2,3-d]-pyrimidine.

EXAMPLE 1275

With the procedure of Example 1, the reaction of 3,4-ethylenedioxyphenethylamine with 4-chloro-2-(pyrazin-2-yl)-6-trifluoromethyl-thieno-[2,3-d]-pyrimidine yields 2-(pyrazin-2-yl)-4-(3,4-ethylenedioxyphenethylamino)-6-trifluoromethyl-thieno-[2,3-d]-pyrimidine.

EXAMPLE 1276

With the procedure of Example 1, the reaction of 3,4-ethylenedioxyphenethylamine with 4-chloro-2-(pyridin-2-yl)-6-methyl-thieno-[2,3-d]-pyrimidine yields 2-(pyridin-2-yl)-4-(3,4-ethylenedioxyphenethylamino)-6-methyl-thieno-[2,3-d]-pyrimidine.

EXAMPLE 1277

With the procedure of Example 1, the reaction of 3,4-ethylenedioxyphenethylamine with 4-chloro-2-(pyridin-2-yl)-5-methyl-thieno-[2,3-d]-pyrimidine yields 2-(pyridin-2-yl)-4-(3,4-ethylenedioxyphenethylamino)-5-methyl-thieno-[2,3-d]-pyrimidine.

EXAMPLE 1278

With the procedure of Example 1, the reaction of 3,4-ethylenedioxyphenethylamine with 4-chloro-2-(pyridin-2-yl)-5,6,7,8-tetrahydro-[1]-benzothieno-[2,3-d]-pyrimidine yields 2-(pyridin-2-yl)-4-(3,4-ethylenedioxyphenethylamino)-5,6,7,8-tetrahydro-thieno-[2,3-d]-pyrimidine.

EXAMPLE 1279

With the procedure of Example 1, the reaction of 3,4-ethylenedioxyphenethylamine with 4-chloro-2-(pyridin-2-yl)-5,6-cyclopenteno-thieno-[2,3-d]-pyrimidine yields 2-(pyridin-2-yl)-4-(3,4-ethylenedioxyphenethylamino)-5,6-cyclopenteno-thieno-[2,3-d]-pyrimidine.

EXAMPLE 1280

With the procedure of Example 1, the reaction of 3,4-ethylenedioxyphenethylamine with 4-chloro-2-(pyridin-2-yl)-5,6-cyclohepteno-thieno-[2,3-d]-pyrimidine yields 2-(pyridin-2-yl)-4-(3,4-ethylenedioxyphenethylamino)-5,6-cyclohepteno-thieno-[2,3-d]-pyrimidine.

EXAMPLE 1281

With the procedure of Example 1, the reaction of 3,4-ethylenedioxyphenethylamine with 4-chloro-2-(pyridin-2-yl)-6-ethyl-thieno-[2,3-d]-pyrimidine yields 2-(pyridin-2-yl)-4-(3,4-ethylenedioxyphenethylamino)-6-ethyl-thieno-[2,3-d]-pyrimidine.

EXAMPLE 1282

With the procedure of Example 1, the reaction of 3,4-ethylenedioxyphenethylamine with 4-chloro-2-(pyridin-2-yl)-6-chloro-thieno-[2,3-d]-pyrimidine yields 2-(pyridin-2-yl)-4-(3,4-ethylenedioxyphenethylamino)-6-chloro-thieno-[2,3-d]-pyrimidine.

EXAMPLE 1283

With the procedure of Example 1, the reaction of 3,4-ethylenedioxyphenethylamine with 4-chloro-2-(pyridin-2-yl)-5-chloro-6-methyl-thieno-[2,3-d]-pyrimidine yields 2-(pyridin-2-yl)-4-(3,4-ethylenedioxyphenethylamino)-5-chlror-6-methyl-thieno-[2,3-d]-pyrimidine.

EXAMPLE 1284

With the procedure of Example 1, the reaction of 3,4-ethylenedioxyphenethylamine with 4-chloro-2-(pyridin-2- yl)-6-nitro-thieno-[2,3-d]-pyrimidine yields 2-(pyridin-2-yl)-4-(3,4-ethylenedioxyphenethylamino)-6-nitro-thieno-[2,3-d]-pyrimidine.

EXAMPLE 1285

With the procedure of Example 1, the reaction of 3,4-ethylenedioxyphenethylamine with 4-chloro-2-(pyridin-2-yl)-5,6-dimethyl-thieno-[2,3-d]-pyrimidine yields 2-(pyridin-2-yl)-4-(3,4-ethylenedioxyphenethylamino)-5,6-dimethyl-thieno-[2,3-d]-pyrimidine.

EXAMPLE 1286

With the procedure of Example 1, the reaction of 3,4-ethylenedioxyphenethylamine with 4-chloro-2-(pyridin-2-yl)-6-trifluoromethyl-thieno-[2,3-d]-pyrimidine yields 2-(pyridin-2-yl)-4-(3,4-ethylenedioxyphenethylamino)-6-trifluoromethyl-thieno-[2,3-d]-pyrimidine.

EXAMPLE 1287

With the procedure of Example 1, the reaction of 3,4-ethylenedioxyphenethylamine with 4-chloro-2-(pyridin-4-yl)-6-methyl-thieno-[2,3-d]-pyrimidine yields 2-(pyridin-4-yl)-4-(3,4-ethylenedioxyphenethylamino)-6-methyl-thieno-[2,3-d]-pyrimidine.

EXAMPLE 1288

With the procedure of Example 1, the reaction of 3,4-ethylenedioxyphenethylamine with 4-chloro-2-(pyridin-4-yl)-5-methyl-thieno-[2,3-d]-pyrimidine yields 2-(pyridin-4-yl)-4-(3,4-ethylenedioxyphenethylamino)-5-methyl-thieno-[2,3-d]-pyrimidine.

EXAMPLE 1289

With the procedure of Example 1, the reaction of 3,4-ethylenedioxyphenethylamine with 4-chloro-2-(pyridin-4-yl)-5,6,7,8-tetrahydro-[1]-benzothieno-[2,3-d]-pyrimidine yields 2-(pyridin-4-yl)-4-(3,4-ethylenedioxyphenethylamino)-5,6,7,8-tetrahydro-thieno-[2,3-d]-pyrimidine.

EXAMPLE 1290

With the procedure of Example 1, the reaction of 3,4-ethylenedioxyphenethylamine with 4-chloro-2-(pyridin-4-yl)-5,6-cyclopenteno-thieno-[2,3-d]-pyrimidine yields 2-(pyridin-4-yl)-4-(3,4-ethylenedioxyphenethylamino)-5,6-cyclopenteno-thieno-[2,3-d]-pyrimidine.

EXAMPLE 1291

With the procedure of Example 1, the reaction of 3,4-ethylenedioxyphenethylamine with 4-chloro-2-(pyridin-4-yl)-5,6-cyclohepteno-thieno-[2,3-d]-pyrimidine yields 2-(pyridin-4-yl)-4-(3,4-ethylenedioxyphenethylamino)-5,6-cyclohepteno-thieno-[2,3-d]-pyrimidine.

EXAMPLE 1292

With the procedure of Example 1, the reaction of 3,4-ethylenedioxyphenethylamine with 4-chloro-2-(pyridin-4-yl)-6-ethyl-thieno-[2,3-d]-pyrimidine yields 2-(pyridin-4-yl)-4-(3,4-ethylenedioxyphenethylamino)-6-ethyl-thieno-[2,3-d]-pyrimidine.

EXAMPLE 1293

With the procedure of Example 1, the reaction of 3,4-ethylenedioxyphenethylamine with 4-chloro-2-(pyridin-4-yl)-6-chloro-thieno-[2,3-d]-pyrimidine yields 2-(pyridin-4-yl)-4-(3,4-ethylenedioxyphenethylamino)-6-chloro-thieno-[2,3-d]-pyrimidine.

EXAMPLE 1294

With the procedure of Example 1, the reaction of 3,4-ethylenedioxyphenethylamine with 4-chloro-2-(pyridin-4-yl)-5-chloro-6-methyl-thieno-[2,3-d]-pyrimidine yields 2-(pyridin-4-yl)-4-(3,4-ethylenedioxyphenethylamino)-5-chlror-6-methyl-thieno-[2,3-d]-pyrimidine.

EXAMPLE 1295

With the procedure of Example 1, the reaction of 3,4-ethylenedioxyphenethylamine with 4-chloro-2-(pyridin-4-yl)-6-nitro-thieno-[2,3-d]-pyrimidine yields 2-(pyridin-4-yl)-4-(3,4-ethylenedioxyphenethylamino)-6-nitro-thieno-[2,3-d]-pyrimidine.

EXAMPLE 1296

With the procedure of Example 1, the reaction of 3,4-ethylenedioxyphenethylamine with 4-chloro-2-(pyridin-4-yl)-5,6-dimethyl-thieno-[2,3-d]-pyrimidine yields 2-(pyridin-4-yl)-4-(3,4-ethylenedioxyphenethylamino)-5,6-dimethyl-thieno-[2,3-d]-pyrimidine.

EXAMPLE 1297

With the procedure of Example 1, the reaction of 3,4-ethylenedioxyphenethylamine with 4-chloro-2-(pyridin-4-yl)-6-trifluoromethyl-thieno-[2,3-d]-pyrimidine yields 2-(pyridin-4-yl)-4-(3,4-ethylenedioxyphenethylamino)-6-trifluoromethyl-thieno-[2,3-d]-pyrimidine.

EXAMPLE 1298

With the procedure of Example 1, the reaction of 3,4-ethylenedioxyphenethylamine with 4-chloro-2-(pyridin-3-yl)-6-methyl-thieno-[2,3-d]-pyrimidine yields 2-(pyridin-3-yl)-4-(3,4-ethylenedioxyphenethylamino)-6-methyl-thieno-[2,3-d]-pyrimidine.

EXAMPLE 1299

With the procedure of Example 1, the reaction of 3,4-ethylenedioxyphenethylamine with 4-chloro-2-(pyridin-3-yl)-5-methyl-thieno-[2,3-d]-pyrimidine yields 2-(pyridin-3-yl)-4-(3,4-ethylenedioxyphenethylamino)-5-methyl-thieno-[2,3-d]-pyrimidine.

EXAMPLE 1300

With the procedure of Example 1, the reaction of 3,4-ethylenedioxyphenethylamine with 4-chloro-2-(pyridin-3-yl)-5,6,7,8-tetrahydro-[1]-benzothieno-[2,3-d]-pyrimidine yields 2-(pyridin-3-yl)-4-(3,4-ethylenedioxyphenethylamino)-5,6,7,8-tetrahydro-thieno-[2,3-d]-pyrimidine.

EXAMPLE 1301

With the procedure of Example 1, the reaction of 3,4-ethylenedioxyphenethylamine with 4-chloro-2-(pyridin-3-yl)-5,6-cyclopenteno-thieno-[2,3-d]-pyrimidine yields 2-(pyridin-3-yl)-4-(3,4-ethylenedioxyphenethylamino)-5,6-cyclopenteno-thieno-[2,3-d]-pyrimidine.

EXAMPLE 1302

With the procedure of Example 1, the reaction of 3,4-ethylenedioxyphenethylamine with 4-chloro-2-(pyridin-3- yl)-5,6-cyclohepteno-thieno-[2,3-d]-pyrimidine yields 2-(pyridin-3-yl)-4-(3,4-ethylenedioxyphenethylamino)-5,6-cyclohepteno-thieno-[2,3-d]-pyrimidine.

EXAMPLE 1303

With the procedure of Example 1, the reaction of 3,4-ethylenedioxyphenethylamine with 4-chloro-2-(pyridin-3-yl)-6-ethyl-thieno-[2,3-d]-pyrimidine yields 2-(pyridin-3-yl)-4-(3,4-ethylenedioxyphenethylamino)-6-ethyl-thieno-[2,3-d]-pyrimidine.

EXAMPLE 1304

With the procedure of Example 1, the reaction of 3,4-ethylenedioxyphenethylamine with 4-chloro-2-(pyridin-3-yl)-6-chloro-thieno-[2,3-d]-pyrimidine yields 2-(pyridin-3-yl)-4-(3,4-ethylenedioxyphenethylamino)-6-chloro-thieno-[2,3-d]-pyrimidine.

EXAMPLE 1305

With the procedure of Example 1, the reaction of 3,4-ethylenedioxyphenethylamine with 4-chloro-2-(pyridin-3-yl)-5-chloro-6-methyl-thieno-[2,3-d]-pyrimidine yields 2-(pyridin-3-yl)-4-(3,4-ethylenedioxyphenethylamino)-5-chlror-6-methyl-thieno-[2,3-d]-pyrimidine.

EXAMPLE 1306

With the procedure of Example 1, the reaction of 3,4-ethylenedioxyphenethylamine with 4-chloro-2-(pyridin-3-yl)-6-nitro-thieno-[2,3-d]-pyrimidine yields 2-(pyridin-3-yl)-4-(3,4-ethylenedioxyphenethylamino)-6-nitro-thieno-[2,3-d]-pyrimidine.

EXAMPLE 1307

With the procedure of Example 1, the reaction of 3,4-ethylenedioxyphenethylamine with 4-chloro-2-(pyridin-3-yl)-5,6-dimethyl-thieno-[2,3-d]-pyrimidine yields 2-(pyridin-3-yl)-4-(3,4-ethylenedioxyphenethylamino)-5,6-dimethyl-thieno-[2,3-d]-pyrimidine.

EXAMPLE 1308

With the procedure of Example 1, the reaction of 3,4-ethylenedioxyphenethylamine with 4-chloro-2-(pyridin-3-yl)-6-trifluoromethyl-thieno-[2,3-d]-pyrimidine yields 2-(pyridin-3-yl)-4-(3,4-ethylenedioxyphenethylamino)-6-trifluoromethyl-thieno-[2,3-d]-pyrimidine.

EXAMPLE 1309

With the procedure of Example 1, the reaction of 3,4-ethylenedioxyphenethylamine with 4-chloro-2-(isoxazol-5-yl)-6-methyl-thieno-[2,3-d]-pyrimidine yields 2-(isoxazol-5-yl)-4-(3,4-ethylenedioxyphenethylamino)-6-methyl-thieno-[2,3-d]-pyrimidine.

EXAMPLE 1310

With the procedure of Example 1, the reaction of 3,4-ethylenedioxyphenethylamine with 4-chloro-2-(isoxazol-5-yl)-5-methyl-thieno-[2,3-d]-pyrimidine yields 2-(isoxazol-5-yl)-4-(3,4-ethylenedioxyphenethylamino)-5-methyl-thieno-[2,3-d]-pyrimidine.

EXAMPLE 1311

With the procedure of Example 1, the reaction of 3,4-ethylenedioxyphenethylamine with 4-chloro-2-(isoxazol-5-yl)-5,6,7,8-tetrahydro-[1]-benzothieno-[2,3-d]-pyrimidine yields 2-(isoxazol-5-yl)-4-(3,4-ethylenedioxyphenethylamino)-5,6,7,8-tetrahydro-thieno-[2,3-d]-pyrimidine.

EXAMPLE 1312

With the procedure of Example 1, the reaction of 3,4-ethylenedioxyphenethylamine with 4-chloro-2-(isoxazol-5-yl)-5,6-cyclopenteno-thieno-[2,3-d]-pyrimidine yields 2-(isoxazol-5-yl)-4-(3,4-ethylenedioxyphenethylamino)-5,6-cyclopenteno-thieno-[2,3-d]-pyrimidine.

EXAMPLE 1313

With the procedure of Example 1, the reaction of 3,4-ethylenedioxyphenethylamine with 4-chloro-2-(isoxazol-5-yl)-5,6-cyclohepteno-thieno-[2,3-d]-pyrimidine yields 2-(isoxazol-5-yl)-4-(3,4-ethylenedioxyphenethylamino)-5,6-cyclohepteno-thieno-[2,3-d]-pyrimidine.

EXAMPLE 1314

With the procedure of Example 1, the reaction of 3,4-ethylenedioxyphenethylamine with 4-chloro-2-(isoxazol-5-yl)-6-ethyl-thieno-[2,3-d]-pyrimidine yields 2-(isoxazol-5-yl)-4-(3,4-ethylenedioxyphenethylamino)-6-ethyl-thieno-[2,3-d]-pyrimidine.

EXAMPLE 1315

With the procedure of Example 1, the reaction of 3,4-ethylenedioxyphenethylamine with 4-chloro-2-(isoxazol-5-yl)-6-chloro-thieno-[2,3-d]-pyrimidine yields 2-(isoxazol-5-yl)-4-(3,4-ethylenedioxyphenethylamino)-6-chloro-thieno-[2,3-d]-pyrimidine.

EXAMPLE 1316

With the procedure of Example 1, the reaction of 3,4-ethylenedioxyphenethylamine with 4-chloro-2-(isoxazol-5-yl)-5-chloro-6-methyl-thieno-[2,3-d]-pyrimidine yields 2-(isoxazol-5-yl)-4-(3,4-ethylenedioxyphenethylamino)-5-chlror-6-methyl-thieno-[2,3-d]-pyrimidine.

EXAMPLE 1317

With the procedure of Example 1, the reaction of 3,4-ethylenedioxyphenethylamine with 4-chloro-2-(isoxazol-5-yl)-6-nitro-thieno-[2,3-d]-pyrimidine yields 2-(isoxazol-5-yl)-4-(3,4-ethylenedioxyphenethylamino)-6-nitro-thieno-[2,3-d]-pyrimidine.

EXAMPLE 1318

With the procedure of Example 1, the reaction of 3,4-ethylenedioxyphenethylamine with 4-chloro-2-(isoxazol-5-yl)-5,6-dimethyl-thieno-[2,3-d]-pyrimidine yields 2-(isoxazol-5-yl)-4-(3,4-ethylenedioxyphenethylamino)-5,6-dimethyl-thieno-[2,3-d]-pyrimidine.

EXAMPLE 1319

With the procedure of Example 1, the reaction of 3,4-ethylenedioxyphenethylamine with 4-chloro-2-(isoxazol-5-yl)-6-trifluoromethyl-thieno-[2,3-d]-pyrimidine yields 2-(isoxazol-5-yl)-4-(3,4-ethylenedioxyphenethylamino)-6-trifluoromethyl-thieno-[2,3-d]-pyrimidine.

EXAMPLE 1320

With the procedure of Example 1, the reaction of 3,4-ethylenedioxyphenethylamine with 4-chloro-2-(pyrazin-2- yl)-6-methyl-thieno-[2,3-d]-pyrimidine yields 2-(pyrazin-2-yl)-4-(3,4-ethylenedioxyphenethylamino)-6-methyl-thieno-[2,3-d]-pyrimidine.

EXAMPLE 1321

With the procedure of Example 1, the reaction of 3,4-ethylenedioxyphenethylamine with 4-chloro-2-(pyrazin-2-yl)-5-methyl-thieno-[2,3-d]-pyrimidine yields 2-(pyrazin-2-yl)-4-(3,4-ethylenedioxyphenethylamino)-5-methyl-thieno-[2,3-d]-pyrimidine.

EXAMPLE 1322

With the procedure of Example 1, the reaction of 3,4-ethylenedioxyphenethylamine with 4-chloro-2-(pyrazin-2-yl)-5,6,7,8-tetrahydro-[1]-benzothieno-[2,3-d]-pyrimidine yields 2-(pyrazin-2-yl)-4-(3,4-ethylenedioxyphenethylamino)-5,6,7,8-tetrahydro-thieno-[2,3-d]-pyrimidine.

EXAMPLE 1323

With the procedure of Example 1, the reaction of 3,4-ethylenedioxyphenethylamine with 4-chloro-2-(pyrazin-2-yl)-5,6-cyclopenteno-thieno-[2,3-d]-pyrimidine yields 2-(pyrazin-2-yl)-4-(3,4-ethylenedioxyphenethylamino)-5,6-cyclopenteno-thieno-[2,3-d]-pyrimidine.

EXAMPLE 1324

With the procedure of Example 1, the reaction of 3,4-ethylenedioxyphenethylamine with 4-chloro-2-(pyrazin-2-yl)-5,6-cyclohepteno-thieno-[2,3-d]-pyrimidine yields 2-(pyrazin-2-yl)-4-(3,4-ethylenedioxyphenethylamino)-5,6-cyclohepteno-thieno-[2,3-d]-pyrimidine.

EXAMPLE 1325

With the procedure of Example 1, the reaction of 3,4-ethylenedioxyphenethylamine with 4-chloro-2-(pyrazin-2-yl)-6-ethyl-thieno-[2,3-d]-pyrimidine yields 2-(pyrazin-2-yl)-4-(3,4-ethylenedioxyphenethylamino)-6-ethyl-thieno-[2,3-d]-pyrimidine.

EXAMPLE 1326

With the procedure of Example 1, the reaction of 3,4-ethylenedioxyphenethylamine with 4-chloro-2-(pyrazin-2-yl)-6-chloro-thieno-[2,3-d]-pyrimidine yields 2-(pyrazin-2-yl)-4-(3,4-ethylenedioxyphenethylamino)-6-chloro-thieno-[2,3-d]-pyrimidine.

EXAMPLE 1326A

With the procedure of Example 1, the reaction of 3,4-ethylenedioxyphenethylamine with 4-chloro-2-(pyrazin-2-yl)-5-chloro-6-methyl-thieno-[2,3-d]-pyrimidine yields 2-(pyrazin-2-yl)-4-(3,4-ethylenedioxyphenethylamino)—S—chlror-6-methyl-thieno-[2,3-d]-pyrimidine.

EXAMPLE 1327

With the procedure of Example 1, the reaction of 3,4-ethylenedioxyphenethylamine with 4-chloro-2-(pyrazin-2-yl)-6-nitro-thieno-[2,3-d]-pyrimidine yields 2-(pyrazin-2-yl)-4-(3,4-ethylenedioxyphenethylamino)-6-nitro-thieno-[2,3-d]-pyrimidine.

EXAMPLE 1328

With the procedure of Example 1, the reaction of 3,4-ethylenedioxyphenethylamine with 4-chloro-2-(pyrazin-2-yl)-5,6-dimethyl-thieno-[2,3-d]-pyrimidine yields 2-(pyrazin-2-yl)-4-(3,4-ethylenedioxyphenethylamino)-5,6-dimethyl-thieno-[2,3-d]-pyrimidine.

EXAMPLE 1329

With the procedure of Example 1, the reaction of 3,4-ethylenedioxyphenethylamine with 4-chloro-2-(pyrazin-2-yl)-6-trifluoromethyl-thieno-[2,3-d]-pyrimidine yields 2-(pyrazin-2-yl)-4-(3,4-ethylenedioxyphenethylamino)-6-trifluoromethyl-thieno-[2,3-d]-pyrimidine.

EXAMPLE 1330

With the procedure of Example 1, the reaction of 3,4-ethylenedioxyphenethylamine with 4-chloro-2-(pyridin-2-yl)-6-methyl-thieno-[2,3-d]-pyrimidine yields 2-(pyridin-2-yl)-4-(3,4-ethylenedioxyphenethylamino)-6-methyl-thieno-[2,3-d]-pyrimidine.

EXAMPLE 1331

With the procedure of Example 1, the reaction of 3,4-ethylenedioxyphenethylamine with 4-chloro-2-(pyridin-2-yl)-5-methyl-thieno-[2,3-d]-pyrimidine yields 2-(pyridin-2-yl)-4-(3,4-ethylenedioxyphenethylamino)-5-methyl-thieno-[2,3-d]-pyrimidine.

EXAMPLE 1332

With the procedure of Example 1, the reaction of 3,4-ethylenedioxyphenethylamine with 4-chloro-2-(pyridin-2-yl)-5,6,7,8-tetrahydro-[1]-benzothieno-[2,3-d]-pyrimidine yields 2-(pyridin-2-yl)-4-(3,4-ethylenedioxyphenethylamino)-5,6,7,8-tetrahydro-thieno-[2,3-d]-pyrimidine.

EXAMPLE 1333

With the procedure of Example 1, the reaction of 3,4-ethylenedioxyphenethylamine with 4-chloro-2-(pyridin-2-yl)-5,6-cyclopenteno-thieno-[2,3-d]-pyrimidine yields 2-(pyridin-2-yl)-4-(3,4-ethylenedioxyphenethylamino)-5,6-cyclopenteno-thieno-[2,3-d]-pyrimidine.

EXAMPLE 1334

With the procedure of Example 1, the reaction of 3,4-ethylenedioxyphenethylamine with 4-chloro-2-(pyridin-2-yl)-5,6-cyclohepteno-thieno-[2,3-d]-pyrimidine yields 2-(pyridin-2-yl)-4-(3,4-ethylenedioxyphenethylamino)-5,6-cyclohepteno-thieno-[2,3-d]-pyrimidine.

EXAMPLE 1335

With the procedure of Example 1, the reaction of 3,4-ethylenedioxyphenethylamine with 4-chloro-2-(pyridin-2-yl)-6-ethyl-thieno-[2,3-d]-pyrimidine yields 2-(pyridin-2-yl)-4-(3,4-ethylenedioxyphenethylamino)-6-ethyl-thieno-[2,3-d]-pyrimidine.

EXAMPLE 1336

With the procedure of Example 1, the reaction of 3,4-ethylenedioxyphenethylamine with 4-chloro-2-(pyridin-2-yl)-6-chloro-thieno-[2,3-d]-pyrimidine yields 2-(pyridin-2-yl)-4-(3,4-ethylenedioxyphenethylamino)-6-chloro-thieno-[2,3-d]-pyrimidine.

EXAMPLE 1337

With the procedure of Example 1, the reaction of 3,4-ethylenedioxyphenethylamine with 4-chloro-2-(pyridin-2- yl)-5-chloro-6-methyl-thieno-[2,3-d]-pyrimidine yields 2-(pyridin-2-yl)-4-(3,4-ethylenedioxyphenethylamino)-5-chlror-6-methyl-thieno-[2,3-d]-pyrimidine.

EXAMPLE 1338

With the procedure of Example 1, the reaction of 3,4-ethylenedioxyphenethylamine with 4-chloro-2-(pyridin-2-yl)-6-nitro-thieno-[2,3-d]-pyrimidine yields 2-(pyridin-2-yl)-4-(3,4-ethylenedioxyphenethylamino)-6-nitro-thieno-[2,3-d]-pyrimidine.

EXAMPLE 1339

With the procedure of Example 1, the reaction of 3,4-ethylenedioxyphenethylamine with 4-chloro-2-(pyridin-2-yl)-5,6-dimethyl-thieno-[2,3-d]-pyrimidine yields 2-(pyridin-2-yl)-4-(3,4-ethylenedioxyphenethylamino)-5,6-dimethyl-thieno-[2,3-d]-pyrimidine.

EXAMPLE 1340

With the procedure of Example 1, the reaction of 3,4-ethylenedioxyphenethylamine with 4-chloro-2-(pyridin-2-yl)-6-trifluoromethyl-thieno-[2,3-d]-pyrimidine yields 2-(pyridin-2-yl)-4-(3,4-ethylenedioxyphenethylamino)-6-trifluoromethyl-thieno-[2,3-d]-pyrimidine.

EXAMPLE 1341

With the procedure of Example 1, the reaction of 3,4-ethylenedioxyphenethylamine with 4-chloro-2-(pyridin-4-yl)-6-methyl-thieno-[2,3-d]-pyrimidine yields 2-(pyridin-4-yl)-4-(3,4-ethylenedioxyphenethylamino)-6-methyl-thieno-[2,3-d]-pyrimidine.

EXAMPLE 1342

With the procedure of Example 1, the reaction of 3,4-ethylenedioxyphenethylamine with 4-chloro-2-(pyridin-4-yl)-5-methyl-thieno-[2,3-d]-pyrimidine yields 2-(pyridin-4-yl)-4-(3,4-ethylenedioxyphenethylamino)-5-methyl-thieno-[2,3-d]-pyrimidine.

EXAMPLE 1343

With the procedure of Example 1, the reaction of 3,4-ethylenedioxyphenethylamine with 4-chloro-2-(pyridin-4-yl)-5,6,7,8-tetrahydro-[1]-benzothieno-[2,3-d]-pyrimidine yields 2-(pyridin-4-yl)-4-(3,4-ethylenedioxyphenethylamino)-5,6,7,8-tetrahydro-thieno-[2,3-d]-pyrimidine.

EXAMPLE 1344

With the procedure of Example 1, the reaction of 3,4-ethylenedioxyphenethylamine with 4-chloro-2-(pyridin-4-yl)-5,6-cyclopenteno-thieno-[2,3-d]-pyrimidine yields 2-(pyridin-4-yl)-4-(3,4-ethylenedioxyphenethylamino)-5,6-cyclopenteno-thieno-[2,3-d]-pyrimidine.

EXAMPLE 1345

With the procedure of Example 1, the reaction of 3,4-ethylenedioxyphenethylamine with 4-chloro-2-(pyridin-4-yl)-5,6-cyclohepteno-thieno-[2,3-d]-pyrimidine yields 2-(pyridin-4-yl)-4-(3,4-ethylenedioxyphenethylamino)-5,6-cyclohepteno-thieno-[2,3-d]-pyrimidine.

EXAMPLE 1346

With the procedure of Example 1, the reaction of 3,4-ethylenedioxyphenethylamine with 4-chloro-2-(pyridin-4-yl)-6-ethyl-thieno-[2,3-d]-pyrimidine yields 2-(pyridin-4-yl)-4-(3,4-ethylenedioxyphenethylamino)-6-ethyl-thieno-[2,3-d]-pyrimidine.

EXAMPLE 1347

With the procedure of Example 1, the reaction of 3,4-ethylenedioxyphenethylamine with 4-chloro-2-(pyridin-4-yl)-6-chloro-thieno-[2,3-d]-pyrimidine yields 2-(pyridin-4-yl)-4-(3,4-ethylenedioxyphenethylamino)-6-chloro-thieno-[2,3-d]-pyrimidine.

EXAMPLE 1348

With the procedure of Example 1, the reaction of 3,4-ethylenedioxyphenethylamine with 4-chloro-2-(pyridin-4-yl)-5-chloro-6-methyl-thieno-[2,3-d]-pyrimidine yields 2-(pyridin-4-yl)-4-(3,4-ethylenedioxyphenethylamino)-5-chlror-6-methyl-thieno-[2,3-d]-pyrimidine.

EXAMPLE 1349

With the procedure of Example 1, the reaction of 3,4-ethylenedioxyphenethylamine with 4-chloro-2-(pyridin-4-yl)-6-nitro-thieno-[2,3-d]-pyrimidine yields 2-(pyridin-4-yl)-4-(3,4-ethylenedioxyphenethylamino)-6-nitro-thieno-[2,3-d]-pyrimidine.

EXAMPLE 1350

With the procedure of Example 1, the reaction of 3,4-ethylenedioxyphenethylamine with 4-chloro-2-(pyridin-4-yl)-5,6-dimethyl-thieno-[2,3-d]-pyrimidine yields 2-(pyridin-4-yl)-4-(3,4-ethylenedioxyphenethylamino)-5,6-dimethyl-thieno-[2,3-d]-pyrimidine.

EXAMPLE 1351

With the procedure of Example 1, the reaction of 3,4-ethylenedioxyphenethylamine with 4-chloro-2-(pyridin-4-yl)-6-trifluoromethyl-thieno-[2,3-d]-pyrimidine yields 2-(pyridin-4-yl)-4-(3,4-ethylenedioxyphenethylamino)-6-trifluoromethyl-thieno-[2,3-d]-pyrimidine.

EXAMPLE 1352

With the procedure of Example 1, the reaction of phenethylamine with 4-chloro-2-(pyridin-3-yl)-6-methyl-thieno-[2,3-d]-pyrimidine yields 2-(pyridin-3-yl)-4-phenethylamino-6-methyl-thieno-[2,3-d]-pyrimidine.

EXAMPLE 1353

With the procedure of Example 1, the reaction of 4-fluorophenethylamine with 4-chloro-2-(pyridin-3-yl)-5-methyl-thieno-[2,3-d]-pyrimidine yields 2-(pyridin-3-yl)-4-phenethylamino-5-methyl-thieno-[2,3-d]-pyrimidine.

EXAMPLE 1354

With the procedure of Example 1, the reaction of 4-fluorophenethylamine with 4-chloro-2-(pyridin-3-yl)-5,6,7,8-tetrahydro-[1]-benzothieno-[2,3-d]-pyrimidine yields 2-(pyridin-3-yl)-4-phenethylamino-5,6,7,8-tetrahydro-thieno-[2,3-d]-pyrimidine.

EXAMPLE 1355

With the procedure of Example 1, the reaction of phenethylamine with 4-chloro-2-(pyridin-3-yl)-5,6-cyclopenteno-thieno-[2,3-d]-pyrimidine yields 2-(pyridin-3-yl)-4-phenethylamino-5,6-cyclopenteno-thieno-[2,3-d]-pyrimidine.

EXAMPLE 1356

With the procedure of Example 1, the reaction of phenethylamine with 4-chloro-2-(pyridin-3-yl)-5,6-cyclohepteno-thieno-[2,3-d]-pyrimidine yields 2-(pyridin-3-yl)-4-phenethylamino-5,6-cyclohepteno-thieno-[2,3-d]-pyrimidine.

EXAMPLE 1357

With the procedure of Example 1, the reaction of phenethylamine with 4-chloro-2-(pyridin-3-yl)-6-ethyl-thieno-[2,3-d]-pyrimidine yields 2-(pyridin-3-yl)-4-phenethylamino-6-ethyl-thieno-[2,3-d]-pyrimidine.

EXAMPLE 1358

With the procedure of Example 1, the reaction of phenethylamine with 4-chloro-2-(pyridin-3-yl)-6-chloro-thieno-[2,3-d]-pyrimidine yields 2-(pyridin-3-yl)-4-phenethylamino-6-chloro-thieno-[2,3-d]-pyrimidine.

EXAMPLE 1359

With the procedure of Example 1, the reaction of phenethylamine with 4-chloro-2-(pyridin-3-yl)-5-chloro-6-methyl-thieno-[2,3-d]-pyrimidine yields 2-(pyridin-3-yl)-4-phenethylamino-5-chlror-6-methyl-thieno-[2,3-d]-pyrimidine.

EXAMPLE 1360

With the procedure of Example 1, the reaction of phenethylamine with 4-chloro-2-(pyridin-3-yl)-6-nitro-thieno-[2,3-d]-pyrimidine yields 2-(pyridin-3-yl)-4-phenethylamino-6-nitro-thieno-[2,3-d]-pyrimidine.

EXAMPLE 1361

With the procedure of Example 1, the reaction of phenethylamine with 4-chloro-2-(pyridin-3-yl)-5,6-dimethyl-thieno-[2,3-d]-pyrimidine yields 2-(pyridin-3-yl)-4-phenethylamino-5,6-dimethyl-thieno-[2,3-d]-pyrimidine.

EXAMPLE 1362

With the procedure of Example 1, the reaction of phenethylamine with 4-chloro-2-(pyridin-3-yl)-6-trifluoromethyl-thieno-[2,3-d]-pyrimidine yields 2-(pyridin-3-yl)-4-phenethylamino-6-trifluoromethyl-thieno-[2,3-d]-pyrimidine.

EXAMPLE 1363

With the procedure of Example 1, the reaction of phenethylamine with 4-chloro-2-(isoxazol-5-yl)-6-methyl-thieno-[2,3-d]-pyrimidine yields 2-(isoxazol-5-yl)-4-phenethylamino-6-methyl-thieno-[2,3-d]-pyrimidine.

EXAMPLE 1364

With the procedure of Example 1, the reaction of phenethylamine with 4-chloro-2-(isoxazol-5-yl)-5-methyl-thieno-[2,3-d]-pyrimidine yields 2-(isoxazol-5-yl)-4-phenethylamino-5-methyl-thieno-[2,3-d]-pyrimidine.

EXAMPLE 1365

With the procedure of Example 1, the reaction of phenethylamine with 4-chloro-2-(isoxazol-5-yl)-5,6,7,8-tetrahydro-[1]-benzothieno-[2,3-d]-pyrimidine yields 2-(isoxazol-5-yl)-4-phenethylamino-5,6,7,8-tetrahydro-thieno-[2,3-d]-pyrimidine.

EXAMPLE 1366

With the procedure of Example 1, the reaction of phenethylamine with 4-chloro-2-(isoxazol-5-yl)-5,6-cyclopenteno-thieno-[2,3-d]-pyrimidine yields 2-(isoxazol-5-yl)-4-phenethylamino-5,6-cyclopenteno-thieno-[2,3-d]-pyrimidine.

EXAMPLE 1367

With the procedure of Example 1, the reaction of phenethylamine with 4-chloro-2-(isoxazol-5-yl)-5,6-cyclohepteno-thieno-[2,3-d]-pyrimidine yields 2-(isoxazol-5-yl)-4-phenethylamino-5,6-cyclohepteno-thieno-[2,3-d]-pyrimidine.

EXAMPLE 1368

With the procedure of Example 1, the reaction of phenethylamine with 4-chloro-2-(isoxazol-5-yl)-6-ethyl-thieno-[2,3-d]-pyrimidine yields 2-(isoxazol-5-yl)-4-phenethylamino-6-ethyl-thieno-[2,3-d]-pyrimidine.

EXAMPLE 1369

With the procedure of Example 1, the reaction of phenethylamine with 4-chloro-2-(isoxazol-5-yl)-6-chloro-thieno-[2,3-d]-pyrimidine yields 2-(isoxazol-5-yl)-4-phenethylamino-6-chloro-thieno-[2,3-d]-pyrimidine.

EXAMPLE 1370

With the procedure of Example 1, the reaction of phenethylamine with 4-chloro-2-(isoxazol-5-yl)-5-chloro-6-methyl-thieno-[2,3-d]-pyrimidine yields 2-(isoxazol-5-yl)-4-phenethylamino-5-chlror-6-methyl-thieno-[2,3-d]-pyrimidine.

EXAMPLE 1371

With the procedure of Example 1, the reaction of phenethylamine with 4-chloro-2-(isoxazol-5-yl)-6-nitro-thieno-[2,3-d]-pyrimidine yields 2-(isoxazol-5-yl)-4-phenethylamino-6-nitro-thieno-[2,3-d]-pyrimidine.

EXAMPLE 1372

With the procedure of Example 1, the reaction of phenethylamine with 4-chloro-2-(isoxazol-5-yl)-5,6-dimethyl-thieno-[2,3-d]-pyrimidine yields 2-(isoxazol-5-yl)-4-phenethylamino-5,6-dimethyl-thieno-[2,3-d]-pyrimidine.

EXAMPLE 1373

With the procedure of Example 1, the reaction of phenethylamine with 4-chloro-2-(isoxazol-5-yl)-6-trifluoromethyl-thieno-[2,3-d]-pyrimidine yields 2-(isoxazol-5-yl)-4-phenethylamino-6-trifluoromethyl-thieno-[2,3-d]-pyrimidine.

EXAMPLE 1374

With the procedure of Example 1, the reaction of phenethylamine with 4-chloro-2-(pyrazin-2-yl)-6-methyl-thieno-[2,3-d]-pyrimidine yields 2-(pyrazin-2-yl)-4-phenethylamino-6-methyl-thieno-[2,3-d]-pyrimidine.

EXAMPLE 1375

With the procedure of Example 1, the reaction of phenethylamine with 4-chloro-2-(pyrazin-2-yl)-5-methyl-thieno-[2,3-d]-pyrimidine yields 2-(pyrazin-2-yl)-4-phenethylamino-5-methyl-thieno-[2,3-d]-pyrimidine.

EXAMPLE 1376

With the procedure of Example 1, the reaction of phenethylamine with 4-chloro-2-(pyrazin-2-yl)-5,6,7,8-tetrahydro-[1]-benzothieno-[2,3-d]-pyrimidine yields 2-(pyrazin-2-yl)-4-phenethylamino-5,6,7,8-tetrahydro-thieno-[2,3-d]-pyrimidine.

EXAMPLE 1377

With the procedure of Example 1, the reaction of phenethylamine with 4-chloro-2-(pyrazin-2-yl)-5,6-cyclopenteno-thieno-[2,3-d]-pyrimidine yields 2-(pyrazin-2-yl)-4-phenethylamino-5,6-cyclopenteno-thieno-[2,3-d]-pyrimidine.

EXAMPLE 1378

With the procedure of Example 1, the reaction of phenethylamine with 4-chloro-2-(pyrazin-2-yl)-5,6-cycloheptheno-thieno-[2,3-d]-pyrimidine yields 2-(pyrazin-2-yl)-4-phenethylamino-5,6-cycloheptheno-thieno-[2,3-d]-pyrimidine.

EXAMPLE 1379

With the procedure of Example 1, the reaction of phenethylamine with 4-chloro-2-(pyrazin-2-yl)-6-ethyl-thieno-[2,3-d]-pyrimidine yields 2-(pyrazin-2-yl)-4-phenethylamino-6-ethyl-thieno-[2,3-d]-pyrimidine.

EXAMPLE 1380

With the procedure of Example 1, the reaction of phenethylamine with 4-chloro-2-(pyrazin-2-yl)-6-chloro-thieno-[2,3-d]-pyrimidine yields 2-(pyrazin-2-yl)-4-phenethylamino-6-chloro-thieno-[2,3-d]-pyrimidine.

EXAMPLE 1381

With the procedure of Example 1, the reaction of phenethylamine with 4-chloro-2-(pyrazin-2-yl)-5-chloro-6-methyl-thieno-[2,3-d]-pyrimidine yields 2-(pyrazin-2-yl)-4-phenethylamino-5-chlror-6-methyl-thieno-[2,3-d]-pyrimidine.

EXAMPLE 1382

With the procedure of Example 1, the reaction of phenethylamine with 4-chloro-2-(pyrazin-2-yl)-6-nitro-thieno-[2,3-d]-pyrimidine yields 2-(pyrazin-2-yl)-4-phenethylamino-6-nitro-thieno-[2,3-d]-pyrimidine.

EXAMPLE 1383

With the procedure of Example 1, the reaction of phenethylamine with 4-chloro-2-(pyrazin-2-yl)-5,6-dimethyl-thieno-[2,3-d]-pyrimidine yields 2-(pyrazin-2-yl)-4-phenethylamino-5,6-dimethyl-thieno-[2,3-d]-pyrimidine.

EXAMPLE 1384

With the procedure of Example 1, the reaction of phenethylamine with 4-chloro-2-(pyrazin-2-yl)-6-trifluoromethyl-thieno-[2,3-d]-pyrimidine yields 2-(pyrazin-2-yl)-4-phenethylamino-6-trifluoromethyl-thieno-[2,3-d]-pyrimidine.

EXAMPLE 1385

With the procedure of Example 1, the reaction of phenethylamine with 4-chloro-2-(pyridin-2-yl)-6-methyl-thieno-[2,3-d]-pyrimidine yields 2-(pyridin-2-yl)-4-phenethylamino-6-methyl-thieno-[2,3-d]-pyrimidine.

EXAMPLE 1386

With the procedure of Example 1, the reaction of phenethylamine with 4-chloro-2-(pyridin-2-yl)-5-methyl-thieno-[2,3-d]-pyrimidine yields 2-(pyridin-2-yl)-4-phenethylamino-5-methyl-thieno-[2,3-d]-pyrimidine.

EXAMPLE 1387

With the procedure of Example 1, the reaction of phenethylamine with 4-chloro-2-(pyridin-2-yl)-5,6,7,8-tetrahydro-[1]-benzothieno-[2,3-d]-pyrimidine yields 2-(pyridin-2-yl)-4-phenethylamino-5,6,7,8-tetrahydro-thieno-[2,3-d]-pyrimidine.

EXAMPLE 1388

With the procedure of Example 1, the reaction of phenethylamine with 4-chloro-2-(pyridin-2-yl)-5,6-cyclopenteno-thieno-[2,3-d]-pyrimidine yields 2-(pyradin-2-yl)-4-phenethylamino-5,6-cyclopenteno-thieno-[2,3-d]-pyrimidine.

EXAMPLE 1389

With the procedure of Example 1, the reaction of phenethylamine with 4-chloro-2-(pyridin-2-yl)-5,6-cycloheptheno-thieno-[2,3-d]-pyrimidine yields 2-(pyradin-2-yl)-4-phenethylamino-5,6-cycloheptheno-thieno-[2,3-d]-pyrimidine.

EXAMPLE 1390

With the procedure of Example 1, the reaction of phenethylamine with 4-chloro-2-(pyridin-2-yl)-6-ethyl-thieno-[2,3-d]-pyrimidine yields 2-(pyridin-2-yl)-4-phenethylamino-6-ethyl-thieno-[2,3-d]-pyrimidine.

EXAMPLE 1391

With the procedure of Example 1, the reaction of phenethylamine with 4-chloro-2-(pyridin-2-yl)-6-chloro-thieno-[2,3-d]-pyrimidine yields 2-(pyridin-2-yl)-4-phenethylamino-6-chloro-thieno-[2,3-d]-pyrimidine.

EXAMPLE 1392

With the procedure of Example 1, the reaction of phenethylamine with 4-chloro-2-(pyridin-2-yl)-5-chloro-6-methyl-thieno-[2,3-d]-pyrimidine yields 2-(pyridin-2-yl)-4-phenethylamino-5-chlror-6-methyl-thieno-[2,3-d]-pyrimidine.

EXAMPLE 1393

With the procedure of Example 1, the reaction of phenethylamine with 4-chloro-2-(pyridin-2-yl)-6-nitro-thieno-[2,3-d]-pyrimidine yields 2-(pyridin-2-yl)-4-phenethylamino-6-nitro-thieno-[2,3-d]-pyrimidine.

EXAMPLE 1394

With the procedure of Example 1, the reaction of phenethylamine with 4-chloro-2-(pyridin-2-yl)-5,6-dimethyl-thieno-[2,3-d]-pyrimidine yields 2-(pyridin-2-yl)-4-phenethylamino-5,6-dimethyl-thieno-[2,3-d]-pyrimidine.

EXAMPLE 1395

With the procedure of Example 1, the reaction of phenethylamine with 4-chloro-2-(pyridin-2-yl)-6- trifluoromethyl-thieno-[2,3-d]-pyrimidine yields 2-(pyridin-2-yl)-4-phenethylamino-6-trifluoromethyl-thieno-[2,3-d]-pyrimidine.

EXAMPLE 1396

With the procedure of Example 1, the reaction of phenethylamine with 4-chloro-2-(pyridin-4-yl)-6-methyl-thieno-[2,3-d]-pyrimidine yields 2-(pyridin-4-yl)-4-phenethylamino-6-methyl-thieno-[2,3-d]-pyrimidine.

EXAMPLE 1397

With the procedure of Example 1, the reaction of phenethylamine with 4-chloro-2-(pyridin-4-yl)-5-methyl-thieno-[2,3-d]-pyrimidine yields 2-(pyridin-4-yl)-4-phenethylamino-5-methyl-thieno-[2,3-d]-pyrimidine.

EXAMPLE 1398

With the procedure of Example 1, the reaction of phenethylamine with 4-chloro-2-(pyridin-4-yl)-5,6,7,8-tetrahydro-[1]-benzothieno-[2,3-d]-pyrimidine yields 2-(pyridin-4-yl)-4-phenethylamino-5,6,7,8-tetrahydro-thieno-[2,3-d]-pyrimidine.

EXAMPLE 1399

With the procedure of Example 1, the reaction of phenethylamine with 4-chloro-2-(pyridin-4-yl)-5,6-cyclopenteno-thieno-[2,3-d]-pyrimidine yields 2-(pyridin-4-yl)-4-phenethylamino-5,6-cyclopenteno-thieno-[2,3-d]-pyrimidine.

EXAMPLE 1400

With the procedure of Example 1, the reaction of phenethylamine with 4-chloro-2-(pyridin-4-yl)-5,6-cyclohepteno-thieno-[2,3-d]-pyrimidine yields 2-(pyridin-4-yl)-4-phenethylamino-5,6-cyclohepteno-thieno-[2,3-d]-pyrimidine.

EXAMPLE 1401

With the procedure of Example 1, the reaction of phenethylamine with 4-chloro-2-(pyridin-4-yl)-6-ethyl-thieno-[2,3-d]-pyrimidine yields 2-(pyridin-4-yl)-4-phenethylamino-6-ethyl-thieno-[2,3-d]-pyrimidine.

EXAMPLE 1402

With the procedure of Example 1, the reaction of phenethylamine with 4-chloro-2-(pyridin-4-yl)-6-chloro-thieno-[2,3-d]-pyrimidine yields 2-(pyridin-4-yl)-4-phenethylamino-6-chloro-thieno-[2,3-d]-pyrimidine.

EXAMPLE 1403

With the procedure of Example 1, the reaction of phenethylamine with 4-chloro-2-(pyridin-4-yl)-5-chloro-6-methyl-thieno-[2,3-d]-pyrimidine yields 2-(pyridin-4-yl)-4-phenethylamino-5-chlror-6-methyl-thieno-[2,3-d]-pyrimidine.

EXAMPLE 1404

With the procedure of Example 1, the reaction of phenethylamine with 4-chloro-2-(pyridin-4-yl)-6-nitro-thieno-[2,3-d]-pyrimidine yields 2-(pyridin-4-yl)-4-phenethylamino-6-nitro-thieno-[2,3-d]-pyrimidine.

EXAMPLE 1405

With the procedure of Example 1, the reaction of phenethylamine with 4-chloro-2-(pyridin-4-yl)-5,6-dimethyl-thieno-[2,3-d]-pyrimidine yields 2-(pyridin-4-yl)-4-phenethylamino-5,6-dimethyl-thieno-[2,3-d]-pyrimidine.

EXAMPLE 1406

With the procedure of Example 1, the reaction of phenethylamine with 4-chloro-2-(pyridin-4-yl)-6-trifluoromethyl-thieno-[2,3-d]-pyrimidine yields 2-(pyridin-4-yl)-4-phenethylamino-6-trifluoromethyl-thieno-[2,3-d]-pyrimidine.

EXAMPLE 1407

With the procedure of Example 1, the reaction of phenethylamine with 4-chloro-2-(pyridin-3-yl)-6-methyl-thieno-[2,3-d]-pyrimidine yields 2-(pyridin-3-yl)-4-phenethylamino-6-methyl-thieno-[2,3-d]-pyrimidine.

EXAMPLE 1408

With the procedure of Example 1, the reaction of phenethylamine with 4-chloro-2-(pyridin-3-yl)-5-methyl-thieno-[2,3-d]-pyrimidine yields 2-(pyridin-3-yl)-4-phenethylamino-5-methyl-thieno-[2,3-d]-pyrimidine.

EXAMPLE 1409

With the procedure of Example 1, the reaction of phenethylamine with 4-chloro-2-(pyridin-3-yl)-5,6,7,8-tetrahydro-[1]-benzothieno-[2,3-d]-pyrimidine yields 2-(pyridin-3-yl)-4-phenethylamino-5,6,7,8-tetrahydro-thieno-[2,3-d]-pyrimidine.

EXAMPLE 1410

With the procedure of Example 1, the reaction of phenethylamine with 4-chloro-2-(pyridin-3-yl)-5,6-cyclopenteno-thieno-[2,3-d]-pyrimidine yields 2-(pyridin-3-yl)-4-phenethylamino-5,6-cyclopenteno-thieno-[2,3-d]-pyrimidine.

EXAMPLE 1411

With the procedure of Example 1, the reaction of phenethylamine with 4-chloro-2-(pyridin-3-yl)-5,6-cyclohepteno-thieno-[2,3-d]-pyrimidine yields 2-(pyridin-3-yl)-4-phenethylamino-5,6-cyclohepteno-thieno-[2,3-d]-pyrimidine.

EXAMPLE 1412

With the procedure of Example 1, the reaction of phenethylamine with 4-chloro-2-(pyridin-3-yl)-6-ethyl-thieno-[2,3-d]-pyrimidine yields 2-(pyridin-3-yl)-4-phenethylamino-6-ethyl-thieno-[2,3-d]-pyrimidine.

EXAMPLE 1413

With the procedure of Example 1, the reaction of phenethylamine with 4-chloro-2-(pyridin-3-yl)-6-chloro-thieno-[2,3-d]-pyrimidine yields 2-(pyridin-3-yl)-4-phenethylamino-6-chloro-thieno-[2,3-d]-pyrimidine.

EXAMPLE 1414

With the procedure of Example 1, the reaction of phenethylamine with 4-chloro-2-(pyridin-3-yl)-5-chloro-6-methyl-thieno-[2,3-d]-pyrimidine yields 2-

EXAMPLE 1415

With the procedure of Example 1, the reaction of phenethylamine with 4-chloro-2-(pyridin-3-yl)-6-nitro-thieno-[2, 3-d]-pyrimidine yields 2-(pyridin-3-yl)-4-phenethylamino-6-nitro-thieno-[2,3-d]-pyrimidine.

EXAMPLE 1416

With the procedure of Example 1, the reaction of phenethylamine with 4-chloro-2-(pyridin-3-yl)-5,6-dimethyl-thieno-[2,3-d]-pyrimidine yields 2-(pyridin-3-yl)-4-phenethylamino-5,6-dimethyl-thieno-[2,3-d]-pyrimidine.

EXAMPLE 1417

With the procedure of Example 1, the reaction of phenethylamine with 4-chloro-2-(pyridin-3-yl)-6-trifluoromethyl-thieno-[2,3-d]-pyrimidine yields 2-(pyridin-3-yl)-4-phenethylamino-6-trifluoromethyl-thieno-[2,3-d]-pyrimidine.

EXAMPLE 1418

With the procedure of Example 1, the reaction of phenethylamine with 4-chloro-2-(isoxazol-5-yl)-6-methyl-thieno-[2,3-d]-pyrimidine yields 2-(isoxazol-5-yl)-4-phenethylamino-6-methyl-thieno-[2,3-d]-pyrimidine.

EXAMPLE 1419

With the procedure of Example 1, the reaction of phenethylamine with 4-chloro-2-(isoxazol-5-yl)-5-methyl-thieno-[2,3-d]-pyrimidine yields 2-(isoxazol-5-yl)-4-phenethylamino-5-methyl-thieno-[2,3-d]-pyrimidine.

EXAMPLE 1420

With the procedure of Example 1, the reaction of phenethylamine with 4-chloro-2-(isoxazol-5-yl)-5,6,7,8-tetrahydro-[1]-benzothieno-[2,3-d]-pyrimidine yields 2-(isoxazol-5-yl)-4-phenethylamino-5,6,7,8-tetrahydro-thieno-[2,3-d]-pyrimidine.

EXAMPLE 1421

With the procedure of Example 1, the reaction of phenethylamine with 4-chloro-2-(isoxazol-5-yl)-5,6-cyclopenteno-thieno-[2,3-d]-pyrimidine yields 2-(isoxazol-5-yl)-4-phenethylamino-5,6-cyclopenteno-thieno-[2,3-d]-pyrimidine.

EXAMPLE 1422

With the procedure of Example 1, the reaction of phenethylamine with 4-chloro-2-(isoxazol-5-yl)-5,6-cyclohepteno-thieno-[2,3-d]-pyrimidine yields 2-(isoxazol-5-yl)-4-phenethylamino-5,6-cyclohepteno-thieno-[2,3-d]-pyrimidine.

EXAMPLE 1423

With the procedure of Example 1, the reaction of phenethylamine with 4-chloro-2-(isoxazol-5-yl)-6-ethyl-thieno-[2,3-d]-pyrimidine yields 2-(isoxazol-5-yl)-4-phenethylamino-6-ethyl-thieno-[2,3-d]-pyrimidine.

EXAMPLE 1424

With the procedure of Example 1, the reaction of phenethylamine with 4-chloro-2-(isoxazol-5-yl)-6-chloro-thieno-[2,3-d]-pyrimidine yields 2-(isoxazol-5-yl)-4-phenethylamino-6-chloro-thieno-[2,3-d]-pyrimidine.

EXAMPLE 1425

With the procedure of Example 1, the reaction of phenethylamine with 4-chloro-2-(isoxazol-5-yl)-5-chloro-6-methyl-thieno-[2,3-d]-pyrimidine yields 2-2-(isoxazol-5-yl)-4-phenethylamino-5-chlror-6-methyl-thieno-[2,3-d]-pyrimidine.

EXAMPLE 1426

With the procedure of Example 1, the reaction of phenethylamine with 4-chloro-2-(isoxazol-5-yl)-6-nitro-thieno-[2,3-d]-pyrimidine yields 2-(isoxazol-5-yl)-4-phenethylamino-6-nitro-thieno-[2,3-d]-pyrimidine.

EXAMPLE 1427

With the procedure of Example 1, the reaction of phenethylamine with 4-chloro-2-(isoxazol-5-yl)-5,6-dimethyl-thieno-[2,3-d]-pyrimidine yields 2-(isoxazol-5-yl)-4-phenethylamino-5,6-dimethyl-thieno-[2,3-d]-pyrimidine.

EXAMPLE 1428

With the procedure of Example 1, the reaction of phenethylamine with 4-chloro-2-(isoxazol-5-yl)-6-trifluoromethyl-thieno-[2,3-d]-pyrimidine yields 2-(isoxazol-5-yl)-4-phenethylamino-6-trifluoromethyl-thieno-[2,3-d]-pyrimidine.

EXAMPLE 1429

With the procedure of Example 1, the reaction of phenethylamine with 4-chloro-2-(pyrazin-2-yl)-6-methyl-thieno-[2,3-d]-pyrimidine yields 2-(pyrazin-2-yl)-4-phenethylamino-6-methyl-thieno-[2,3-d]-pyrimidine.

EXAMPLE 1430

With the procedure of Example 1, the reaction of phenethylamine with 4-chloro-2-(pyrazin-2-yl)-5-methyl-thieno-[2,3-d]-pyrimidine yields 2-(pyrazin-2-yl)-4-phenethylamino-5-methyl-thieno-[2,3-d]-pyrimidine.

EXAMPLE 1431

With the procedure of Example 1, the reaction of phenethylamine with 4-chloro-2-(pyrazin-2-yl)-5,6,7,8-tetrahydro-[1]-benzothieno-[2,3-d]-pyrimidine yields 2-(pyrazin-2-yl)-4-phenethylamino-5,6,7,8-tetrahydro-thieno-[2,3-d]-pyrimidine.

EXAMPLE 1432

With the procedure of Example 1, the reaction of phenethylamine with 4-chloro-2-(pyrazin-2-yl)-5,6-cyclopenteno-thieno-[2,3-d]-pyrimidine yields 2-(pyrazin-2-yl)-4-phenethylamino-5,6-cyclopenteno-thieno-[2,3-d]-pyrimidine.

EXAMPLE 1433

With the procedure of Example 1, the reaction of phenethylamine with 4-chloro-2-(pyrazin-2-yl)-5,6-cyclohepteno-thieno-[2,3-d]-pyrimidine yields 2-(pyrazin-2-yl)-4-phenethylamino-5,6-cyclohepteno-thieno-[2,3-d]-pyrimidine.

EXAMPLE 1434

With the procedure of Example 1, the reaction of phenethylamine with 4-chloro-2-(pyrazin-2-yl)-6-ethyl-thieno-[2,3-d]-pyrimidine yields 2-(pyrazin-2-yl)-4-phenethylamino-6-ethyl-thieno-[2,3-d]-pyrimidine.

EXAMPLE 1435

With the procedure of Example 1, the reaction of phenethylamine with 4-chloro-2-(pyrazin-2-yl)-6-chloro-thieno-

[2,3-d]-pyrimidine yields 2-(pyrazin-2-yl)-4-phenethylamino-6-chloro-thieno-[2,3-d]-pyrimidine.

EXAMPLE 1436

With the procedure of Example 1, the reaction of phenethylamine with 4-chloro-2-(pyrazin-2-yl)-5-chloro-6-methyl-thieno-[2,3-d]-pyrimidine yields 2-(pyrazin-2-yl)-4-phenethylamino-5-chlror-6-methyl-thieno-[2,3-d]-pyrimidine.

EXAMPLE 1437

With the procedure of Example 1, the reaction of phenethylamine with 4-chloro-2-(pyrazin-2-yl)-6-nitro-thieno-[2,3-d]-pyrimidine yields 2-(pyrazin-2-yl)-4-phenethylamino-6-nitro-thieno-[2,3-d]-pyrimidine.

EXAMPLE 1438

With the procedure of Example 1, the reaction of phenethylamine with 4-chloro-2-(pyrazin-2-yl)-5,6-dimethyl-thieno-[2,3-d]-pyrimidine yields 2-(pyrazin-2-yl)-4-phenethylamino-5,6-dimethyl-thieno-[2,3-d]-pyrimidine.

EXAMPLE 1439

With the procedure of Example 1, the reaction of phenethylamine with 4-chloro-2-(pyrazin-2-yl)-6-trifluoromethyl-thieno-[2,3-d]-pyrimidine yields 2-(pyrazin-2-yl)-4-phenethylamino-6-trifluoromethyl-thieno-[2,3-d]-pyrimidine.

EXAMPLE 1440

With the procedure of Example 1, the reaction of phenethylamine with 4-chloro-2-(pyridin-2-yl)-6-methyl-thieno-[2,3-d]-pyrimidine yields 2-(pyridin-2-yl)-4-phenethylamino-6-methyl-thieno-[2,3-d]-pyrimidine.

EXAMPLE 1441

With the procedure of Example 1, the reaction of phenethylamine with 4-chloro-2-(pyridin-2-yl)-5-methyl-thieno-[2,3-d]-pyrimidine yields 2-(pyridin-2-yl)-4-phenethylamino-5-methyl-thieno-[2,3-d]-pyrimidine.

EXAMPLE 1442

With the procedure of Example 1, the reaction of phenethylamine with 4-chloro-2-(pyridin-2-yl)-5,6,7,8-tetrahydro-[1]-benzothieno-[2,3-d]-pyrimidine yields 2-(pyridin-2-yl)-4-phenethylamino-5,6,7,8-tetrahydro-thieno-[2,3-d]-pyrimidine.

EXAMPLE 1443

With the procedure of Example 1, the reaction of phenethylamine with 4-chloro-2-(pyridin-2-yl)-5,6-cyclopenteno-thieno-[2,3-d]-pyrimidine yields 2-(pyradin-2-yl)-4-phenethylamino-5,6-cyclopenteno-thieno-[2,3-d]-pyrimidine.

EXAMPLE 1444

With the procedure of Example 1, the reaction of phenethylamine with 4-chloro-2-(pyridin-2-yl)-5,6-cyclohepteno-thieno-[2,3-d]-pyrimidine yields 2-(pyradin-2-yl)-4-phenethylamino-5,6-cyclohepteno-thieno-[2,3-d]-pyrimidine.

EXAMPLE 1445

With the procedure of Example 1, the reaction of phenethylamine with 4-chloro-2-(pyridin-2-yl)-6-ethyl-thieno-[2,3-d]-pyrimidine yields 2-(pyridin-2-yl)-4-phenethylamino-6-ethyl-thieno-[2,3-d]-pyrimidine.

EXAMPLE 1446

With the procedure of Example 1, the reaction of phenethylamine with 4-chloro-2-(pyridin-2-yl)-6-chloro-thieno-[2,3-d]-pyrimidine yields 2-(pyridin-2-yl)-4-phenethylamino-6-chloro-thieno-[2,3-d]-pyrimidine.

EXAMPLE 1447

With the procedure of Example 1, the reaction of phenethylamine with 4-chloro-2-(pyridin-2-yl)-5-chloro-6-methyl-thieno-[2,3-d]-pyrimidine yields 2-(pyridin-2-yl)-4-phenethylamino-5-chlror-6-methyl-thieno-[2,3-d]-pyrimidine.

EXAMPLE 1448

With the procedure of Example 1, the reaction of phenethylamine with 4-chloro-2-(pyridin-2-yl)-6-nitro-thieno-[2,3-d]-pyrimidine yields 2-(pyridin-2-yl)-4-phenethylamino-6-nitro-thieno-[2,3-d]-pyrimidine.

EXAMPLE 1449

With the procedure of Example 1, the reaction of phenethylamine with 4-chloro-2-(pyridin-2-yl)-5,6-dimethyl-thieno-[2,3-d]-pyrimidine yields 2-(pyridin-2-yl)-4-phenethylamino-5,6-dimethyl-thieno-[2,3-d]-pyrimidine.

EXAMPLE 1450

With the procedure of Example 1, the reaction of phenethylamine with 4-chloro-2-(pyridin-2-yl)-6-trifluoromethyl-thieno-[2,3-d]-pyrimidine yields 2-(pyradin-2-yl)-4-phenethylamino-6-trifluoromethyl-thieno-[2,3-d]-pyrimidine.

EXAMPLE 1451

With the procedure of Example 1, the reaction of phenethylamine with 4-chloro-2-(pyridin-4-yl)-6-methyl-thieno-[2,3-d]-pyrimidine yields 2-(pyridin-4-yl)-4-phenethylamino-6-methyl-thieno-[2,3-d]-pyrimidine.

EXAMPLE 1452

With the procedure of Example 1, the reaction of phenethylamine with 4-chloro-2-(pyridin-4-yl)-5-methyl-thieno-[2,3-d]-pyrimidine yields 2-(pyridin-4-yl)-4-phenethylamino-5-methyl-thieno-[2,3-d]-pyrimidine.

EXAMPLE 1453

With the procedure of Example 1, the reaction of phenethylamine with 4-chloro-2-(pyridin-4-yl)-5,6,7,8-tetrahydro-[1]-benzothieno-[2,3-d]-pyrimidine yields

EXAMPLE 1454

With the procedure of Example 1, the reaction of phenethylamine with 4-chloro-2-(pyridin-4-yl)-5,6-cyclopenteno-thieno-[2,3-d]-pyrimidine yields 2-(pyridin-4-yl)-4-phenethylamino-5,6-cyclopenteno-thieno-[2,3-d]-pyrimidine.

EXAMPLE 1455

With the procedure of Example 1, the reaction of phenethylamine with 4-chloro-2-(pyridin-4-yl)-5,6- cyclohepteno-thieno-[2,3-d]-pyrimidine yields 2-(pyridin-4-yl)-4-phenethylamino-5,6-cyclohepteno-thieno-[2,3-d]-pyrimidine.

EXAMPLE 1456

With the procedure of Example 1, the reaction of phenethylamine with 4-chloro-2-(pyridin-4-yl)-6-ethyl-thieno-[2,3-d]-pyrimidine yields 2-(pyridin-4-yl)-4-phenethylamino-6-ethyl-thieno-[2,3-d]-pyrimidine.

EXAMPLE 1457

With the procedure of Example 1, the reaction of phenethylamine with 4-chloro-2-(pyridin-4-yl)-6-chloro-thieno-[2,3-d]-pyrimidine yields 2-(pyridin-4-yl)-4-phenethylamino-6-chloro-thieno-[2,3-d]-pyrimidine.

EXAMPLE 1458

With the procedure of Example 1, the reaction of phenethylamine with 4-chloro-2-(pyridin-4-yl)-5-chloro-6-methyl-thieno-[2,3-d]-pyrimidine yields 2-(pyridin-4-yl)-4-phenethylamino-5-chlror-6-methyl-thieno-[2,3-d]-pyrimidine.

EXAMPLE 1459

With the procedure of Example 1, the reaction of phenethylamine with 4-chloro-2-(pyridin-4-yl)-6-nitro-thieno-[2,3-d]-pyrimidine yields 2-(pyridin-4-yl)-4-phenethylamino-6-nitro-thieno-[2,3-d]-pyrimidine.

EXAMPLE 1460

With the procedure of Example 1, the reaction of phenethylamine with 4-chloro-2-(pyridin-4-yl)-5,6-dimethyl-thieno-[2,3-d]-pyrimidine yields 2-(pyridin-4-yl)-4-phenethylamino-5,6-dimethyl-thieno-[2,3-d]-pyrimidine.

EXAMPLE 1461

With the procedure of Example 1, the reaction of phenethylamine with 4-chloro-2-(pyridin-4-yl)-6-trifluoromethyl-thieno-[2,3-d]-pyrimidine yields 2-(pyridin-4-yl)-4-phenethylamino-6-trifluoromethyl-thieno-[2,3-d]-pyrimidine.

EXAMPLE 1462

A solution of 2-(Imidazol-1-yl)-6-methyl-4-(3-nitrobenzylamino)-thieno-[2,3-d]-pyrimidine in methanol is hydrogenated in the presence of Raney-nickel. The catalyst is filtered off and the solution is concentrated. Recrystallization yields 2-(imidazol-1-yl)-6-methyl-4-(3-aminobenzylamino)-thieno-[2,3-d]-pyrimidine.

EXAMPLE 1463

A solution of 2-(Imidazol-1-yl)-6-methyl-4-(3-aminobenzylamino)-thieno-[2,3-d]-pyrimidine (6 g) and titantetrachloride (0.5 g) in methanol (100 ml) is charged with freshly distilled acetaldehyde (1 ml). Natriumcyanborhydride (4 g) is added and the mixture is stirred 30 hours. Semi concentrated HCl is added. The usual workup yields 2-(Imidazol-1-yl)-6-methyl-4-(3-N-ethylamino-benzylamino)-thieno-[2,3-d]-pyrimidine.

EXAMPLE 1464

In analogy to Example 2 the following compounds are obtained.

2-(Imidazol-1-yl)-5,6,7,8-tetrahydro-4-(3,4-difluorobenzylamino)-[1]-benzothieno-[2,3-d]-pyrimidine m.p. 212° C.

2-(Imidazol-1-yl)-5,6-cyclopenteno-4-benzylamino-thieno-[2,3-d]-pyrimidine m.p. 221° C.

2-(Imidazol-1-yl)-6-methyl-4-benzylamino-thieno-[2,3-d]-pyrimidine m.p. 241° C.

2-(Imidazol-1-yl)-6-methyl-4-(3,4-dimethoxybenzylamino)-thieno-[2,3-d]-pyrimidine m.p. 217° C.

2-(Imidazol-1-yl)-6-chloro-5-methyl-4-(3,4-methylendioxybenzylamino)-thieno-[2,3-d]-pyrimidine m.p. 250° C.

2-(Imidazol-1-yl)-5,6,7,8-tetrahydro-4-benzylamino-[1]-benzothieno-[2,3-d]-pyrimidine m.p. 190° C.

2-(1,2,4-Triazol-1-yl)-6-methyl-4-(3,4-methylendioxybenzylamino)-thieno-[2,3-d]-pyrimidine m.p. 231° C.

2-(Imidazol-1-yl)-6-isopropyl-4-(3,4-methylendioxybenzylamino)-thieno-[2,3-d]-pyrimidine m.p. 192° C.

2-(Imidazol-1-yl)-6-propyl-4-(3,4-methylendioxybenzylamino)-thieno-[2,3-d]-pyrimidine m.p. 183° C.

We claim:

1. A method of treating a mammal having precancerous lesions sensitive to treatment with a compound of Formula I comprising administering a pharmacologically effective amount of a compound of Formula I or pharmaceutically acceptable salt thereof:

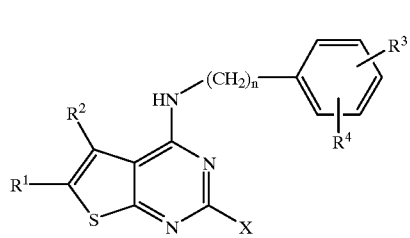

(I)

wherein $R_1$ and $R_2$ are independently selected from the group consisting of hydrogen, hydroxy, A, OA, alkenyl, alkynyl, —NO$_2$, —CF$_3$ or halogen, with the proviso that one of $R_1$ or $R_2$ is not hydrogen;

$R_3$ and $R_4$ are independently selected from the group consisting of hydrogen, A, —OA, halogen, —NO$_2$, —NH$_2$, —NHA or —NAA', or $R_3$ and $R_4$ are together form a moiety selected from the group consisting of —O—CH$_2$—CH$_2$—, —O—CH$_2$—O— or —O—CH$_2$—CH$_2$—O, X is selected from the group consisting of an unsubstituted or a substituted 5–7 membered saturated or unsaturated ring, wherein the ring is selected from the group consisting of phenyl, cyclopentyl, cyclohexyl, cycloheptyl, furyl, dioxolanyl, thienyl, pyrrolyl, pyrrolidinyl, imidazolyl, pyrazolyl, pyridyl, piperidinyl, morpholinyl, pyranyl, dioxanyl, pyridazinyl, pyrimidinyl, piperazinyl, quinolyl, and isoquinolyl and wherein the substitutents on the "X" ring are one or two selected from the group consisting of -lower alkyl, COOH, —COOA, —CONH$_2$, —CONAA', —CONHA, —CN, —CH$_2$COOH or —CH$_2$CH$_2$COOH;

A and A' are independently selected from the group consisting of C$_{1-6}$ alkyl; and n is 0, 1, 2 or 3; and
physiologically acceptable salts thereof.

2. The method according to claim 1 wherein X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH.

3. The method according to claim 1 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; X is as defined in Group 1; and n is 1.

4. The method according to claim 1 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ are independently selected from the group consisting of hydrogen, A, OA, halogen, —NO$_2$, —NH$_2$, —NHA or —NAA'; X is as defined in group 1; and n is 1.

5. A method for inducing apoptosis in human neoplastic cells comprising exposing said cells to an effective amount of a compound of the formula:

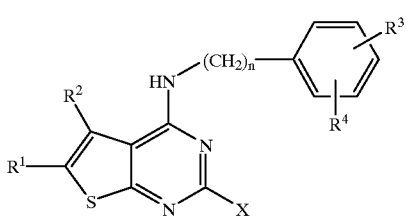

(I)

wherein $R_1$ and $R_2$ are independently selected from the group consisting of hydrogen, hydroxy A, OA, alkenyl, alkynyl, —NO$_2$, —CF$_3$ or halogen, with the proviso that one of $R_1$ or $R_2$ is not hydrogen;

$R_3$ and $R_4$ are independently selected from the group consisting of hydrogen, A,—OA, halogen, —NO$_2$, —NH$_2$, —NHA or —NAA', or $R_3$ and $R_4$ are together form a moiety selected from the group consisting of —O—CH$_2$—CH$_2$—, —O—CH$_2$—O— or —O—CH$_2$—CH$_2$—O, X is selected from the group consisting of an unsubstituted or a substituted 5–7 membered saturated or unsaturated ring, wherein the ring is selected from the group consisting of phenyl, cyclopentyl, cyclohexyl, cycloheptyl, furyl, dioxolanyl, thienyl, pyrrolyl, pyrrolidinyl, imidazolyl, pyrazolyl, pyridyl, piperidinyl, morpholinyl, pyranyl, dioxanyl, pyridazinyl, pyrimidinyl, piperazinyl, quinolyl, and isoquinolyl and wherein the substitutents on the "X" ring are one or two selected from the group consisting of —lower alkyl, COOH, —COOA, —CONH$_2$, —CONAA', —CONHA, —CN, —CH$_2$COOH or —CH$_2$CH$_2$COOH;

A and A' are independently selected from the group consisting of C$_{1-6}$ alkyl; and n is 0, 1, 2 or 3; and
physiologically acceptable salts thereof.

6. The method according to claim 5 wherein X is single or double substituted phenyl, 1-piperidinyl or cyclohexyl wherein said substitutents are selected from the group consisting of —COOH, —COOA, —CONH$_2$, —CONAA', —CONHA, —CN, —CH$_2$COOH or —CH$_2$CH$_2$COOH.

7. The method according to claim 5 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; X is as defined in Group 1; and n is 1.

8. The method according to claim 5 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ are independently selected from the group consisting of hydrogen, A, OA, halogen, —NO$_2$, —NH$_2$, —NHA, or —NAA'; X is as defined in group 1; and n is 1.

9. A method for inhibiting the growth of neoplastic cells sensitive to treatment with a compound of Formula I comprising exposing the cells to a growth inhibiting effective amount of a compound of Formula I or pharmaceutically acceptable salt thereof:

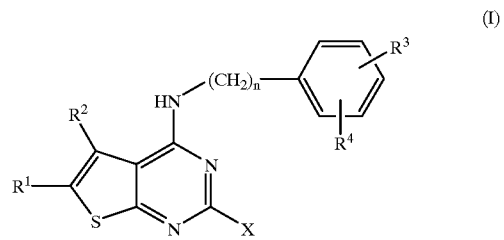

(I)

wherein $R_1$ and $R_2$ are independently selected from the group consisting of hydrogen, hydroxy, A, OA, alkenyl, alkynyl, —NO$_2$, —CF$_3$ or halogen, with the proviso that one of $R_1$ or $R_2$ is not hydrogen;

$R_3$ and $R_4$ are independently selected from the group consisting of hydrogen, A, —OA, halogen, —NO$_2$, —NH$_2$, —NHA or —NAA', or $R_3$ and $R_4$ are together form a moiety selected from the group consisting of —O—CH$_2$—CH$_2$—, —O—CH$_2$—O— or —O—CH$_2$—CH$_2$—O, X is selected from the group consisting of an unsubstituted or a substituted 5–7 membered saturated or unsaturated ring, wherein the ring is selected from the group consisting of phenyl, cyclopentyl, cyclohexyl, cycloheptyl, furyl, dioxolanyl, thienyl, pyrrolyl, pyrrolidinyl, imidazolyl, pyrazolyl, pyridyl, piperidinyl, morpholinyl, pyranyl, dioxanyl, pyridazinyl, pyrimidinyl, piperazinyl, quinolyl, and isoquinolyl and wherein the substitutents on the "X" ring are one or two selected from the group consisting of -lower alkyl, COOH, —COOA, —CONH$_2$, —CONAA', —CONHA, —CN, —CH$_2$COOH or —CH$_2$CH$_2$COOH;

A and A' are independently selected from the group consisting of C$_{1-6}$ alkyl; and n is 0, 1, 2 or 3; and
physiologically acceptable salts thereof.

10. The method according to claim 9 wherein X is single or double substituted phenyl, 1-piperidinyl or cyclohexyl wherein said substitutents are selected from the group consisting of —COOH, —COOA, —CONH$_2$; —CONAA', —CONHA, —CN, —CH$_2$COOH or —CH$_2$CH$_2$COOH.

11. The method according to claim 9 wherein $R_1$ and $R_2$ are independently selected from the group consisting of hydrogen, A, OA, NO$_2$, CF$_3$ or halogen, with the proviso that one of $R_1$ and $R_2$ is not hydrogen; $R_3$ and $R_4$ together form a moiety selected from the group consisting of —O—CH$_2$—CH$_2$—, —O—CH$_2$—O— or —O—CH$_2$—CH$_2$—O; X is as defined in Group 1; and n is 1.

12. The method according to claim 9 wherein R$_1$ and R$_2$ are independently selected from the group consisting of hydrogen, A, OA, NO$_2$, CF$_3$ or halogen, with the proviso that one of R$_1$ and R$_2$ is not hydrogen; R$_3$ and R$_4$ are independently selected from the group consisting of hydrogen, A, OA, halogen, —NO$_2$, —NH$_2$, —NHA or —NAA'; X is as defined in group 1; and n is 1.

* * * * *